United States Patent
Pujala et al.

(10) Patent No.: US 11,504,364 B2
(45) Date of Patent: Nov. 22, 2022

(54) INHIBITORS OF FIBROBLAST ACTIVATION PROTEIN

(71) Applicant: Praxis Biotech LLC, San Francisco, CA (US)

(72) Inventors: Brahmam Pujala, Uttar Pradesh (IN); Dayanand Panpatil, Uttar Pradesh (IN); Sebastian Bernales, Piedmont, CA (US); Sebastian Belmar, Santiago (CL); Gonzalo Andrés Ureta Díaz, Santiago (CL)

(73) Assignee: PRAXIS BIOTECH LLC, San Francisco, CA (US)

( * ) Notice: Subject to any disclaimer, the term of this patent is extended or adjusted under 35 U.S.C. 154(b) by 0 days.

(21) Appl. No.: 16/724,198

(22) Filed: Dec. 21, 2019

(65) Prior Publication Data

US 2020/0206216 A1    Jul. 2, 2020

Related U.S. Application Data

(60) Provisional application No. 62/863,853, filed on Jun. 19, 2019, provisional application No. 62/784,291, filed on Dec. 21, 2018.

(51) Int. Cl.
| | |
|---|---|
| C07D 405/14 | (2006.01) |
| A61K 31/4709 | (2006.01) |
| A61K 31/192 | (2006.01) |
| C07D 401/12 | (2006.01) |
| C07D 401/14 | (2006.01) |
| A61P 35/00 | (2006.01) |

(52) U.S. Cl.
CPC ........ *A61K 31/4709* (2013.01); *A61K 31/192* (2013.01); *A61P 35/00* (2018.01); *C07D 401/12* (2013.01); *C07D 401/14* (2013.01); *C07D 405/14* (2013.01)

(58) Field of Classification Search
CPC .................................................... A61K 31/47
See application file for complete search history.

(56) References Cited

U.S. PATENT DOCUMENTS

| | | | |
|---|---|---|---|
| 8,183,280 | B2 | 5/2012 | Evans |
| 9,346,814 | B2 | 5/2016 | Jansen et al. |
| 2006/0276435 | A1 | 12/2006 | Cohen |
| 2007/0098781 | A1 | 5/2007 | Loeffler |
| 2010/0081701 | A1 | 4/2010 | Evans |
| 2010/0291020 | A1 | 11/2010 | Arora |
| 2012/0045509 | A1 | 2/2012 | Loeffler |
| 2014/0357650 | A1 | 12/2014 | Jansen et al. |
| 2019/0185451 | A1 | 6/2019 | Alfaro |
| 2020/0216417 | A1 | 7/2020 | Bernales |

FOREIGN PATENT DOCUMENTS

| | | |
|---|---|---|
| EA | 028422 81 | 11/2017 |
| RU | 2447063 C2 | 4/2012 |
| WO | 2003002553 A2 | 1/2003 |
| WO | 2004071454 A2 | 8/2004 |
| WO | 2007085895 A2 | 8/2007 |
| WO | 2009116067 A2 | 9/2009 |
| WO | 2010083570 A1 | 7/2010 |
| WO | 2013107820 A1 | 7/2013 |
| WO | 2017011831 A1 | 1/2017 |
| WO | 2017189569 A1 | 11/2017 |
| WO | 2018111969 A1 | 6/2018 |
| WO | 2018111989 A1 | 6/2018 |
| WO | 2019083990 A2 | 5/2019 |
| WO | 2019118932 A1 | 6/2019 |
| WO | 2019154886 A1 | 8/2019 |

OTHER PUBLICATIONS

Pinedo et al. (2000).*
McMahon et al. (2000).*
Aertgeerts, K. et al. (May 2005). "Structural and Kinetic Analysis of the Substrate Specificity of Human Fibroblast Activation Protein α," J. Biol. Chem. 280(20):19441-19444.
Brokopp, C.E. et al. (2011, e-pub. Feb. 2, 2011). "Fibroblast Activation Protein is induced By Inflammation and degrades Type I Collagen in Thin-Cap Fibroatheromata," Eur. Heart J. 32(21):2713-2722.
Camacho, R.C. et al. (Sep. 5, 2013, e-pub. Jul. 3, 2013). "Pegylated Fgf21 Rapidly Normalizes Insulin-Stimulated Glucose Utilization In Diet-Induced insulin Resistant Mice," Eur. J. Pharmacol. 715(1-3):41-45.
Chen, L. et al. (Aug. 9, 2017). "PKM2 Aggravates Palmitate-Induced Insulin Resistance in HepG2 Celis via STAT3 Pathway," Biochem. Biophys. Res. Commun. 492(1):109-115.
Cohen, S.J. et al. (Aug. 2008). "Fibroblast Activation Protein and Its Relationship to Clinical Outcome in Pancreatic Adenocarcinoma," Pancreas 37(2):154-158.
Coppage, A.L. et al. (Mar. 10, 2016). "Human FGF-21 Is a Substrate of Fibroblast Activation Protein," PLoSOne 11(3):e0151269, 10 pages.
Cunningham, C.C. (Sep. 2007). "Talabostat," Expert Opin Investig Drugs 16(9):1459-1465.
Dong, J.Q., et al. (2 015, e-pub. May 2, 2015). "Pharmacokinetics and Pharmacodynamics of PF-05231023, A Novel Long-Acting FGF21 Mimetic, In a First-In-Human Study," Br. J. Clin. Pharmacol. 80(5):1051-1063.
Dunshee, D.R. et al. (Mar. 11, 2016). "Fibroblast Activation Protein Cleaves and Inactivates Fibroblast Growth Factor 21," J. Biol. Chem. 291(11):5986-5995.
Eager, R.M. et al. (Jul. 30, 2009). "Phase II Assessment of Talabostat and Cisplatin in Second-Line Stage IV Melanoma," BMC Cancer 9:263, 11 pages.
Eager, R.M., et al. (Aug. 2009, e-pub. Jun. 5, 2009). "Phase II Trial of Talabostat and Docetaxel in Advanced Non-Small Cell Lung Cancer," Clin. Oneal. R. Coll. Radiol. 21(6):464-472.
Gaich, G. et al. (Sep. 3, 2013). "The Effects of LY2405319, an FGF21 Arsalog, In Obese Human Subjects with Type 2 Diabetes," Cell Metab 18(3):333-340.

(Continued)

*Primary Examiner* — Paul V Ward
(74) *Attorney, Agent, or Firm* — Morrison & Foerster LLP

(57) ABSTRACT

Compounds and compositions for modulating fibroblast activation protein (FAP) are described. The compounds and compositions may find use as therapeutic agents for the treatment of diseases, including hyperproliferative diseases.

37 Claims, 3 Drawing Sheets

(56) References Cited

OTHER PUBLICATIONS

Hager, T., et al. (Feb. 4, 2013). "Differential Enzyme-Linked Immunosorbent Assay And Ligand-Binding Mass Spectrometry For Analysis of Biotransformation of Protein Therapeutics: Application To Various FGF21 Modalities," Anal Chem. 85(5):2731-2738.

Hecht, R. et al. (Nov. 27, 2012). "Rationale-Based Engineering of a Potent Long-Acting FGF21 Analog for the Treatment of Type 2 Diabetes," PLoS One 7(11):e49345, 13 pages.

Henry, L.R. et al. (Mar. 15, 2007). "Clinical implications of Fibroblast Activation Protein in Patients With Colon Cancer," Clin Cancer Res. 13(6):1736-1741.

Hugo, W. et al. (Mar. 24, 2016). "Genomic and Transcriptomic Features of Response To Anti-PD-1 Therapy In Metastatic Melanoma," Cell 165(1):35-44.

International Preliminary Report on Patentability, dated Jun. 16, 2020, for PCT Appiication No. PCT/US2018/65859, filed Dec. 14, 2018, 10 pages.

International Search Report and Written Opinion of the International Searching Authority, dated Apr. 29, 2020, for PCT Application No. PCT/US2020/012260, filed Jan. 3, 2020, 10 pages.

International Search Report and Written Opinion of the International Searching Authority, dated Feb. 27, 2019, for PCT Application No. PCT/US2018/65859, filed Dec. 14, 2018, 15 pages.

International Search Report and Written Opinion of the international Searching Authority, dated Jun. 8, 2020, for PCT Application No. PCT/US2019/68189, filed Dec. 21, 2019, 11 pages.

Jansen, K. et al. (Mar. 11, 2014). "Extended Structure-Activity Relationship and Pharmacokinetic Investigation of (4-Quinolinoyl)glycyl-2-cyanopyrrolidine Inhibitors of Fibroblast Activation Protein (FAP)," J. Med. Chem. 57(7):3053-3074.

Ju, M.J. et al. (2009). "Perltumoral Activated Hepatic Stellate Cells Predict Poor Clinical Outcome in Hepatocellular Carcinoma After Curative Resection," Am. J. Clin. Pathol. 131(4):498-510.

Kharitonenkov, A, et al. (Feb. 2007, e-pub. Oct. 26, 2006). "The Metabolic State of Diabetic Monkeys Is Regulated by Fibroblast Growth Factor-21," Endocrinology 148(2):774-781.

Kharitonenkov, A. et al. (Jun. 2005). "FGF-21 As A Novel Metabolic Regulator," J. Clin. Invest. 115(6):1627-1635.

Lee, K.N. et al. (2011). "Enhancement of Fibrinolysis By Inhibiting Enzymatic Cieavage of Precursor α2-Antiplasmin," J. Thromb. Haemost 9(5):987-996.

Lee, K.N. et al. (Jun. 16, 2009). "Using Substrate Specificity ofAntiplasmin-Cleaving Enzyme for Fibroblast Activation Protein Inhibitor Design," Biochemistry, 48(23):5149-5158, 22 pages.

Levy, M.T. et al. (1999). "Fibroblast Activation Protein: A Cell Surface Dipeptidyl Peptidase and Gelatinase Expressed by Stellate Cells at the Tissue Remodelling interface in Human Cirrhosis," Hepatology 29(6):1768-1778.

Li, J. et al. (Aug. 15, 2012). "An Activatable Near Infrared Fluorescent Probe for In Vivo Imaging of Fibroblast Activation Protein-alpha," Bioconjug Chem. 23(8):1704-1711, 17 pages.

Markan, K.R. et al. (May 2016). "Metabolic Fibroblast Growth Factors (FGFs): Mediators of Energy Homeostasis," Semin. Cell Dev. Biol. 53:85-93, 21 pages.

Micanovic, R., et al. (May 2009. e-pub. Dec. 30, 2008). "Differentef N- and C- Termini In The Functional Activity of FGF21," Cell Physiol. 219(2):227-234.

Mu, J. et al. (Feb. 2012). "FGF21 Analogs of Sustained Action Enabled by Orthogonal Biosynthesis Demonstrate Enhanced Antidiabetic Pharmacology in Rodents," Diabetes 61(2):505-512.

Narra, K. et al. (2007, e-pub. Nov. 1, 2007). "Phase II Trial of Single Agent Val-Boropro (Talabostat) Inhibiting Fibroblast Activation Protein In Patients With Metastatic Colorectal Cancer," Cancer Biol. Ther. 6(11):1691-1699.

Niedermeyer, J. et al. (Feb. 2000). "Targeted Disruption of Mouse Fibroblast Activation Protein," Mol. Cell Biol. 20(3):1089-1094.

O'Brien, P. et al. (2008). "Seprase; An Overview of An Important Matrix Serine Protease," Biochim. Biophys. Acta 1784(9):1130-1145, 57 pages.

Park, J.E. et al. (Dec. 17, 1999). "Fibroblast Activation Protein, a Dual Specificity Serine Protease Expressed in Reactive Human Tumor Stromal Fibroblasts," J. Biol. Chem. 274(51):36505-36512.

PubChem SID 104103293, Substance Record CHEBI:558344, seven pages.

PubChem-CID-1 0376593. Create date Oct. 25, 2006 (modify date Apr. 18, 2020). "1-[(2S)-2-Amino-3-methylpentanoyl]-3,3-difluoroazetidine-2-carbonitrile," 11 pages.

Ryantsova, O. et al. (2012, e-pub. Apr. 4, 2012). "Acylated Gly-(2-Cyano)Pyrrolidines As Inhibitor of Fibroblast Activation Protein (FAP) and the issued of FAP/Proly Oligopeptidase (PREP)-Selectivity," Bioorganic & Medicinal Chemistry Letters 22:3412-3417.

Santos, A.M. et al. (Dec. 2009). "Targeting Fibroblast Activation Protein Inhibits Tumor Stromagenesis and Growth in Mice," Clin. Invest. 119(12):3613-3625.

Sánchez-Garrido, M.A. et al. (2016). "Fibroblast Activation Protein (FAP) as a Novel Metabolic Target," Molecular Metabolism pp. 1-44.

Tsu, H. et al. (2006). "2-[3-[2-[(2S)-2-Cyano-1Pyrrolidinyl]-2-Oxoethylamino]-3-Methyl-1-Oxobutyl]-1,2,3,4-Tetrahydroisoquinoline:A Potent, Selective, and Orally Bioavailable Dipeptide-Derived inhibitor of Dipeptidyl Peptidase IV," Journal of Medicinal Chemistry 49(1):373-380, 2 pages. (English Abstract Only).

Wen, X. et al. (2016). "Fibroblast Activation Protein-α-Positive Fibroblasts Promote Gastric Cancer Progression and Resistance to Immune Checkpoint Blockade," Oncol Res. 25:629-640.

Xu, J. et al. (2009, e-pub. Aug. 25, 2009). "Acute Glucose-Lowering And Insulin-Sensitizing Action of FGF21 in Insulin-Resistant Mouse Models—Association With Liver and Adipose Tissue Effects," Am. J. Physiol. Endocrinol. Metab. 297(5):E1105-1114.

Yellapu, N. et al. (Jan. 2014, e-pub. May 31, 2013). Design, Synthesis, In Silico, and In Vitro evaluation of Novel Pyrimidine Phosphonates with Cytotoxicity against Breast Cancer Cells, Med. Chem. Res. 23:317-328.

Yie, J. et al. (2009, e-pub. Dec. 4, 2008). "FGF21 N- and C-Termini Play Different Roles In Receptor Interaction and Activation," FEES Lett. 583(1):19-24.

Zhen, E.Y. et al. (2016). "Circulating FGF21 Proteolytic Processing Mediated By Fibroblast Activation Protein," Biochem J. 473(5):605-614.

Fitzgerald, A.A. et al. (2020). "The Role of Fibroblast Activation Protein in Health and Malignancy," Cancer and Metastasis Reviews 39:783-803.

Gura, T. (Nov. 1997). "Systems for Identifying New Drugs are Often Faulty," Science 278(5340):1041-1042.

Hamson, E.J. et al. (2014). "Understanding Fibroblast Activation Protein (FAP): Substrates, Activities, Expression and Targeting for Cancer Therapy," Proteomics Clin. Appl. 8:454-463.

International Preliminary Report on Patentability, dated Jun. 16, 2021, dated Apr. 29, 2020, for PCT Application No. PCT/US2020/012260, filed Jan. 3, 2020, 6 pages.

International Preliminary Report on Patentability, dated Jun. 16, 2021, dated Jun. 8, 2020, for PCT Application No. PCT/US2019/068189, filed Dec. 21, 2019, 7 pages.

Invitation to Pay Additional Fees form PCT/ISA/206 dated Feb. 21, 2020, for International Patent Application No. PCT/US2020/012260 filed Jan. 3, 2020, two pages.

Invitation to Pay Additional Fees form PCT/ISA/206 dated Mar. 11, 2020, for International Patent Application No. PCT/US19/68189 filed Dec. 21, 2019, two pages.

Johnson, J. et al. (2001). "Relationships between drug activity in NCI preclinicai in vitro and in vivo models and early clinical trials," British Journal of Cancer 84(10): 1424-1431.

Juillerat-Jeannert, L. et al. (2017). "Fibroblast Activation Protein-α In Fibrogenic Disorders And Cancer: More Than A Prolyl-Specific Peptidase?," Expert Opinion on Therapeutic Targets 21(10):977-991.

Kelly, T. (2012). "Fibroblast Activation Protein-α: A Key Modulator of the Microenvironment in Multiple Pathologies," Chapters, International Review of Cell and Molecular Biology 297:83-116.

(56) References Cited

OTHER PUBLICATIONS

Kelly, T. (2005). "Fibroblast Activation Protein-α and Dipeptidly Peptidase IV (CD26): Cell-surface Proteases that Activate Cell Signaling and are Potential Targets for Cancer Therapy," Drug Resistance Updates 8:51-58.
Martinez-Garza, et al. (Sep. 21, 2019). "Fibroblast Growth Factor 21 and the Adaptive Response to Nutritional Challenges," Int. J. Mol. Sci. 20:1-21.
Pearce, H. et al. (2008). "Failure modes in anticancer drug discovery and development," Cancer Drug Design and Discovery, ed. Stephen Neidle, Chapter 18, 424-435.
Pure, E. et al. (2018, e-pub. May 3, 2018). "Pro-Tumorigenic Roles of Fibroblast Activation Protein in Cancer: Back to the Basics," Oncogene 37:4343-4357.
Schuppan, D. et al. (2018). "Liver Fibrosis: Direct Antifibrotic Agents and Targeted Therapies," Matrix Biol, 68-69:435-451.
Simone, J.V. et al. (1996). "Oncology," Part XIV in Cecil Textbook of Medicine, 20th edition, Bennet, J.C. et al. eds., W.B. Saunders Company, pp. 1004-1010.
Vliegen, G. et al. (2017). "The Expression of Proline-Specific Enzymes In The Human Lung," Annals of Translational Medicine 5(6):1-13.
Wauman, Y. et al. (Aug. 7, 2015). "The Dipeptidyl Peptidase Family, Prolyl Oligopeptidase and Prolyl Carboxypeptidase in The Immune System and inflammatory Disease, including Atherosclerosis," Frontiers in Immunology 6(387), 18 pages.
Jansen, K. et al. (May 9, 2013). "Selective Inhibitors Of Fibroblast Activation Protein (FAP) With A (4-Quinolinoyl)-Glycyl-2-Cyanopyrrolidine Scaffold," ACS Medicinal Chemistry Letters 4(5):491-496.
Third Party Observations Against EP Application 18887574.4, Applicant Praxis Biotech LLC, dated Nov. 15, 2021, 19 pages.
Third Party Observations Against EP Application 199012881.1, Applicant Praxis Biotech LLC, dated Dec. 1, 2021, 22 pages.
Jansen, K. (2014). "Potent and Selective Inhibitors of Fibroblast Activation Protein (FAP)," Dissertation University of Antwerp, Chapter 1 to Chapter 9, 279 pages.
Poplawski, S.E. et al. (May 9, 2013). "Identification Of Selective And Potent Inhibitors Of Fibroblast Activation Protein And Prolyl Oiigopeptidase," Journal Of Medicinal Chemistry 56(9):3467-3477, pp. A-K.

\* cited by examiner

INHIBITORS OF FIBROBLAST ACTIVATION PROTEIN

CROSS REFERENCE TO RELATED APPLICATIONS

This application claims priority to U.S. Provisional Application Ser. No. 62/784,291, filed Dec. 21, 2018, and U.S. Provisional Application Ser. No. 62/863,853, filed Jun. 19, 2019, both of which are hereby incorporated by reference in its entirety.

FIELD OF THE INVENTION

The present disclosure relates generally to therapeutic agents that may be useful in modulating fibroblast activation protein.

BACKGROUND

Fibroblast activation protein (FAP), also referred to as FAPα, Seprase or α2-antiplasmin converting enzyme, is a type II integral membrane serine protease that belongs to the prolyl oligopeptidase family S9, which also includes DPPII, DPPIV, DPP8, DPP9, and PREP enzymes. This family is characterized for having an exo-dipeptidyl peptidase (DPP) activity. FAP is the only member that also has an endopeptidase activity (Aertgeerts, K., et al. J Biol Chem, 2005. 280(20): p. 19441-4). FAP has a high degree of homology with DPPIV. It is mainly found as a cell surface homodimer but it has also been reported to form heterodimers with DPPIV in vivo (O'Brien, P., et al. Biochim Biophys Acta, 2008. 1784(9): p. 1130-45). Purported physiological substrates of FAP endopeptidase activity include α2-antiplasmin, type I collagen, gelatin, and Fibroblast growth factor 21 (FGF21) (Lee, K. N., et al., Biochemistry, 2009. 48(23): p. 5149-58), and for the exopeptidase activity include Neuropeptide Y, B-type natriuretic peptide, substance P and peptide YY (Brokopp, C. E., et al., Eur Heart J, 2011. 32(21): p. 2713-22; Coppage, A. L., et al., PLoS One, 2016. 11(3): p. e0151269; Dunshee, D. R., et al., J Biol Chem, 2016. 291(11): p. 5986-96; Lee, K. N., et al., J Thromb Haemost, 2011. 9(5): p. 987-96).

FAP has been implicated in diseases involving proliferation, tissue remodeling, chronic inflammation and/or fibrosis, including but not limited to fibrotic disease, wound healing, keloid formation, osteoarthritis, rheumatoid arthritis and related disorders involving cartilage degradation, atherosclerotic disease, and Crohn's disease.

FAP expression is related to poor prognosis in several types of cancer including gastric cancer, pancreatic adenocarcinoma and hepatocellular carcinoma, (Wen, X., et al., Oncol Res, 2016; Cohen, S. J., et al., Pancreas, 2008. 37(2): p. 154-8; Ju, M. J., et al., Am J Clin Pathol, 2009. 131(4): p. 498-510) and in colon cancer, increased FAP expression has been associated with a more aggressive disease (Henry, L. R., et al., Clin Cancer Res, 2007. 13(6): p. 1736-41). Purportedly, FAPα on CAFs has critical roles in regulating antitumor immune response by inducing tumor-promoting inflammation (Chen, L., et al., Biochem Biophys Res Commun, 2017; Wen, X., et al., Oncol Res, 2016; Hugo, W., et al., Cell, 2016. 165(1): p. 35-44).

Val-boroPro (Talabostat, PT-100) is the only FAP inhibitor that reached clinical stages. This compound was originally developed as a DPPIV inhibitor and subsequently evaluated as a FAP inhibitor regardless of its lack of selectivity (Cunningham, C. C., Expert Opin Investig Drugs, 2007. 16(9): p. 1459-65). This agent was tested in Phase II in a variety of cancers in combination with standard cytotoxic chemotherapy, however endpoints for efficacy were not met (Eager, R. M., et al., BMC Cancer, 2009. 9: p. 263; Narra, K., et al., Cancer Biol Ther, 2007. 6(11): p. 1691-9; Eager, R. M., et al., Clin Oncol R Coll Radiol, 2009. 21(6): p. 464-72). Two Phase III trials were early terminated, apparently because of both safety and efficacy concerns (Jansen, K., et al., J Med Chem, 2014. 57(7): p. 3053-74). Since Val-boroPro rapidly loses protease inhibitory activity due to cyclization upon standing in pH 7.8, effective concentrations were difficult to achieve in patients given the clinical toxicities seen with this agent at higher doses (Narra, K., et al., Cancer Biol Ther, 2007. 6(11): p. 1691-9).

There is scope to improve FAP inhibitor selectivity and the properties of the inhibitors to improve safety and efficacy in vivo.

BRIEF SUMMARY

Provided herein are compounds, salts thereof, pharmaceutical compositions of the foregoing and methods of making and using the same. In one aspect is provided a compound of formula (A):

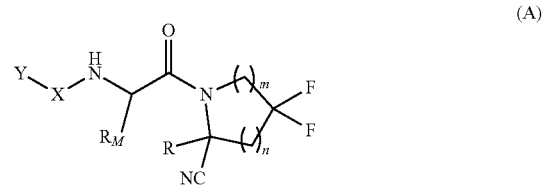

(A)

a pharmaceutically acceptable salt, stereoisomer or tautomer thereof, wherein R, $R_M$, m, n, X, and Y are as detailed herein.

In one aspect is provided a compound of formula (I):

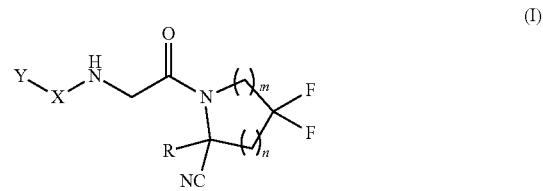

(I)

a pharmaceutically acceptable salt, stereoisomer or tautomer thereof, wherein R, m, n, X, and Y are as detailed herein.

Also provided is a pharmaceutical composition comprising a compound of any formula herein, including formula (A) or (I), a pharmaceutically acceptable salt, stereoisomer or tautomer thereof, and a pharmaceutically acceptable carrier.

Also provided is a method of treating a disease or disorder mediated by fibroblast activation protein (FAP) in an individual in need thereof comprising administering to the individual a therapeutically effective amount of a compound as detailed herein, including but not limited to a compound of formula (A) or (I), a pharmaceutically acceptable salt, stereoisomer or tautomer thereof, or a pharmaceutical composition comprising such compound or salt. Such disease or disorder in one aspect is characterized by proliferation, tissue remodeling, chronic inflammation, obesity, glucose intolerance, or insulin insensitivity. In one aspect, the disease or disorder is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In a particular aspect, the disease or disorder is metastatic kidney cancer, chronic lymphocytary leukemia, pancreatic adenocarcinoma, or non-small cell lung cancer. In a further aspect, the disease or disorder is a fibrotic disease, wound healing, keloid formation, osteoarthritis, rheumatoid arthritis and related disorders involving cartilage degradation, atherosclerotic disease, Crohn's disease, or Type II diabetes. In another particular aspect is provided a method of reducing tumor growth, tumor proliferation, or tumorigenicity in an individual in need thereof, comprising administering to the individual a compound as detailed herein, such as a compound of formula (A) or (I), a pharmaceutically acceptable salt, stereoisomer or tautomer thereof, or a pharmaceutical composition of the foregoing.

DETAILED DESCRIPTION

Figure 1A:
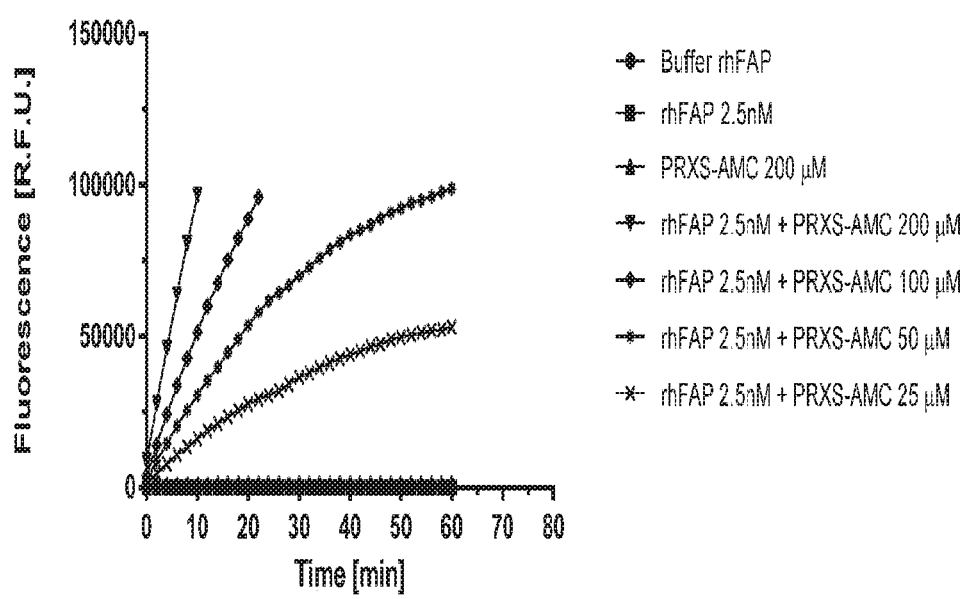
FIG. 1A shows PRXS-AMC degradation over time by rhFAP.

Described herein are compounds according to formula (A):

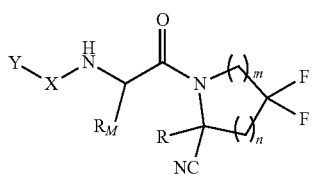

and pharmaceutically acceptable salts, stereoisomers or tautomers thereof.

Described herein are compounds according to formula (I):

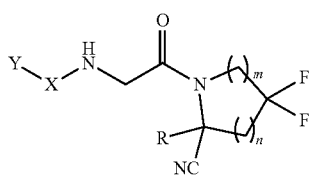

and pharmaceutically acceptable salts, stereoisomers or tautomers thereof.

The compounds can be useful for inhibiting fibroblast activation protein (FAPα). In certain embodiments, the compound is used to treat a disease or a disorder mediated by FAPα in an individual. Such diseases or disorders can include or be characterized by proliferation, tissue remodeling, chronic inflammation, obesity, glucose intolerance, and/or insulin insensitivity. In some embodiments, the compound is used to treat cancer.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl ($-CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($-OCF_3$).

"Carbonyl" refers to the group C=O.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. Beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods described herein contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

In one aspect, provided is a compound of formula (A):

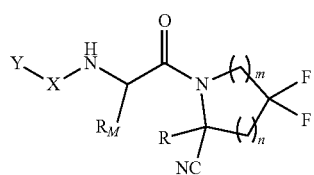

(A)

a pharmaceutically acceptable salt, stereoisomer or tautomer thereof, wherein:

R is hydrogen, $C_1$-$C_6$ alkyl, $C_1$-$C_6$ alkoxy, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_1$-$C_6$ alkoxy, $C_3$-$C_8$ cycloalkyl, 3- to 12-membered heterocyclyl, 5- to 10-membered heteroaryl, and $C_6$-$C_{14}$ aryl of R are independently optionally substituted by $R^d$;

$R_M$ is hydrogen or optionally substituted $C_1$-$C_6$ alkyl;

m is 0, 1, 2, 3, or 4;

n is 0, 1, 2, 3, or 4, wherein m+n is 1, 2, 3, or 4;

X is —C(=O)—, —O—, —CH(OH)—, —S—, —S(=O)—, or —S(=O)$_2$—;

Y is

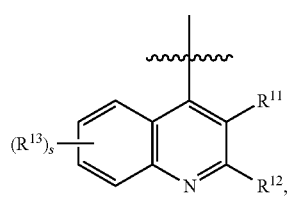

wherein:

the wavyline represents the point of attachment to the rest of the molecule, s is 1, 2, 3, or 4, $R^{11}$ and $R^{12}$ are each independently hydrogen, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, —$OR^{14}$, —$NR^{15}R^{16}$, —$SR^{14}$, —$NO_2$, —C=NH($OR^{14}$), —C(O)$R^{14}$, —OC(O)$R^{14}$, —C(O)$OR^{14}$, —C(O)$NR^{15}R^{16}$, —$NR^{14}$C(O)$R^{15}$, —$NR^{14}$C(O)$OR^{15}$, —$NR^{14}$C(O)$NR^{15}R^{16}$, —S(O)$R^{14}$, —S(O)$_2R^{14}$, —$NR^{14}$S(O)$R^{15}$, —$NR^{14}$S(O)$_2R^{15}$, —S(O)$NR^{15}R^{16}$, —S(O)$_2NR^{15}R^{16}$, or —P(O)($OR^{15}$)($OR^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{11}$ and $R^{12}$ are each independently optionally substituted by one of more of $R^L$;

each $R^{13}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, —$NR^{15}R^{16}$, —$NO_2$, —C=NH($OR^{14}$), —C(O)$R^{14}$, —OC(O)$R^{14}$, —C(O)$OR^{14}$, —C(O)$NR^{15}R^{16}$, —$NR^{14}$C(O)$R^{15}$, —$NR^{14}$C(O)$OR^{15}$, —$NR^{14}$C(O)$NR^{15}R^{16}$, —S(O)$R^{14}$, —S(O)$_2R^{14}$, —$NR^{14}$S(O)$R^{15}$, —$NR^{14}$S(O)$_2R^{15}$, —S(O)$NR^{15}R^{16}$, —S(O)$_2NR^{15}R^{16}$, or —P(O)($OR^{15}$)($OR^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{13}$ are each independently optionally substituted by one or more $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo;

$R^d$, independently at each occurrence, is halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —$OR^{14}$, —$NR^{15}R^{16}$, cyano, or nitro; and each $R^L$ is independently halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, —C(O)$R^{14}$, —OC(O)$R^{14}$, —C(O)$OR^{14}$, —C(O)$NR^{15}R^{16}$, —$NR^{14}$C(O)$R^{15}$, —$NR^{14}$C(O)$OR^{15}$, —$NR^{14}$C(O)$NR^{15}R^{16}$, —S(O)$R^{14}$, —S(O)$_2R^{14}$, —$NR^{14}$S(O)$R^{15}$, —$NR^{14}$S(O)$_2R^{15}$, —S(O)$NR^{15}R^{16}$, S(O)$_2NR^{15}R^{16}$, or —P(O)($OR^{15}$)($OR^{16}$), —$NR^{15}R^{16}$, cyano, oxo, or nitro, wherein (1) the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo, (2) the $C_1$-$C_6$ alkyl is optionally substituted by 5- to 10-membered heteroaryl, or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl.

In some embodiments, the compound of formula (A) is of the formula (I),

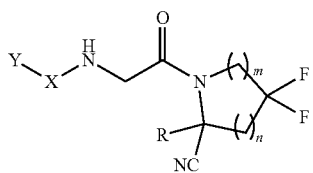
(I)

a pharmaceutically acceptable salt, stereoisomer or tautomer thereof, wherein $R_M$ is hydrogen, and R, m, n, X, and Y are as defined for formula (A).

Also provided is a compound of formula (I), a pharmaceutically acceptable salt, stereoisomer or tautomer thereof, wherein:

R is hydrogen, $C_1$-$C_6$ alkyl, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_3$-$C_8$ cycloalkyl, 3- to 12-membered heterocyclyl, 5- to 10-membered heteroaryl, and $C_6$-$C_{14}$ aryl of R are independently optionally substituted by $R^d$;

m is 0, 1, 2, 3, or 4;

n is 0, 1, 2, 3, or 4, wherein m+n is 1, 2, 3, or 4;

X is —C(═O)—, —O—, —CH(OH)—, —S—, —S(═O)—, or —S(═O)$_2$—;

Y is

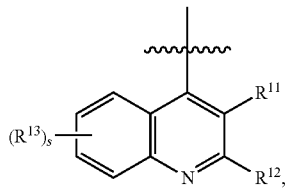

wherein:

the wavyline represents the point of attachment to the rest of the molecule, s is 1, 2, 3, or 4, $R^{11}$ and $R^{12}$ are each independently hydrogen, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, —OR$^{14}$, —NR$^{15}$R$^{16}$, —SR$^{14}$, —NO$_2$, —C═NH(OR$^{14}$), —C(O)R$^{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$, or —P(O)(OR$^{15}$)(OR$^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{11}$ and $R^{12}$ are each independently optionally substituted by $R^L$;

each $R^{13}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, —NR$^{15}$R$^{16}$, —NO$_2$, —C═NH(OR$^{14}$), —C(O)R$^{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$, or —P(O)(OR$^{15}$)(OR$^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{13}$ are each independently optionally substituted by $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo;

$R^d$, independently at each occurrence, is halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —OR$^{14}$, —NR$^{15}$R$^{16}$, cyano, or nitro; and each $R^L$ is independently halogen, $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, —C(O)R$^{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$ or —P(O)(OR$^{15}$)(OR$^{16}$), —NR$^{15}$R$^{16}$, cyano, oxo, or nitro.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to R of formula (A) or (I) may be combined with every description, variation, embodiment or aspect of Y, X, L, m, and/or n the same as if each and every combination were specifically and individually listed. It is also understood that all descriptions, variations, embodiments or aspects of formula (A) or (I), where applicable, apply equally to other formulae detailed herein, and are equally described, the same as if each and every description, variation, embodiment or aspect were separately and individually listed for all formulae. For example, all descriptions, variations, embodiments or aspects of formula (A) or (I), where applicable, apply equally to any applicable formulae herein, such as formulae Ia, Ib, II, IIa, IIb, IIc, IIc-1 and IIc-2, as detailed herein, and are equally described, the same as if each and every description, variation, embodiment or aspect were separately and individually listed for all formulae.

In some embodiments, the compound of formula (I) is of the formula (Ia):

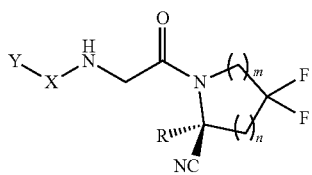

(Ia)

a pharmaceutically acceptable salt, stereoisomer or tautomer thereof, wherein R, m, n, X, and Y are as defined for formula (I).

In some embodiments, the compound of formula (I) is of the formula (Ib):

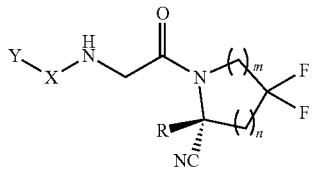

(Ib)

a pharmaceutically acceptable salt, stereoisomer or tautomer thereof, wherein R, m, n, X, and Y are as defined for formula (I).

In some embodiments of the compound of formula (I), where m is 1 and n is 1, the compound is of the formula (II):

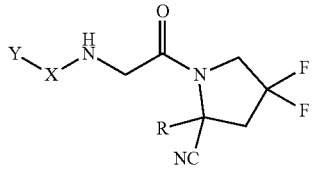

(II)

a pharmaceutically acceptable salt, stereoisomer or tautomer thereof, wherein Y, X, and R are as defined for formula (I).

In some embodiments, the compound of formula (II) is of the formula (IIa):

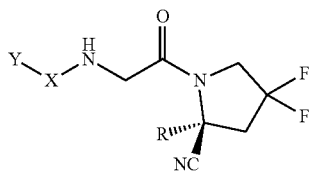

(IIa)

a pharmaceutically acceptable salt, stereoisomer or tautomer thereof, wherein Y, X, and R are as defined for formula (I).

In some embodiments, the compound of formula (II) is of the formula (IIb):

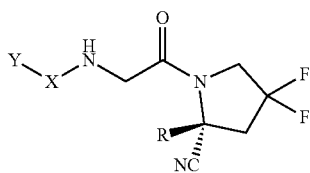

(IIb)

a pharmaceutically acceptable salt, stereoisomer or tautomer thereof, wherein Y, X, and R are as defined for formula (I).

In some embodiments, the compound of formula (II) is of the formula (IIc):

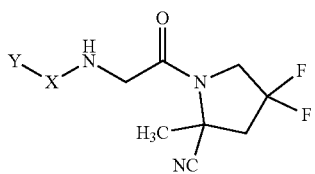

(IIc)

a pharmaceutically acceptable salt, stereoisomer or tautomer thereof, wherein Y and X are as defined for formula (I).

In some embodiments, the compound of formula (II) is of the formula (IIc-1):

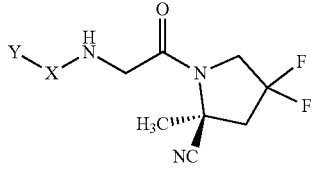

(IIc-1)

a pharmaceutically acceptable salt, stereoisomer or tautomer thereof, wherein Y and X are as defined for formula (I).

In some embodiments, the compound of formula (II) is of the formula (IIc-2):

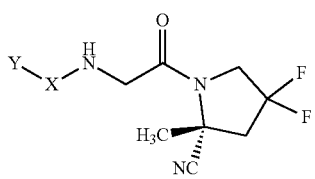

(IIc-2)

a pharmaceutically acceptable salt, stereoisomer or tautomer thereof, wherein Y and X are as defined for formula (I).

In some embodiments, a compound of formula (A), a pharmaceutically acceptable salt, stereoisomer or tautomer thereof, is of formula (I), wherein $R_M$ is hydrogen. In some embodiments of the compound of formula (A), a pharmaceutically acceptable salt, stereoisomer or tautomer thereof, $R_M$ is optionally substituted $C_1$-$C_6$ alkyl, such as propyl.

In some embodiments, a compound of formula (A) or (I), a pharmaceutically acceptable salt, stereoisomer or tautomer thereof, is provided wherein X is —C(=O)—, —O— or —CH(OH)—. In some embodiments, a compound of formula (A) or (I), or a salt thereof, is provided wherein X is —S—, —S(=O)—, or —S(=O)$_2$—. In some embodiments of the compound of formula (A) or (I), or a salt thereof, X is —C(=O)—. In other embodiments of the compound of formula (A) or (I), or a salt thereof, X is —O—. All variations of X apply equally to any applicable formulae herein, such as formulae Ia, Ib, II, IIa, IIb, IIc, IIc-1 and IIc-2.

In some embodiments of the compound of formula (A) or (I), a pharmaceutically acceptable salt, stereoisomer or tautomer thereof, R is hydrogen. In some embodiments, R is $C_1$-$C_6$ alkyl optionally substituted by $R^d$, such as methyl, ethyl, n-propyl, isopropyl, n-butyl, t-butyl, isobutyl, or sec-butyl, each of which is optionally substituted by $R^d$. In some embodiments, R is $C_1$-$C_6$ alkoxy optionally substituted by $R^d$, such as cyclopropyl, cyclobutyl, cyclopentyl, cyclohexyl, or cycloheptyl, each of which is optionally substituted by $R^d$. In some embodiments, R is $C_3$-$C_8$ cycloalkyl optionally substituted by $R^d$, such as cyclopropyl, cyclobutyl, cyclopentyl, cyclohexyl, or cycloheptyl, each of which is optionally substituted by $R^d$. In some embodiments, R is 3- to 12-membered heterocyclyl optionally substituted by $R^d$. In some embodiments, R is 5- to 10-membered heteroaryl optionally substituted by $R^d$. In some embodiments, R is $C_6$-$C_{14}$ aryl optionally substituted by $R^d$.

In some embodiments of the compound of formula (A) or (I), a pharmaceutically acceptable salt, stereoisomer or tautomer thereof, m is 0. In some embodiments, m is 1. In some embodiments, m is 2. In some embodiments, m is 3. In some embodiments, m is 4. In some embodiments, n is 0. In some embodiments, n is 1. In some embodiments, n is 2. In some embodiments, n is 3. In some embodiments, n is 4.

In some embodiments of the compound of formula (A) or (I), a pharmaceutically acceptable salt, stereoisomer or tautomer thereof, $R^{11}$ is hydrogen. In some embodiments, $R^{11}$ is $C_1$-$C_6$ alkyl optionally substituted with $R^L$ such as methyl, ethyl, n-propyl, isopropyl, n-butyl, t-butyl, isobutyl, or sec-butyl, each of which is optionally substituted with $R^L$. In some embodiments, $R^{11}$ is halogen such as fluoro, chloro, bromo, or iodo. In some embodiments, $R^{11}$ is $C_3$-$C_8$ cycloalkyl optionally substituted with $R^L$, such as cyclopropyl, cyclobutyl, cyclopentyl, cyclohexyl, or cycloheptyl, each of which is optionally substituted with $R^L$. In some embodiments, $R^{11}$ is 3- to 12-membered heterocyclyl optionally substituted with $R^L$. In some embodiments, $R^{11}$ is 5- to 10-membered heteroaryl optionally substituted with $R^L$. In some embodiments, $R^{11}$ is $C_6$-$C_{14}$ aryl optionally substituted with $R^L$.

In some embodiments of the compound of formula (A) or (I), a pharmaceutically acceptable salt, stereoisomer or tautomer thereof, $R^{12}$ is hydrogen. In some embodiments, $R^{12}$ is $C_1$-$C_6$ alkyl optionally substituted with $R^L$, such as methyl, ethyl, n-propyl, isopropyl, n-butyl, t-butyl, isobutyl, or sec-butyl, each of which is optionally substituted with $R^L$. In some embodiments, $R^{12}$ is halogen such as fluoro, chloro, bromo, and iodo. In some embodiments, $R^{12}$ is $C_3$-$C_8$ cycloalkyl optionally substituted with $R^L$, such as cyclopropyl, cyclobutyl, cyclopentyl, cyclohexyl, cycloheptyl, each of which is optionally substituted with $R^L$. In some embodiments, $R^{12}$ is 3- to 12-membered heterocyclyl optionally substituted with $R^L$. In some embodiments, $R^{12}$ is 5- to 10-membered heteroaryl optionally substituted with $R^L$. In some embodiments, $R^{12}$ is $C_6$-$C_{14}$ aryl optionally substituted with $R^L$.

In some embodiments of the compound of formula (A) or (I), a pharmaceutically acceptable salt, stereoisomer or tautomer thereof, both $R^{11}$ and $R^{12}$ are hydrogen. In some embodiments, $R^{11}$ is hydrogen; and $R^{12}$ is $C_1$-$C_6$ alkyl or halogen. In some embodiments, $R^{11}$ is $C_1$-$C_6$ alkyl or halogen; and $R^{12}$ is hydrogen.

In some embodiments of the compound of formula (A) or (I), a pharmaceutically acceptable salt, stereoisomer or tautomer thereof, s is 1, 2, or 3. In some embodiments, s is 1 or 2. In some embodiments, s is 1. In some embodiments, s is 2. In some embodiments, s is 3. In some embodiments, s is 4.

In some embodiments of the compound of formula (A) or (I), a pharmaceutically acceptable salt, stereoisomer or tautomer thereof, each $R^{13}$ is independently $C_1$-$C_6$ alkyl optionally substituted with $R^L$, such as methyl, ethyl, n-propyl, isopropyl, n-butyl, t-butyl, isobutyl, or sec-butyl, each of which is optionally substituted with $R^L$. In some embodiments of the compound of formula (A) or (I), or a salt thereof, each $R^{13}$ is independently $C_3$-$C_8$ cycloalkyl, 3- to 12-membered heterocyclyl, 5- to 10-membered heteroaryl, or $C_6$-$C_{14}$ aryl, wherein the $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{13}$ are each independently optionally substituted by $R^L$.

In some embodiments, each $R^{13}$ is independently $C_3$-$C_8$ cycloalkyl optionally substituted with $R^L$, such as cyclopropyl, cyclobutyl, cyclopentyl, cyclohexyl, or cycloheptyl, each of which is optionally substituted with $R^L$. In some embodiments, each $R^{13}$ is independently 3- to 12-membered heterocyclyl optionally substituted with $R^L$.

In some embodiments of the compound of formula (A) or (I), a pharmaceutically acceptable salt, stereoisomer or tautomer thereof, each $R^{13}$ is independently $C_6$-$C_{14}$ aryl optionally substituted with $R^L$. In some embodiments, each $R^{13}$ is independently phenyl optionally substituted with $R^L$. In some embodiments, each $R^{13}$ is unsubstituted phenyl. In some embodiments, each $R^{13}$ is independently phenyl substituted with one or more $R^L$. In some embodiments, $R^{13}$ is phenyl substituted with one or more halogen or $C_1$-$C_6$ alkyl. In some embodiments, $R^{13}$ is bicyclic $C_6$-$C_{14}$ aryl optionally substituted with $R^L$. In some embodiments, each $R^{13}$ is independently unsubstituted bicyclic $C_6$-$C_{14}$ aryl. In some embodiments, each $R^{13}$ is independently bicyclic $C_6$-$C_{14}$ aryl substituted with one or more $R^L$. In some embodiments, each $R^{13}$ is independently bicyclic $C_6$-$C_{14}$ aryl substituted with one or more halogen or $C_1$-$C_6$ alkyl.

In some embodiments of the compound of formula (A) or (I), a pharmaceutically acceptable salt, stereoisomer or tautomer thereof, each $R^{13}$ is independently 5- to 10-membered heteroaryl optionally substituted with $R^L$. In some embodiments, each $R^{13}$ is independently monocyclic 5- to 10-membered heteroaryl optionally substituted with $R^L$. In some embodiments, each $R^{13}$ is independently unsubstituted monocyclic 5- to 10-membered heteroaryl. In some embodiments, each $R^{13}$ is independently monocyclic 5- to 10-membered heteroaryl substituted with one or more $R^L$. In some embodiments, each $R^{13}$ is independently monocyclic 5- to 10-membered heteroaryl substituted with one or more halogen or $C_1$-$C_6$ alkyl. In some embodiments, each $R^{13}$ is independently bycyclic 5- to 10-membered heteroaryl optionally substituted with $R^L$. In some embodiments, each $R^{13}$ is independently unsubstituted bycyclic 5- to 10-membered heteroaryl. In some embodiments, each $R^{13}$ is independently bycyclic 5- to 10-membered heteroaryl substituted with one or more $R^L$. In some embodiments, each $R^{13}$ is independently bycyclic 5- to 10-membered heteroaryl substituted with one or more halogen or $C_1$-$C_6$ alkyl.

In some embodiments of the compound of formula (A) or (I), a pharmaceutically acceptable salt, stereoisomer or tautomer thereof, each $R^{13}$ is independently selected from the groups consisting of:

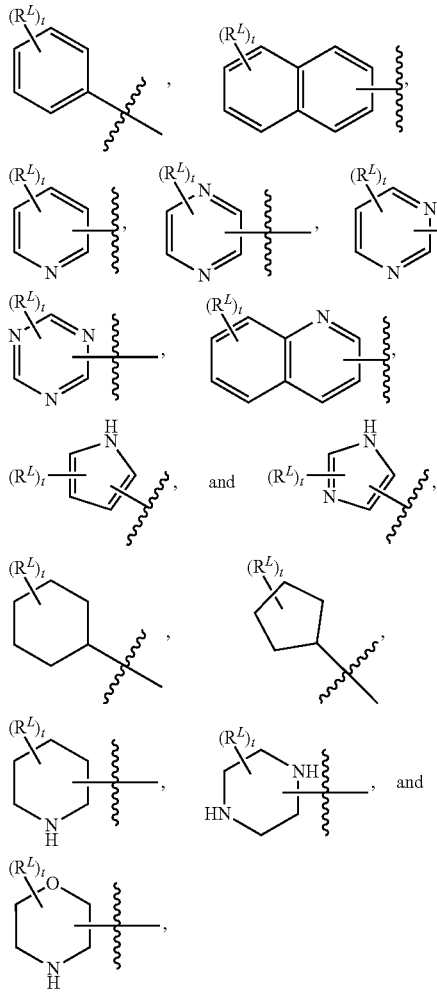

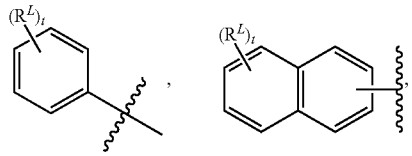

wherein t is 0, 1, 2, 3, 4, or 5; and the wavyline represents the point of attachment to the rest of the molecule. In some embodiments, t is 0. In some embodiments, t is 1. In some embodiments, t is 2. In some embodiments, t is 3. In some embodiments, t is 4. In some embodiments, t is 5. In some embodiments, $R^L$ is halogen, such as fluoro, chloro, or bromo. In some embodiments, $R^L$ is $C_1$-$C_6$ alkyl such as methyl, ethyl, n-propyl, or isopropyl.

In some embodiments of the compound of formula (A) or (I), a pharmaceutically acceptable salt, stereoisomer or tautomer thereof, at least one $R^{13}$ is selected from the groups consisting of:

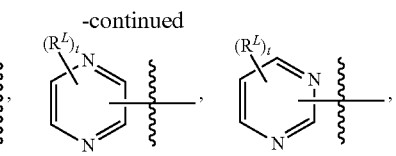

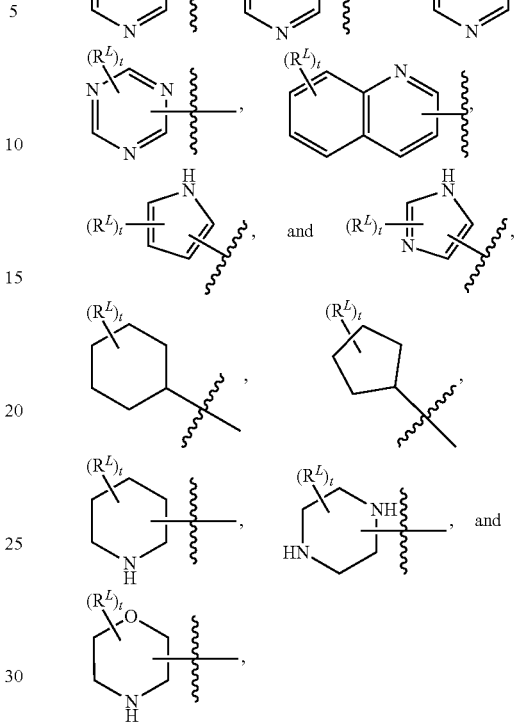

wherein t is 0, 1, 2, 3, 4, or 5, the wavyline represents the point of attachment to the rest of the molecule. In some embodiments, t is 0. In some embodiments, t is 1. In some embodiments, t is 2. In some embodiments, t is 3. In some embodiments, t is 4. In some embodiments, t is 5. In some embodiments, $R^L$ is halogen, such as fluoro, chloro, or bromo. In some embodiments, $R^L$ is $C_1$-$C_6$ alkyl such as methyl, ethyl, n-propyl, or isopropyl. In some embodiments, at least one $R^{13}$ is

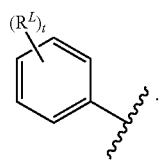

In some embodiments of the compound of formula (A) or (I), a pharmaceutically acceptable salt, stereoisomer or tautomer thereof, each $R^L$ is independently $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, —C(O)$R^{14}$, —OC(O)$R^{14}$, —C(O)O$R^{14}$, —C(O)N$R^{15}R^{16}$, —N$R^{14}$C(O)$R^{15}$, —N$R^{14}$C(O)O$R^{15}$, —N$R^{14}$C(O)N$R^{15}R^{16}$, —S(O)$R^{14}$, —S(O)$_2R^{14}$, —N$R^{14}$S(O)$R^{15}$, —N$R^{14}$S(O)$_2R^{15}$, —S(O)N$R^{15}R^{16}$, —S(O)$_2$N$R^{15}R^{16}$, or —P(O)(O$R^{15}$)(O$R^{16}$), —N$R^{15}R^{16}$, cyano, oxo, or nitro, wherein (1) the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo, (2) the $C_1$-$C_6$ alkyl is optionally substituted by 5- to 10-membered heteroaryl, or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl. In some embodiments, $R^L$ is $C_1$-$C_6$ alkoxy, wherein the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo. In some embodiments, $R^L$ is $C_1$-$C_6$ alkyl, wherein the $C_1$-$C_6$ alkyl is optionally substituted by 5- to 10-membered heteroaryl, or 3- to 12-membered heterocyclyl. In some embodiments, $R^L$ is $C_1$-$C_6$ alkyl, wherein the $C_1$-$C_6$ alkyl is optionally substituted by 5- to 10-membered heteroaryl, or 3- to 12-membered heterocyclyl, wherein the 3- to 12-membered heterocyclyl is further optionally substituted by $C_1$-$C_6$ alkyl. In some embodiments, $R^L$ is 5- to 10-membered heteroaryl, wherein the 5- to 10-membered heteroaryl is optionally substituted by oxo. In some embodiments, $R^L$ is $C_3$-$C_8$ cycloalkenyl, wherein the $C_3$-$C_8$ cycloalkenyl is optionally substituted by halogen, —OH, oxo, cyano, $C_1$-$C_6$ alkoxy, or $C_1$-$C_6$ alkyl.

In some embodiments of the compound of formula (A) or (I), a pharmaceutically acceptable salt, stereoisomer or tautomer thereof, $R^{13}$ is optionally substituted $C_2$-$C_6$ alkenyl. In some embodiments of the compound of formula (A) or (I), a pharmaceutically acceptable salt, stereoisomer or tautomer thereof, $R^{13}$ is a substituted $C_2$-$C_6$ alkenyl, such as a substituted $C_2$-$C_3$ alkenyl. In some embodiments of the compound of formula (A) or (I), a pharmaceutically acceptable salt, stereoisomer or tautomer thereof, $R^{13}$ is a $C_2$-$C_6$ alkenyl substituted by a moiety selected from the group consisting of halogen, $C_1$-$C_6$ alkyl, $C_1$-$C_6$ alkoxy, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, or —C(O)OR$^{14}$, wherein (1) the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo, (2) the $C_1$-$C_6$ alkyl is optionally substituted by 5- to 10-membered heteroaryl or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl. In certain such embodiments, $R^{11}$ and $R^{12}$ are each H and s is 1.

In some embodiments of the compound of formula (A) or (I), a pharmaceutically acceptable salt, stereoisomer or tautomer thereof, $R^{13}$ is optionally substituted $C_6$-$C_{14}$ aryl. In some embodiments of the compound of formula (A) or (I), a pharmaceutically acceptable salt, stereoisomer or tautomer thereof, $R^{13}$ is optionally substituted $C_6$-$C_{14}$ aryl, such as phenyl. In some embodiments of the compound of formula (A) or (I), a pharmaceutically acceptable salt, stereoisomer or tautomer thereof, $R^{13}$ is a phenyl substituted by a moiety selected from the group consisting of halogen, $C_1$-$C_6$ alkyl, $C_1$-$C_6$ alkoxy, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, —C(O)OR$^{14}$, —C(O)NR$^{15}$R$^{16}$, —NR$^{14}$C(O)$^{15}$, wherein (1) the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo, (2) the $C_1$-$C_6$ alkyl is optionally substituted by 5- to 10-membered heteroaryl or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl. In certain such embodiments, $R^{11}$ and $R^{12}$ are each H and s is 1.

In some embodiments of the compound of formula (A) or (I), a pharmaceutically acceptable salt, stereoisomer or tautomer thereof, $R^{13}$ is optionally substituted 5- to 10-membered heteroaryl. In some embodiments of the compound of formula (A) or (I), a pharmaceutically acceptable salt, stereoisomer or tautomer thereof, $R^{13}$ is a substituted 5- to 10-membered heteroaryl, such as a substituted imidazolyl, pyrazolyl, isoxazolyl, furyl, pyridyl, pyranyl, tetrahydroquinolinyl, isoindolinyl, benzofuranyl, benzoxazine, benzothiazolyl, or benzimidazolyl. In some embodiments of the compound of formula (A) or (I), a pharmaceutically acceptable salt, stereoisomer or tautomer thereof, $R^{13}$ is 5- to 10-membered heteroaryl substituted by a moiety selected from the group consisting of halogen, $C_1$-$C_6$ alkyl, $C_1$-$C_6$ alkoxy, $C_3$-$C_8$ cycloalkyl cyano, oxo, or nitro, wherein (1) the $C_1$-$C_6$ alkoxy is optionally substituted by halogen, —OH, oxo, cyano, $C_1$-$C_6$ alkoxy, or $C_1$-$C_6$ alkyl optionally substituted by halogen, —OH, or oxo, (2) the $C_1$-$C_6$ alkyl is optionally substituted by 5- to 10-membered heteroaryl or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl. In certain such embodiments, $R^{11}$ and $R^{12}$ are each H and s is 1.

It is understood that, every description, variation, embodiment or aspect provided herein with respect to $R^{13}$ of Formula (A) or (I), applicable formulae herein, such as formulae Ia, Ib, II, IIa, IIb, IIc, IIc-1 and IIc-2, may be combined with every description, variation, embodiment or aspect of Y, X, L, m, and/or n the same as if each and every combination were specifically and individually listed. For example, in some embodiments, R is hydrogen; m is 1; n is 1; X is —C(=O)—; $R^{11}$, is hydrogen; $R^{12}$ is hydrogen; s is 1; and $R^{13}$ is phenyl optionally substituted with halogen.

It is understood that compounds with tautomeric forms are described and embraced herein. For example, a compound with moiety A below may exist in equilibrium with a tautomeric form of imidic acid moiety B, and amide C may exist in equilibrium with a tautomeric form of imidic acid D. All such tautomers are provided.

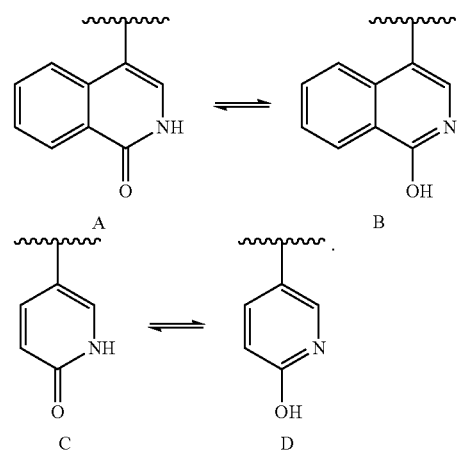

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1A and Table 1B.

TABLE 1A

| Compound No. | Structure |
|---|---|
| 1 | 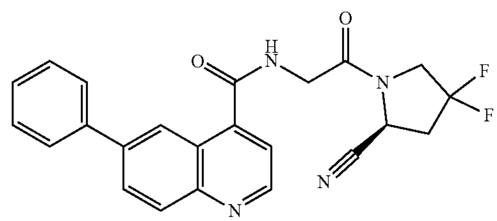 [SMILES: N#C[C@@H]1CC(F)(F)CN1C(=O)CNC(=O)c1ccnc2ccc(-c3ccccc3)cc12] |
| 2 | 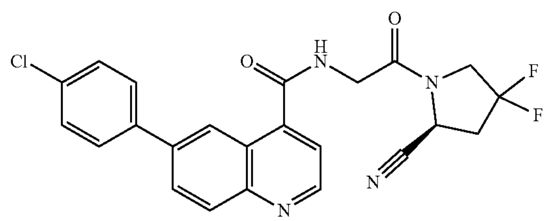 [SMILES: N#C[C@@H]1CC(F)(F)CN1C(=O)CNC(=O)c1ccnc2ccc(-c3ccc(Cl)cc3)cc12] |
| 3 | 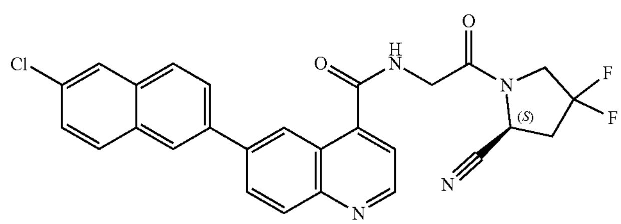 |
| 4 | 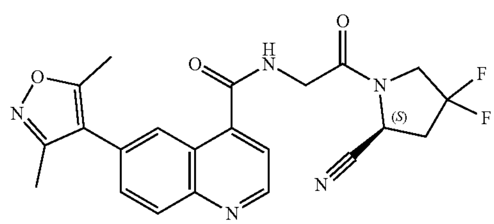 |
| 5 | 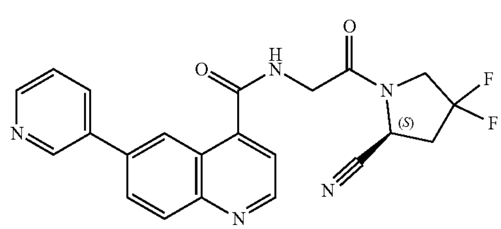 |

TABLE 1A-continued
Compound No. Structure
6 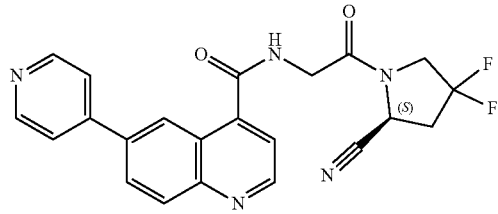
7 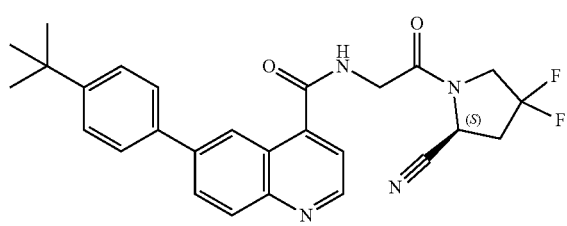
8 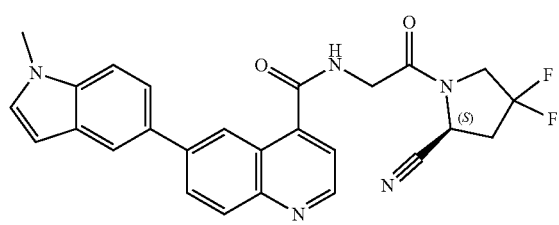
9 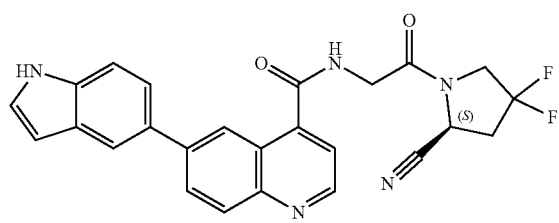
10 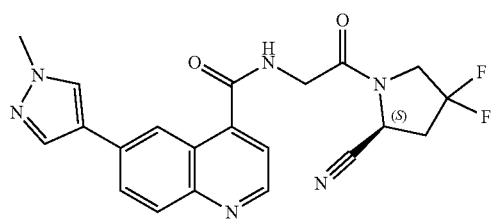
11 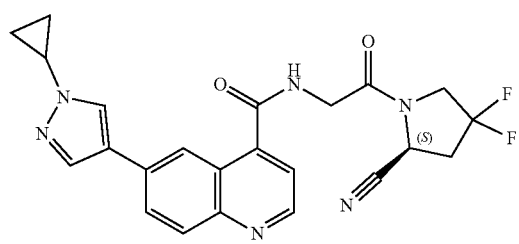

TABLE 1A-continued
| Compound No. | Structure |
|---|---|
| 12 | 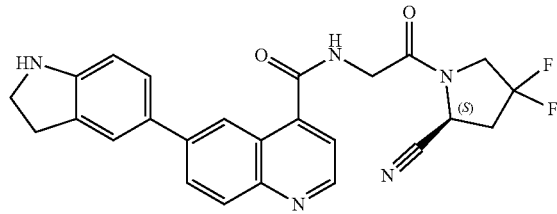 |
| 13 | 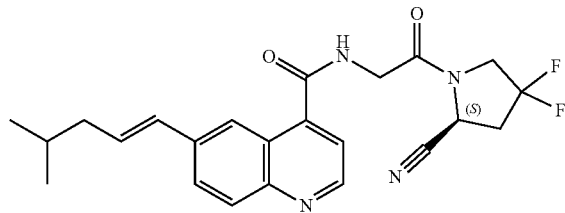 |
| 14 | 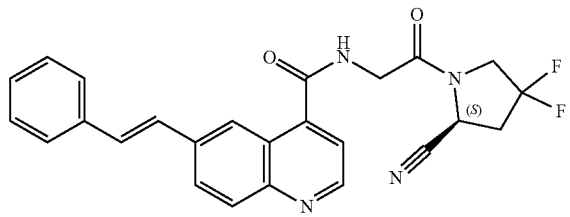 |
| 15 | 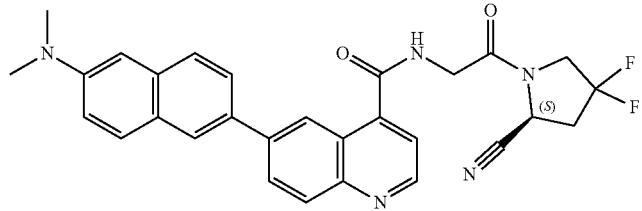 |
| 16 | 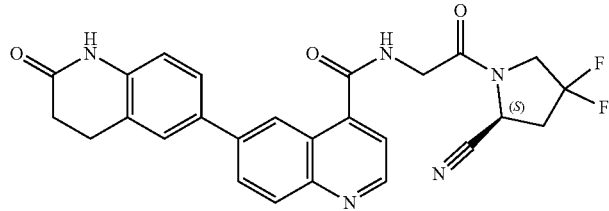 |
| 17 | 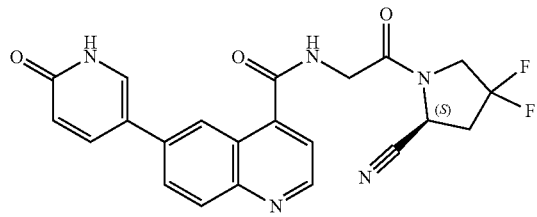 |
| 18 | 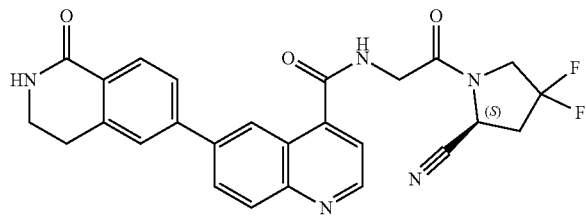 |

TABLE 1A-continued
| Compound No. | Structure |
|---|---|
| 19 | 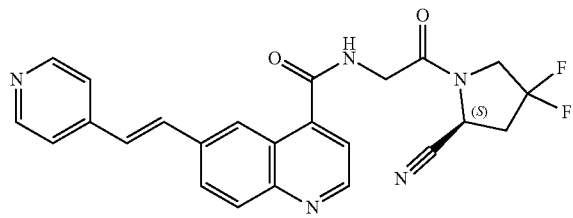 |
| 20 | 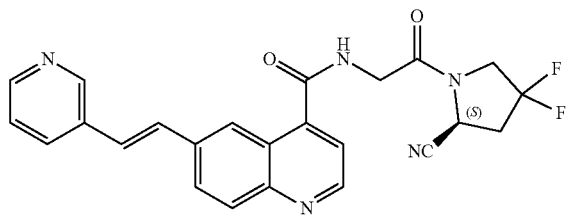 |
| 21 | 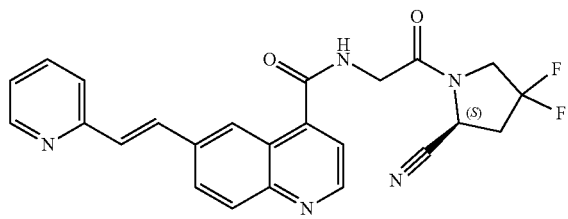 |
| 22 | 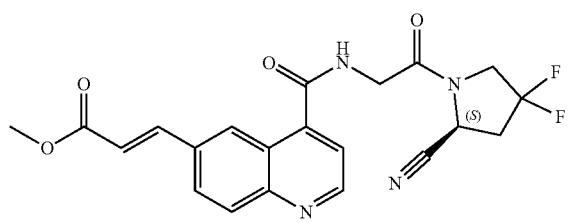 |
| 23 | 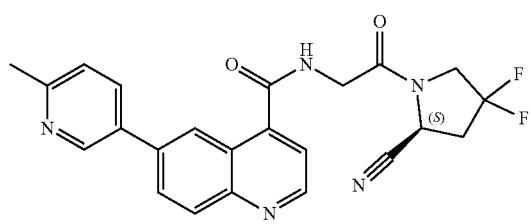 |
| 24 | 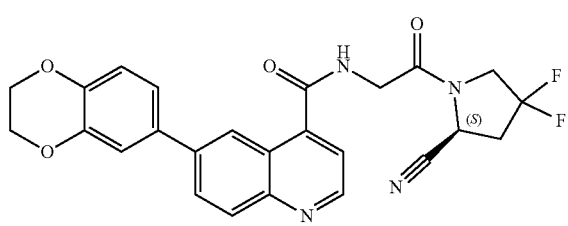 |

TABLE 1A-continued
| Compound No. | Structure |
|---|---|
| 25 | 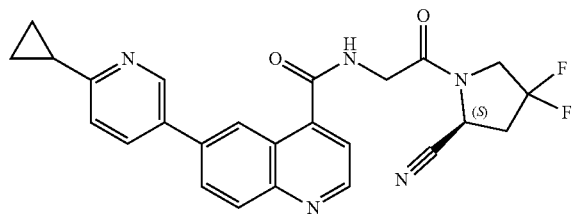 |
| 26 | 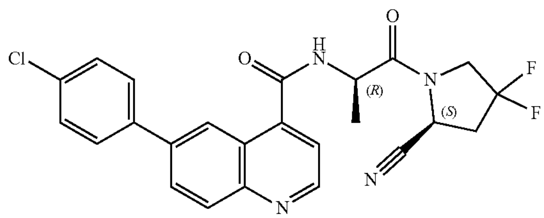 |
| 27 | 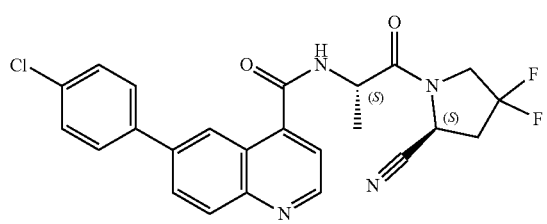 |
| 28 | 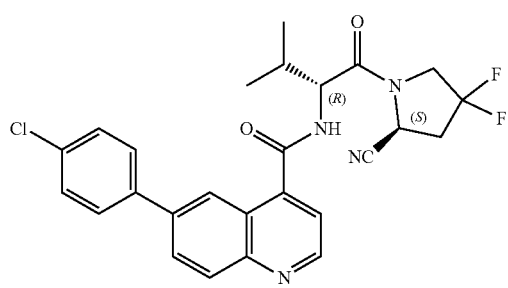 |
| 29 | 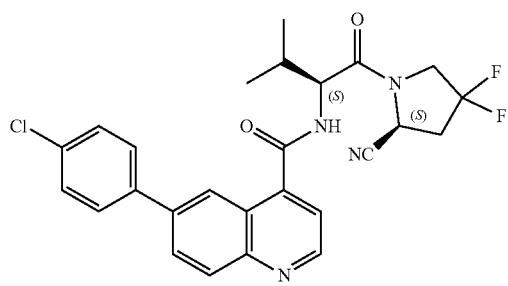 |
| 30 | 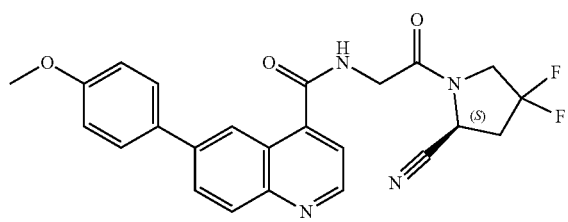 |

TABLE 1A-continued
| Compound No. | Structure |
|---|---|
| 31 | 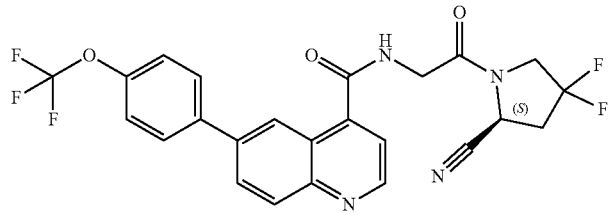 |
| 32 | 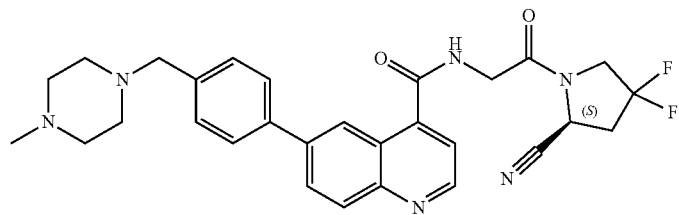 |
| 33 | 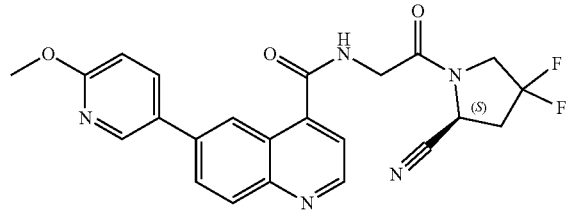 |
| 34 | 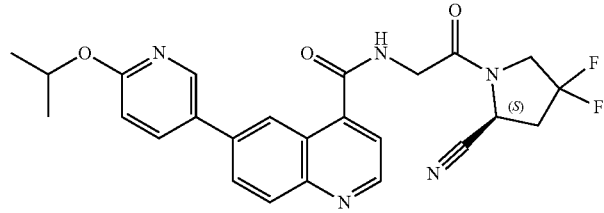 |
| 35 | 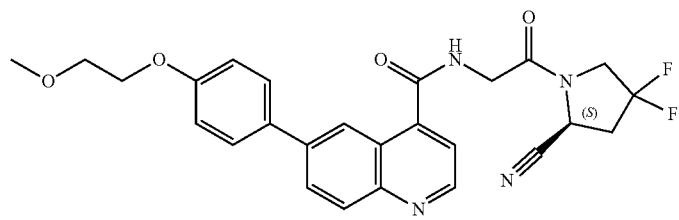 |
| 36 | 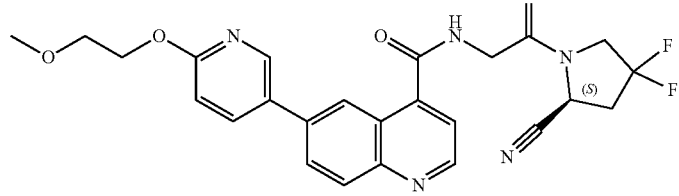 |
| 37 | 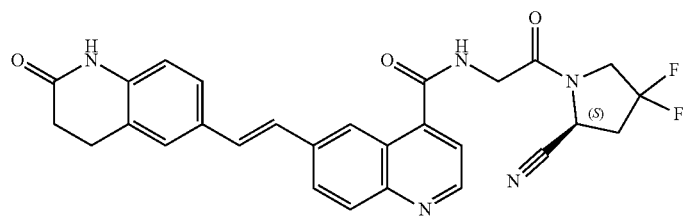 |

TABLE 1A-continued
| Compound No. | Structure |
|---|---|
| 38 | 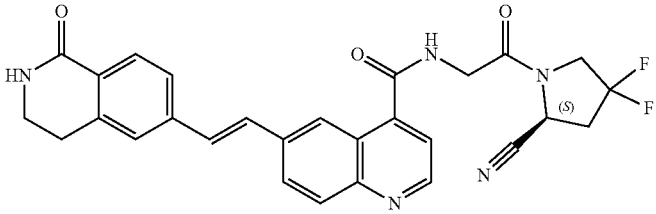 |
| 39 | 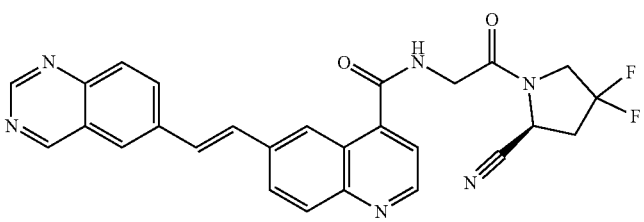 [SMILES: N#C[C@@H]1CC(F)(F)CN1C(=O)CNC(=O)c1ccnc2ccc(/C=C/c3ccc4ncncc4c3)cc12] |
| 40 | 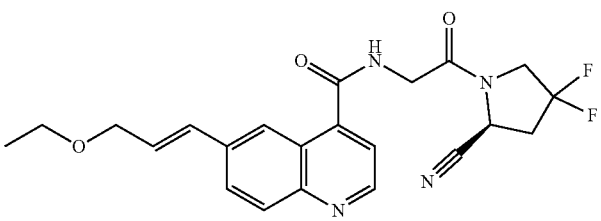 [SMILES: CCOC/C=C/c1ccc2nccc(C(=O)NCC(=O)N3CC(F)(F)C[C@H]3C#N)c2c1] |
| 41 | 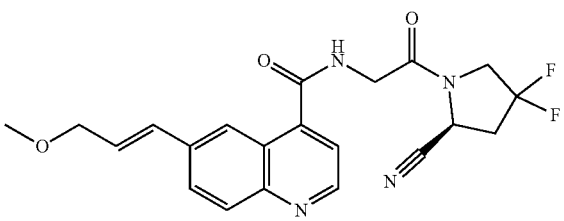 [SMILES: COC/C=C/c1ccc2nccc(C(=O)NCC(=O)N3CC(F)(F)C[C@H]3C#N)c2c1] |
| 42 | 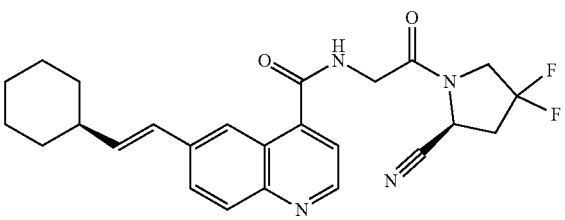 |
| 43 | 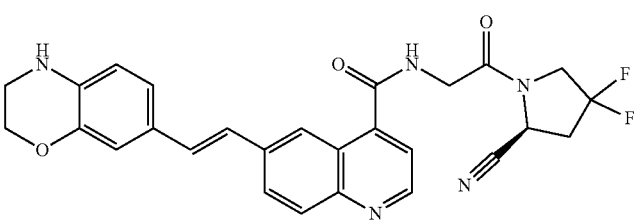 [SMILES: N#C[C@@H]1CC(F)(F)CN1C(=O)CNC(=O)c1ccnc2ccc(/C=C/c3ccc4c(c3)OCCN4)cc12] |

TABLE 1A-continued

| Compound No. | Structure |
|---|---|
| 44 | *(4-chlorophenyl)-quinoline-4-carboxamide linked via NH-CH2-C(O) to 5,5-difluoro-2-cyanopiperidine)* |
| 45 | *(6-(4-methylpiperazin-1-yl)quinoline-4-carboxamide linked via NH-CH2-C(O) to 4,4-difluoro-2-cyanopyrrolidine)* |
| 46 | *(6-(6-chloronaphthalen-2-yl)quinoline-4-carboxamide linked via NH-CH2-C(O) to 3,3-difluoro-2-cyanoazetidine)* |
| 47 | *(6-((E)-2-cyclohexylvinyl)quinoline-4-carboxamide linked via NH-CH2-C(O) to 4,4-difluoro-2-cyanopyrrolidine)* |
| 48 | *(6-(2-oxo-1,2,3,4-tetrahydroquinolin-6-yl)quinoline-4-carboxamide linked via NH-CH2-C(O) to 4,4-difluoro-2-cyanopiperidine)* |
| 49 | *(6-((E)-2-(piperazin-1-yl)vinyl)quinoline-4-carboxamide linked via NH-CH2-C(O) to 4,4-difluoro-2-cyanopyrrolidine)* |
| 50 | *(6-(6-chloronaphthalen-2-yl)quinoline-4-carboxamide linked via NH-CH2-C(O) to 4,4-difluoro-2-cyano-2-ethylpyrrolidine)* |

TABLE 1A-continued
| Compound No. | Structure |
|---|---|
| 51 | 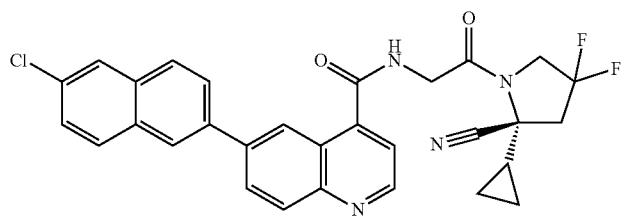 [SMILES: N#C[C@]1(C2CC2)CC(F)(F)CN1C(=O)CNC(=O)c1ccnc2ccc(-c3ccc4cc(Cl)ccc4c3)cc12] |
| 52 | 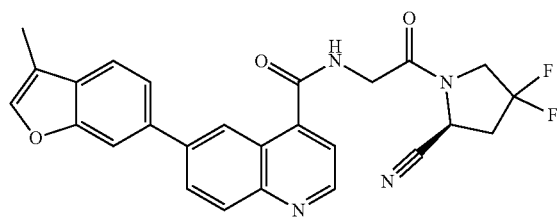 [SMILES: Cc1coc2cc(-c3ccc4nccc(C(=O)NCC(=O)N5CC(F)(F)C[C@H]5C#N)c4c3)ccc12] |
| 53 | 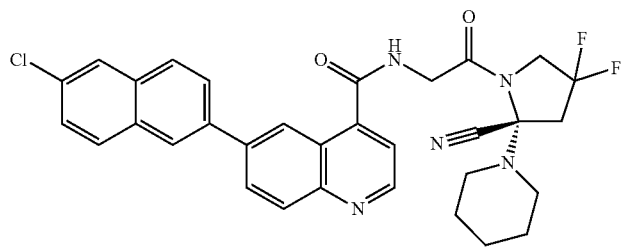 [SMILES: N#C[C@]1(N2CCCCC2)CC(F)(F)CN1C(=O)CNC(=O)c1ccnc2ccc(-c3ccc4cc(Cl)ccc4c3)cc12] |
| 54 | 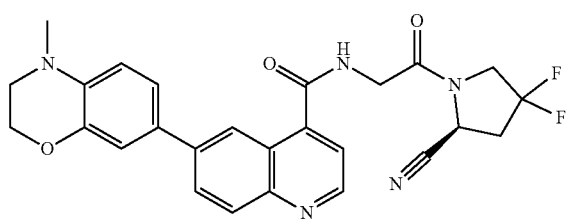 [SMILES: CN1CCOc2cc(-c3ccc4nccc(C(=O)NCC(=O)N5CC(F)(F)C[C@H]5C#N)c4c3)ccc21] |
| 55 | 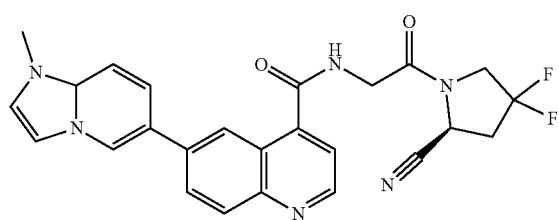 [SMILES: CN1C=CN2C=C(c3ccc4nccc(C(=O)NCC(=O)N5CC(F)(F)C[C@H]5C#N)c4c3)C=CC12] |
| 56 | 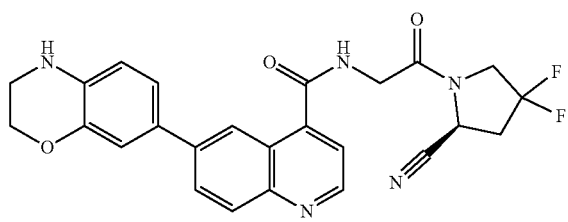 [SMILES: N#C[C@@H]1CC(F)(F)CN1C(=O)CNC(=O)c1ccnc2ccc(-c3ccc4c(c3)OCCN4)cc12] |

TABLE 1A-continued
| Compound No. | Structure |
|---|---|
| 57 | 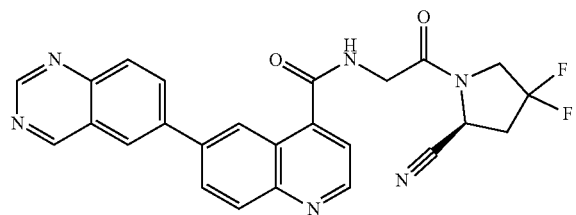 [SMILES: N#C[C@@H]1CC(F)(F)CN1C(=O)CNC(=O)c1ccnc2ccc(-c3ccc4ncncc4c3)cc12] |
| 58 | 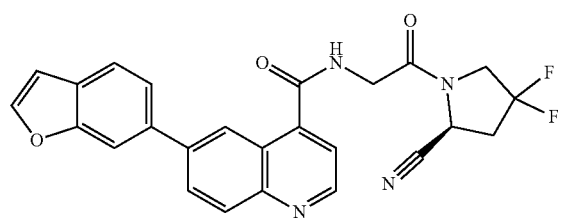 [SMILES: N#C[C@@H]1CC(F)(F)CN1C(=O)CNC(=O)c1ccnc2ccc(-c3ccc4ccoc4c3)cc12] |
| 59 | 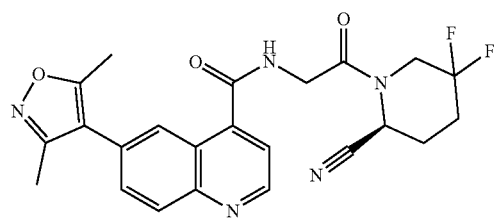 [SMILES: Cc1noc(C)c1-c1ccc2nccc(C(=O)NCC(=O)N3CC(F)(F)CC[C@H]3C#N)c2c1] |
| 60 | 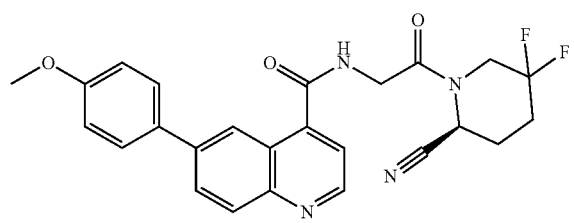 [SMILES: COc1ccc(-c2ccc3nccc(C(=O)NCC(=O)N4CC(F)(F)CC[C@H]4C#N)c3c2)cc1] |
| 61 | 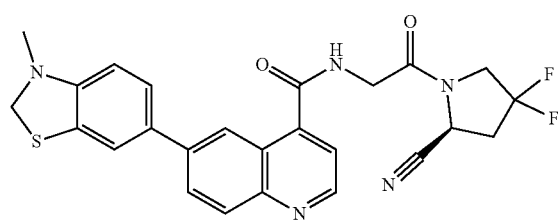 [SMILES: CN1CSc2cc(-c3ccc4nccc(C(=O)NCC(=O)N5CC(F)(F)C[C@H]5C#N)c4c3)ccc21] |
| 62 | 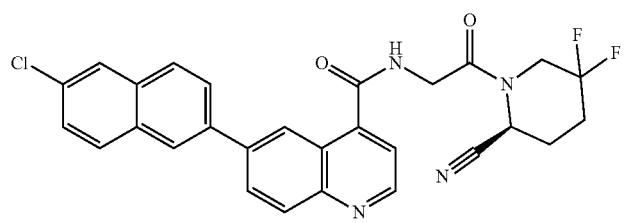 [SMILES: N#C[C@@H]1CCC(F)(F)CN1C(=O)CNC(=O)c1ccnc2ccc(-c3ccc4cc(Cl)ccc4c3)cc12] |
| 63 | 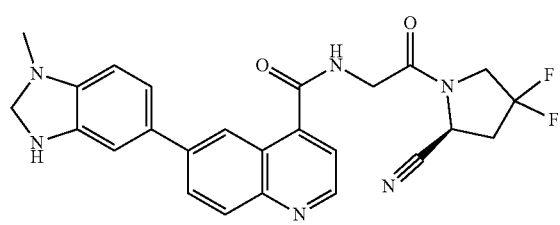 [SMILES: CN1CNc2cc(-c3ccc4nccc(C(=O)NCC(=O)N5CC(F)(F)C[C@H]5C#N)c4c3)ccc21] |

TABLE 1A-continued
| Compound No. | Structure |
|---|---|
| 64 | 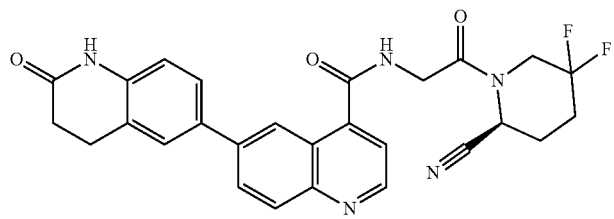 [SMILES: N#C[C@@H]1CCC(F)(F)CN1C(=O)CNC(=O)c1ccnc2ccc(-c3ccc4c(c3)CCC(=O)N4)cc12] |
| 65 | 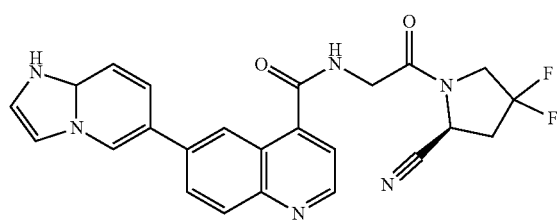 [SMILES: N#C[C@@H]1CC(F)(F)CN1C(=O)CNC(=O)c1ccnc2ccc(C3=CN4C=CNC4C=C3)cc12] |
| 66 | 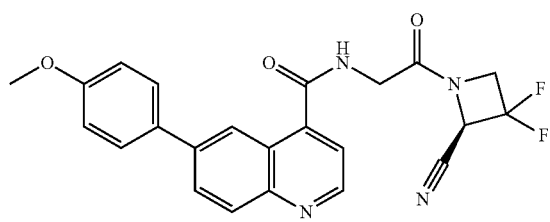 [SMILES: COc1ccc(-c2ccc3nccc(C(=O)NCC(=O)N4CC(F)(F)[C@H]4C#N)c3c2)cc1] |
| 67 | 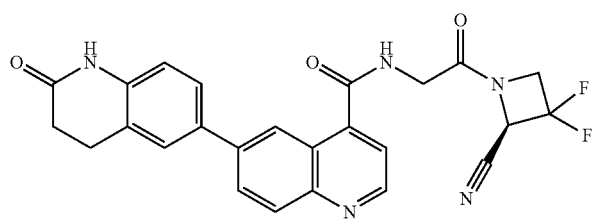 [SMILES: N#C[C@H]1N(C(=O)CNC(=O)c2ccnc3ccc(-c4ccc5c(c4)CCC(=O)N5)cc23)CC1(F)F] |
| 68 | 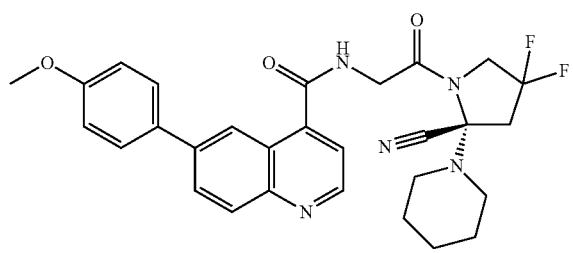 [SMILES: COc1ccc(-c2ccc3nccc(C(=O)NCC(=O)N4CC(F)(F)C[C@]4(C#N)N4CCCCC4)c3c2)cc1] |
| 69 | 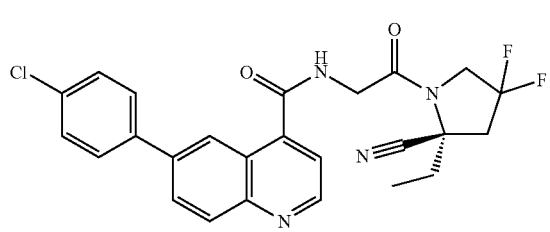 [SMILES: CC[C@@]1(C#N)CC(F)(F)CN1C(=O)CNC(=O)c1ccnc2ccc(-c3ccc(Cl)cc3)cc12] |

TABLE 1A-continued
| Compound No. | Structure |
|---|---|
| 70 | 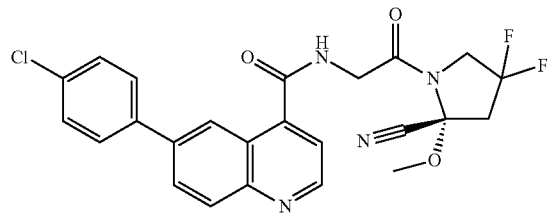 [SMILES: CO[C@@]1(C#N)CC(F)(F)CN1C(=O)CNC(=O)c1ccnc2ccc(-c3ccc(Cl)cc3)cc12] |
| 71 | 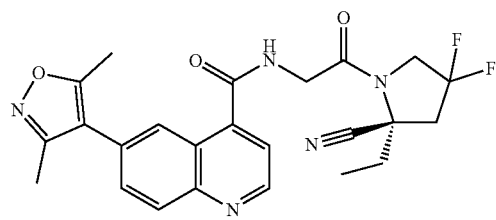 [SMILES: CC[C@@]1(C#N)CC(F)(F)CN1C(=O)CNC(=O)c1ccnc2ccc(-c3c(C)noc3C)cc12] |
| 72 | 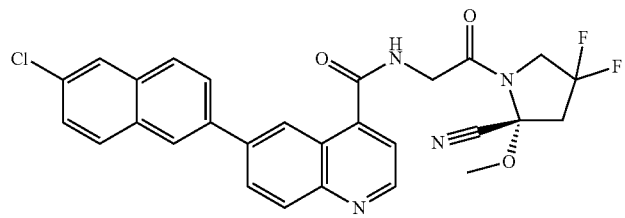 [SMILES: CO[C@@]1(C#N)CC(F)(F)CN1C(=O)CNC(=O)c1ccnc2ccc(-c3ccc4cc(Cl)ccc4c3)cc12] |
| 73 | 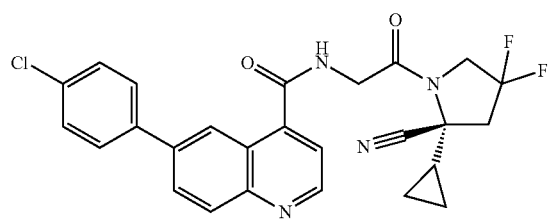 [SMILES: N#C[C@]1(C2CC2)CC(F)(F)CN1C(=O)CNC(=O)c1ccnc2ccc(-c3ccc(Cl)cc3)cc12] |
| 74 | 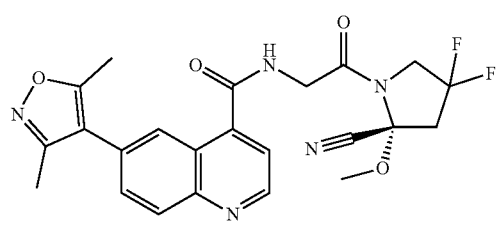 |
| 75 | 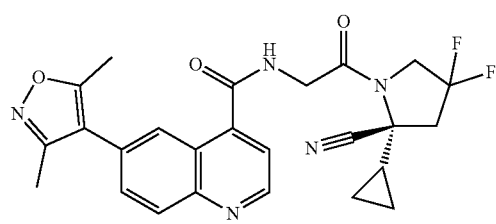 [SMILES: Cc1noc(C)c1-c1ccc2nccc(C(=O)NCC(=O)N3CC(F)(F)C[C@]3(C#N)C3CC3)c2c1] |
| 76 | 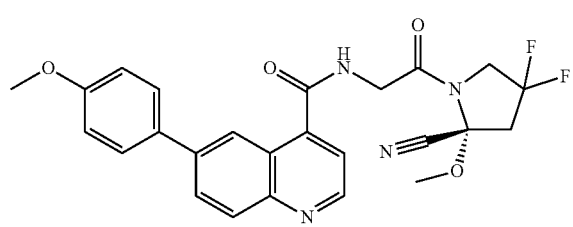 [SMILES: COc1ccc(-c2ccc3nccc(C(=O)NCC(=O)N4CC(F)(F)C[C@]4(C#N)OC)c3c2)cc1] |

TABLE 1A-continued
| Compound No. | Structure |
|---|---|
| 77 | 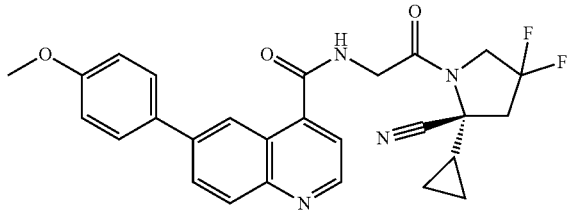 [SMILES: COc1ccc(-c2ccc3nccc(C(=O)NCC(=O)N4CC(F)(F)C[C@]4(C#N)C4CC4)c3c2)cc1] |
| 78 | 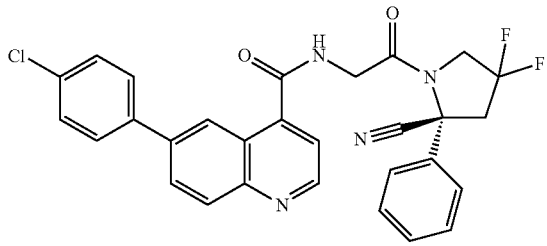 [SMILES: N#C[C@]1(c2ccccc2)CC(F)(F)CN1C(=O)CNC(=O)c1ccnc2ccc(-c3ccc(Cl)cc3)cc12] |
| 79 | 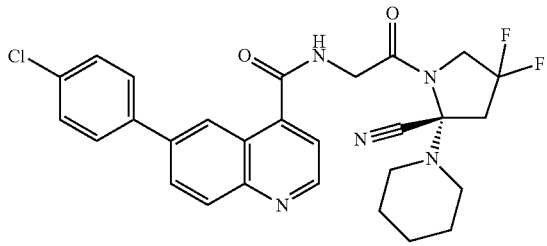 [SMILES: N#C[C@]1(N2CCCCC2)CC(F)(F)CN1C(=O)CNC(=O)c1ccnc2ccc(-c3ccc(Cl)cc3)cc12] |
| 80 | 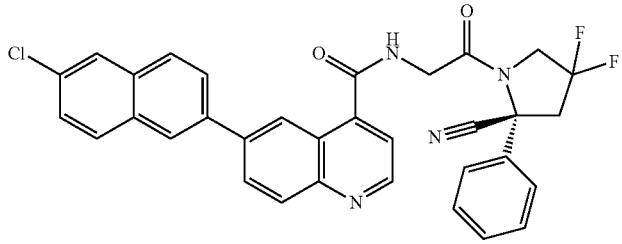 [SMILES: N#C[C@]1(c2ccccc2)CC(F)(F)CN1C(=O)CNC(=O)c1ccnc2ccc(-c3ccc4cc(Cl)ccc4c3)cc12] |
| 81 | 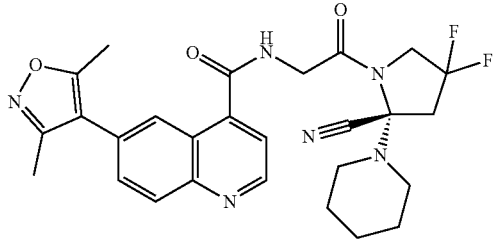 [SMILES: Cc1noc(C)c1-c1ccc2nccc(C(=O)NCC(=O)N3CC(F)(F)C[C@]3(C#N)N3CCCCC3)c2c1] |
| 82 | 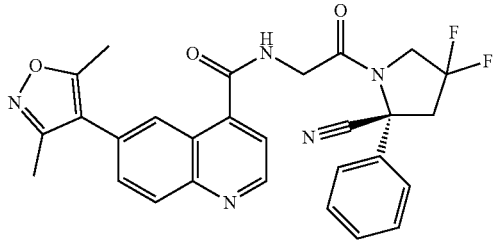 [SMILES: Cc1noc(C)c1-c1ccc2nccc(C(=O)NCC(=O)N3CC(F)(F)C[C@]3(C#N)c3ccccc3)c2c1] |

TABLE 1A-continued

| Compound No. | Structure |
|---|---|
| 83 | 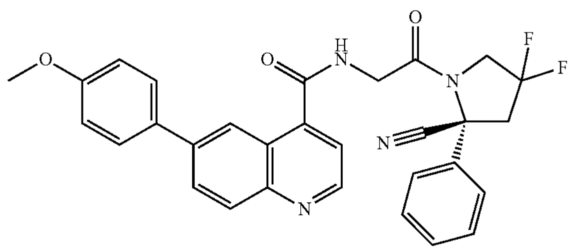 [SMILES: COc1ccc(-c2ccc3nccc(C(=O)NCC(=O)N4CC(F)(F)C[C@]4(C#N)c4ccccc4)c3c2)cc1] |
| 84 | 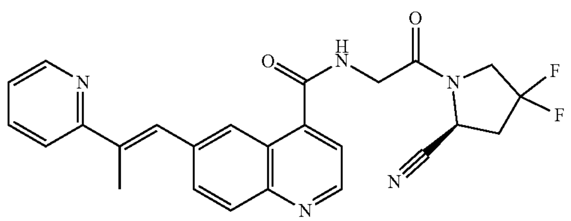 [SMILES: C/C(=C\c1ccc2nccc(C(=O)NCC(=O)N3CC(F)(F)C[C@H]3C#N)c2c1)c1ccccn1] |
| 85 | 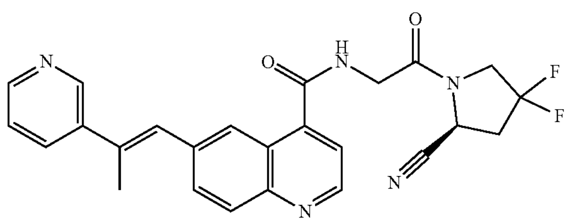 [SMILES: C/C(=C\c1ccc2nccc(C(=O)NCC(=O)N3CC(F)(F)C[C@H]3C#N)c2c1)c1cccnc1] |
| 86 | 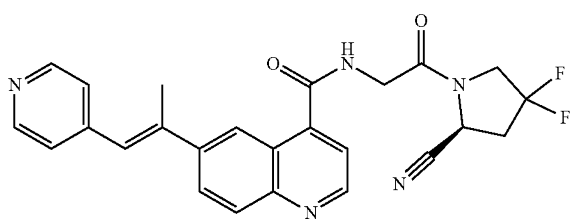 [SMILES: C/C(=C\c1ccncc1)c1ccc2nccc(C(=O)NCC(=O)N3CC(F)(F)C[C@H]3C#N)c2c1] |
| 87 | 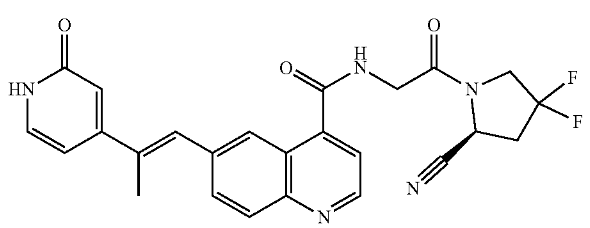 [SMILES: C/C(=C\c1ccc2nccc(C(=O)NCC(=O)N3CC(F)(F)C[C@H]3C#N)c2c1)c1cc[nH]c(=O)c1] |
| 88 | 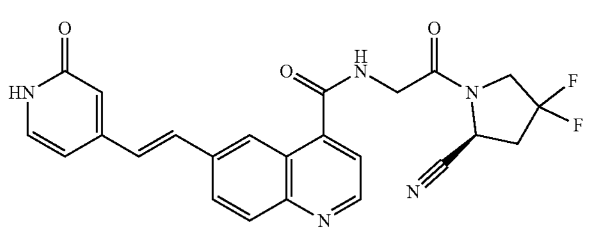 [SMILES: N#C[C@@H]1CC(F)(F)CN1C(=O)CNC(=O)c1ccnc2ccc(/C=C/c3cc[nH]c(=O)c3)cc12] |

TABLE 1A-continued

| Compound No. | Structure |
|---|---|
| 89 | 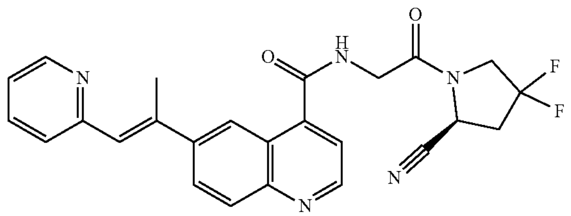 [SMILES: C/C(=C\c1ccccn1)c1ccc2nccc(C(=O)NCC(=O)N3CC(F)(F)C[C@H]3C#N)c2c1] |
| 90 | 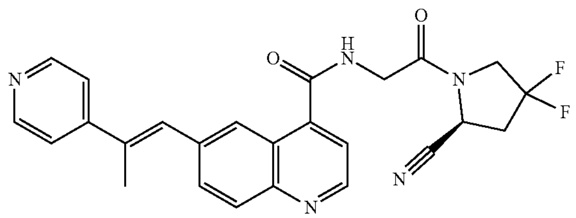 [SMILES: C/C(=C\c1ccc2nccc(C(=O)NCC(=O)N3CC(F)(F)C[C@H]3C#N)c2c1)c1ccncc1] |
| 91 | 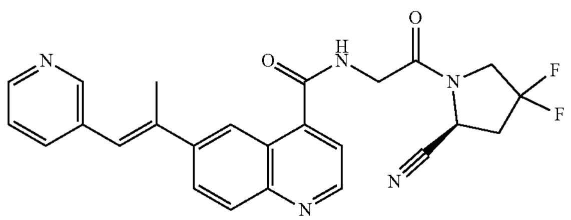 [SMILES: C/C(=C\c1cccnc1)c1ccc2nccc(C(=O)NCC(=O)N3CC(F)(F)C[C@H]3C#N)c2c1] |
| 92 | 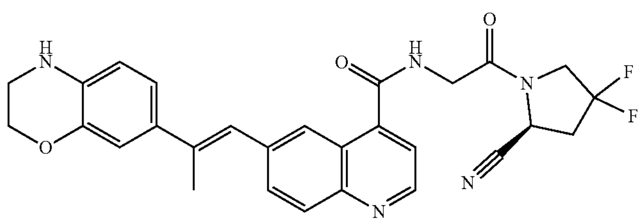 [SMILES: C/C(=C\c1ccc2nccc(C(=O)NCC(=O)N3CC(F)(F)C[C@H]3C#N)c2c1)c1ccc2c(c1)OCCN2] |
| 93 | 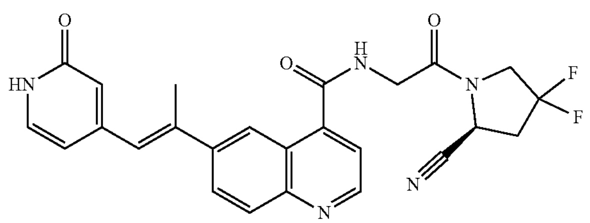 [SMILES: C/C(=C\c1cc[nH]c(=O)c1)c1ccc2nccc(C(=O)NCC(=O)N3CC(F)(F)C[C@H]3C#N)c2c1] |
| 94 | 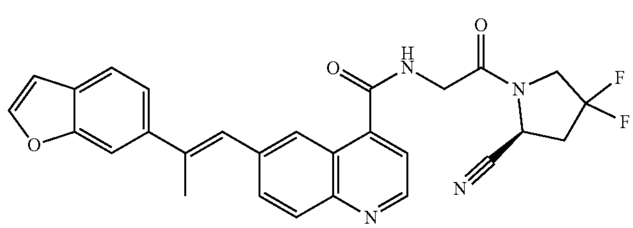 [SMILES: C/C(=C\c1ccc2nccc(C(=O)NCC(=O)N3CC(F)(F)C[C@H]3C#N)c2c1)c1ccc2ccoc2c1] |
| 95 | 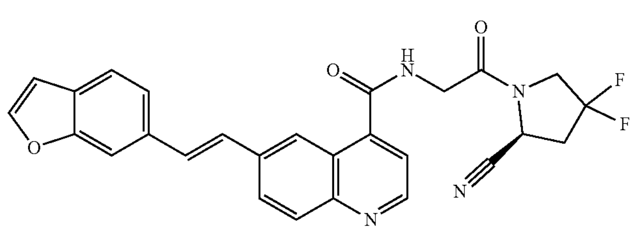 [SMILES: N#C[C@@H]1CC(F)(F)CN1C(=O)CNC(=O)c1ccnc2ccc(/C=C/c3ccc4ccoc4c3)cc12] |

TABLE 1A-continued

| Compound No. | Structure |
|---|---|
| 96 | *(chemical structure)* |
| 97 | *(chemical structure)* |
| 98 | *(chemical structure)* |
| 99 | *(chemical structure)* |
| 100 | *(chemical structure)* |
| 101 | *(chemical structure)* |

TABLE 1A-continued

| Compound No. | Structure |
|---|---|
| 102 | 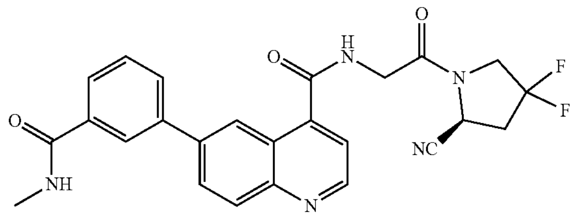 [SMILES: CNC(=O)c1cccc(-c2ccc3nccc(C(=O)NCC(=O)N4CC(F)(F)C[C@H]4C#N)c3c2)c1] |
| 103 | 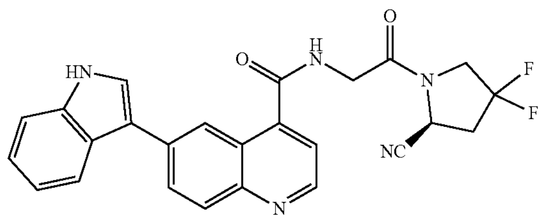 [SMILES: N#C[C@@H]1CC(F)(F)CN1C(=O)CNC(=O)c1ccnc2ccc(-c3c[nH]c4ccccc34)cc12] |
| 104 | 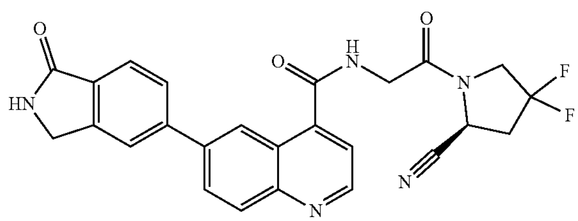 [SMILES: N#C[C@@H]1CC(F)(F)CN1C(=O)CNC(=O)c1ccnc2ccc(-c3ccc4c(c3)CNC4=O)cc12] |
| 105 | 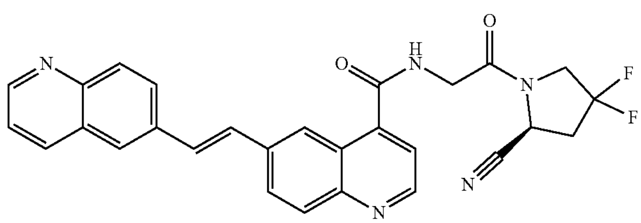 [SMILES: N#C[C@@H]1CC(F)(F)CN1C(=O)CNC(=O)c1ccnc2ccc(/C=C/c3ccc4ncccc4c3)cc12] |
| 106 | 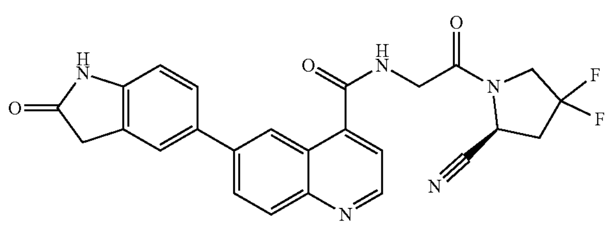 [SMILES: N#C[C@@H]1CC(F)(F)CN1C(=O)CNC(=O)c1ccnc2ccc(-c3ccc4c(c3)CC(=O)N4)cc12] |
| 107 | 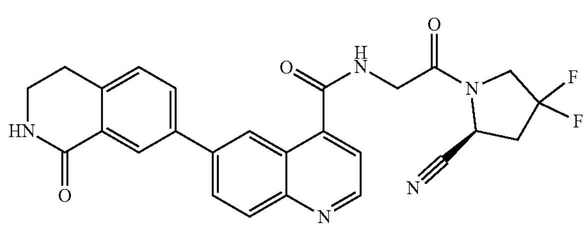 [SMILES: N#C[C@@H]1CC(F)(F)CN1C(=O)CNC(=O)c1ccnc2ccc(-c3ccc4c(c3)C(=O)NCC4)cc12] |
| 108 | 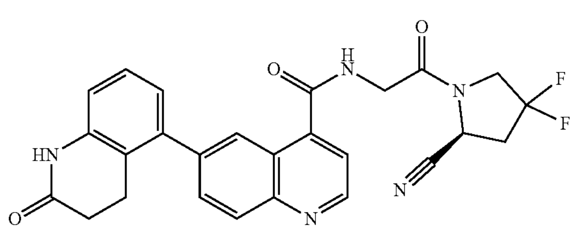 [SMILES: N#C[C@@H]1CC(F)(F)CN1C(=O)CNC(=O)c1ccnc2ccc(-c3cccc4c3CCC(=O)N4)cc12] |

TABLE 1A-continued
| Compound No. | Structure |
|---|---|
| 109 | 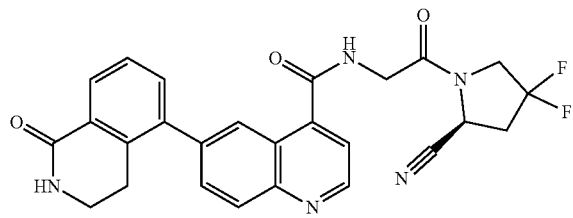 [SMILES: N#C[C@@H]1CC(F)(F)CN1C(=O)CNC(=O)c1ccnc2ccc(-c3cccc4c3CCNC4=O)cc12] |
| 110 | 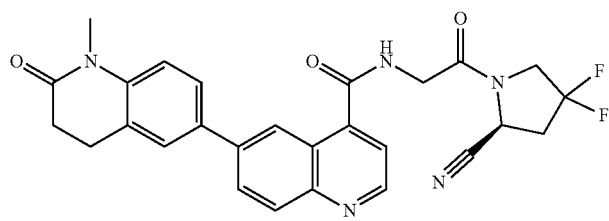 [SMILES: CN1C(=O)CCc2cc(-c3ccc4nccc(C(=O)NCC(=O)N5CC(F)(F)C[C@H]5C#N)c4c3)ccc21] |
| 111 | 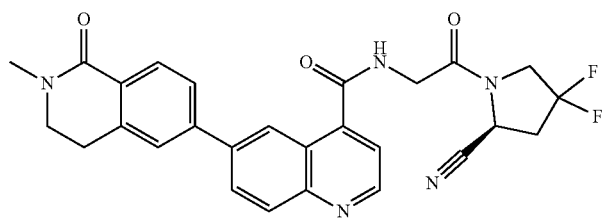 [SMILES: CN1CCc2cc(-c3ccc4nccc(C(=O)NCC(=O)N5CC(F)(F)C[C@H]5C#N)c4c3)ccc2C1=O] |
| 112 | 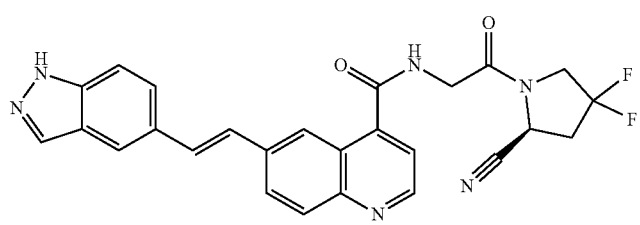 [SMILES: N#C[C@@H]1CC(F)(F)CN1C(=O)CNC(=O)c1ccnc2ccc(/C=C/c3ccc4[nH]ncc4c3)cc12] |
| 113 | 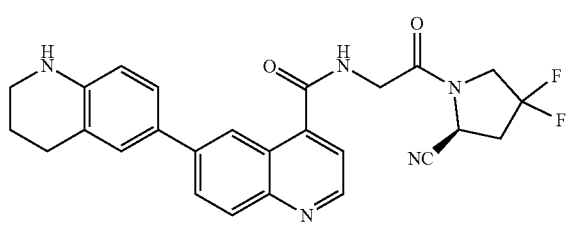 [SMILES: N#C[C@@H]1CC(F)(F)CN1C(=O)CNC(=O)c1ccnc2ccc(-c3ccc4c(c3)CCCN4)cc12] |
| 114 | 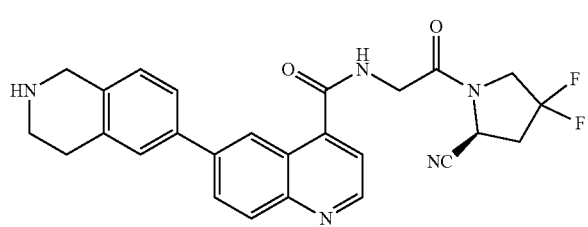 [SMILES: N#C[C@@H]1CC(F)(F)CN1C(=O)CNC(=O)c1ccnc2ccc(-c3ccc4c(c3)CCNC4)cc12] |

TABLE 1A-continued

| Compound No. | Structure |
|---|---|
| 115 | 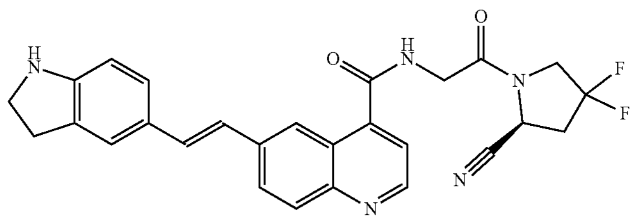 [SMILES: N#C[C@@H]1CC(F)(F)CN1C(=O)CNC(=O)c1ccnc2ccc(/C=C/c3ccc4c(c3)CCN4)cc12] |
| 116 | 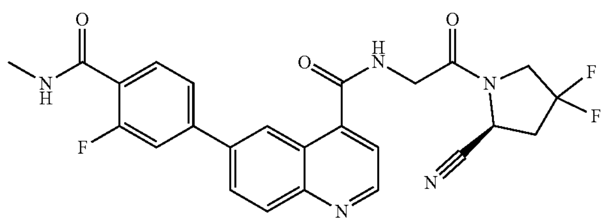 [SMILES: CNC(=O)c1ccc(-c2ccc3nccc(C(=O)NCC(=O)N4CC(F)(F)C[C@H]4C#N)c3c2)cc1F] |
| 117 | 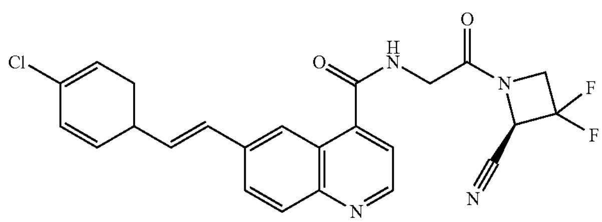 [SMILES: N#C[C@H]1N(C(=O)CNC(=O)c2ccnc3ccc(/C=C/C4C=CC(Cl)=CC4)cc23)CC1(F)F] |
| 118 | 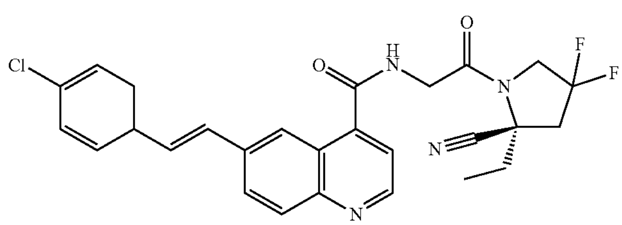 [SMILES: CC[C@@]1(C#N)CC(F)(F)CN1C(=O)CNC(=O)c1ccnc2ccc(/C=C/C3C=CC(Cl)=CC3)cc12] |
| 119 | 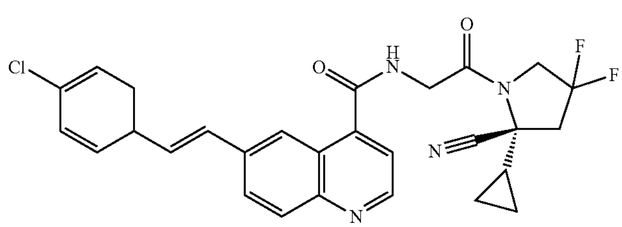 [SMILES: N#C[C@]1(C2CC2)CC(F)(F)CN1C(=O)CNC(=O)c1ccnc2ccc(/C=C/C3C=CC(Cl)=CC3)cc12] |
| 120 | 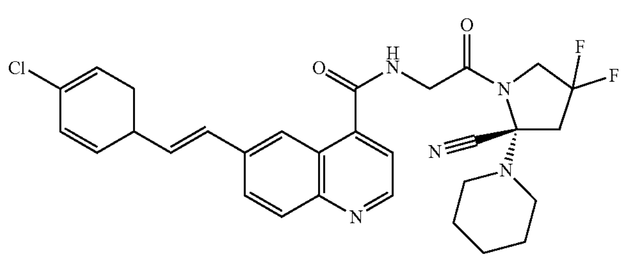 [SMILES: N#C[C@]1(N2CCCCC2)CC(F)(F)CN1C(=O)CNC(=O)c1ccnc2ccc(/C=C/C3C=CC(Cl)=CC3)cc12] |

TABLE 1A-continued
| Compound No. | Structure |
|---|---|
| 121 | 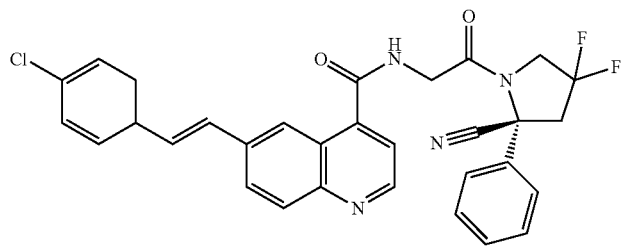 [SMILES: N#C[C@]1(c2ccccc2)CC(F)(F)CN1C(=O)CNC(=O)c1ccnc2ccc(/C=C/C3C=CC(Cl)=CC3)cc12] |
TABLE 1B
| Compound No. | Structure |
|---|---|
| 122 | 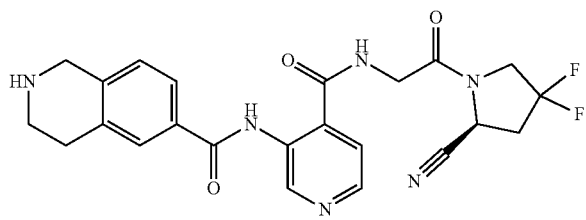 [SMILES: N#C[C@@H]1CC(F)(F)CN1C(=O)CNC(=O)c1ccncc1NC(=O)c1ccc2c(c1)CCNC2] |
| 123 | 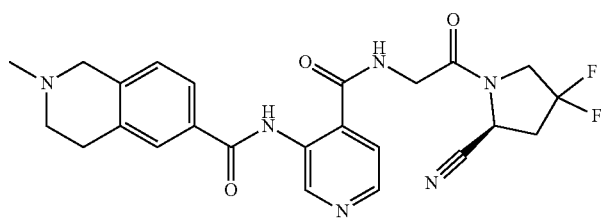 [SMILES: CN1CCc2cc(C(=O)Nc3cnccc3C(=O)NCC(=O)N3CC(F)(F)C[C@H]3C#N)ccc2C1] |
| 124 | 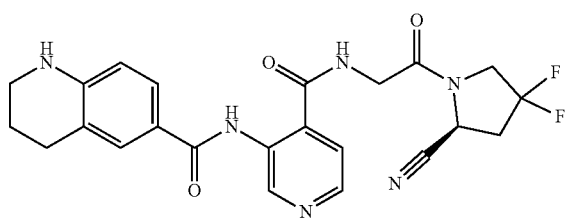 [SMILES: N#C[C@@H]1CC(F)(F)CN1C(=O)CNC(=O)c1ccncc1NC(=O)c1ccc2c(c1)CCCN2] |
| 125 | 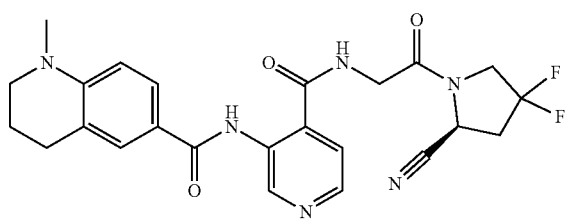 [SMILES: CN1CCCc2cc(C(=O)Nc3cnccc3C(=O)NCC(=O)N3CC(F)(F)C[C@H]3C#N)ccc21] |
| 126 | 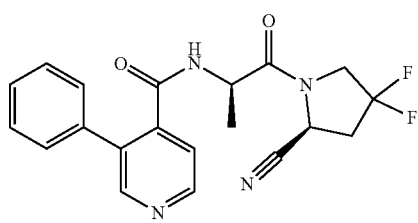 [SMILES: C[C@@H](NC(=O)c1ccncc1-c1ccccc1)C(=O)N1CC(F)(F)C[C@H]1C#N] |

TABLE 1B-continued

| Compound No. | Structure |
|---|---|
| 127 | 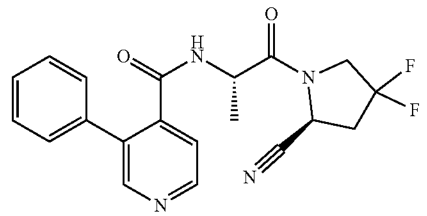 [SMILES: C[C@H](NC(=O)c1ccncc1-c1ccccc1)C(=O)N1CC(F)(F)C[C@H]1C#N] |
| 128 | 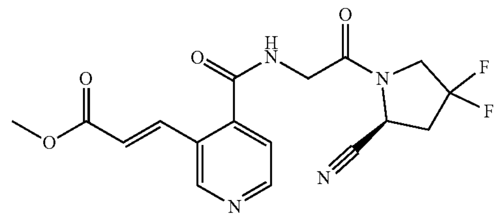 [SMILES: COC(=O)/C=C/c1cnccc1C(=O)NCC(=O)N1CC(F)(F)C[C@H]1C#N] |
| 129 | 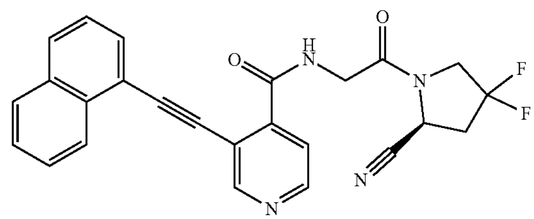 [SMILES: N#C[C@@H]1CC(F)(F)CN1C(=O)CNC(=O)c1ccncc1C#Cc1cccc2ccccc12] |
| 130 | 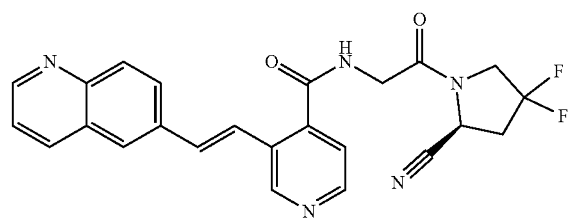 [SMILES: N#C[C@@H]1CC(F)(F)CN1C(=O)CNC(=O)c1ccncc1/C=C/c1ccc2ncccc2c1] |
| 131 | 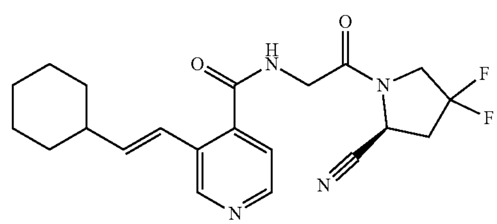 [SMILES: N#C[C@@H]1CC(F)(F)CN1C(=O)CNC(=O)c1ccncc1/C=C/C1CCCCC1] |
| 132 | 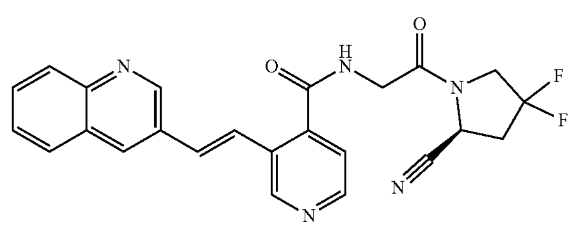 [SMILES: N#C[C@@H]1CC(F)(F)CN1C(=O)CNC(=O)c1ccncc1/C=C/c1cnc2ccccc2c1] |
| 133 | 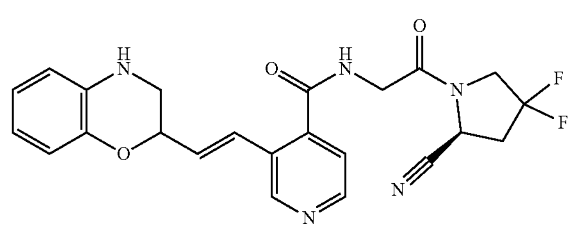 [SMILES: N#C[C@@H]1CC(F)(F)CN1C(=O)CNC(=O)c1ccncc1/C=C/C1CNc2ccccc2O1] |

TABLE 1B-continued
| Compound No. | Structure |
|---|---|
| 134 | 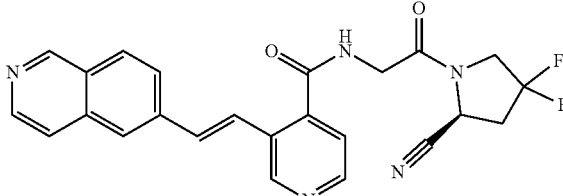 |
| 135 | 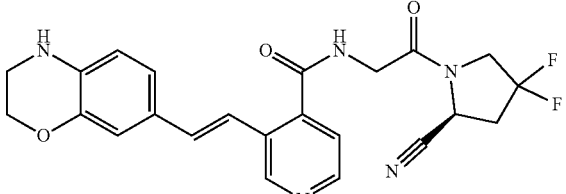 |
| 136 | 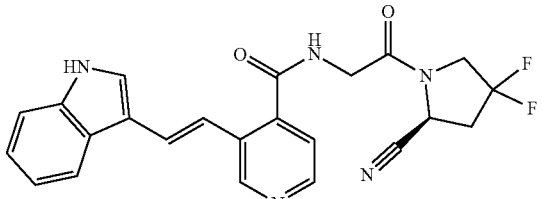 |
| 137 | 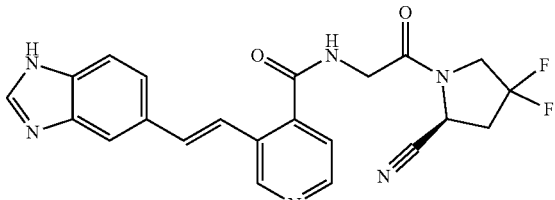 |
| 138 | 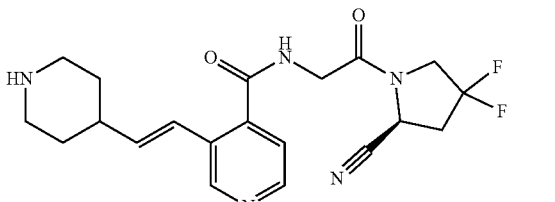 |
| 139 | 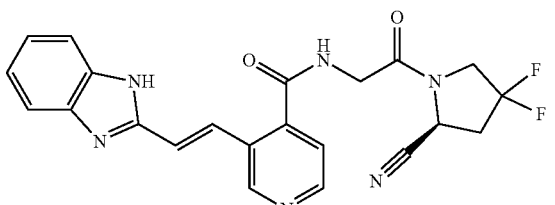 |
| 140 | 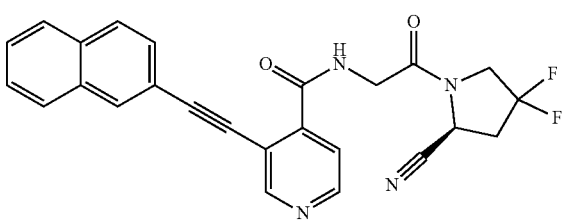 [SMILES: N#C[C@@H]1CC(F)(F)CN1C(=O)CNC(=O)c1ccncc1C#Cc1ccc2ccccc2c1] |

TABLE 1B-continued

| Compound No. | Structure |
|---|---|
| 141 | 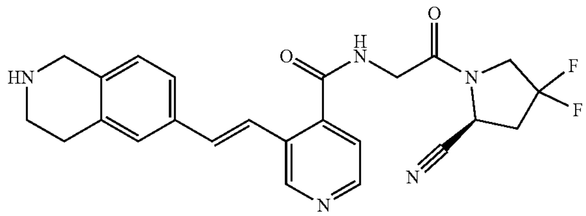 [SMILES: N#C[C@@H]1CC(F)(F)CN1C(=O)CNC(=O)c1ccncc1/C=C/c1ccc2c(c1)CCNC2] |
| 142 | 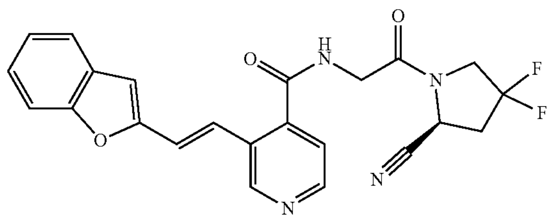 [SMILES: N#C[C@@H]1CC(F)(F)CN1C(=O)CNC(=O)c1ccncc1/C=C/c1cc2ccccc2o1] |
| 143 | 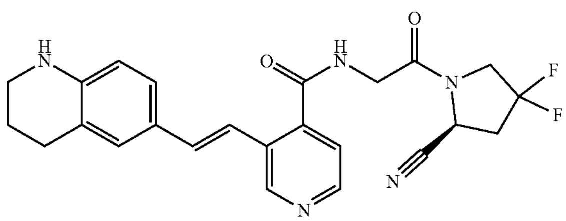 [SMILES: N#C[C@@H]1CC(F)(F)CN1C(=O)CNC(=O)c1ccncc1/C=C/c1ccc2c(c1)CCCN2] |
| 144 | 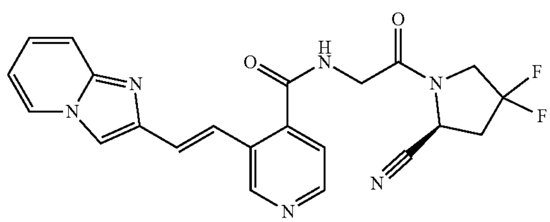 [SMILES: N#C[C@@H]1CC(F)(F)CN1C(=O)CNC(=O)c1ccncc1/C=C/c1cn2ccccc2n1] |
| 145 | 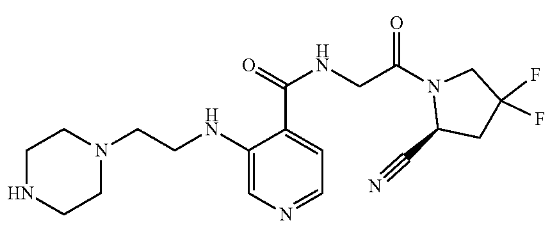 [SMILES: N#C[C@@H]1CC(F)(F)CN1C(=O)CNC(=O)c1ccncc1NCCN1CCNCC1] |
| 146 | 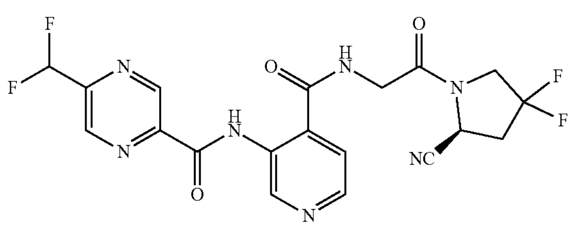 [SMILES: N#C[C@@H]1CC(F)(F)CN1C(=O)CNC(=O)c1ccncc1NC(=O)c1cnc(C(F)F)cn1] |
| 147 | 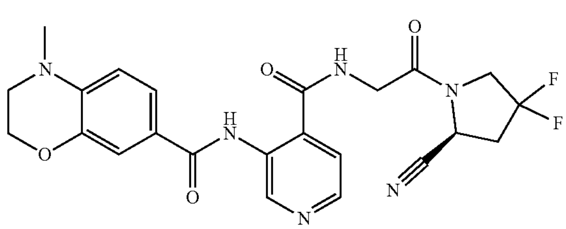 [SMILES: CN1CCOc2cc(C(=O)Nc3cnccc3C(=O)NCC(=O)N3CC(F)(F)C[C@H]3C#N)ccc21] |

TABLE 1B-continued

| Compound No. | Structure |
|---|---|
| 148 | 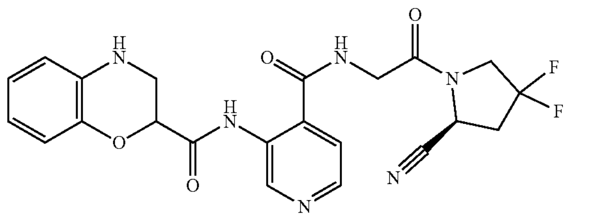 [SMILES: N#C[C@@H]1CC(F)(F)CN1C(=O)CNC(=O)c1ccncc1NC(=O)C1CNc2ccccc2O1] |
| 149 | 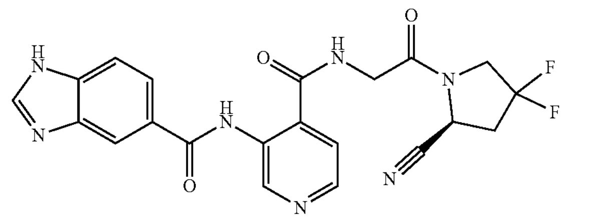 [SMILES: N#C[C@@H]1CC(F)(F)CN1C(=O)CNC(=O)c1ccncc1NC(=O)c1ccc2[nH]cnc2c1] |
| 150 | 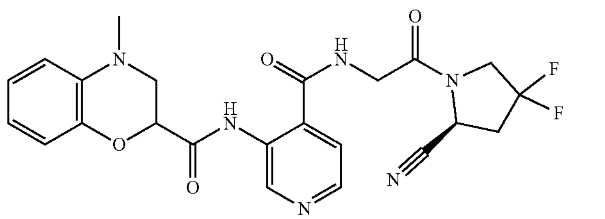 [SMILES: CN1CC(C(=O)Nc2cnccc2C(=O)NCC(=O)N2CC(F)(F)C[C@H]2C#N)Oc2ccccc21] |
| 151 | 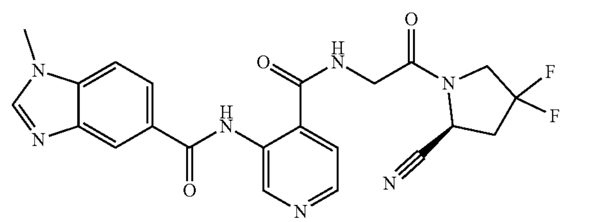 [SMILES: Cn1cnc2cc(C(=O)Nc3cnccc3C(=O)NCC(=O)N3CC(F)(F)C[C@H]3C#N)ccc21] |
| 152 | 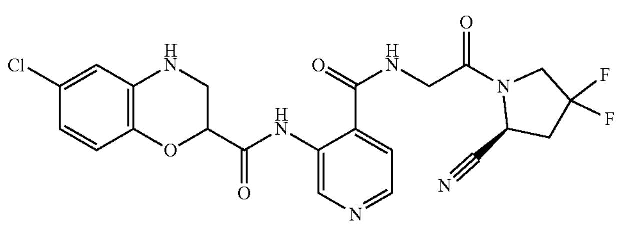 [SMILES: N#C[C@@H]1CC(F)(F)CN1C(=O)CNC(=O)c1ccncc1NC(=O)C1CNc2cc(Cl)ccc2O1] |
| 153 | 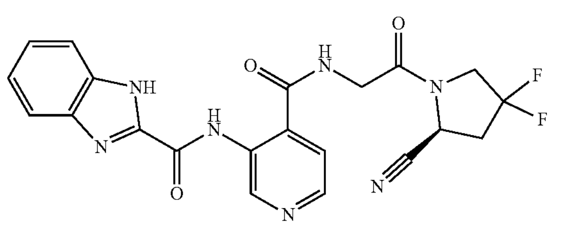 [SMILES: N#C[C@@H]1CC(F)(F)CN1C(=O)CNC(=O)c1ccncc1NC(=O)c1nc2ccccc2[nH]1] |
| 154 | 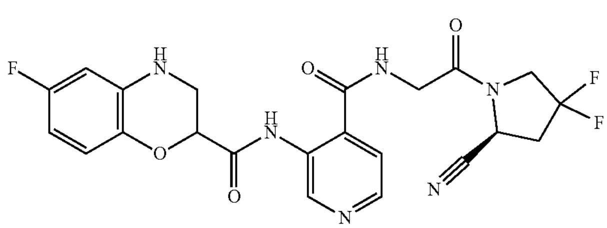 [SMILES: N#C[C@@H]1CC(F)(F)CN1C(=O)CNC(=O)c1ccncc1NC(=O)C1CNc2cc(F)ccc2O1] |

TABLE 1B-continued

| Compound No. | Structure |
|---|---|
| 155 | 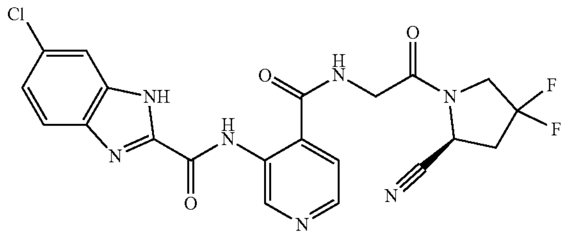 [SMILES: N#C[C@@H]1CC(F)(F)CN1C(=O)CNC(=O)c1ccncc1NC(=O)c1nc2ccc(Cl)cc2[nH]1] |
| 156 | 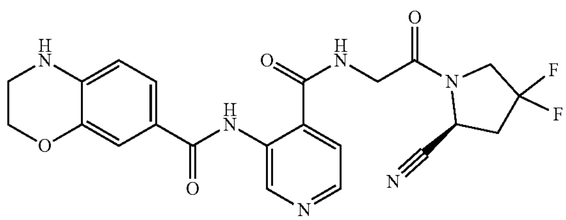 [SMILES: N#C[C@@H]1CC(F)(F)CN1C(=O)CNC(=O)c1ccncc1NC(=O)c1ccc2c(c1)OCCN2] |
| 157 | 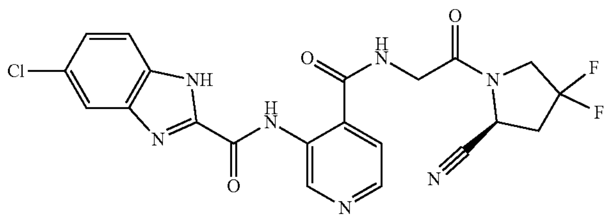 [SMILES: N#C[C@@H]1CC(F)(F)CN1C(=O)CNC(=O)c1ccncc1NC(=O)c1nc2cc(Cl)ccc2[nH]1] |
| 158 | 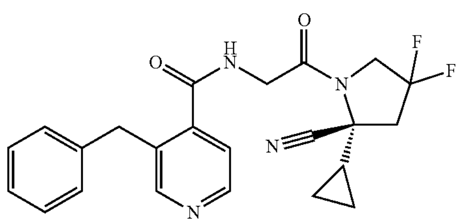 [SMILES: N#C[C@]1(C2CC2)CC(F)(F)CN1C(=O)CNC(=O)c1ccncc1Cc1ccccc1] |
| 159 | 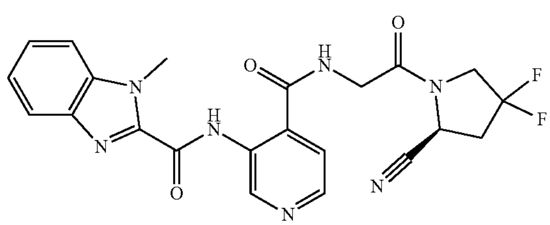 [SMILES: Cn1c(C(=O)Nc2cnccc2C(=O)NCC(=O)N2CC(F)(F)C[C@H]2C#N)nc2ccccc21] |
| 160 | 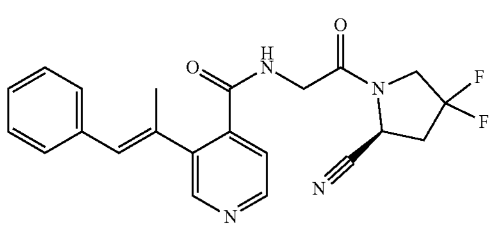 [SMILES: C/C(=C\c1ccccc1)c1cnccc1C(=O)NCC(=O)N1CC(F)(F)C[C@H]1C#N] |
| 161 | 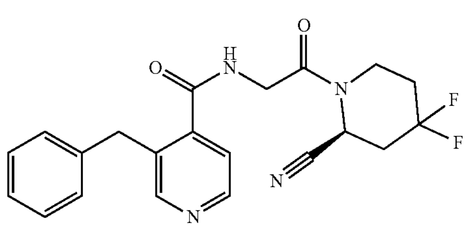 [SMILES: N#C[C@@H]1CC(F)(F)CCN1C(=O)CNC(=O)c1ccncc1Cc1ccccc1] |

TABLE 1B-continued
| Compound No. | Structure |
|---|---|
| 162 | 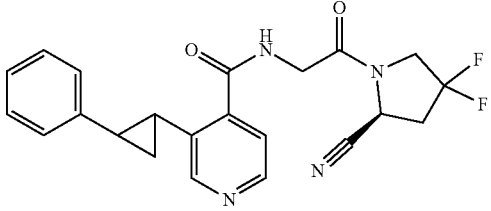 [SMILES: N#C[C@@H]1CC(F)(F)CN1C(=O)CNC(=O)c1ccncc1C1CC1c1ccccc1] |
| 163 | 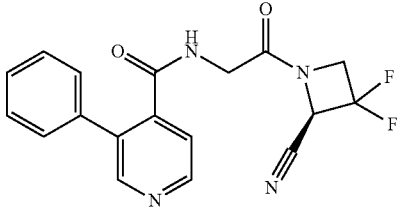 [SMILES: N#C[C@H]1N(C(=O)CNC(=O)c2ccncc2-c2ccccc2)CC1(F)F] |
| 164 | 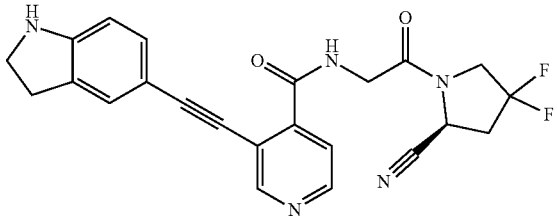 [SMILES: N#C[C@@H]1CC(F)(F)CN1C(=O)CNC(=O)c1ccncc1C#Cc1ccc2c(c1)CCN2] |
| 165 | 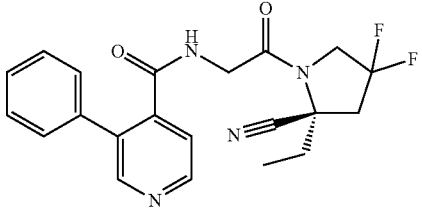 [SMILES: CC[C@@]1(C#N)CC(F)(F)CN1C(=O)CNC(=O)c1ccncc1-c1ccccc1] |
| 166 | 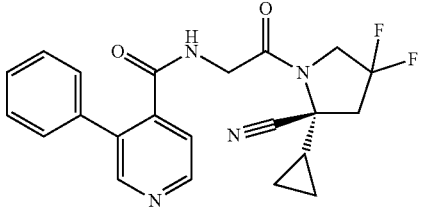 [SMILES: N#C[C@]1(C2CC2)CC(F)(F)CN1C(=O)CNC(=O)c1ccncc1-c1ccccc1] |
| 167 | 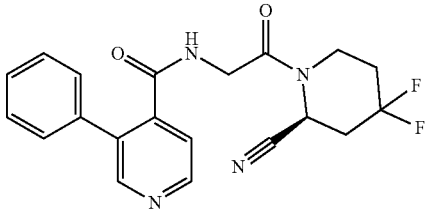 [SMILES: N#C[C@@H]1CC(F)(F)CCN1C(=O)CNC(=O)c1ccncc1-c1ccccc1] |

TABLE 1B-continued
| Compound No. | Structure |
|---|---|
| 168 | 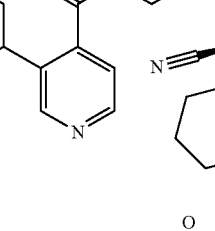 |
| 169 | 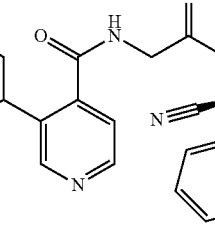 |
| 170 | 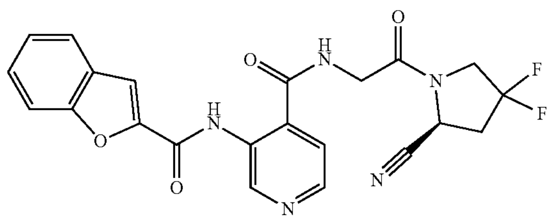 [SMILES: N#C[C@@H]1CC(F)(F)CN1C(=O)CNC(=O)c1ccncc1NC(=O)c1cc2ccccc2o1] |
| 171 | 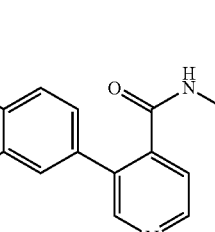 |
| 172 | 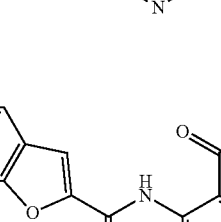 |
| 173 | 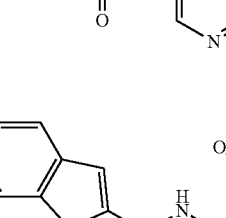 |

TABLE 1B-continued

| Compound No. | Structure |
|---|---|
| 174 | 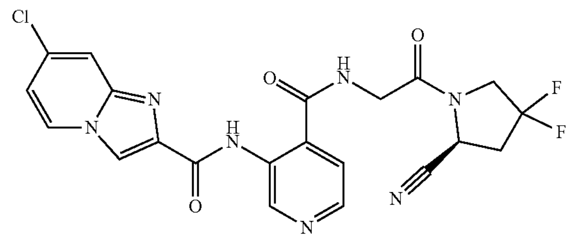 [SMILES: N#C[C@@H]1CC(F)(F)CN1C(=O)CNC(=O)c1ccncc1NC(=O)c1cn2ccc(Cl)cc2n1] |
| 175 | 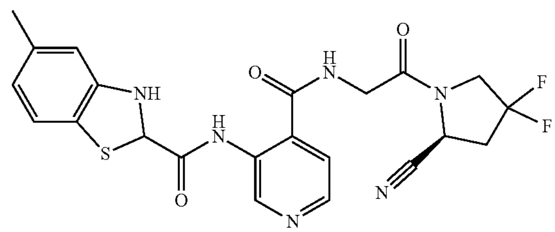 [SMILES: Cc1ccc2c(c1)NC(C(=O)Nc1cnccc1C(=O)NCC(=O)N1CC(F)(F)C[C@H]1C#N)S2] |
| 176 | 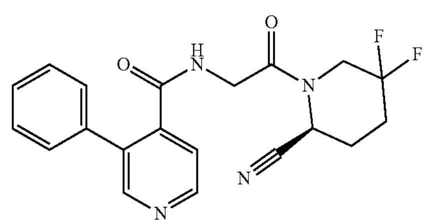 [SMILES: N#C[C@@H]1CCC(F)(F)CN1C(=O)CNC(=O)c1ccncc1-c1ccccc1] |
| 177 | 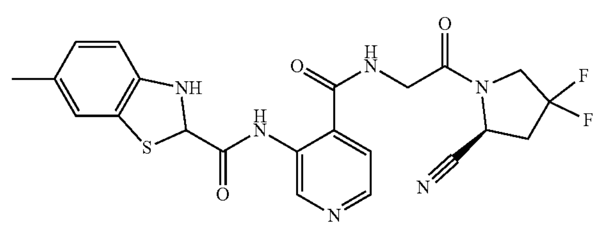 [SMILES: Cc1ccc2c(c1)SC(C(=O)Nc1cnccc1C(=O)NCC(=O)N1CC(F)(F)C[C@H]1C#N)N2] |
| 178 | 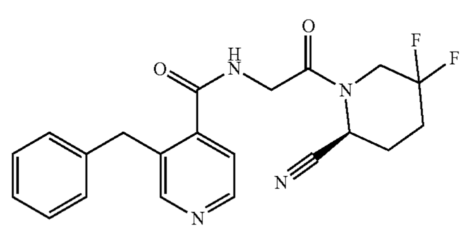 [SMILES: N#C[C@@H]1CCC(F)(F)CN1C(=O)CNC(=O)c1ccncc1Cc1ccccc1] |
| 179 | 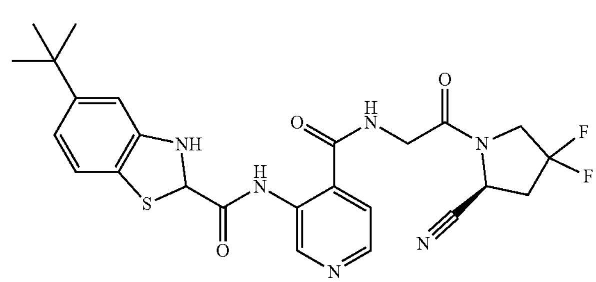 [SMILES: CC(C)(C)c1ccc2c(c1)NC(C(=O)Nc1cnccc1C(=O)NCC(=O)N1CC(F)(F)C[C@H]1C#N)S2] |

TABLE 1B-continued
| Compound No. | Structure |
|---|---|
| 180 | 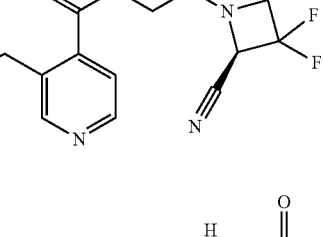 |
| 181 | 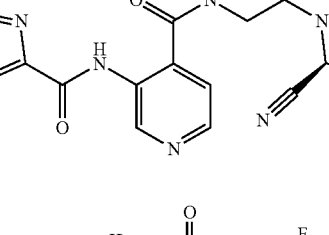 |
| 182 | 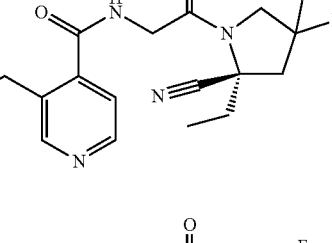 |
| 183 | 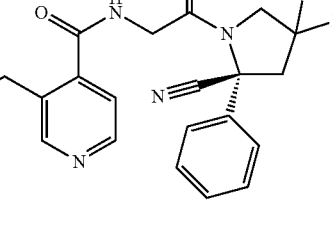 |
| 184 | 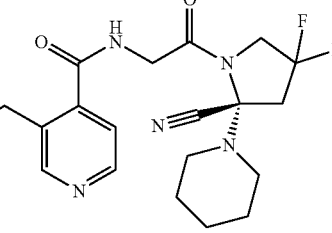 |
| 185 | 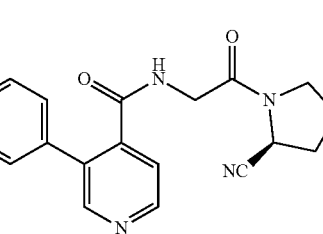 |

TABLE 1B-continued

| Compound No. | Structure |
|---|---|
| 186 | 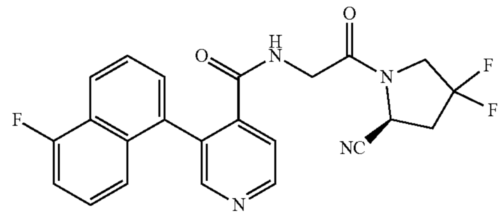 [SMILES: N#C[C@@H]1CC(F)(F)CN1C(=O)CNC(=O)c1ccncc1-c1cccc2c(F)cccc12] |
| 187 | 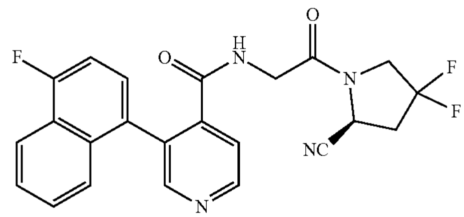 [SMILES: N#C[C@@H]1CC(F)(F)CN1C(=O)CNC(=O)c1ccncc1-c1ccc(F)c2ccccc12] |
| 188 | 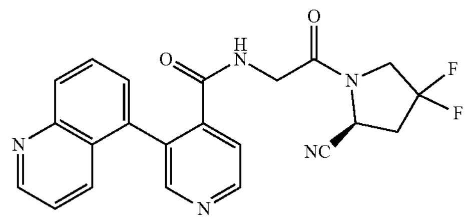 [SMILES: N#C[C@@H]1CC(F)(F)CN1C(=O)CNC(=O)c1ccncc1-c1cccc2ncccc12] |
| 189 | 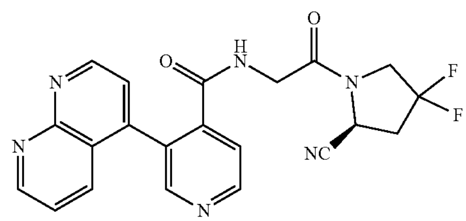 |
| 190 | 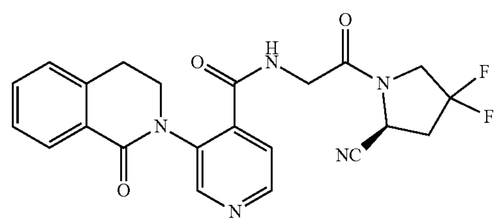 [SMILES: N#C[C@@H]1CC(F)(F)CN1C(=O)CNC(=O)c1ccncc1N1CCc2ccccc2C1=O] |
| 191 | 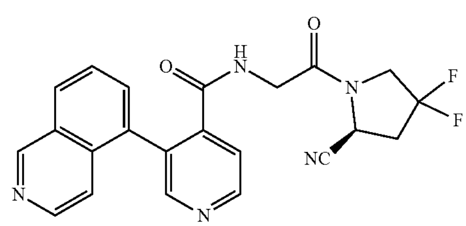 |
| 192 | 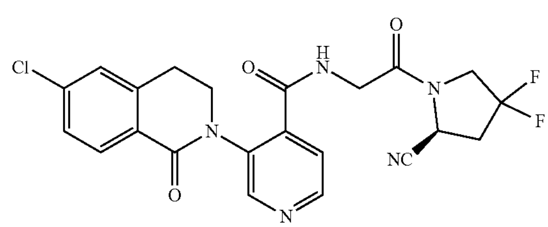 [SMILES: N#C[C@@H]1CC(F)(F)CN1C(=O)CNC(=O)c1ccncc1N1CCc2cc(Cl)ccc2C1=O] |

TABLE 1B-continued

| Compound No. | Structure |
|---|---|
| 193 | 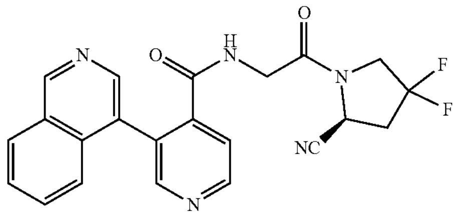 [SMILES: N#C[C@@H]1CC(F)(F)CN1C(=O)CNC(=O)c1ccncc1-c1cncc2ccccc12] |
| 194 | 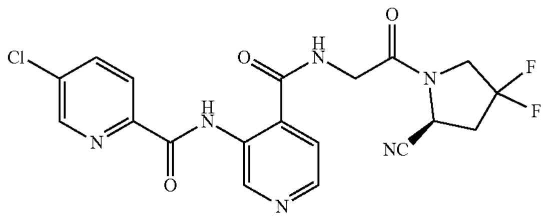 [SMILES: N#C[C@@H]1CC(F)(F)CN1C(=O)CNC(=O)c1ccncc1NC(=O)c1ccc(Cl)cn1] |
| 195 | 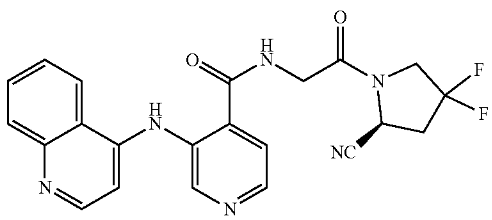 [SMILES: N#C[C@@H]1CC(F)(F)CN1C(=O)CNC(=O)c1ccncc1Nc1ccnc2ccccc12] |
| 196 | 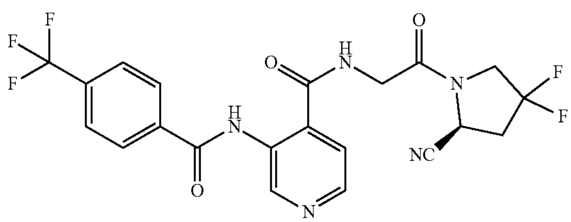 [SMILES: N#C[C@@H]1CC(F)(F)CN1C(=O)CNC(=O)c1ccncc1NC(=O)c1ccc(C(F)(F)F)cc1] |
| 197 | 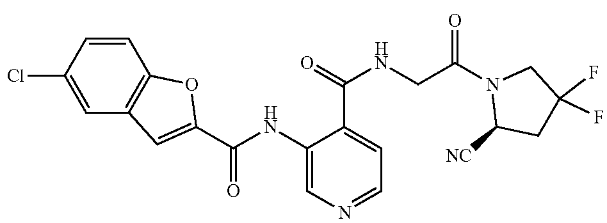 [SMILES: N#C[C@@H]1CC(F)(F)CN1C(=O)CNC(=O)c1ccncc1NC(=O)c1cc2cc(Cl)ccc2o1] |
| 198 | 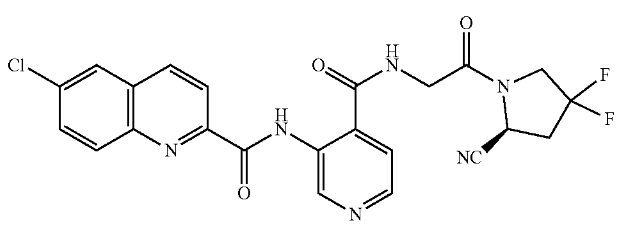 [SMILES: N#C[C@@H]1CC(F)(F)CN1C(=O)CNC(=O)c1ccncc1NC(=O)c1ccc2cc(Cl)ccc2n1] |
| 199 | 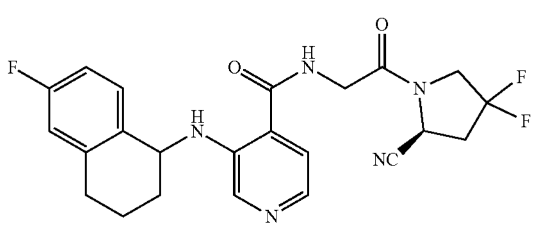 [SMILES: N#C[C@@H]1CC(F)(F)CN1C(=O)CNC(=O)c1ccncc1NC1CCCc2cc(F)ccc21] |

TABLE 1B-continued

| Compound No. | Structure |
|---|---|
| 200 | 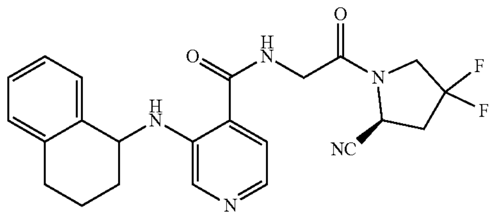 [SMILES: N#C[C@@H]1CC(F)(F)CN1C(=O)CNC(=O)c1ccncc1NC1CCCc2ccccc21] |
| 201 | 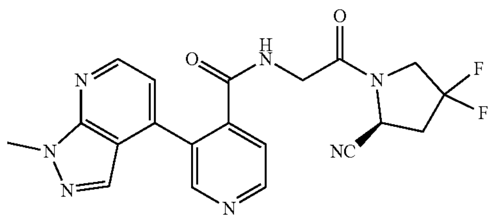 [SMILES: Cn1ncc2c(-c3cnccc3C(=O)NCC(=O)N3CC(F)(F)C[C@H]3C#N)ccnc21] |
| 202 | 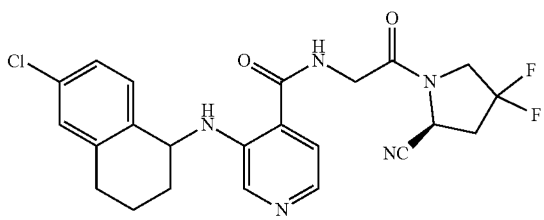 [SMILES: N#C[C@@H]1CC(F)(F)CN1C(=O)CNC(=O)c1ccncc1NC1CCCc2cc(Cl)ccc21] |
| 203 | 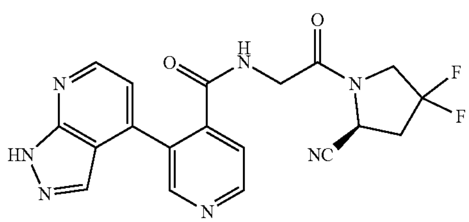 [SMILES: N#C[C@@H]1CC(F)(F)CN1C(=O)CNC(=O)c1ccncc1-c1ccnc2[nH]ncc12] |
| 204 | 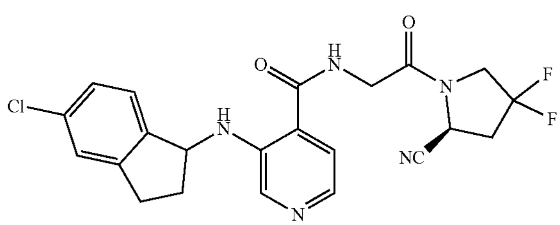 [SMILES: N#C[C@@H]1CC(F)(F)CN1C(=O)CNC(=O)c1ccncc1NC1CCc2cc(Cl)ccc21] |
| 205 | 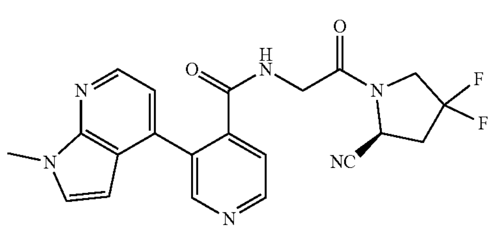 [SMILES: Cn1ccc2c(-c3cnccc3C(=O)NCC(=O)N3CC(F)(F)C[C@H]3C#N)ccnc21] |
| 206 | 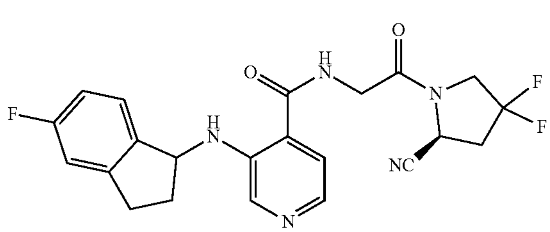 [SMILES: N#C[C@@H]1CC(F)(F)CN1C(=O)CNC(=O)c1ccncc1NC1CCc2cc(F)ccc21] |

TABLE 1B-continued

| Compound No. | Structure |
|---|---|
| 207 | 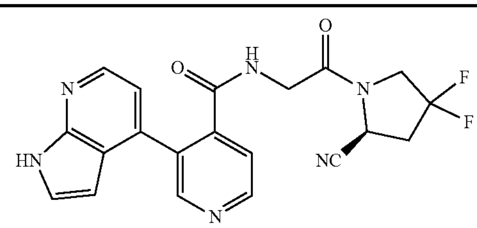 |
| 208 | 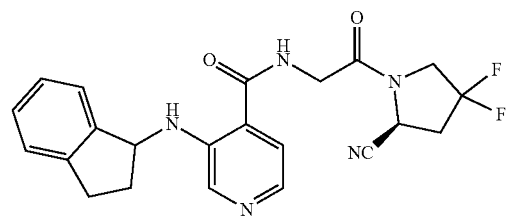 [SMILES: N#C[C@@H]1CC(F)(F)CN1C(=O)CNC(=O)c1ccncc1NC1CCc2ccccc21] |
| 209 | 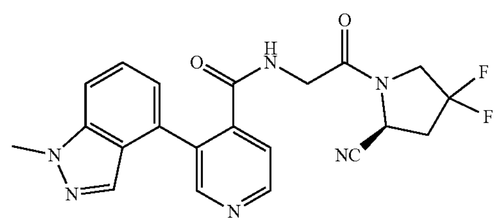 [SMILES: Cn1ncc2c(-c3cnccc3C(=O)NCC(=O)N3CC(F)(F)C[C@H]3C#N)cccc21] |
| 210 | 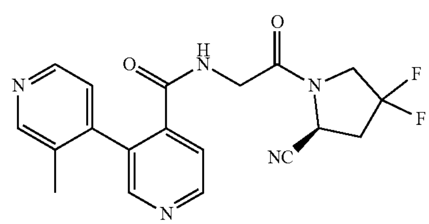 [SMILES: Cc1cnccc1-c1cnccc1C(=O)NCC(=O)N1CC(F)(F)C[C@H]1C#N] |
| 211 | 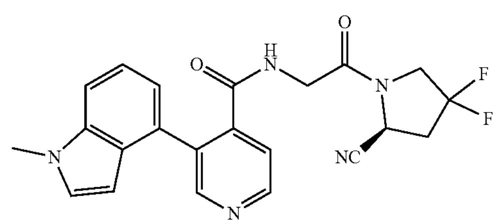 [SMILES: Cn1ccc2c(-c3cnccc3C(=O)NCC(=O)N3CC(F)(F)C[C@H]3C#N)cccc21] |
| 212 | 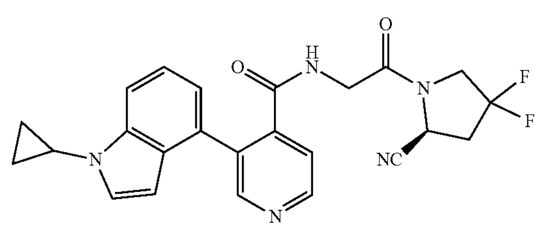 [SMILES: N#C[C@@H]1CC(F)(F)CN1C(=O)CNC(=O)c1ccncc1-c1cccc2c1ccn2C1CC1] |
| 213 | 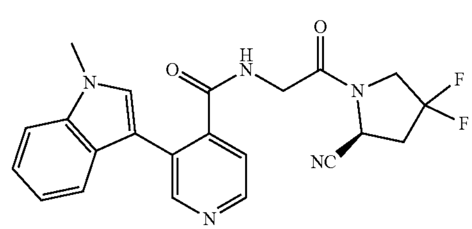 [SMILES: Cn1cc(-c2cnccc2C(=O)NCC(=O)N2CC(F)(F)C[C@H]2C#N)c2ccccc21] |

TABLE 1B-continued

| Compound No. | Structure |
|---|---|
| 214 | 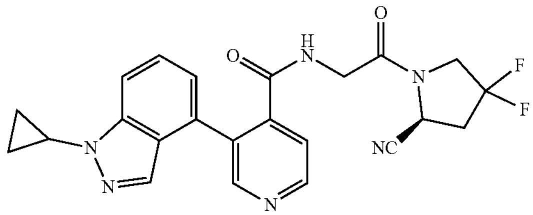 [SMILES: N#C[C@@H]1CC(F)(F)CN1C(=O)CNC(=O)c1ccncc1-c1cccc2c1cnn2C1CC1] |
| 215 | 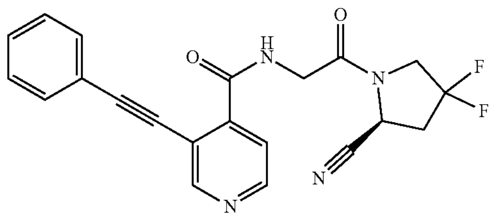 [SMILES: N#C[C@@H]1CC(F)(F)CN1C(=O)CNC(=O)c1ccncc1C#Cc1ccccc1] |
| 216 | 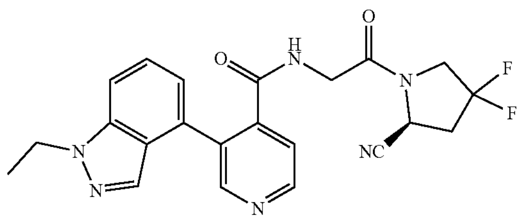 [SMILES: CCn1ncc2c(-c3cnccc3C(=O)NCC(=O)N3CC(F)(F)C[C@H]3C#N)cccc21] |
| 217 | 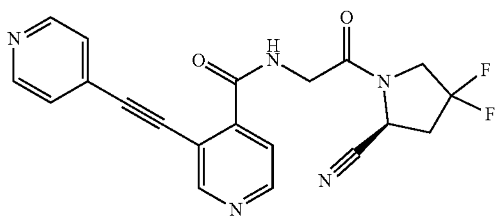 [SMILES: N#C[C@@H]1CC(F)(F)CN1C(=O)CNC(=O)c1ccncc1C#Cc1ccncc1] |
| 218 | 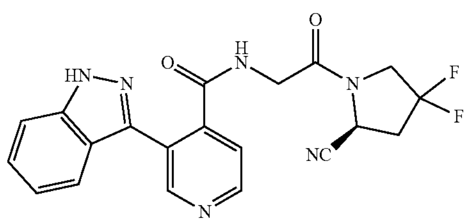 [SMILES: N#C[C@@H]1CC(F)(F)CN1C(=O)CNC(=O)c1ccncc1-c1n[nH]c2ccccc12] |
| 219 | 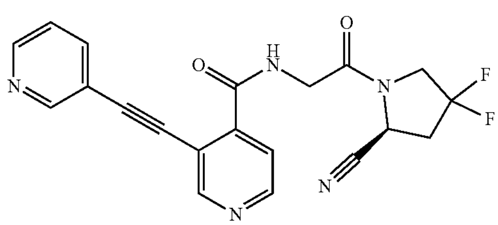 [SMILES: N#C[C@@H]1CC(F)(F)CN1C(=O)CNC(=O)c1ccncc1C#Cc1cccnc1] |
| 220 | 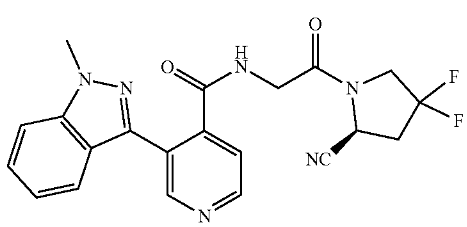 |

TABLE 1B-continued

| Compound No. | Structure |
|---|---|
| 221 | 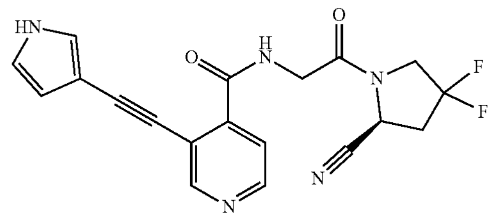 [SMILES: N#C[C@@H]1CC(F)(F)CN1C(=O)CNC(=O)c1ccncc1C#Cc1cc[nH]c1] |
| 222 | 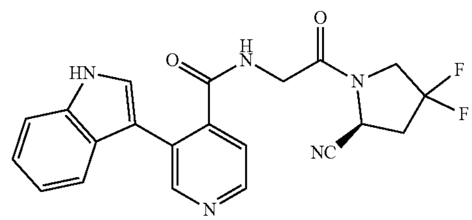 [SMILES: N#C[C@@H]1CC(F)(F)CN1C(=O)CNC(=O)c1ccncc1-c1c[nH]c2ccccc12] |
| 223 | 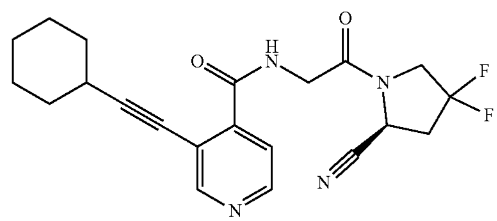 [SMILES: N#C[C@@H]1CC(F)(F)CN1C(=O)CNC(=O)c1ccncc1C#CC1CCCCC1] |

In some embodiments, provided herein is a compound described in Table 1A or Table 1B, or a tautomer thereof, or a salt of any of the foregoing, and uses thereof. In some embodiments, provided herein is a compound described in Table 1A or Table 1B, or a pharmaceutically acceptable salt thereof.

In some embodiments, provided is a compound selected from Compound Nos. 1-223, or a stereoisomer thereof (including a mixture of two or more stereoisomers thereof), or a salt thereof. In some embodiments, the compound is a salt of a compound selected from Compound Nos. 1-223, or a stereoisomer thereof.

Provided herein is a compound selected from the group consisting of:

N-(2-(2-cyano-4,4-difluoropyrrolidin-1-yl)-2-oxoethyl)-6-phenylquinoline-4-carboxamide;
6-(4-chlorophenyl)-N-(2-(2-cyano-4,4-difluoropyrrolidin-1-yl)-2-oxoethyl)quinoline-4-carboxamide;
6-(6-chloronaphthalen-2-yl)-N-(2-(2-cyano-4,4-difluoropyrrolidin-1-yl)-2-oxoethyl)quinoline-4-carboxamide;
6-(4-chlorophenyl)-N-(1-(2-cyano-4,4-difluoropyrrolidin-1-yl)-1-oxopropan-2-yl)quinoline-4-carboxamide;
6-(4-chlorophenyl)-N-(1-(2-cyano-4,4-difluoropyrrolidin-1-yl)-3-methyl-1-oxobutan-2-yl)quinoline-4-carboxamide;
N-(2-(2-cyano-4,4-difluoropyrrolidin-1-yl)-2-oxoethyl)-6-(3,5-dimethylisoxazol-4-yl)quinoline-4-carboxamide;
N-(2-(2-cyano-4,4-difluoropyrrolidin-1-yl)-2-oxoethyl)-6-(4-methoxyphenyl)quinoline-4-carboxamide;
N-(2-(2-cyano-4,4-difluoropyrrolidin-1-yl)-2-oxoethyl)-6-(pyridin-3-yl)quinoline-4-carboxamide;
N-(2-(2-cyano-4,4-difluoropyrrolidin-1-yl)-2-oxoethyl)-6-(pyridin-4-yl)quinoline-4-carboxamide;
6-(4-(tert-butyl)phenyl)-N-(2-(2-cyano-4,4-difluoropyrrolidin-1-yl)-2-oxoethyl)quinoline-4-carboxamide;
N-(2-(2-cyano-4,4-difluoropyrrolidin-1-yl)-2-oxoethyl)-6-(1-methyl-1H-indol-5-yl)quinoline-4-carboxamide;
N-(2-(2-cyano-4,4-difluoropyrrolidin-1-yl)-2-oxoethyl)-6-(1H-indol-5-yl)quinoline-4-carboxamide;
N-(2-(2-cyano-4,4-difluoropyrrolidin-1-yl)-2-oxoethyl)-6-(1-methyl-1H-pyrazol-4-yl)quinoline-4-carboxamide;
N-(2-(2-cyano-4,4-difluoropyrrolidin-1-yl)-2-oxoethyl)-6-(1-cyclopropyl-1H-pyrazol-4-yl)quinoline-4-carboxamide;
N-(2-(2-cyano-4,4-difluoropyrrolidin-1-yl)-2-oxoethyl)-6-(4-(trifluoromethoxy)phenyl)quinoline-4-carboxamide;
N-(2-(2-cyano-4,4-difluoropyrrolidin-1-yl)-2-oxoethyl)-6-(indolin-5-yl)quinoline-4-carboxamide;
N-(2-(2-cyano-4,4-difluoropyrrolidin-1-yl)-2-oxoethyl)-6-(4-methylpent-1-en-1-yl)quinoline-4-carboxamide;
N-(2-(2-cyano-4,4-difluoropyrrolidin-1-yl)-2-oxoethyl)-6-styrylquinoline-4-carboxamide;
N-(2-(2-cyano-4,4-difluoropyrrolidin-1-yl)-2-oxoethyl)-6-(6-(dimethylamino)naphthalen-2-yl)quinoline-4-carboxamide;
N-(2-(2-cyano-4,4-difluoropyrrolidin-1-yl)-2-oxoethyl)-2'-oxo-1',2',3',4'-tetrahydro-[6,6'-biquinoline]-4-carboxamide;
N-(2-(2-cyano-4,4-difluoropyrrolidin-1-yl)-2-oxoethyl)-6-(6-oxo-1,6-dihydropyridin-3-yl)quinoline-4-carboxamide;
N-(2-(2-cyano-4,4-difluoropyrrolidin-1-yl)-2-oxoethyl)-6-(1-oxo-1,2,3,4-tetrahydroisoquinolin-6-yl)quinoline-4-carboxamide;
N-(2-(2-cyano-4,4-difluoropyrrolidin-1-yl)-2-oxoethyl)-6-(4-((4-methylpiperazin-1-yl)methyl)phenyl)quinoline-4-carboxamide;
N-(2-(2-cyano-4,4-difluoropyrrolidin-1-yl)-2-oxoethyl)-6-(2-(pyridin-4-yl)vinyl)quinoline-4-carboxamide;

N-(2-(2-cyano-4,4-difluoropyrrolidin-1-yl)-2-oxoethyl)-6-(2-(pyridin-3-yl)vinyl)quinoline-4-carboxamide;

N-(2-(2-cyano-4,4-difluoropyrrolidin-1-yl)-2-oxoethyl)-6-(2-(pyridin-2-yl)vinyl)quinoline-4-carboxamide;

methyl 3-(4-((2-(2-cyano-4,4-difluoropyrrolidin-1-yl)-2-oxoethyl)carbamoyl)quinolin-6-yl)acrylate;

N-(2-(2-cyano-4,4-difluoropyrrolidin-1-yl)-2-oxoethyl)-6-(6-methylpyridin-3-yl)quinoline-4-carboxamide;

N-(2-(2-cyano-4,4-difluoropyrrolidin-1-yl)-2-oxoethyl)-6-(6-methoxypyridin-3-yl)quinoline-4-carboxamide;

N-(2-(–2-cyano-4,4-difluorocyclopentyl)-2-oxoethyl)-6-(6-isopropoxypyridin-3-yl)quinoline-4-carboxamide;

N-(2-(2-cyano-4,4-difluoropyrrolidin-1-yl)-2-oxoethyl)-6-(2,3-dihydrobenzo[b][1,4]dioxin-6-yl)quinoline-4-carboxamide;

N-(2-(2-cyano-4,4-difluoropyrrolidin-1-yl)-2-oxoethyl)-6-(4-(2-methoxyethoxy)phenyl)quinoline-4-carboxamide;

N-(2-(2-cyano-4,4-difluoropyrrolidin-1-yl)-2-oxoethyl)-6-(6-(2-methoxyethoxy)pyridin-3-yl)quinoline-4-carboxamide;

N-(2-(2-cyano-4,4-difluoropyrrolidin-1-yl)-2-oxoethyl)-6-(6-cyclopropylpyridin-3-yl)quinoline-4-carboxamide;

N-(2-(2-cyano-4,4-difluoropyrrolidin-1-yl)-2-oxoethyl)-6-(2-(2-oxo-1,2,3,4-tetrahydroquinolin-6-yl)vinyl)quinoline-4-carboxamide;

N-(2-(2-cyano-4,4-difluoropyrrolidin-1-yl)-2-oxoethyl)-6-(2-(1-oxo-1,2,3,4-tetrahydroisoquinolin-6-yl)vinyl)quinoline-4-carboxamide;

N-(2-(2-cyano-4,4-difluoropyrrolidin-1-yl)-2-oxoethyl)-6-(2-(quinazolin-6-yl)vinyl)quinoline-4-carboxamide;

N-(2-(2-cyano-4,4-difluoropyrrolidin-1-yl)-2-oxoethyl)-6-(3-ethoxyprop-1-en-1-yl)quinoline-4-carboxamide;

N-(2-(2-cyano-4,4-difluoropyrrolidin-1-yl)-2-oxoethyl)-6-(3-methoxyprop-1-en-1-yl)quinoline-4-carboxamide;

N-(2-(2-cyano-4,4-difluoropyrrolidin-1-yl)-2-oxoethyl)-6-(2-cyclohexylvinyl)quinoline-4-carboxamide;

N-(2-(2-cyano-4,4-difluoropyrrolidin-1-yl)-2-oxoethyl)-6-(2-(3,4-dihydro-2H-benzo[b][1,4]oxazin-7-yl)vinyl)quinoline-4-carboxamide;

6-(4-chlorophenyl)-N-(2-(2-cyano-5,5-difluoropiperidin-1-yl)-2-oxoethyl)quinoline-4-carboxamide;

N-(2-(2-cyano-4,4-difluoropyrrolidin-1-yl)-2-oxoethyl)-6-(4-methylpiperazin-1-yl)quinoline-4-carboxamide;

6-(6-chloronaphthalen-2-yl)-N-(2-(2-cyano-3,3-difluoroazetidin-1-yl)-2-oxoethyl)quinoline-4-carboxamide;

N-(2-(2-cyano-4,4-difluoropiperidin-1-yl)-2-oxoethyl)-2'-oxo-1',2',3',4'-tetrahydro-[6,6'-biquinoline]-4-carboxamide;

N-(2-(2-cyano-4,4-difluoropyrrolidin-1-yl)-2-oxoethyl)-6-(2-(piperazin-1-yl)vinyl)quinoline-4-carboxamide;

6-(6-chloronaphthalen-2-yl)-N-(2-(2-cyano-2-ethyl-4,4-difluoropyrrolidin-1-yl)-2-oxoethyl)quinoline-4-carboxamide;

6-(6-chloronaphthalen-2-yl)-N-(2-(2-cyano-2-cyclopropyl-4,4-difluoropyrrolidin-1-yl)-2-oxoethyl)quinoline-4-carboxamide;

N-(2-(2-cyano-4,4-difluoropyrrolidin-1-yl)-2-oxoethyl)-6-(3-methylbenzofuran-6-yl)quinoline-4-carboxamide;

6-(6-chloronaphthalen-2-yl)-N-(2-(2-cyano-4,4-difluoro-2-(piperidin-1-yl)pyrrolidin-1-yl)-2-oxoethyl)quinoline-4-carboxamide;

N-(2-(2-cyano-4,4-difluoropyrrolidin-1-yl)-2-oxoethyl)-6-(4-methyl-3,4-dihydro-2H-benzo[b][1,4]oxazin-7-yl)quinoline-4-carboxamide;

N-(4-((2-(2-cyano-4,4-difluoropyrrolidin-1-yl)-2-oxoethyl)carbamoyl)pyridin-3-yl)-1,2,3,4-tetrahydroisoquinoline-6-carboxamide;

N-(4-((2-(2-cyano-4,4-difluoropyrrolidin-1-yl)-2-oxoethyl)carbamoyl)pyridin-3-yl)-2-methyl-1,2,3,4-tetrahydroisoquinoline-6-carboxamide;

N-(2-(2-cyano-4,4-difluoropyrrolidin-1-yl)-2-oxoethyl)-6-(1-methyl-1,8a-dihydroimidazo[1,2-a]pyridin-6-yl)quinoline-4-carboxamide;

N-(4-((2-(2-cyano-4,4-difluoropyrrolidin-1-yl)-2-oxoethyl)carbamoyl)pyridin-3-yl)-1,2,3,4-tetrahydroquinoline-6-carboxamide;

N-(2-(2-cyano-4,4-difluoropyrrolidin-1-yl)-2-oxoethyl)-6-(3,4-dihydro-2H-benzo[I][1,4]oxazin-7-yl)quinoline-4-carboxamide;

N-(4-((2-(2-cyano-4,4-difluoropyrrolidin-1-yl)-2-oxoethyl)carbamoyl)pyridin-3-yl)-1-methyl-1,2,3,4-tetrahydroquinoline-6-carboxamide;

N-(2-(2-cyano-4,4-difluoropyrrolidin-1-yl)-2-oxoethyl)-6-(quinazolin-6-yl)quinoline-4-carboxamide;

6-(benzofuran-6-yl)-N-(2-(2-cyano-4,4-difluoropyrrolidin-1-yl)-2-oxoethyl)quinoline-4-carboxamide;

N-(2-(2-cyano-5,5-difluoropiperidin-1-yl)-2-oxoethyl)-6-(3,5-dimethylisoxazol-4-yl)quinoline-4-carboxamide;

N-(2-(2-cyano-5,5-difluoropiperidin-1-yl)-2-oxoethyl)-6-(4-methoxyphenyl)quinoline-4-carboxamide;

N-(2-(2-cyano-4,4-difluoropyrrolidin-1-yl)-2-oxoethyl)-6-(3-methyl-2,3-dihydrobenzo[d]thiazol-6-yl)quinoline-4-carboxamide;

6-(6-chloronaphthalen-2-yl)-N-(2-(2-cyano-5,5-difluoropiperidin-1-yl)-2-oxoethyl)quinoline-4-carboxamide;

N-(2-(2-cyano-4,4-difluoropyrrolidin-1-yl)-2-oxoethyl)-6-(1-methyl-2,3-dihydro-1H-benzo[d]imidazol-5-yl)quinoline-4-carboxamide;

N-(2-(2-cyano-5,5-difluoropiperidin-1-yl)-2-oxoethyl)-2'-oxo-1',2',3',4'-tetrahydro-[6,6'-biquinoline]-4-carboxamide;

N-(2-(2-cyano-4,4-difluoropyrrolidin-1-yl)-2-oxoethyl)-6-(1,8a-dihydroimidazo[1,2-a]pyridin-6-yl)quinoline-4-carboxamide;

N-(2-(2-cyano-3,3-difluoroazetidin-1-yl)-2-oxoethyl)-6-(4-methoxyphenyl)quinoline-4-carboxamide;

N-(2-(2-cyano-3,3-difluoroazetidin-1-yl)-2-oxoethyl)-2'-oxo-1',2',3',4'-tetrahydro-[6,6'-biquinoline]-4-carboxamide;

N-(2-(2-cyano-4,4-difluoro-2-(piperidin-1-yl)pyrrolidin-1-yl)-2-oxoethyl)-6-(4-methoxyphenyl)quinoline-4-carboxamide;

6-(4-chlorophenyl)-N-(2-(2-cyano-2-ethyl-4,4-difluoropyrrolidin-1-yl)-2-oxoethyl)quinoline-4-carboxamide;

6-(4-chlorophenyl)-N-(2-(2-cyano-4,4-difluoro-2-methoxypyrrolidin-1-yl)-2-oxoethyl)quinoline-4-carboxamide;

N-(2-(2-cyano-2-ethyl-4,4-difluoropyrrolidin-1-yl)-2-oxoethyl)-6-(3,5-dimethylisoxazol-4-yl)quinoline-4-carboxamide;

6-(6-chloronaphthalen-2-yl)-N-(2-(2-cyano-4,4-difluoro-2-methoxypyrrolidin-1-yl)-2-oxoethyl)quinoline-4-carboxamide;

6-(4-chlorophenyl)-N-(2-(2-cyano-2-cyclopropyl-4,4-difluoropyrrolidin-1-yl)-2-oxoethyl)quinoline-4-carboxamide;

N-(2-(2-cyano-4,4-difluoro-2-methoxypyrrolidin-1-yl)-2-oxoethyl)-6-(3,5-dimethylisoxazol-4-yl)quinoline-4-carboxamide;

N-(2-(2-cyano-2-cyclopropyl-4,4-difluoropyrrolidin-1-yl)-2-oxoethyl)-6-(3,5-dimethylisoxazol-4-yl)quinoline-4-carboxamide;

N-(2-(2-cyano-4,4-difluoro-2-methoxypyrrolidin-1-yl)-2-oxoethyl)-6-(4-methoxyphenyl)quinoline-4-carboxamide;

N-(2-(2-cyano-2-cyclopropyl-4,4-difluoropyrrolidin-1-yl)-2-oxoethyl)-6-(4-methoxyphenyl)quinoline-4-carboxamide;
6-(4-chlorophenyl)-N-(2-(2-cyano-4,4-difluoro-2-phenylpyrrolidin-1-yl)-2-oxoethyl)quinoline-4-carboxamide;
6-(4-chlorophenyl)-N-(2-(2-cyano-4,4-difluoro-2-(piperidin-1-yl)pyrrolidin-1-yl)-2-oxoethyl)quinoline-4-carboxamide;
6-(6-chloronaphthalen-2-yl)-N-(2-(2-cyano-4,4-difluoro-2-phenylpyrrolidin-1-yl)-2-oxoethyl)quinoline-4-carboxamide;
N-(2-(2-cyano-4,4-difluoro-2-(piperidin-1-yl)pyrrolidin-1-yl)-2-oxoethyl)-6-(3,5-dimethylisoxazol-4-yl)quinoline-4-carboxamide;
N-(2-(2-cyano-4,4-difluoro-2-phenylpyrrolidin-1-yl)-2-oxoethyl)-6-(3,5-dimethylisoxazol-4-yl)quinoline-4-carboxamide;
N-(2-(2-cyano-4,4-difluoro-2-phenylpyrrolidin-1-yl)-2-oxoethyl)-6-(4-methoxyphenyl)quinoline-4-carboxamide;
N-(2-(2-cyano-4,4-difluoropyrrolidin-1-yl)-2-oxoethyl)-6-(2-(pyridin-2-yl)prop-1-en-1-yl)quinoline-4-carboxamide;
N-(2-(2-cyano-4,4-difluoropyrrolidin-1-yl)-2-oxoethyl)-6-(2-(pyridin-3-yl)prop-1-en-1-yl)quinoline-4-carboxamide;
N-(2-(2-cyano-4,4-difluoropyrrolidin-1-yl)-2-oxoethyl)-6-(1-(pyridin-4-yl)prop-1-en-2-yl)quinoline-4-carboxamide;
N-(2-(2-cyano-4,4-difluoropyrrolidin-1-yl)-2-oxoethyl)-6-(2-(2-oxo-1,2-dihydropyridin-4-yl)prop-1-en-1-yl)quinoline-4-carboxamide;
N-(2-(2-cyano-4,4-difluoropyrrolidin-1-yl)-2-oxoethyl)-6-(2-(2-oxo-1,2-dihydropyridin-4-yl)vinyl)quinoline-4-carboxamide;
N-(2-(2-cyano-4,4-difluoropyrrolidin-1-yl)-2-oxoethyl)-6-(1-(pyridin-2-yl)prop-1-en-2-yl)quinoline-4-carboxamide;
N-(2-(2-cyano-4,4-difluoropyrrolidin-1-yl)-2-oxoethyl)-6-(2-(pyridin-4-yl)prop-1-en-1-yl)quinoline-4-carboxamide;
N-(2-(2-cyano-4,4-difluoropyrrolidin-1-yl)-2-oxoethyl)-6-(1-(pyridin-3-yl)prop-1-en-2-yl)quinoline-4-carboxamide;
N-(2-(2-cyano-4,4-difluoropyrrolidin-1-yl)-2-oxoethyl)-6-(2-(3,4-dihydro-2H-benzo[b][1,4]oxazin-7-yl)prop-1-en-1-yl)quinoline-4-carboxamide;
N-(2-(2-cyano-4,4-difluoropyrrolidin-1-yl)-2-oxoethyl)-6-(1-(2-oxo-1,2-dihydropyridin-4-yl)prop-1-en-2-yl)quinoline-4-carboxamide;
6-(2-(benzofuran-6-yl)prop-1-en-1-yl)-N-(2-(2-cyano-4,4-difluoropyrrolidin-1-yl)-2-oxoethyl)quinoline-4-carboxamide;
6-(2-(benzofuran-6-yl)vinyl)-N-(2-(2-cyano-4,4-difluoropyrrolidin-1-yl)-2-oxoethyl)quinoline-4-carboxamide;
N-(2-(2-cyano-4,4-difluoropyrrolidin-1-yl)-2-oxoethyl)-6-(2-(1,8a-dihydroimidazo[1,2-a]pyridin-6-yl)prop-1-en-1-yl)quinoline-4-carboxamide;
N-(1-(2-cyano-4,4-difluoropyrrolidin-1-yl)-1-oxopropan-2-yl)-3-phenylisonicotinamide;
methyl 3-(4-((2-(2-cyano-4,4-difluoropyrrolidin-1-yl)-2-oxoethyl)carbamoyl)pyridin-3-yl)acrylate;
N-(2-(2-cyano-4,4-difluoropyrrolidin-1-yl)-2-oxoethyl)-3-(naphthalen-1-ylethynyl)isonicotinamide;
N-(2-(2-cyano-4,4-difluoropyrrolidin-1-yl)-2-oxoethyl)-3-(2-(quinolin-6-yl)vinyl)isonicotinamide;
N-(2-(2-cyano-4,4-difluoropyrrolidin-1-yl)-2-oxoethyl)-3-(2-(quinolin-3-yl)vinyl)isonicotinamide;
N-(2-(2-cyano-4,4-difluoropyrrolidin-1-yl)-2-oxoethyl)-3-(2-(3,4-dihydro-2H-benzo[b][1,4]oxazin-2-yl)vinyl)isonicotinamide;
N-(2-(2-cyano-4,4-difluoropyrrolidin-1-yl)-2-oxoethyl)-3-(2-(isoquinolin-6-yl)vinyl)isonicotinamide;
N-(2-(2-cyano-4,4-difluoropyrrolidin-1-yl)-2-oxoethyl)-3-(2-(3,4-dihydro-2H-benzo[b][1,4]oxazin-7-yl)vinyl)isonicotinamide;
3-(2-(1H-indol-3-yl)vinyl)-N-(2-(2-cyano-4,4-difluoropyrrolidin-1-yl)-2-oxoethyl)isonicotinamide;
3-(2-(1H-benzo[d]imidazol-5-yl)vinyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(2-(piperidin-4-yl)vinyl)isonicotinamide;
3-(2-(1H-benzo[d]imidazol-2-yl)vinyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(naphthalen-2-ylethynyl)isonicotinamide;
N-(2-(2-cyano-4,4-difluoropyrrolidin-1-yl)-2-oxoethyl)-3-(2-(1,2,3,4-tetrahydroisoquinolin-6-yl)vinyl)isonicotinamide;
3-(2-(benzofuran-2-yl)vinyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(2-(1,2,3,4-tetrahydroquinolin-6-yl)vinyl)isonicotinamide;
N-(2-(2-cyano-4,4-difluoropyrrolidin-1-yl)-2-oxoethyl)-3-(2-(imidazo[1,2-a]pyridin-2-yl)vinyl)isonicotinamide;
N-(2-(2-cyano-4,4-difluoropyrrolidin-1-yl)-2-oxoethyl)-3-((2-(piperazin-1-yl)ethyl)amino)isonicotinamide;
N-(4-((2-(2-cyano-4,4-difluoropyrrolidin-1-yl)-2-oxoethyl)carbamoyl)pyridin-3-yl)-5-(difluoromethyl)pyrazine-2-carboxamide;
N-(4-((2-(2-cyano-4,4-difluoropyrrolidin-1-yl)-2-oxoethyl)carbamoyl)pyridin-3-yl)-4-methyl-3,4-dihydro-2H-benzo[b][1,4]oxazine-7-carboxamide;
N-(4-((2-(2-cyano-4,4-difluoropyrrolidin-1-yl)-2-oxoethyl)carbamoyl)pyridin-3-yl)-3,4-dihydro-2H-benzo[b][1,4]oxazine-2-carboxamide;
N-(4-((2-(2-cyano-4,4-difluoropyrrolidin-1-yl)-2-oxoethyl)carbamoyl)pyridin-3-yl)-1H-benzo[d]imidazole-5-carboxamide;
N-(4-((2-(2-cyano-4,4-difluoropyrrolidin-1-yl)-2-oxoethyl)carbamoyl)pyridin-3-yl)-4-methyl-3,4-dihydro-2H-benzo[b][1,4]oxazine-2-carboxamide;
N-(4-((2-(2-cyano-4,4-difluoropyrrolidin-1-yl)-2-oxoethyl)carbamoyl)pyridin-3-yl)-1-methyl-1H-benzo[d]imidazole-5-carboxamide;
6-chloro-N-(4-((2-(2-cyano-4,4-difluoropyrrolidin-1-yl)-2-oxoethyl)carbamoyl)pyridin-3-yl)-3,4-dihydro-2H-benzo[b][1,4]oxazine-2-carboxamide;
N-(4-((2-(2-cyano-4,4-difluoropyrrolidin-1-yl)-2-oxoethyl)carbamoyl)pyridin-3-yl)-1H-benzo[d]imidazole-2-carboxamide;
N-(4-((2-(2-cyano-4,4-difluoropyrrolidin-1-yl)-2-oxoethyl)carbamoyl)pyridin-3-yl)-6-fluoro-3,4-dihydro-2H-benzo[b][1,4]oxazine-2-carboxamide;
6-chloro-N-(4-((2-(2-cyano-4,4-difluoropyrrolidin-1-yl)-2-oxoethyl)carbamoyl)pyridin-3-yl)-1H-benzo[d]imidazole-2-carboxamide;
N-(4-((2-(2-cyano-4,4-difluoropyrrolidin-1-yl)-2-oxoethyl)carbamoyl)pyridin-3-yl)-3,4-dihydro-2H-benzo[b][1,4]oxazine-7-carboxamide;

5-chloro-N-(4-((2-(2-cyano-4,4-difluoropyrrolidin-1-yl)-2-oxoethyl)carbamoyl)pyridin-3-yl)-1H-benzo[d]imidazole-2-carboxamide;
3-benzyl-N-(2-(2-cyano-2-cyclopropyl-4,4-difluoropyrrolidin-1-yl)-2-oxoethyl)isonicotinamide;
N-(4-((2-(2-cyano-4,4-difluoropyrrolidin-1-yl)-2-oxoethyl)carbamoyl)pyridin-3-yl)-1-methyl-1H-benzo[d]imidazole-2-carboxamide;
N-(2-(2-cyano-4,4-difluoropyrrolidin-1-yl)-2-oxoethyl)-3-(1-phenylprop-1-en-2-yl)isonicotinamide;
3-benzyl-N-(2-(2-cyano-4,4-difluoropiperidin-1-yl)-2-oxoethyl)isonicotinamide;
N-(2-(2-cyano-4,4-difluoropyrrolidin-1-yl)-2-oxoethyl)-3-(2-phenylcyclopropyl)isonicotinamide;
N-(2-(2-cyano-3,3-difluoroazetidin-1-yl)-2-oxoethyl)-3-phenylisonicotinamide;
N-(2-(2-cyano-4,4-difluoropyrrolidin-1-yl)-2-oxoethyl)-3-(indolin-5-ylethynyl)isonicotinamide;
N-(2-(2-cyano-2-ethyl-4,4-difluoropyrrolidin-1-yl)-2-oxoethyl)-3-phenylisonicotinamide;
N-(2-(2-cyano-4,4-difluoropyrrolidin-1-yl)-2-oxoethyl)-3-(2-cyclohexylvinyl)isonicotinamide;
N-(2-(2-cyano-2-cyclopropyl-4,4-difluoropyrrolidin-1-yl)-2-oxoethyl)-3-phenylisonicotinamide;
N-(2-(2-cyano-4,4-difluoropiperidin-1-yl)-2-oxoethyl)-3-phenylisonicotinamide;
N-(2-(2-cyano-4,4-difluoro-2-(piperidin-1-yl)pyrrolidin-1-yl)-2-oxoethyl)-3-phenylisonicotinamide;
N-(2-(2-cyano-4,4-difluoro-2-phenylpyrrolidin-1-yl)-2-oxoethyl)-3-phenylisonicotinamide;
3-(benzofuran-2-carboxamido)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(quinolin-6-yl)isonicotinamide;
N-(2-(2-cyano-4,4-difluoropyrrolidin-1-yl)-2-oxoethyl)-3-(5-fluorobenzofuran-2-carboxamido)isonicotinamide;
N-(2-(2-cyano-4,4-difluoropyrrolidin-1-yl)-2-oxoethyl)-3-(6-fluorobenzofuran-2-carboxamido)isonicotinamide;
7-chloro-N-(4-((2-(2-cyano-4,4-difluoropyrrolidin-1-yl)-2-oxoethyl)carbamoyl)pyridin-3-yl)imidazo[1,2-a]pyridine-2-carboxamide;
N-(4-((2-(2-cyano-4,4-difluoropyrrolidin-1-yl)-2-oxoethyl)carbamoyl)pyridin-3-yl)-5-methyl-2,3-dihydrobenzo[d]thiazole-2-carboxamide;
N-(2-(2-cyano-5,5-difluoropiperidin-1-yl)-2-oxoethyl)-3-phenylisonicotinamide;
N-(4-((2-(2-cyano-4,4-difluoropyrrolidin-1-yl)-2-oxoethyl)carbamoyl)pyridin-3-yl)-6-methyl-2,3-dihydrobenzo[d]thiazole-2-carboxamide;
3-benzyl-N-(2-(2-cyano-5,5-difluoropiperidin-1-yl)-2-oxoethyl)isonicotinamide;
5-(tert-butyl)-N-(4-((2-(2-cyano-4,4-difluoropyrrolidin-1-yl)-2-oxoethyl)carbamoyl)pyridin-3-yl)-2,3-dihydrobenzo[d]thiazole-2-carboxamide;
3-benzyl-N-(2-(2-cyano-3,3-difluoroazetidin-1-yl)-2-oxoethyl)isonicotinamide;
N-(4-((2-(2-cyano-4,4-difluoropyrrolidin-1-yl)-2-oxoethyl)carbamoyl)pyridin-3-yl)imidazo[1,2-a]pyridine-2-carboxamide;
3-benzyl-N-(2-(2-cyano-2-ethyl-4,4-difluoropyrrolidin-1-yl)-2-oxoethyl)isonicotinamide;
3-benzyl-N-(2-(2-cyano-4,4-difluoro-2-phenylpyrrolidin-1-yl)-2-oxoethyl)isonicotinamide;
3-benzyl-N-(2-(2-cyano-4,4-difluoro-2-(piperidin-1-yl)pyrrolidin-1-yl)-2-oxoethyl)isonicotinamide;
N-(2-(2-cyano-4,4-difluoropyrrolidin-1-yl)-2-oxoethyl)-3-(isoquinolin-6-yl)isonicotinamide;
N-(2-(2-cyano-4,4-difluoropyrrolidin-1-yl)-2-oxoethyl)-3-(5-fluoronaphthalen-1-yl)isonicotinamide;
N-(2-(2-cyano-4,4-difluoropyrrolidin-1-yl)-2-oxoethyl)-3-(4-fluoronaphthalen-1-yl)isonicotinamide;
N-(2-(2-cyano-4,4-difluoropyrrolidin-1-yl)-2-oxoethyl)-3-(quinolin-5-yl)isonicotinamide;
N-(2-(2-cyano-4,4-difluoropyrrolidin-1-yl)-2-oxoethyl)-3-(1,8-naphthyridin-4-yl)isonicotinamide;
N-(2-(2-cyano-4,4-difluoropyrrolidin-1-yl)-2-oxoethyl)-3-(1-oxo-3,4-dihydroisoquinolin-2(1H)-yl)isonicotinamide;
N-(2-(2-cyano-4,4-difluoropyrrolidin-1-yl)-2-oxoethyl)-3-(isoquinolin-5-yl)isonicotinamide;
3-(6-chloro-1-oxo-3,4-dihydroisoquinolin-2(1H)-yl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(isoquinolin-4-yl)isonicotinamide;
5-chloro-N-(4-((2-(2-cyano-4,4-difluoropyrrolidin-1-yl)-2-oxoethyl)carbamoyl)pyridin-3-yl)picolinamide;
N-(2-(2-cyano-4,4-difluoropyrrolidin-1-yl)-2-oxoethyl)-3-(quinolin-4-ylamino)isonicotinamide;
N-(2-(2-cyano-4,4-difluoropyrrolidin-1-yl)-2-oxoethyl)-3-(4-(trifluoromethyl)benzamido)isonicotinamide;
3-(5-chlorobenzofuran-2-carboxamido)-N-(2-(2-cyano-4,4-difluoropyrrolidin-1-yl)-2-oxoethyl)isonicotinamide;
6-chloro-N-(4-((2-(2-cyano-4,4-difluoropyrrolidin-1-yl)-2-oxoethyl)carbamoyl)pyridin-3-yl)quinoline-2-carboxamide;
N-(2-(2-cyano-4,4-difluoropyrrolidin-1-yl)-2-oxoethyl)-3-((6-fluoro-1,2,3,4-tetrahydronaphthalen-1-yl)amino)isonicotinamide;
N-(2-(2-cyano-4,4-difluoropyrrolidin-1-yl)-2-oxoethyl)-3-((1,2,3,4-tetrahydronaphthalen-1-yl)amino)isonicotinamide;
N-(2-(2-cyano-4,4-difluoropyrrolidin-1-yl)-2-oxoethyl)-3-(1-methyl-1H-pyrazolo[3,4-b]pyridin-4-yl)isonicotinamide;
3-((6-chloro-1,2,3,4-tetrahydronaphthalen-1-yl)amino)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(1H-pyrazolo[3,4-b]pyridin-4-yl)isonicotinamide;
3-((5-chloro-2,3-dihydro-1H-inden-1-yl)amino)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(1-methyl-1H-pyrrolo[2,3-b]pyridin-4-yl)isonicotinamide;
N-(2-(2-cyano-4,4-difluoropyrrolidin-1-yl)-2-oxoethyl)-3-((5-fluoro-2,3-dihydro-1H-inden-1-yl)amino)isonicotinamide;
N-(2-(2-cyano-4,4-difluoropyrrolidin-1-yl)-2-oxoethyl)-3-(1H-pyrrolo[2,3-b]pyridin-4-yl)isonicotinamide;
N-(2-(2-cyano-4,4-difluoropyrrolidin-1-yl)-2-oxoethyl)-3-((2,3-dihydro-1H-inden-1-yl)amino)isonicotinamide;
N-(2-(2-cyano-4,4-difluoropyrrolidin-1-yl)-2-oxoethyl)-3-(1-methyl-1H-indazol-4-yl)isonicotinamide;
N-(2-(2-cyano-4,4-difluoropyrrolidin-1-yl)-2-oxoethyl)-3'-methyl-[3,4'-bipyridine]-4-carboxamide;
N-(2-(2-cyano-4,4-difluoropyrrolidin-1-yl)-2-oxoethyl)-3-(1-methyl-1H-indol-4-yl)isonicotinamide;
N-(2-(2-cyano-4,4-difluoropyrrolidin-1-yl)-2-oxoethyl)-3-(1-cyclopropyl-1H-indol-4-yl)isonicotinamide;
N-(2-(2-cyano-4,4-difluoropyrrolidin-1-yl)-2-oxoethyl)-3-(1-methyl-1H-indol-3-yl)isonicotinamide;

N-(2-(2-cyano-4,4-difluoropyrrolidin-1-yl)-2-oxoethyl)-3-(1-cyclopropyl-1H-indazol-4-yl)isonicotinamide;
N-(2-(2-cyano-4,4-difluoropyrrolidin-1-yl)-2-oxoethyl)-3-(phenylethynyl)isonicotinamide;
N-(2-(2-cyano-4,4-difluoropyrrolidin-1-yl)-2-oxoethyl)-3-(1-ethyl-1H-indazol-4-yl)isonicotinamide;
N-(2-(2-cyano-4,4-difluoropyrrolidin-1-yl)-2-oxoethyl)-3-(pyridin-4-ylethynyl)isonicotinamide;
N-(2-(2-cyano-4,4-difluoropyrrolidin-1-yl)-2-oxoethyl)-3-(1H-indazol-3-yl)isonicotinamide;
N-(2-(2-cyano-4,4-difluoropyrrolidin-1-yl)-2-oxoethyl)-3-(pyridin-3-ylethynyl)isonicotinamide;
N-(2-(2-cyano-4,4-difluoropyrrolidin-1-yl)-2-oxoethyl)-3-(1-methyl-1H-indazol-3-yl)isonicotinamide;
3-((1H-pyrrol-3-yl)ethynyl)-N-(2-(2-cyano-4,4-difluoropyrrolidin-1-yl)-2-oxoethyl)isonicotinamide;
N-(2-(2-cyano-4,4-difluoropyrrolidin-1-yl)-2-oxoethyl)-3-(1H-indol-3-yl)isonicotinamide;
N-(2-(2-cyano-4,4-difluoropyrrolidin-1-yl)-2-oxoethyl)-3-(cyclohexylethynyl)isonicotinamide;
6-(4-acetamidophenyl)-N-(2-(2-cyano-4,4-difluoropyrrolidin-1-yl)-2-oxoethyl)quinoline-4-carboxamide;
6-(3-acetamidophenyl)-N-(2-(2-cyano-4,4-difluoropyrrolidin-1-yl)-2-oxoethyl)quinoline-4-carboxamide;
6-(2-acetamidophenyl)-N-(2-(2-cyano-4,4-difluoropyrrolidin-1-yl)-2-oxoethyl)quinoline-4-carboxamide;
N-(2-(2-cyano-4,4-difluoropyrrolidin-1-yl)-2-oxoethyl)-6-(4-(methylcarbamoyl)phenyl)quinoline-4-carboxamide;
N-(2-(2-cyano-4,4-difluoropyrrolidin-1-yl)-2-oxoethyl)-6-(1H-indazol-5-yl)quinoline-4-carboxamide;
N-(2-(2-cyano-4,4-difluoropyrrolidin-1-yl)-2-oxoethyl)-6-(3-(methylcarbamoyl)phenyl)quinoline-4-carboxamide;
N-(2-(2-cyano-4,4-difluoropyrrolidin-1-yl)-2-oxoethyl)-6-(1H-indol-3-yl)quinoline-4-carboxamide;
N-(2-(2-cyano-4,4-difluoropyrrolidin-1-yl)-2-oxoethyl)-6-(1-oxoisoindolin-5-yl)quinoline-4-carboxamide;
N-(2-(2-cyano-4,4-difluoropyrrolidin-1-yl)-2-oxoethyl)-6-(2-(quinolin-6-yl)vinyl)quinoline-4-carboxamide;
N-(2-(2-cyano-4,4-difluoropyrrolidin-1-yl)-2-oxoethyl)-6-(2-oxoindolin-5-yl)quinoline-4-carboxamide
N-(2-(2-cyano-4,4-difluoropyrrolidin-1-yl)-2-oxoethyl)-6-(1-oxo-1,2,3,4-tetrahydroisoquinolin-7-yl)quinoline-4-carboxamide
N-(2-(2-cyano-4,4-difluoropyrrolidin-1-yl)-2-oxoethyl)-2-oxo-1,2,3,4-tetrahydro-[5,6'-biquinoline]-4'-carboxamide;
N-(2-(2-cyano-4,4-difluoropyrrolidin-1-yl)-2-oxoethyl)-6-(1-oxo-1,2,3,4-tetrahydroisoquinolin-5-yl)quinoline-4-carboxamide;
N-(2-(2-cyano-4,4-difluoropyrrolidin-1-yl)-2-oxoethyl)-1'-methyl-2'-oxo-1',2',3',4'-tetrahydro-[6,6'-biquinoline]-4-carboxamide;
N-(2-(2-cyano-4,4-difluoropyrrolidin-1-yl)-2-oxoethyl)-6-(2-methyl-1-oxo-1,2,3,4-tetrahydroisoquinolin-6-yl)quinoline-4-carboxamide;
6-(2-(1H-indazol-5-yl)vinyl)-N-(2-(2-cyano-4,4-difluoropyrrolidin-1-yl)-2-oxoethyl)quinoline-4-carboxamide;
N-(2-(2-cyano-4,4-difluoropyrrolidin-1-yl)-2-oxoethyl)-1',2',3',4'-tetrahydro-[6,6'-biquinoline]-4-carboxamide;
N-(2-(2-cyano-4,4-difluoropyrrolidin-1-yl)-2-oxoethyl)-6-(1,2,3,4-tetrahydroisoquinolin-6-yl)quinoline-4-carboxamide;
N-(2-(2-cyano-4,4-difluoropyrrolidin-1-yl)-2-oxoethyl)-6-(2-(indolin-5-yl)vinyl)quinoline-4-carboxamide;
N-(2-(2-cyano-4,4-difluoropyrrolidin-1-yl)-2-oxoethyl)-6-(3-fluoro-4-(methylcarbamoyl)phenyl)quinoline-4-carboxamide;
6-(2-(4-chlorocyclohexa-2,4-dien-1-yl)vinyl)-N-(2-(2-cyano-3,3-difluoroazetidin-1-yl)-2-oxoethyl)quinoline-4-carboxamide;
6-(2-(4-chlorocyclohexa-2,4-dien-1-yl)vinyl)-N-(2-(2-cyano-2-ethyl-4,4-difluoropyrrolidin-1-yl)-2-oxoethyl)quinoline-4-carboxamide;
6-(2-(4-chlorocyclohexa-2,4-dien-1-yl)vinyl)-N-(2-(2-cyano-2-cyclopropyl-4,4-difluoropyrrolidin-1-yl)-2-oxoethyl)quinoline-4-carboxamide;
6-(2-(4-chlorocyclohexa-2,4-dien-1-yl)vinyl)-N-(2-(2-cyano-4,4-difluoro-2-(piperidin-1-yl)pyrrolidin-1-yl)-2-oxoethyl)quinoline-4-carboxamide; and
6-(2-(4-chlorocyclohexa-2,4-dien-1-yl)vinyl)-N-(2-(2-cyano-4,4-difluoro-2-phenylpyrrolidin-1-yl)-2-oxoethyl)quinoline-4-carboxamide,
or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described, such as the compounds of Table 1A and Table 1B. The structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (A) or (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) is useful in compound or substrate tissue distribution studies. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

Compounds of the Formula (A) or (I) can be prepared according to Scheme 1, wherein R, Y, m, and n are as detailed herein for formula (A) or (I), or any variation thereof detailed herein; Z and $Z^1$ are leaving groups; and $PG^1$ is an amine protecting group.

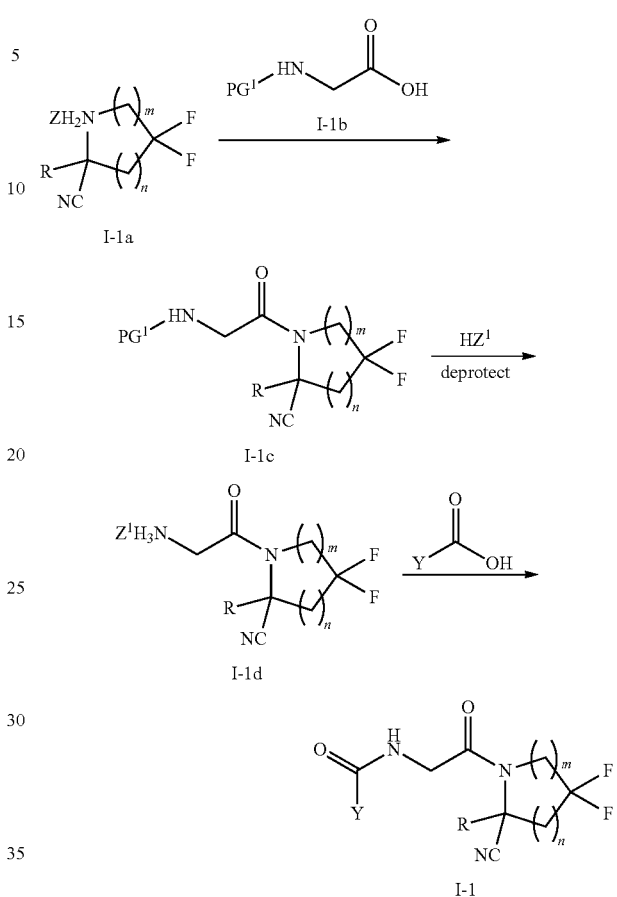

Scheme 1

Coupling of a compound of formula (I-1a) with a compound of formula (I-1b) in the presence of a coupling agent (e.g., HATU, HOBt, or PyBOP) yields a compound of formula (I-1c). Deprotection of the amine of the compound of formula (I-1c) under acidic conditions (e.g., HCl or pTsOH) provides the compound of formula (I-1d) as a salt, which is coupled with a carboxylic acid in the presence of a coupling agent (e.g., HATU, HOBt, or PyBOP) to yield a compound of formula (1-1).

An exemplary embodiment of the preparative method in Scheme 1 is shown in Scheme 1a.

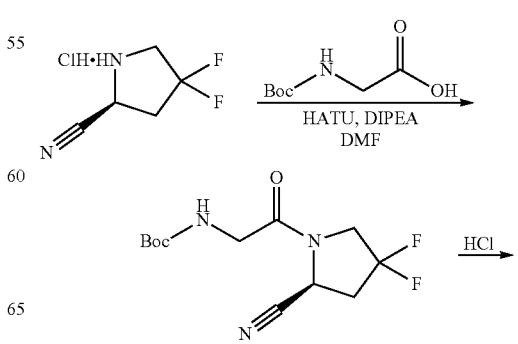

Scheme 1a

-continued

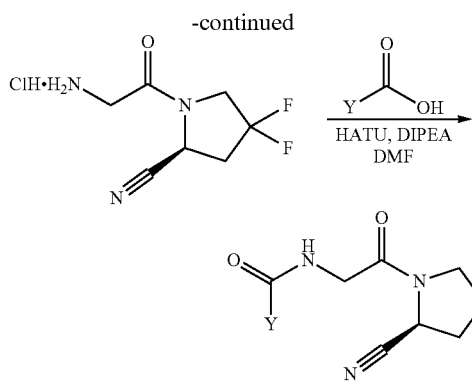

In some embodiments, Y is quinoline-4-yl optionally substituted by $R^{13}$, wherein

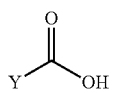

is represented by the compound of formula (II-1).

Scheme 2

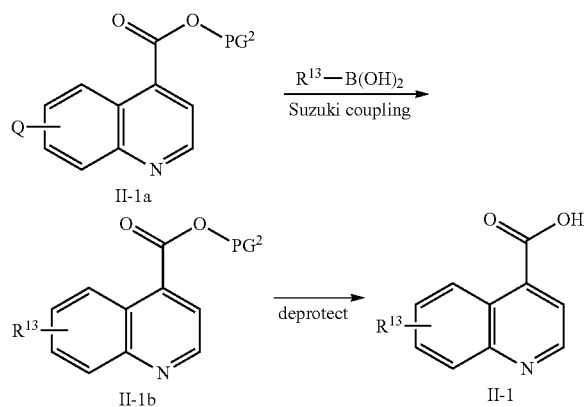

It is understood that the schemes above may be modified to arrive at various compounds of the invention by selection of appropriate reagents and starting materials. For a general description of protecting groups and their use, see P.G.M. Wuts and T.W. Greene, Greene's Protective Groups in Organic Synthesis 4$^{th}$ edition, Wiley-Interscience, New York, 2006.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Compositions comprising a compound provided herein are also described. In one variation, the composition comprises a compound or salt thereof and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound describes herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

The compounds or salts thereof described herein and compositions described herein are believed to be effective for treating a variety of diseases and disorders. In some embodiments, a compound or salt thereof described herein or a composition described herein may be used in a method of treating a disease or disorder mediated by fibroblast activation protein (FAP). In some embodiments, the disease or disorder is characterized by proliferation, tissue remodeling, fibrosis, chronic inflammation, excess alcohol consumption, or abnormal metabolism.

In some embodiments, a compound or salt thereof described herein or a composition described herein may be used in a method of treating a disease or disorder mediated by a physiological substrate of FAP peptidase activity. In some embodiments the FAP peptidase activity is endopeptidase activity. In some embodiments, the physiological substrate of FAP endopeptidase activity is α2-antiplasmin, type I collagen, gelatin, and Fibroblast growth factor 21 (FGF21). In some embodiments the FAP peptidase activity is exopeptidase activity. In some embodiments, the physiological substrate of FAP exopeptidase activity is Neuropeptide Y, B-type natriuretic peptide, substance P and peptide YY. In some embodiments, a compound or salt thereof described herein or a composition described herein may be used in a method of treating a disease or disorder mediated by FGF21.

In some embodiments, a compound or salt thereof described herein or a composition described herein may be used in a method of treating a FGF21-associated disorder, such as obesity, type I-and type II diabetes, pancreatitis, dyslipidemia, hyperlipidemia conditions, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders. In some embodiments, the FGF21-associated disorder is diabetes, obesity, dyslipidemia, metabolic syndrome, non-alcoholic fatty liver disease, non-alcoholic steatohepatitis or cardiovascular diseases.

In some embodiments, a compound or salt thereof described herein or a composition described herein may be used in a method of treating a disease or disorder characterized by proliferation, tissue remodeling, fibrosis, chronic inflammation, excess alcohol consumption, or abnormal metabolism.

In some embodiments, a compound or salt thereof described herein or a composition described herein may be used in a method of treating cancer, such as breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, the compound, salt, or composition may be used in a method of treating metastatic kidney cancer, chronic lymphocytary leukemia, pancreatic adenocarcinoma, or non-small cell lung cancer.

In some embodiments, the administration of the compound, salt, or composition reduces tumor growth, tumor proliferation, or tumorigenicity in the individual. In some embodiments, the compound, salt, or composition may be used in a method of reducing tumor growth, tumor proliferation, or tumorigenicity in an individual in need thereof. In some embodiments, tumor growth is slowed or arrested. In some embodiments, tumor growth is reduced at least about 10%, 20%, 30%, 40%, 50%, 60%, 70%, 80%, 90% or more. In some embodiments, the tumor is reduced in size. In some embodiments, tumor metastasis is prevented or slowed. In some embodiments, the tumor growth, tumor proliferation, or tumorigenicity is compared to the tumor growth, tumor proliferation, or tumorigenicity in the individual prior to the administration of the compound, salt, or composition. In some embodiments, the tumor growth, tumor proliferation, or tumorigenicity is compared to the tumor growth, tumor proliferation, or tumorigenicity in a similar individual or group of individuals. Methods of measuring tumor growth, tumor proliferation, and tumorigenicity are known in the art, for example by repeated imaging of the individual.

In some embodiments, a compound or salt thereof described herein or a composition described herein may be used in in a method of treating fibrotic disease, thrombosis, wound healing, keloid formation, osteoarthritis, rheumatoid arthritis and related disorders involving cartilage degradation, atherosclerotic disease, Crohn's disease, hepatic cirrhosis, idiopathic pulmonary fibrosis, myocardial hypertrophy, diastolic dysfunction, obesity, glucose intolerance, insulin insensitivity, or diabetes mellitus. In some embodiments, the hepatic cirrhosis is viral hepatitis-induced, alcohol-induced, or biliary cirrhosis. In some embodiments, the diabetes mellitus is type II diabetes. In some embodiments, the disease or disorder is fibrotic liver degeneration.

In some embodiments, provided herein is a method of inhibiting FAP. The compounds or salts thereof described herein and compositions described herein are believed to be effective for inhibiting FAP.

In some embodiments, the method of inhibiting FAP comprises inhibiting FAP in a cell by administering or delivering to the cell a compound described herein, or a pharmaceutically acceptable salt thereof, or a pharmaceutical composition described herein. In some embodiments, the cell is a fibroblast, such as a myofibroblast, a keloid fibroblast, a cancer associated fibroblast (CAF), or a reactive stromal fibroblast, among others cells with FAP expression.

In some embodiments, the method of inhibiting FAP comprises inhibiting FAP in a tumor or in plasma by administering or delivering to the tumor or plasma a compound described herein, or a pharmaceutically acceptable salt thereof, or a pharmaceutical composition described herein.

In some embodiments, the inhibition of FAP comprises inhibiting an endopeptidase and/or exopeptidase activity of FAP. In some embodiments, FAP is inhibited by at least about 10%, 20%, 30%, 40%, 50%, 60%, 70%, 80%, 90%, 95%, 98% or more. Inhibition of FAP can be determined by methods known in the art.

In some embodiments, the compound, salt thereof, or composition inhibits FAP with an $IC_{50}$ of less than about 1 µM, such as less than about 750 nM, 600 nM, 500 nM, 300 nM, 200 nM, 100 nM, 80 nM, 60 nM, 40 nM, 25 nM, or less. In some embodiments, the compound, salt thereof, or composition inhibits FAP with an $IC_{50}$ between about 7 nM and 1 µM, such between about 10 nM and 600 nM, 15 nM and 200 nM, or 20 nM and 180 nM. In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the compounds or salts thereof described herein and compositions described herein are administered in an amount wherein DPPII, DPPIV, DPP8, DPP9, and/or PREP activity is not inhibited or is inhibited to a lesser extent. In some embodiments, inhibition of FAP is at least or at least about 2 fold greater than inhibition of DPPII, DPPIV, DPP8, DPP9, and/or PREP activity, for example at least or at least about 3 fold, 4 fold, 5 fold, 8 fold, 10 fold, 15 fold, 30 fold, 50 fold, 60 fold, 75 fold, or 100 fold greater.

By way of example and not wishing to be bound by theory, DPP9 is believed to be a cytoplasmic DPP and belongs to S9B sub-family of proline-selective soluble proteases too. Inhibition of DPP9 activity in macrophages activates the Nlrp1b inflammasome. Activation of this pathway leads to pyroptosis, a proinflammatory form of cell death (Okondo M C et al. 2017; Okondo M C et al. 2018) concomitant with the activation of caspase-1 and subsequent activation of pro-IL-1β and pro-IL-18. In MC38 syngeneic mouse model, Val-boroPro a non-selective DPP inhibitor, has shown to inhibit cancer growth with concomitant up-regulation of immune-stimulatory cytokines and tumor infiltration of anti-cancer cell types including CD8+ T cells, Ml-macrophages and NK cells when combined with the immune checkpoint anti-PD1. The cytoplasmic RU134-42 tumor antigen is a natural substrate of DPP9 and endogenous DPP9 limits the presentation of the RU134-42 peptide. These findings suggest a role for DPP9 in antigen presentation (Geiss-Friedlander R et al, 2009). In human myeloid cells, CARD8 mediates DPP8/9 inhibitor-induced pro-caspase-1β-dependent pyroptosis. DPP8/9 inhibitors induce pyroptosis in the majority of human acute myeloid leukemia (AML) cell lines and primary AML samples, but not in cells from many other lineages, and that these inhibitors inhibit human AML progression in mouse models. Val-boroPro afforded a 97% reduction in tumor burden relative to the vehicle control in a model of disseminated MV4; 11 leukemia cells in NSG mice (Johnson et al., 2018).

Provided herein is a method of enhancing an immune response in an individual comprising administering to the individual a compound described herein, or a pharmaceutically acceptable salt thereof, or a pharmaceutical composition described herein. In some embodiments, the individual has cancer. In some embodiments, the enhanced immune response is directed to a tumor or cancerous cell. By way of example and not wishing to be bound by theory, FAP is believed to suppress immune responses, especially in the context of cancer, therefore inhibiting FAP may enhancing the immune response of an individual. Accordingly, provided herein are methods of treating cancer in an individual in need thereof comprising administering to the individual a compound described herein, or a pharmaceutically acceptable salt thereof, or a pharmaceutical composition described herein, wherein an immune response of the individual is increased.

Provided herein is a method of increasing the level of FGF21 expression in an individual comprising administering to the individual a compound described herein, or a pharmaceutically acceptable salt thereof, or a pharmaceutical composition described herein. FGF21 stimulates glucose uptake in adipocytes and is believed to protective against obesity and insulin insensitivity. By way of example and not wishing to be bound by theory, FAP is believed to be the enzyme responsible for cleavage and inactivation of FGF21; therefore inhibiting FAP may increase levels of FGF21 expression. Accordingly, provided herein are methods of treating diabetes mellitus, insulin insensitivity, and/or obesity in an individual in need thereof comprising administering to the individual a compound described herein, or a pharmaceutically acceptable salt thereof, or a pharmaceutical composition described herein, wherein FGF21 expression is increased. In some embodiments, the diabetes mellitus is type II diabetes.

FGF21 is a peptidic endocrine hormone secreted primarily by the liver (Markan, K. R. et al. Semin Cell Dev Biol, 2016, 53: 85-93). Upon entering circulation, FGF21 functions by signaling to specific tissues regulating carbohydrate and lipid metabolism (Kharitonenkov, A., et al., J Clin Invest, 2005, 115(6): 1627-35). FGF21 stimulates glucose uptake in adipocytes and is believed to protective against obesity and insulin insensitivity. Pharmacological administration of FGF21 to diabetic and obese animal models markedly ameliorates obesity, insulin resistance, dyslipidemia, fatty liver, and hyperglycemia in rodents (Markan, K. R. et al. Semin Cell Dev Biol, 2016, 53: 85-93). Small clinical trials have demonstrated that FGF21 analogs are efficacious in inducing weight loss and correcting hyperinsulinemia, dyslipidemia, and hypoadiponectinemia in obese individuals with type 2 diabetes (Gaich, G., et al., Cell Metab, 2013, 18(3): p. 333-40; Dong, J. Q., et al., Br J Clin Pharmacol, 2015, 80(5): 1051-63.

By way of example and not wishing to be bound by theory, FAP is believed to be the enzyme responsible for cleavage and inactivation of FGF21; therefore inhibiting FAP may increase levels of FGF21 expression and may augment endogenous and/or exogenous FGF21 action. FGF21 interacts with FGFR1 through its N-terminus and with β-Klotho through its C-terminus. This C-terminal region of FGF21 is essential to activate the receptor complex to initiate signaling (Micanovic, R., et al., J Cell Physiol, 2009, 219(2): 227-34; Yie, J., et al., FEBS Lett, 2009, 583(1): 19-24). Recently, FAPα has been identified as the protease responsible for the inactivation of circulating FGF21 through the C-terminal cleavage at Pro171 (Dunshee, D. R., et al., J Biol Chem, 2016, 291(11): 5986-96; Coppage, A. L., et al., PLoS One, 2016, 11(3): e0151269; Zhen, E. Y., et al., Biochem J, 2016, 473(5): 605-14). In rodents and primates, the half-life of exogenously administrated human FGF21 is short (~0.5-2 h) as result of FAP-mediated enzymatic degradation and susceptibility to renal clearance (Hager, T., et al., Anal Chem, 2013, 85(5): 2731-8; Xu, J., et al., Am J Physiol Endocrinol Metab, 2009, 297(5): E1105-14; Kharitonenkov, A., et al., Endocrinology, 2007, 148(2): 774-81). Common half-life extension strategies have improved significantly the PK properties of these FGF21 analogs in vivo; however, proteolytic processing still persists in these analogs (Hecht, R., et al., PLoS One, 2012, 7(11): e49345; Mu, J., et al., Diabetes, 2012, 61(2): 505-12; Camacho, R. C., et al., Eur J Pharmacol, 2013, 715(1-3): 41-5).

Accordingly, provided herein are methods of treating diabetes mellitus, insulin insensitivity, and/or obesity in an individual in need thereof comprising administering to the individual a compound described herein, or a pharmaceutically acceptable salt thereof, or a pharmaceutical composition described herein. In some embodiments, the method further comprises administering FGF21 or an FGF21 analog. In some embodiments, the FGF21 analog is pegylated FGF21, PF-05231023, or LY2405319. Also provided herein are methods of treating diabetes mellitus, insulin insensitivity, and/or obesity in an individual in need thereof comprising administering to the individual a compound described herein, or a pharmaceutically acceptable salt thereof, or a pharmaceutical composition described herein, wherein FGF21 expression is increased. In some embodiments, the diabetes mellitus is type II diabetes.

In some embodiments, the individual is a mammal. In some embodiments, the individual is a primate, bovine, ovine, porcine, equine, canine, feline, lapine, or rodent. In some embodiments, the individual is a human. In some embodiments, the individual has any of the diseases or disorders disclosed herein. In some embodiments, the individual is a risk for developing any of the diseases or disorders disclosed herein.

In some embodiments, the individual is human. In some embodiments, the human is at least about or is about any of 21, 25, 30, 35, 40, 45, 50, 55, 60, 65, 70, 75, 80, or 85 years old. In some embodiments, the human is a child. In some embodiments, the human is less than about or about any of 21, 18, 15, 12, 10, 8, 6, 5, 4, 3, 2, or 1 years old.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by FAP.

Combination Therapy

As provided herein, compounds or salts thereof described herein and compositions described herein may be administered with an additional agent to treat any of the diseases and disorders disclosed herein.

In some embodiments, (a) a compound described herein, or a pharmaceutically acceptable salt thereof, or a pharmaceutical composition described herein and (b) an additional agent are sequentially administered, concurrently administered or simultaneously administered. In certain embodiments, (a) a compound described herein, or a pharmaceutically acceptable salt thereof, or a pharmaceutical composition described herein and (b) an additional agent are administered with a time separation of about 15 minutes or less, such as about any of 10, 5, or 1 minutes or less. In certain embodiments, (a) a compound described herein, or a pharmaceutically acceptable salt thereof, or a pharmaceutical composition described herein and (b) an additional agent are administered with a time separation of about 15 minutes or more, such as about any of 20, 30, 40, 50, 60, or more minutes. Either (a) a compound described herein, or a pharmaceutically acceptable salt thereof, or a pharmaceutical composition described herein and (b) an additional agent may be administered first. In certain embodiments, (a) a compound described herein, or a pharmaceutically acceptable salt thereof, or a pharmaceutical composition described herein and (b) an additional agent are administered simultaneously.

In some embodiments, the agent targets an immune checkpoint protein. In some embodiments, the agent is an antibody that targets an immune checkpoint protein. In some embodiments, the additional agent targets PD-1, PD-L1, PD-L2, CTLA4, TIM3, LAG3, CCR4, OX40, OX40L, IDO, and A2AR. In some embodiments, the agent is an anti-PD-1 antibody, an anti-PD-L1 antibody, or an anti-CTLA-4 antibody.

In some embodiments, the agent is an inducer of FGF21 expression, such as a PPARα agonist. In some embodiment, the PPARα agonist is fibrate or fenofibrate.

Provided herein is a method of enhancing an immune response in an individual comprising administering to the individual (a) a compound described herein, or a pharmaceutically acceptable salt thereof, or a pharmaceutical composition described herein and (b) an agent that targets an immune checkpoint protein and. In some embodiments, the individual has cancer. In some embodiments, the enhanced immune response is directed to a tumor or cancerous cell.

Also provided herein are methods of treating cancer in an individual in need thereof comprising administering to the individual (a) a compound described herein, or a pharmaceutically acceptable salt thereof, or a pharmaceutical composition described herein and (b) an agent that targets an immune checkpoint protein, wherein an immune response of the individual is increased.

Provided herein is a method of increasing the level of FGF21 expression in an individual comprising administering to the individual (a) a compound described herein, or a pharmaceutically acceptable salt thereof, or a pharmaceutical composition described herein and (b) an agent that induces FGF21 expression.

Also provided herein are methods of treating diabetes mellitus, insulin insensitivity, and/or obesity in an individual in need thereof comprising administering to the individual (a) a compound described herein, or a pharmaceutically acceptable salt thereof, or a pharmaceutical composition described herein and (b) an agent that induces FGF21 expression, wherein FGF21 expression is increased. In some embodiments, the diabetes mellitus is type II diabetes.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

All references throughout, such as publications, patents, patent applications and published patent applications, are incorporated herein by reference in their entireties.

EXAMPLES

Synthetic Examples

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Example S-1

Synthesis of (S)—N-(2-(2-cyano-4,4-difluoropyrrolidin-1-yl)-2-oxoethyl)-6-phenylquinoline-4-carboxamide

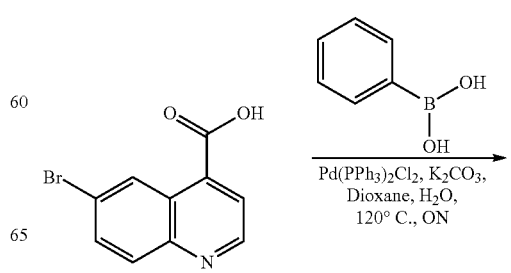

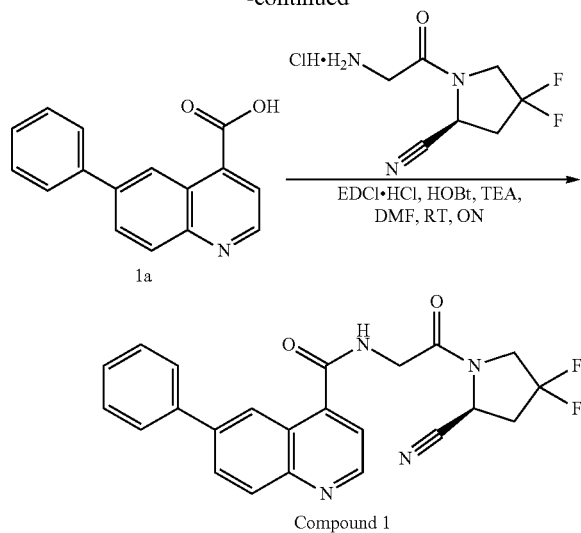

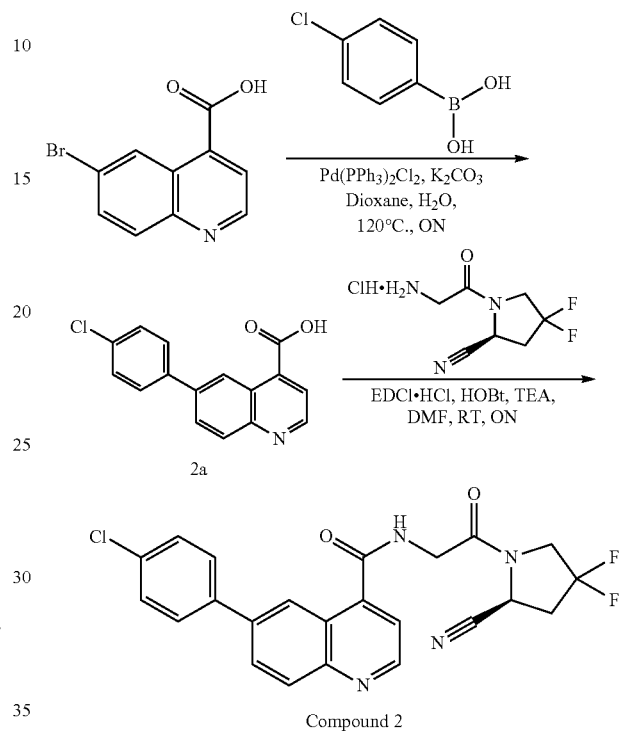

Example S-2

Synthesis of (S)-6-(4-chlorophenyl)-N-(2-(2-cyano-4,4-difluoropyrrolidin-1-yl)-2-oxoethyl)quinoline-4-carboxamide Compound 1a. To a solution of 6-bromoquinoline-4-carboxylic acid (0.05 g, 0.199 mmol, 1.0 equiv) in Dioxan (4 mL) and water (2 mL) was added phenyl boronic acid (0.046 g, 0.298 mmol, 1.5 equiv), $K_2CO_3$ (0.055 g, 0.397 mmol, 2.0 equiv) and resulting reaction mixture purged with $N_2$ gas for 10 minute, followed by the addition of Pd(PPh$_2$)Cl$_2$ (0.008 g, 0.009 mmol. 0.05 equiv). The resulting reaction mixture was heated at 120° C. for overnight. Product formation was confirmed by LCMS. After the completion of reaction, the mixture was quenched with water (10 mL) and aqueous layer washed with ethyl acetate (10 mL). Filtrate was concentrated under reduced pressure. Aqueous layer was separated and freeze dried on lyophilyzer to obtained 6-phenyl-quinoline-4-carboxylic acid (0.048 g, 98% Yield) as an off white solid.

LCMS 250.1 [M+H]$^+$

Compound 1. To a stirred solution of 6-phenyl-quinoline-4-carboxylic acid (0.12 g, 0.485 mmol, 1.0 equiv) in DMF (3 mL), was added (S)-4,4-difluoro-1-glycylpyrrolidine-2-carbonitrile hydrochloride (0.16 g, 0.727 mmol, 1.5 equiv), EDCI.HCl (0.086 g, 0.727 mmol, 1.5 equiv) & HOBt (0.098 g, 0.727 mmol, 1.5 equiv). The mixture was allowed to stir at RT for 10 min. Triethylamine (0.3 mL) was added and the mixture was allowed to stir at RT for overnight. Product formation was confirmed by LCMS and TLC. After completion of reaction, the mixture was diluted with water (10 mL) and extracted with ethyl acetate (10 mL×2). Combined organic extracts were washed with water (10 mL×4), dried over anhydrous $Na_2SO_4$ and concentrated. The crude product obtained was purified by flash chromatography (5% Methanol in DCM as an eluent) followed by reversed phase prep purification to obtain (S)—N-(2-(2-cyano-4,4-difluoropyrrolidin-1-yl)-2-oxoethyl)-6-phenylquinoline-4-carboxamide (0.030 g, 15% Yield) as an off-white solid.

LCMS 421.2 [M+H]$^+$ $^1$H NMR (400 MHz, DMSO-d$_6$) δ 9.19 (br. s., 1H), 9.00 (d, J=3.9 Hz, 1H), 8.77 (s, 1H), 8.27-8.14 (m, 2H), 7.92 (d, J=7.0 Hz, 1H), 7.61 (d, J=4.4 Hz, 1H), 7.54 (t, J=7.9 Hz, 1H), 7.45 (d, J=7.5 Hz, 1H), 5.18 (d, J=6.1 Hz, 1H), 4.40-4.25 (m, 2H), 4.21 (br. s., 1H), 4.16 (br. s., 1H), 2.83 (br. s., 3H).

Compound 2a. To a solution of 6-bromoquinoline-4-carboxylic acid (0.05 g, 0.199 mmol, 1.0 equiv) in dioxane (4 mL) and water (2 mL) was added (4-chlorophenyl) boronic acid (0.046 g, 0.298 mmol, 1.5 equiv), $K_2CO_3$ (0.055 g, 0.397 mmol, 2.0 equiv) and resulting reaction mixture purged with $N_2$ gas for 10 minute, followed by the addition of Pd(PPh$_2$)Cl$_2$ (0.008 g, 0.009 mmol. 0.05 equiv). The resulting reaction mixture was heated at 120° C. for overnight. Product formation was confirmed by LCMS. After the completion of reaction, the mixture was quenched with water (10 mL) and aqueous layer washed with ethyl acetate (10 mL). Filtrate was concentrated under reduced pressure. Aqueous layer was separated and freeze dried on lyophilyzer to obtained 6-(4-chlorophenyl)quinoline-4-carboxylic acid (0.052 g, 93% Yield) as an off white solid.

LCMS 283.9 [M+H]+

1H NMR (DMSO-d$_6$, 400 MHz) δ 9.12 (s, 1H), 8.63 (d, J=5.4 Hz, 1H), 7.65-7.77 (m, 2H), 7.61 (d, J=7.3 Hz, 2H), 7.38-7.49 (m, 2H), 7.26-7.38 (m, 2H), 3.83-3.96 ppm (m, 3H).

Compound 2. To a stirred solution of 6-(4-chlorophenyl)quinoline-4-carboxylic acid (0.05 g, 0.176 mmol, 1.0 equiv) in DMF (3 mL), was added (S)-4,4-difluoro–1-glycylpyrrolidine-2-carbonitrile hydrochloride (0.06 g, 0.265 mmol, 1.5 equiv), EDCI.HCl (0.051 g, 0.265 mmol, 1.5 equiv) & HOBt (0.036 g, 0.265 mmol, 1.5 equiv). The mixture was allowed to stir at RT for 10 min. Triethylamine (0.1 mL) was added and the mixture was allowed to stir at RT for overnight. Product formation was confirmed by LCMS and TLC. After completion of reaction, the mixture was diluted with water (10 mL) and extracted with ethyl acetate (10 mL×2). Combined organic extracts were washed with water (10 mL×4), dried over anhydrous $Na_2SO_4$ and concentrated. The crude product obtained was purified by flash chromatography (5% Methanol in DCM as an eluent) followed by reversed phase prep purification to obtain (S)-6-(4-chlorophenyl)-N-(2-(2-cyano-4,4-difluoropyrrolidin-1-yl)-2-oxoethyl)quinoline-4-carboxamide (0.022 g, 27.5% Yield) as a white solid.

LCMS 455.2 $[M+H]^+$ $^1$H NMR (DMSO-$d_6$, 400 MHz) δ 9.19 (t, J=5.9 Hz, 1H), 8.99 (d, J=4.4 Hz, 1H), 8.86 (d, J=1.8 Hz, 1H), 8.09-8.30 (m, 2H), 7.99 (d, J=8.8 Hz, 2H), 7.92 (d, J=7.5 Hz, 1H), 7.51-7.65 (m, 2H), 5.21 (d, J=6.6 Hz, 1H), 4.31-4.44 (m, 1H), 4.22-4.31 (m, 2H), 4.03-4.22 (m, 2H), 2.79-3.06 ppm (m, 2H).

Example S-3

Synthesis of (S)-6-(6-chloronaphthalen-2-yl)-N-(2-(2-cyano-4,4-difluoropyrrolidin-1-yl)-2-oxoethyl)quinoline-4-carboxamide

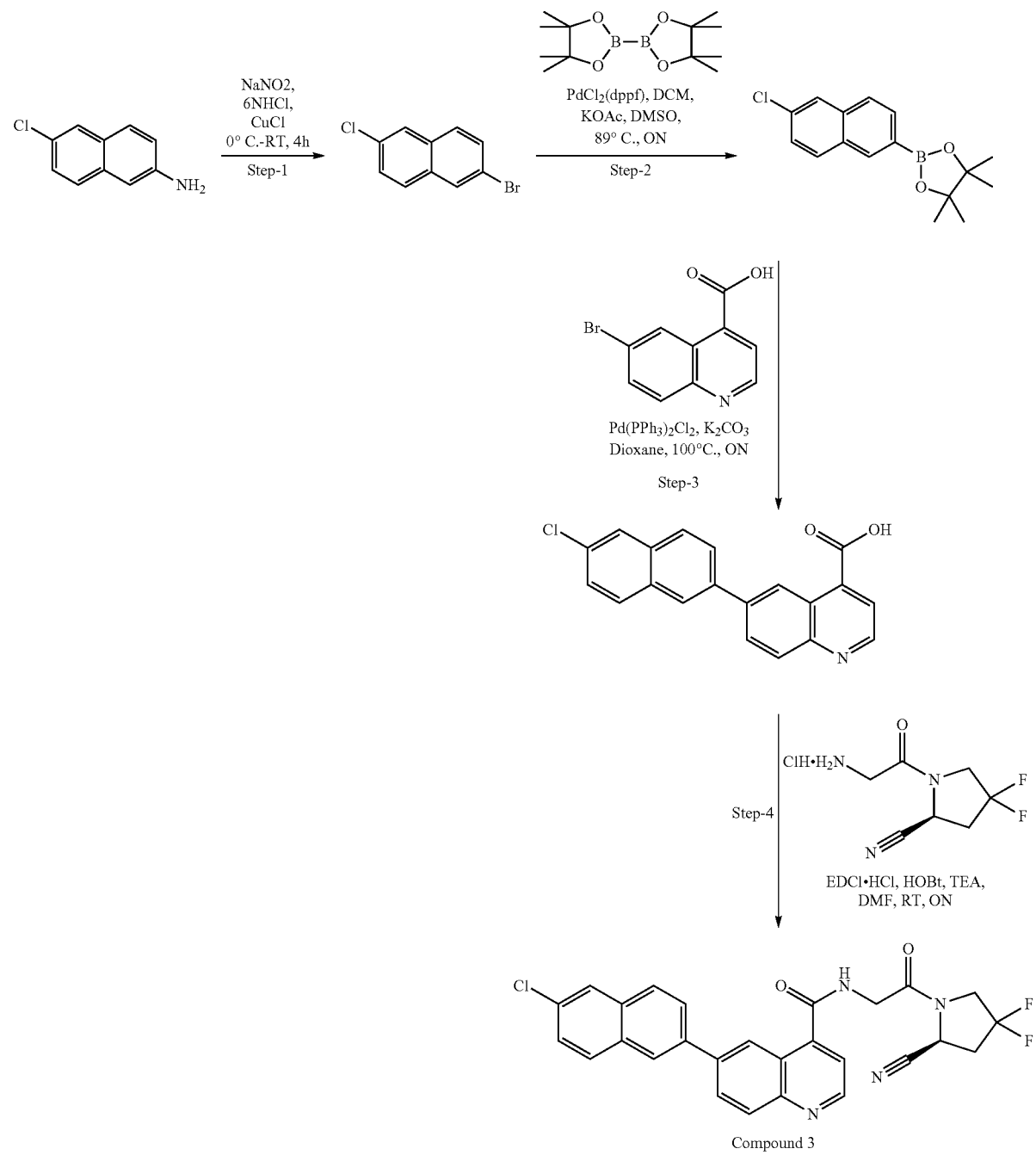

Compound 3

Step 1: Synthesis of 2-bromo-6-chloronaphthalene. To a solution of 6-chloronaphthalen-2-amine (0.5 g, 2.272 mmol, 1.0 equiv) in 6N HCl (7 mL) was added NaNO$_2$ (0.19 g, 2.727 mmol, 1.2 equiv) dissolved in water (10 mL) at 0° C. and resulting reaction mixture was allowed to stir at RT for 1 h. The reaction mixture was again cooled to 0° C. and solution of CuCl (1.3 g, 13.636 mmol, and 5.0 equiv) in 6N HCl (10 mL) was added and allowed to stir at RT for 4 hour. After the completion of reaction (monitored by TLC), the reaction mixture was diluted with water (100 mL) and extracted with ethyl acetate (150 mL×2). Combined organic extracts were washed with water (100 mL×2) and brine (100 mL), dried over anhydrous Na$_2$SO$_4$ and concentrated. The crude product obtained was purified by flash chromatography (100% hexane as an eluent) to obtain 2-bromo-6-chloronaphthalene (0.280 g, 51.4% Yield) as a white solid.

LCMS 242.2 [M+H]$^+$ $^1$H NMR (DMSO-d$_6$, 400 MHz) δ 8.27 (d, J=1.8 Hz, 1H), 8.10 (d, J=2.2 Hz, 1H), 7.97 (d, J=8.8 Hz, 1H), 7.90 (d, J=8.8 Hz, 1H), 7.69 (d, J=1.8 Hz, 1H), 7.59 ppm (dd, J=8.8, 2.2 Hz, 1H).

Step 2: Synthesis of 2-(6-chloronaphthalen-2-yl)-4,4,5,5-tetramethyl-1,3,2-dioxaborolane. To a solution of 2-bromo-6-chloronaphthalene (0.5 g, 2.08 mmol, 1.0 equiv) in DMSO (4 mL) was added 4,4,4',4',5,5,5',5'-octamethyl-2,2'-bi(1,3,2-dioxaborolane) (0.790 g, 3.12 mmol, 1.5 equiv), KOAc (0.4 g, 4.16 mmol, 2.0 equiv) and resulting reaction mixture purged with N$_2$ gas for 10 minute, followed by the addition of PdCl$_2$(dppf).DCM (0.17 g, 0.21 mmol. 0.1 equiv). The resulting reaction mixture was heated at 80° C. for overnight. After the completion of reaction (monitored by TLC & LCMS), the mixture was diluted with water (100 mL) and extracted with ethyl acetate (2×100 mL). Combined organic extracts were washed with water (100 mL×2) & brine (100 mL), dried over anhydrous Na$_2$SO$_4$ and concentrated. The crude product was purified by flash chromatography (20% EtOAc/hexane as an eluent) to obtain 2-(6-chloronaphthalen-2-yl)-4,4,5,5-tetramethyl-1,3,2-dioxaborolan (0.370 g, 61.6% Yield) as an off white solid.

$^1$H NMR (DMSO-d$_6$, 400 MHz) δ 8.44 (s, 1H), 8.25-8.37 (m, 1H), 8.04-8.15 (m, 1H), 7.90 (d, J=8.3 Hz, 1H), 7.76 (d, J=8.3 Hz, 1H), 7.49-7.61 (m, 1H), 1.11-1.41 (m, 12H).

Step 3: Synthesis of 6-(6-chloronaphthalen-2-yl)quinoline-4-carboxylic acid. To a solution of 6-bromoquinoline-4-carboxylic acid (0.1 g, 0.397 mmol, 1.0 equiv) in Dioxan (5 mL) and water (5 mL) was added 2-(6-chloronaphthalen-2-yl)-4,4,5,5-tetramethyl-1,3,2-dioxaborolane (0.172 g, 0.595 mmol, 1.5 equiv), K$_2$CO$_3$ (0.109 g, 0.794 mmol, 2.0 equiv) and resulting reaction mixture purged with N$_2$ gas for 10 minute, followed by the addition of Pd(PPh$_3$)Cl$_2$ (0.014 g, 0.0198 mmol. 0.05 equiv). The resulting reaction mixture was heated at 100° C. for overnight. Product formation was confirmed by LCMS. After the completion of reaction, the mixture was quenched with water (10 mL) and aqueous layer was washed with ethyl acetate (10 mL). Aqueous layer acidify with 6N HCl (pH~5 to 6), solid precipitate formed which was filtered off and dried under vacuum to obtained 6-(6-chloronaphthalen-2-yl)quinoline-4-carboxylic acid (0.050 g, 37.9% Yield) as a dark brown solid.

LCMS 334.1 [M+H]$^+$

Step 4: Synthesis of (S)-6-(6-chloronaphthalen-2-yl)-N-(2-(2-cyano-4,4-difluoropyrrolidin-1-yl)-2-oxoethyl)quinoline-4-carboxamide. To a stirred solution of 6-(6-chloronaphthalen-2-yl)quinoline-4-carboxylic acid (0.05 g, 0.15 mmol, 1.0 equiv) in DMF (3 mL), was added (S)-4,4-difluoro−1-glycylpyrrolidine-2-carbonitrile hydrochloride (0.04 g, 0.15 mmol, 1.0 equiv), EDCI.HCl (0.043 g, 0.225 mmol, 1.5 equiv) & HOBt (0.031 g, 0.225 mmol, 1.5 equiv). The mixture was allowed to stir at RT for 10 min. TEA (0.1 mL) was added and the reaction mixture was allowed to stir at RT for overnight. Product formation was confirmed by LCMS and TLC. After completion of reaction, the mixture was diluted with water (10 mL) and extracted with ethyl acetate (10 mL×2). Combined organic extracts were washed with water (10 mL×4), dried over anhydrous Na$_2$SO$_4$ and concentrated. The crude product was purified by flash chromatography (5% MeOH in DCM as an eluent) to obtain (S)-6-(6-chloronaphthalen-2-yl)-N-(2-(2-cyano-4,4-difluoropyrrolidin-1-yl)-2-oxoethyl)quinoline-4-carboxamide (0.03 g, 39.47% Yield) as a yellow solid.

LCMS 505.3 [M+H]$^+$ $^1$H NMR (DMSO-d$_6$, 400 MHz) δ 9.26 (br. s., 1H), 9.01 (d, J=3.9 Hz, 1H), 8.95 (s, 1H), 8.59 (s, 1H), 8.38 (d, J=9.2 Hz, 1H), 7.99-8.27 (m, 5H), 7.48-7.64 (m, 2H), 5.22 (d, J=9.6 Hz, 1H), 4.26-4.47 (m, 2H), 4.19 (d, J=12.3 Hz, 1H), 2.95 (d, J=8.8 Hz, 1H), 2.87 (d, J=14.0 Hz, 2H).

Example S-4

Synthesis of (S)—N-(2-(2-cyano-4,4-difluoropyrrolidin-1-yl)-2-oxoethyl)-6-(3,5-dimethylisoxazol-4-yl)quinoline-4-carboxamide

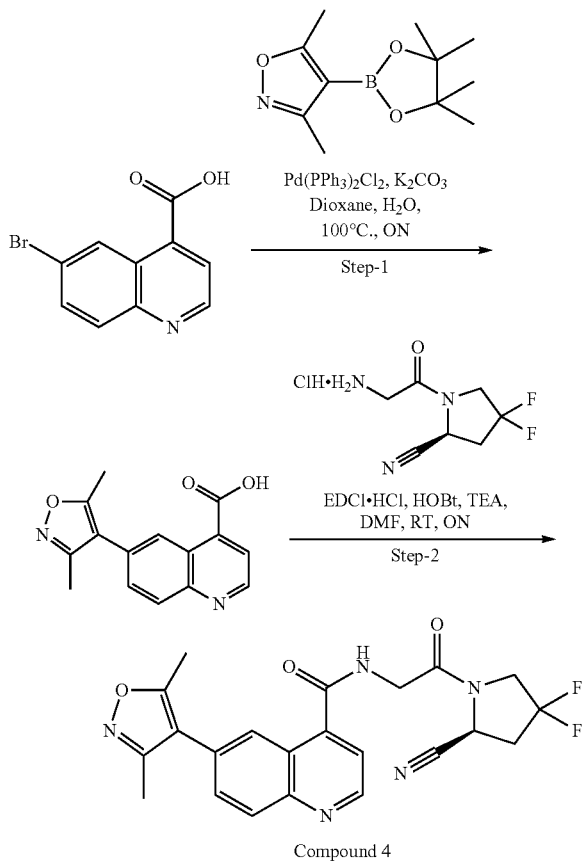

Compound 4

Step 1: Synthesis of 6-(3,5-dimethylisoxazol-4-yl)quinoline-4-carboxylic acid. To a solution of 6-bromoquinoline-4-carboxylic acid (0.05 g, 0.199 mmol, 1.0 equiv) in dioxane (4 mL) and water (2 mL) was added 3,5-dimethyl-4-(4,4,5,5-tetramethyl-1,3,2-dioxaborolan-2-yl)isoxazole (0.057 g, 0.298 mmol, 1.5 equiv), K₂CO₃ (0.055 g, 0.397 mmol, 2.0 equiv) and resulting reaction mixture was purged with N₂ gas for 10 min, followed by the addition of Pd(PPh₂)Cl₂ (0.008 g, 0.009 mmol. 0.05 equiv). The resulting reaction mixture was heated at 100° C. for overnight. Product formation was confirmed by LCMS. After completion of reaction, the reaction mixture was quenched with water (10 mL) and aqueous layer washed with ethyl acetate (10 mL). Aqueous layer was separated and acidified with 6N HCl (pH~5 to 6), solid precipitate formed was filtered off and dried under vacuum to obtain 6-(3,5-dimethylisoxazol-4-yl) quinoline-4-carboxylic acid (0.05 g, 94.33% Yield) as an off white solid.

LCMS 269.1 [M+H]⁺

Step 2: Synthesis of (S)—N-(2-(2-cyano-4,4-difluoropyrrolidin-1-yl)-2-oxoethyl)-6-(3,5-dimethylisoxazol-4-yl) quinoline-4-carboxamide. To a stirred solution of 6-(3,5-dimethylisoxazol-4-yl)quinoline-4-carboxylic acid (0.06 g, 0.223 mmol, 1.0 equiv) in DMF (3 mL), was added (S)-4,4-difluoro-1-glycylpyrrolidine-2-carbonitrile hydrochloride (0.050 g, 0.223 mmol, 1.5 equiv), EDCI.HCl (0.064 g, 0.3345 mmol, 1.5 equiv) and HOBt (0.045 g, 0.3345 mmol, 1.5 equiv). The mixture was allowed to stir at RT for 10 min. Triethylamine (0.2 mL) was added and the resulting reaction mixture was allowed to stir at RT for overnight. Product formation was confirmed by LCMS and TLC. After completion of reaction, the mixture was diluted with water (10 mL) and extracted with ethyl acetate (20 mL×2). Combined organic extracts were washed with water (10 mL×4), dried over anhydrous Na₂SO₄ and concentrated. The crude product was purified by flash chromatography (5% Methanol in DCM as an eluent) followed by reversed phase HPLC purification to obtain (S)—N-(2-(2-cyano-4,4-difluoropyrrolidin-1-yl)-2-oxoethyl)-6-(3,5-dimethylisoxazol-4-yl)quinoline-4-carboxamide (0.008 g, 8.16% Yield) as a yellow solid.

LCMS 440.2 [M+H]⁺

¹H NMR (400 MHz, DMSO-d₆) δ 9.19 (br. s., 1H), 9.01 (d, J=4.38 Hz, 1H), 8.44 (s, 1H), 8.17 (d, J=8.77 Hz, 1H), 7.88 (d, J=8.77 Hz, 1H), 7.60 (d, J=4.39 Hz, 1H), 5.15 (d, J=6.58 Hz, 1H), 4.19-4.44 (m, 3H), 4.15 (d, J=10.96 Hz, 1H), 2.92 (br. s., 1H), 2.83 (d, J=17.54 Hz, 3H), 2.32 (s, 3H).

Example S-5

Synthesis of (S)—N-(2-(2-cyano-4,4-difluoropyrrolidin-1-yl)-2-oxoethyl)-6-(pyridin-3-yl)quinoline-4-carboxamide

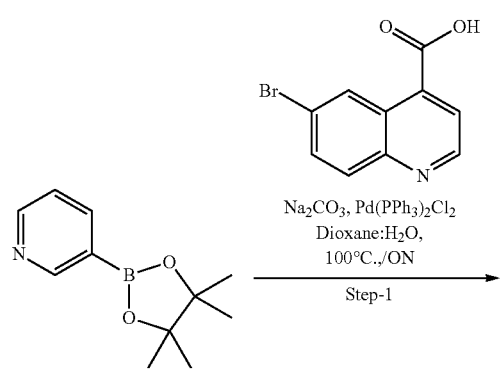

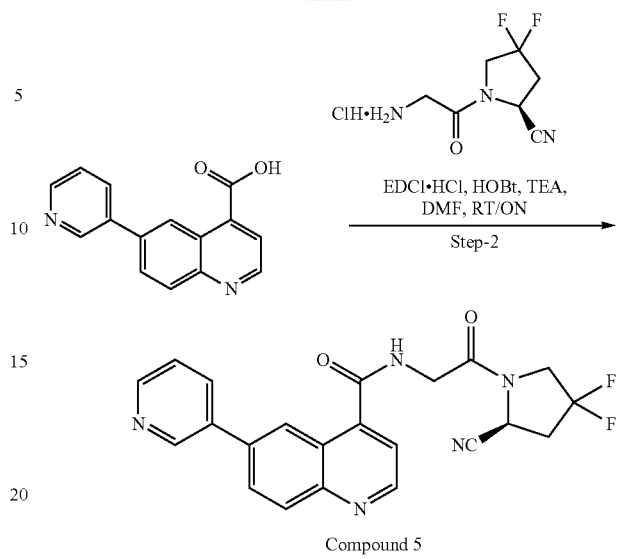

Compound 5

Step 1: Synthesis of 6-(pyridin-3-yl)quinoline-4-carboxylic acid. To the solution of 3-(4,4,5,5-tetramethyl-1,3,2-dioxaborolan-2-yl)pyridine (100 mg, 0.48 mmol, 1.0 equiv) in Dioxane: water (05:02 mL), was added 6-bromoquinoline-4-carboxylic acid (123 mg, 0.48 mmol, 1.0 equiv), Na₂CO₃ (102 mg, 0.96 mmol, 2.0 equiv) followed by the addition of Pd(PPh₃)₂Cl₂(17 mg, 0.024 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and freeze dried over lyophilizer to obtain 6-(pyridin-3-yl)quinoline-4-carboxylic acid (100 mg, 80% Yield) as an off white solid.

LCMS 251.1 [M+H]⁺

Step 2: Synthesis of (S)—N-(2-(2-cyano-4,4-difluoropyrrolidin-1-yl)-2-oxoethyl)-4-phenylquinoline-6-carboxamide. To a stirred solution of 6-(pyridin-3-yl)quinoline-4-carboxylic acid (100 mg, 0.40 mmol, 1.0 equiv) in DMF (05 mL), was added (S)-4,4-difluoro-1-glycylpyrrolidine-2-carbonitrile hydrochloride (90 mg, 0.40 mmol, 1.0 equiv), HOBT (81 mg, 0.60 mmol, 1.5 equiv) and EDC.HCl (115 mg, 0.60 mmol, 1.5 equiv). The mixture was allowed to stir at RT for 10 min. Triethyl amine (0.20 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous Na₂SO₄ and concentrated. The crude product obtained was purified reversed phase HPLC to obtain (S)—N-(2-(2-cyano-4,4-difluoropyrrolidin-1-yl)-2-oxoethyl)-6-(pyridin-3-yl)quinoline-4-carboxamide (05 mg, 04% Yield) as a yellow solid.

LCMS 422.3 [M+H]⁺

¹H NMR (400 MHz, DMSO-d₆) δ 9.23 (t, J=5.48 Hz, 1H), 9.14 (br. s., 1H), 9.03 (d, J=4.38 Hz, 1H), 8.86 (s, 1H), 8.69 (d, J=3.95 Hz, 1H), 8.44 (d, J=7.89 Hz, 1H), 8.16-8.34 (m, 2H), 7.64 (d, J=4.38 Hz, 2H), 5.19 (d, J=6.58 Hz, 1H), 4.27-4.37 (m, 2H), 4.08-4.25 (m, 2H), 2.82-2.97 (m, 2H).

Example S-6

Synthesis of (S)—N-(2-(2-cyano-4,4-difluoropyrrolidin-1-yl)-2-oxoethyl)-6-(pyridin-4-yl)quinoline-4-carboxamide

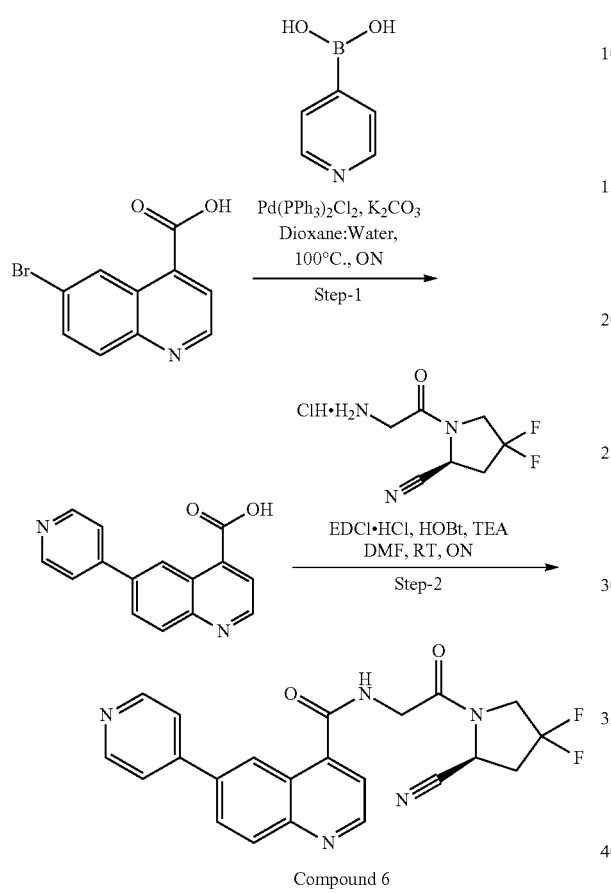

Compound 6

Step 1: Synthesis of 6-(pyridin-4-yl)quinoline-4-carboxylic acid. To a stirred solution of 6-bromoquinoline-4-carboxylic acid (1.02 g, 4.065 mmol, 1.0 equiv) in Dioxane (10 mL) was added 4-Pyridineboronic Acid (0.500 g 4.065 mmol, 1.0 equiv) and a solution of K$_2$CO$_3$ (1.12 g, 8.13 mmol, 2.0 equiv) in water (5 mL), and resulting reaction mixture purged with N$_2$ gas for 10 minute, followed by the addition of Pd(PPh$_3$)$_2$Cl$_2$ (0.142 g, 0.203 mmol. 0.05 equiv). The resulting reaction mixture was heated at 100° C. for overnight. Product formation was confirmed by LCMS. Reaction mixture was cool to RT, diluted with water (100 mL) washed with ethyl acetate (100 mL×3). Aqueous layer was separated and freeze dried on lyophilizer to obtain 6-(pyridin-4-yl)quinoline-4-carboxylic acid (0.350 g, 35.28% Yield) as an off white solid.

LCMS 251.2 [M+H]$^+$ $^1$H NMR (400 MHz, DMSO-d$_6$) δ 9.24 (s, 1H) 8.83 (d, J=4.38 Hz, 1H) 8.65-8.71 (m, 2H) 8.25-8.34 (m, 1H) 8.05-8.10 (m, 2H) 7.74-7.80 (m, 2H) 7.56 (d, J=3.95 Hz, 1H).

Step 2: Synthesis of (S)—N-(2-(2-cyano-4,4-difluoropyrrolidin-1-yl)-2-oxoethyl)-6-(pyridin-4-yl)quinoline-4-carboxamide. To a stirred solution of 6-(pyridin-4-yl)quinoline-4-carboxylic acid (0.200 g, 0.800 mmol, 1.0 equiv) in DMF (5 mL), was added (S)-4,4-difluoro–1-glycylpyrrolidine-2-carbonitrile hydrochloride (0.270 g, 1.200 mmol, 1.5 equiv), HOBt (0.162 g, 1.200 mmol, 1.5 equiv) & EDCI.HCl (0.229 g, 1.200 mmol, 1.5 equiv). The mixture was allowed to stir at RT for 2 min. TEA (0.2 mL) was added and the mixture was allowed to stir at RT for overnight. Product formation was confirmed by LCMS and TLC. After completion of reaction, the mixture was diluted with water (50 mL) and extracted with ethyl acetate (100 mL×2). Combined organic extracts were washed with water (50 mL×2) and brine (50 mL), dried over anhydrous Na$_2$SO$_4$ and concentrated. The crude product obtained was purified by reversed phase chromatography to obtained (S)—N-(2-(2-cyano-4,4-difluoropyrrolidin-1-yl)-2-oxoethyl)-6-(pyridin-4-yl)quinoline-4-carboxamide (0.060 g, 18% Yield) as an off white solid.

LCMS 422.3 [M+H]$^+$ $^1$H NMR (400 MHz, DMSO-d$_6$) δ9.18-9.28 (m, 1H) 8.94-9.10 (m, 2H) 8.71 (d, J=5.70 Hz, 2H) 8.32 (d, J=10.52 Hz, 1H) 8.18-8.27 (m, 1H) 7.98 (d, J=5.70 Hz, 2H) 7.63 (d, J=3.95 Hz, 1H) 5.22 (d, J=7.02 Hz, 1H) 4.07-4.23 (m, 2H) 3.86-4.07 (m, 2H) 2.75-2.92 (m, 2H).

Example S-7

Synthesis of (S)-6-(4-(tert-butyl)phenyl)-N-(2-(2-cyano-4,4-difluoropyrrolidin-1-yl)-2-oxoethyl)quinoline-4-carboxamide

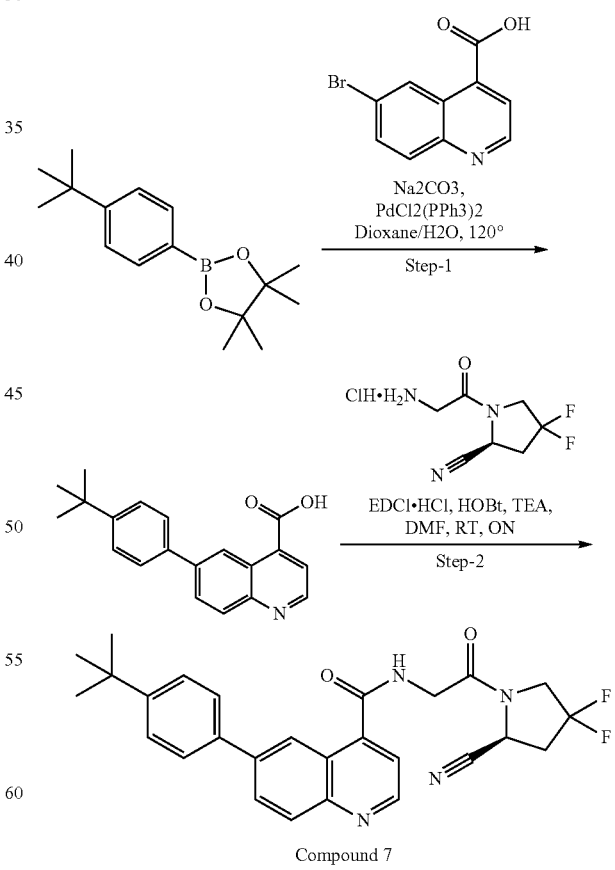

Compound 7

Step 1: Synthesis of 6-(4-(tert-butyl)phenyl)quinoline-4-carboxylic acid. To a solution of 2-(4-(tert-butyl)phenyl)-4,4,5,5-tetramethyl-1,3,2-dioxaborolane (0.1 g, 0.384 mmol, 1.0 equiv) in dioxane (4 mL) and water (1 ml) was added 6-bromoquinoline-4-carboxylic acid (0.096 g, 0.384 mmol, 1.0 equiv), Na$_2$CO$_3$ (0.081 g, 0.769 mmol, 2.0 equiv) and the resulting reaction mixture was purged with N$_2$ gas for 10 min, followed by the addition of Pd(PPh$_2$)Cl$_2$(0.013 g, 0.019 mmol. 0.05 equiv). The resulting reaction mixture was heated at 120° C. for overnight. Product formation was confirmed by LCMS. After completion of reaction the reaction mixture was diluted with water (30 mL) and washed with ethyl acetate (50 mL×2). Aqueous layer was separated and freeze dried over lyophilizer to obtain 6-(4-(tert-butyl)phenyl)quinoline-4-carboxylic acid (0.150 g, Quant. Yield) as a yellow solid.

LCMS 306.1 [M+H]$^+$ $^1$H NMR (400 MHz, DMSO-d$_6$) δ 9.02 (d, J=1.32 Hz, 1H) 8.77 (d, J=4.39 Hz, 1H) 7.90-8.08 (m, 2H) 7.67 (d, J=8.33 Hz, 2H) 7.39-7.61 (m, 3H) 1.34 (s, 9H).

Step 2: Synthesis of (S)-6-(4-(tert-butyl)phenyl)-N-(2-(2-cyano-4,4-difluoropyrrolidin-1-yl)-2-oxoethyl)quinoline-4-carboxamide. To a stirred solution of (6-(4-(tert-butyl)phenyl)quinoline-4-carboxylic acid (0.150 g, 0.490 mmol, 1.0 equiv) in DMF (5 mL), was added (S)-4,4-difluoro-1-glycylpyrrolidine-2-carbonitrile hydrochloride (0.11 g, 0.490 mmol, 1.0 equiv), EDCI.HCl (0.140 g, 0.735 mmol, 1.5 equiv) and HOBt (0.099 g, 0.735 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (20 mL) and extracted with ethyl acetate (50 mL×2). Combined organic extracts were washed with water (20 mL×4), dried over anhydrous Na$_2$SO$_4$ and concentrated. The crude product was purified by flash chromatography (0-5% MeOH in DCM as an eluent) to obtain (S)-6-(4-(tert-butyl)phenyl)-N-(2-(2-cyano-4,4-difluoropyrrolidin-1-yl)-2-oxoethyl)quinoline-4-carboxamide (0.007 g, 3.0% Yield) as a an off-white solid.

LCMS 427.4 [M+H]$^+$ $^1$H NMR (400 MHz, DMSO-d$_6$) δ 9.18 (d, J=6.14 Hz, 1H) 8.97 (d, J=4.38 Hz, 1H) 8.76 (s, 1H) 8.09-8.38 (m, 2H) 7.85 (d, J=8.33 Hz, 2H) 7.46-7.72 (m, 3H) 5.19 (d, J=6.58 Hz, 1H) 4.48 (s, 2H) 4.10-4.39 (m, 2H) 2.95 (br. s., 1H) 2.86 (d, J=19.73 Hz, 1H) 1.49 (s, 9H).

Example S-8

Synthesis of (S)—N-(2-(2-cyano-4,4-difluoropyrrolidin-1-yl)-2-oxoethyl)-6-(1-methyl-1H-indol-5-yl) quinoline-4-carboxamide

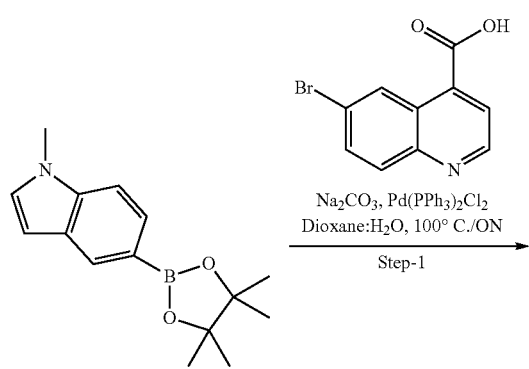

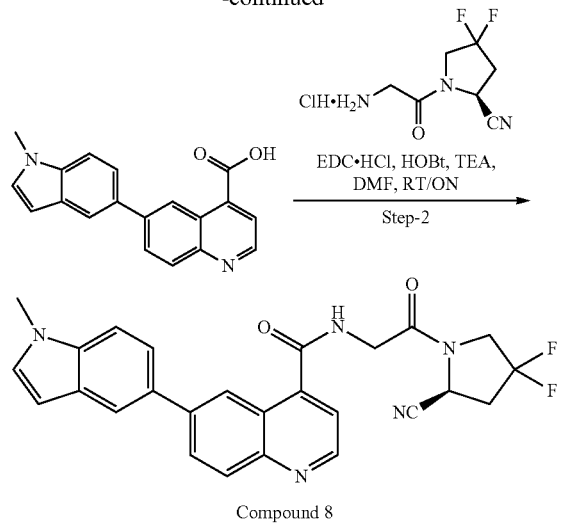

Compound 8

Step 1: Synthesis of 6-(1-methyl-1H-indol-5-yl)quinoline-4-carboxylic acid. To the solution of 1-methyl-5-(4,4,5,5-tetramethyl-1,3,2-dioxaborolan-2-yl)-1H-indole (100 mg, 0.38 mmol, 1.0 equiv) in Dioxane: water (05:02 mL), was added 6-bromoquinoline-4-carboxylic acid (98 mg, 0.38 mmol, 1.0 equiv), Na$_2$CO$_3$ (81 mg, 0.76 mmol, 2.0 equiv) followed by the addition of Pd(PPh$_3$)$_2$Cl$_2$ (14 mg, 0.019 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(1-methyl-1H-indol-5-yl)quinoline-4-carboxylic acid (100 mg, 85% Yield) as an off white solid.

LCMS 303.0 [M+H]$^+$

Step 2: Synthesis of (S)—N-(2-(2-cyano-4,4-difluoropyrrolidin-1-yl)-2-oxoethyl)-6-(1-methyl-1H-indol-5-yl)quinoline-4-carboxamide. To a stirred solution of 6-(1-methyl-1H-indol-5-yl)quinoline-4-carboxylic acid (100 mg, 0.33 mmol, 1.0 equiv) in DMF (05 mL), was added (S)-4,4-difluoro-1-glycylpyrrolidine-2-carbonitrile hydrochloride (75 mg, 0.33 mmol, 1.0 equiv), HOBT (66 mg, 0.49 mmol, 1.5 equiv) and EDC.HCl (95 mg, 0.49 mmol, 1.5 equiv). The mixture was allowed to stir at RT for 10 min. Triethyl amine (0.13 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous Na$_2$SO$_4$ and concentrated. The crude product obtained was purified reverse phase HPLC to obtain (S)—N-(2-(2-cyano-4,4-difluoropyrrolidin-1-yl)-2-oxoethyl)-6-(1-methyl-1H-indol-5-yl)quinoline-4-carboxamide (20 mg, 13% Yield) as an off-white solid.

LCMS 474.4 [M+H]$^+$ $^1$H NMR (400 MHz, DMSO-d$_6$) δ 9.18 (br. s., 1H), 8.94 (d, J=3.95 Hz, 1H), 8.71 (d, J=1.75 Hz, 1H), 8.22-8.30 (m, 1H), 8.06-8.19 (m, 2H), 7.71 (d, J=7.02 Hz, 1H), 7.46-7.65 (m, 3H), 7.39 (d, J=3.07 Hz, 1H), 6.57 (d, J=3.51 Hz, 1H), 5.19 (d, J=6.58 Hz, 1H), 4.30-4.41 (m, 2H), 4.28 (d, J=5.26 Hz, 3H), 2.67 (m, 3H).

Example S-9

Synthesis of (S)—N-(2-(2-cyano-4,4-difluoropyrrolidin-1-yl)-2-oxoethyl)-6-(1H-indol-5-yl)quinoline-4-carboxamide

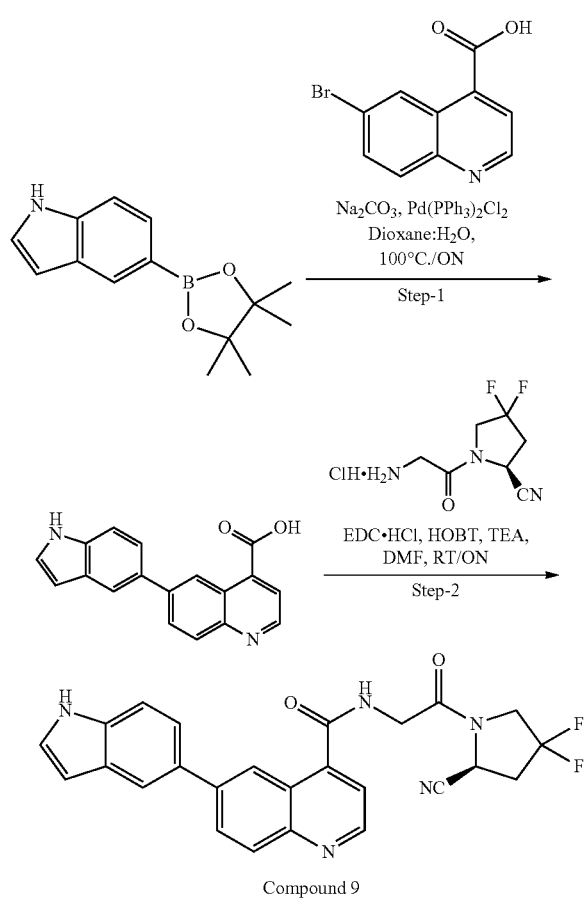

Compound 9

Step 1: Synthesis of 6-(1H-indol-5-yl) quinoline-4-carboxylic acid. To the solution of 5-(4,4,5,5-tetramethyl-1,3,2-dioxaborolan-2-yl)-1H-indole (100 mg, 0.41 mmol, 1.0 equiv) in Dioxane: water (05:02 mL), was added 6-bromoquinoline-4-carboxylic acid (104 mg, 0.41 mmol, 1.0 equiv), $Na_2CO_3$ (87 mg, 0.82 mmol, 2.0 equiv) and followed by the addition of $Pd(PPh_3)_2Cl_2$ (15 mg, 0.020 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(1H-indol-5-yl) quinoline-4-carboxylic acid (100 mg, 83% Yield) as an off white solid.

LCMS 289.0 [M+H]$^+$

Step 2: Synthesis of (S)—N-(2-(2-cyano-4,4-difluoropyrrolidin-1-yl)-2-oxoethyl)-6-(1H-indol-5-yl)quinoline-4-carboxamide. To a stirred solution of 6-(1H-indol-5-yl) quinoline-4-carboxylic acid (100 mg, 0.34 mmol, 1.0 equiv) in DMF (05 mL), was added (S)-4,4-difluoro-1-glycylpyrrolidine-2-carbonitrile hydrochloride (78 mg, 0.34 mmol, 1.0 equiv), HOBT (69 mg, 0.51 mmol, 1.5 equiv) and EDC.HCl (98 mg, 0.51 mmol, 1.5 equiv). The mixture was allowed to stir at RT for 10 min. Triethyl amine (0.14 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous $Na_2SO_4$ and concentrated. The crude product obtained was purified reverse phase HPLC to obtain (S)—N-(2-(2-cyano-4,4-difluoropyrrolidin-1-yl)-2-oxoethyl)-6-(1H-indol-5-yl)quinoline-4-carboxamide (20 mg, 13% Yield) as an off-white solid.

LCMS 460.4 [M+H]$^+$ $^1$H NMR (400 MHz, DMSO-d$_6$) δ 11.22 (br. s., 1H), 9.14-9.23 (m, 1H), 8.94 (d, J=4.38 Hz, 1H), 8.71 (s, 1H), 8.21-8.30 (m, 1H), 8.03-8.16 (m, 2H), 7.66 (d, J=8.33 Hz, 1H), 7.49-7.61 (m, 2H), 7.41 (t, J=2.63 Hz, 1H), 6.57 (br. s., 1H), 5.19 (d, J=6.58 Hz, 1H), 4.27-4.38 (m, 2H), 4.08-4.24 (m, 2H), 2.79-2.92 (m, 2H).

Example S-10

Synthesis of (S)—N-(2-(2-cyano-4,4-difluoropyrrolidin-1-yl)-2-oxoethyl)-6-(1-methyl-1H-pyrazol-4-yl)quinoline-4-carboxamide

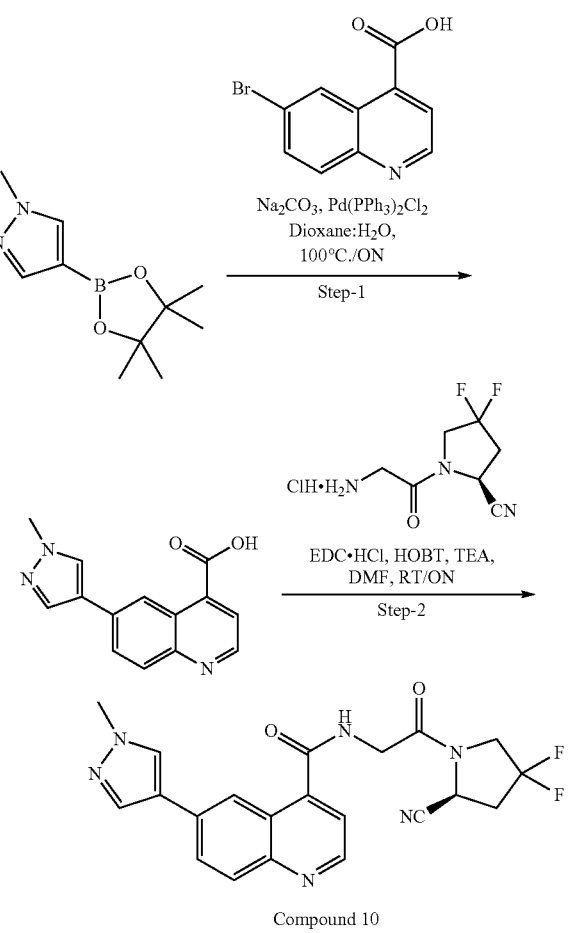

Compound 10

Step 1: synthesis of 6-(1-methyl-1H-pyrazol-4-yl)quinoline-4-carboxylic acid. To the solution of 1-methyl-4-(4,4,5,5-tetramethyl-1,3,2-dioxaborolan-2-yl)-1H-pyrazole (100 mg, 0.48 mmol, 1.0 equiv) in Dioxane:water (05:02 mL), was added 6-bromoquinoline-4-carboxylic acid (121 mg, 0.48 mmol, 1.0 equiv), Na₂CO₃ (108 mg, 0.96 mmol, 2.0 equiv) followed by the addition of Pd(PPh₃)₂Cl₂ (17 mg, 0.024 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(1-methyl-1H-pyrazol-4-yl)quinoline-4-carboxylic acid (100 mg, 82% Yield) as an off white solid.

LCMS 254.1 [M+H]⁺

Step 2: Synthesis of (S)—N-(2-(2-cyano-4,4-difluoropyrrolidin-1-yl)-2-oxoethyl)-6-(1-methyl-1H-pyrazol-4-yl)quinoline-4-carboxamide. To a stirred solution of 6-(1-methyl-1H-pyrazol-4-yl)quinoline-4-carboxylic acid (100 mg, 0.39 mmol, 1.0 equiv) in DMF (05 mL), was added (S)-4,4-difluoro-1-glycylpyrrolidine-2-carbonitrile hydrochloride (89 mg, 0.39 mmol, 1.0 equiv), HOBT (71 mg, 0.52 mmol, 1.5 equiv) and EDC.HCl (99 mg, 0.52 mmol, 1.5 equiv). The mixture was allowed to stir at RT for 10 min. Triethyl amine (0.16 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous Na₂SO₄ and concentrated. The crude product obtained was purified reversed phase HPLC to obtain (S)—N-(2-(2-cyano-4,4-difluoropyrrolidin-1-yl)-2-oxoethyl)-6-(1-methyl-1H-pyrazol-4-yl)quinoline-4-carboxamide (20 mg, 12% Yield) as an off white solid.

LCMS 425.4 [M+H]⁺

$^1$H NMR (400 MHz, DMSO-d₆) δ 9.16 (t, J=5.92 Hz, 1H) 8.88 (d, J=4.38 Hz, 1H) 8.75 (d, J=1.32 Hz, 1H) 8.38 (s, 1H) 8.01-8.13 (m, 3H) 7.50 (d, J=3.95 Hz, 1H) 5.25 (dd, J=9.21, 2.63 Hz, 1H) 4.28-4.40 (m, 2H) 4.13-4.28 (m, 2H) 3.92 (s, 3H) 2.77-3.05 (m, 2H).

Example S-11

Synthesis of (S)—N-(2-(2-cyano-4,4-difluoropyrrolidin-1-yl)-2-oxoethyl)-6-(1-cyclopropyl-1H-pyrazol-4-yl)quinoline-4-carboxamide

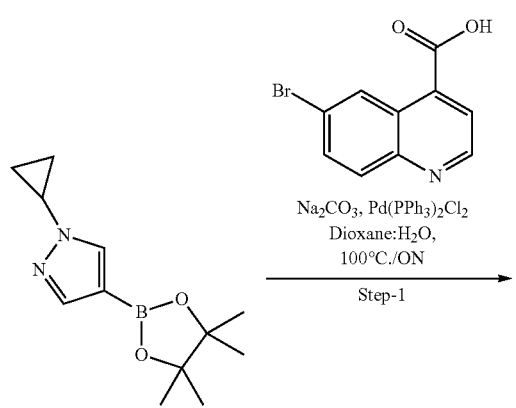

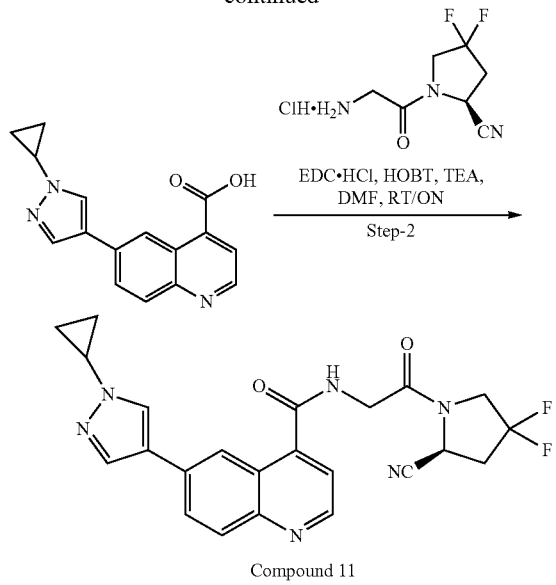

Compound 11

Step 1: Synthesis of 6-(1-cyclopropyl-1H-pyrazol-4-yl)quinoline-4-carboxylic acid. To the solution of 1-cyclopropyl-4-(4,4,5,5-tetramethyl-1,3,2-dioxaborolan-2-yl)-1H-pyrazole (100 mg, 0.42 mmol, 1.0 equiv) in Dioxane:water (05:02 mL), was added 6-bromoquinoline-4-carboxylic acid (108 mg, 0.42 mmol, 1.0 equiv), Na₂CO₃ (90 mg, 0.84 mmol, 2.0 equiv) followed by the addition of Pd(PPh₃)₂Cl₂ (15 mg, 0.021 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(1-cyclopropyl-1H-pyrazol-4-yl)quinoline-4-carboxylic acid (100 mg, 84% Yield) as an off white solid.

LCMS 280.0 [M+H]⁺

Step 2: Synthesis of (S)—N-(2-(2-cyano-4,4-difluoropyrrolidin-1-yl)-2-oxoethyl)-6-(1-cyclopropyl-1H-pyrazol-4-yl)quinoline-4-carboxamide. To a stirred solution of 6-(1-cyclopropyl-1H-pyrazol-4-yl)quinoline-4-carboxylic acid (100 mg, 0.35 mmol, 1.0 equiv) in DMF (05 mL), was added (S)-4,4-difluoro-1-glycylpyrrolidine-2-carbonitrile hydrochloride (81 mg, 0.35 mmol, 1.0 equiv), HOBT (70 mg, 0.52 mmol, 1.5 equiv) and EDC.HCl (101 mg, 0.52 mmol, 1.5 equiv). The mixture was allowed to stir at RT for 10 min. Triethyl amine (0.14 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous Na₂SO₄ and concentrated. The crude product obtained was purified reversed phase HPLC to obtain (S)—N-(2-(2-cyano-4,4-difluoropyrrolidin-1-yl)-2-oxoethyl)-6-(1-cyclopropyl-1H-pyrazol-4-yl)quinoline-4-carboxamide (05 mg, 03% Yield) as a yellow solid.

LCMS 451.3 [M+H]⁺

$^1$H NMR (400 MHz, DMSO-d₆) δ 9.17-9.23 (m, 1H), 8.89 (d, J=4.38 Hz, 1H), 8.72 (s, 1H), 8.48 (s, 1H), 7.99-8.16 (m, 3H), 7.51 (d, J=4.39 Hz, 1H), 5.25 (d, J=6.58 Hz, 1H), 4.35 (d, J=16.22 Hz, 2H), 4.11-4.22 (m, 2H), 3.17 (s, 1H), 2.84-2.91 (m, 2H), 1.10-1.16 (m, 4H).

Example 5-12

Synthesis of (S)—N-(2-(2-cyano-4,4-difluoropyrrolidin-1-yl)-2-oxoethyl)-6-(indolin-5-yl)quinoline-4-carboxamide

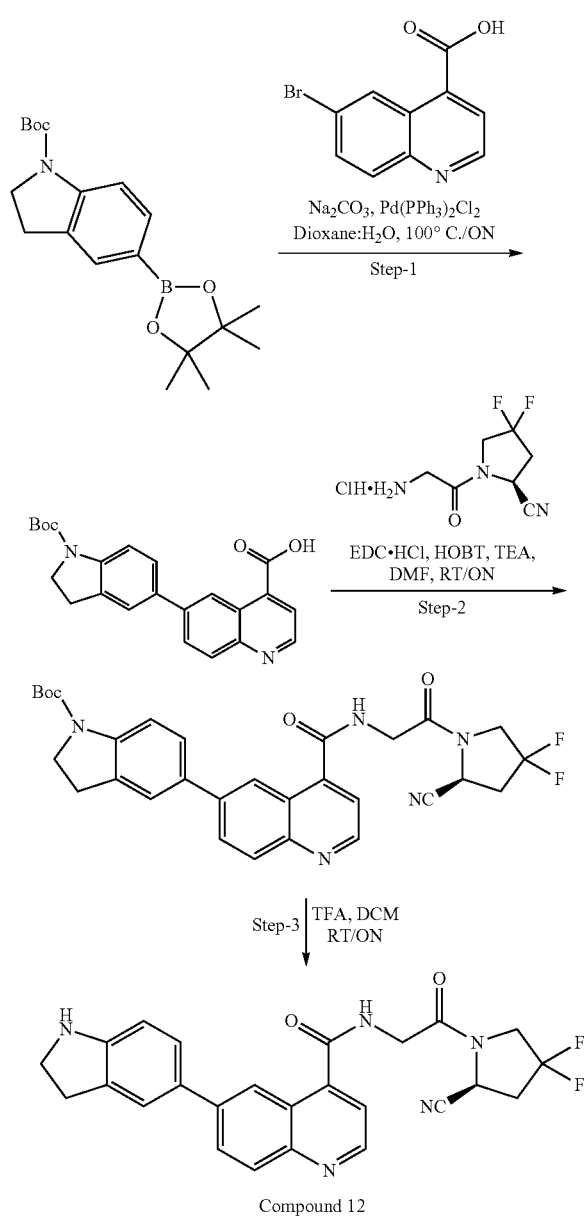

Compound 12

Step 1: Synthesis of 6-(1-(tert-butoxycarbonyl)indolin-5-yl)quinoline-4-carboxylic acid. To the solution of tert-butyl 5-(4,4,5,5-tetramethyl-1,3,2-dioxaborolan-2-yl)indoline-1-carboxylate (100 mg, 0.28 mmol, 1.0 equiv) in Dioxane: water (05:02 mL), was added 6-bromoquinoline-4-carboxylic acid (73 mg, 0.28 mmol, 1.0 equiv), $Na_2CO_3$ (60 mg, 0.56 mmol, 2.0 equiv) followed by the addition of Pd(PPh$_3$)$_2$Cl$_2$ (10 mg, 0.014 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(1-(tert-butoxycarbonyl)indolin-5-yl)quinoline-4-carboxylic acid (100 mg, 88% Yield) as an off white solid.
LCMS 391.2 [M+H]$^+$ Step 2: Synthesis of tert-butyl (S)-5-(4-((2-(2-cyano-4,4-difluoropyrrolidin-1-yl)-2-oxoethyl)carbamoyl)quinolin-6-yl)indoline-1-carboxylate. To a stirred solution of 6-(1-(tert-butoxycarbonyl)indolin-5-yl)quinoline-4-carboxylic acid (100 mg, 0.25 mmol, 1.0 equiv) in DMF (05 mL), was added (S)-4,4-difluoro-1-glycylpyrrolidine-2-carbonitrile hydrochloride (58 mg, 0.25 mmol, 1.0 equiv), HOBT (50 mg, 0.37 mmol, 1.5 equiv) and EDC.HCl (72 mg, 0.37 mmol, 1.5 equiv). The mixture was allowed to stir at RT for 10 min. Triethyl amine (0.10 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous $Na_2SO_4$ and concentrated. The crude product obtained was purified by reversed phase HPLC to obtain tert-butyl (S)-5-(4-((2-(2-cyano-4,4-difluoropyrrolidin-1-yl)-2-oxoethyl)carbamoyl)quinolin-6-yl)indoline-1-carboxylate (20 mg, 14% Yield) as an yellow solid.
LCMS 562.3 [M+H]$^+$
$^1$H NMR (400 MHz, DMSO-d$_6$) δ 9.19 (s, 1H), 8.95 (d, J=3.95 Hz, 1H), 8.71 (br. s., 1H), 8.03-8.29 (m, 3H), 7.82 (s, 1H), 7.71 (d, J=5.70 Hz, 1H), 7.56 (d, J=4.38 Hz, 1H), 5.19 (d, J=7.02 Hz, 1H), 4.24-4.32 (m, 2H), 4.09-4.24 (m, 2H), 3.97 (t, J=8.77 Hz, 2H), 3.18 (d, J=7.89 Hz, 2H), 2.86 (d, J=19.29 Hz, 2H), 1.53 (br. s., 9H).

Step 3: Synthesis of (S)—N-(2-(2-cyano-4,4-difluoropyrrolidin-1-yl)-2-oxoethyl)-6-(indolin-5-yl)quinoline-4-carboxamide. To a stirred solution of tert-butyl (S)-5-(4-((2-(2-cyano-4,4-difluoropyrrolidin-1-yl)-2-oxoethyl)carbamoyl)quinolin-6-yl)indoline-1-carboxylate (20 mg, 0.035 mmol, 1.0 equiv) in DCM (5 mL), was added trifloroacetic acid (0.2 mL). The mixture was allowed to stir at RT overnight. Product formation was confirmed by LCMS. The reaction mixture was concentrated and the crude was crystallized in diethyl ether to obtain (S)—N-(2-(2-cyano-4,4-difluoropyrrolidin-1-yl)-2-oxoethyl)-6-(indolin-5-yl)quinoline-4-carboxamide (05 mg, 31% Yield) as a light brown solid.
LCMS 462.4 [M+H]$^+$
$^1$H NMR (400 MHz, DMSO-d$_6$) δ 9.17 (br. s., 1H), 8.93 (d, J=4.39 Hz, 1H), 8.66 (s, 1H), 8.05-8.18 (m, 2H), 7.77 (br. s., 1H), 7.51-7.64 (m, 2H), 6.87 (br. s., 1H), 5.19 (d, J=8.33 Hz, 1H), 4.35 (br. s., 1H), 4.27 (br. s., 1H), 4.06-4.21 (m, 2H), 3.57 (d, J=7.89 Hz, 2H), 3.05-3.17 (m, 2H), 2.86 (d, J=11.84 Hz, 2H).

Example 5-13

Synthesis of (S,E)-N-(2-(2-cyano-4,4-difluoropyrrolidin-1-yl)-2-oxoethyl)-6-(4-methylpent-1-en-1-yl)quinoline-4-carboxamide

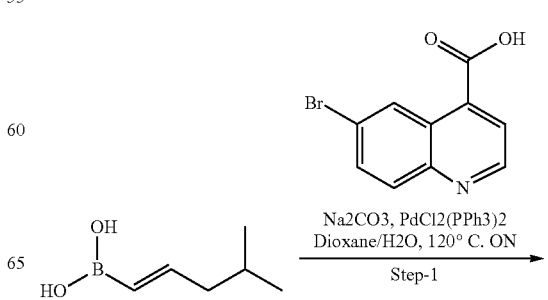

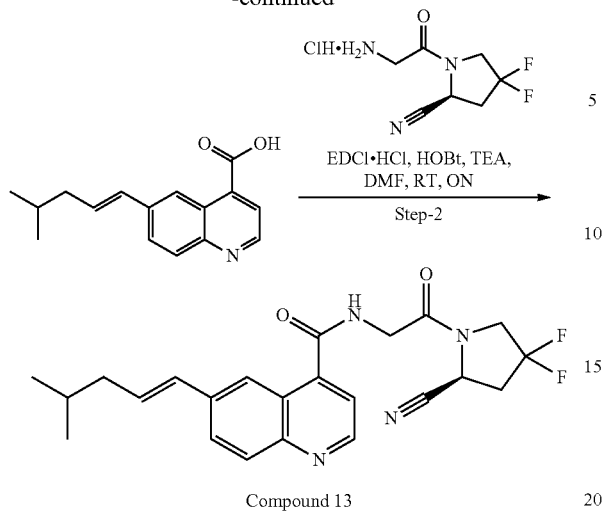

Compound 13

Step 1: Synthesis of (E)-6-(4-methylpent-1-en-1-yl)quinoline-4-carboxylic acid. To a solution of (E)-(4-methylpent-1-en-1-yl)boronic acid (0.1 g, 0.781 mmol, 1.0 equiv) in dioxane (4 mL) and water (2 mL) was added 6-bromoquinoline-4-carboxylic acid (0.19 g, 0.781 mmol, 1.0 equiv), $Na_2CO_3$ (0.165 g, 1.562 mmol, 2.0 equiv) and the resulting mixture was purged with $N_2$ gas for 10 min, followed by the addition of $Pd(PPh_2)Cl_2$ (0.027 g, 0.039 mmol. 0.05 equiv). The resulting reaction mixture was heated at 120° C. for overnight. Product formation was confirmed by LCMS. After the completion of reaction the reaction mixture was diluted with water (30 mL) and washed with ethyl acetate (50 mL×2). Aqueous layer was separated and dried over lyophilizer to obtain (E)-6-(4-methylpent-1-en-1-yl)quinoline-4-carboxylic acid (0.120 g, 62% Yield) as a yellow solid.

LCMS 256.0 [M+H]+

$^1$H NMR (400 MHz, DMSO-$d_6$) δ 8.71 (d, J=4.38 Hz, 1H) 8.59 (s, 1H) 7.74-7.89 (m, 2H) 7.41-7.52 (m, 1H) 6.51 (s, 1H) 6.34-6.46 (m, 1H) 2.13 (t, J=6.80 Hz, 2H) 1.73-1.79 (m, 1H) 0.94 (d, J=7.02 Hz, 5H) 0.75-0.89 (m, 1H).

Step 2: Synthesis of (S,E)-N-(2-(2-cyano-4,4-difluoropyrrolidin-1-yl)-2-oxoethyl)-6-(4-methylpent-1-en-1-yl)quinoline-4-carboxamide. To a stirred solution of (E)-6-(4-methylpent-1-en-1-yl)quinoline-4-carboxylic acid (0.1 g, 0.308 mmol, 1.0 equiv) in DMF (5 mL), was added (S)-4,4-difluoro-1-glycylpyrrolidine-2-carbonitrile hydrochloride (0.087 g, 0.390 mmol, 1.0 equiv), EDCI.HCl (0.089 g, 0.468 mmol, 1.2 equiv) and HOBt (0.063 g, 0.468 mmol, 1.2 equiv) followed by the addition of TEA (0.1 mL). The resulting reaction mixture was allowed to stir at RT for overnight. Product formation was confirmed by LCMS and TLC. After completion of reaction, the reaction mixture was diluted with water (20 mL) and extracted with ethyl acetate (50 mL×2). Combined organic extracts were washed with water (20 mL×4), dried over anhydrous $Na_2SO_4$ and concentrated. The crude product was purified by flash chromatography (0-5% MeOH in DCM as an eluent) to obtain (S,E)-N-(2-(2-cyano-4,4-difluoropyrrolidin-1-yl)-2-oxoethyl)-6-(4-methylpent-1-en-1-yl)quinoline-4-carboxamide (0.016 g, 10% Yield) as an off-white solid.

LCMS 427.4 [M+H]+

$^1$H NMR (400 MHz, DMSO-$d_6$) δ 9.13 (d, J=6.14 Hz, 1H) 8.90 (d, J=4.39 Hz, 1H) 8.32 (s, 1H) 7.84-8.09 (m, 2H) 7.52 (d, J=4.38 Hz, 1H) 6.46-6.65 (m, 2H) 5.16 (t, J=7.02 Hz, 1H) 4.09-4.38 (m, 4H) 2.85 (d, J=17.98 Hz, 2H) 2.15 (t, J=6.36 Hz, 2H) 1.71-1.82 (m, 1H) 0.95 (d, J=6.58 Hz, 3H) 0.86 (br. s., 3H).

Example 5-14

Synthesis of (S,E)-N-(2-(2-cyano-4,4-difluoropyrrolidin-1-yl)-2-oxoethyl)-6-styrylquinoline-4-carboxamide Compound 14

Step 1: Synthesis of (E)-6-styrylquinoline-4-carboxylic acid. To a solution of 6-bromoquinoline-4-carboxylic acid (0.2 g, 0.8 mmol, 1.0 equiv) and (E)-2-styryl)-4,4,5,5-tetramethyl-1,3,2-dioxaborolane (0.22 g, 0.96 mmol, 1.2 equiv) in dioxane (10 ml) and water (2 ml) was added in $K_2CO_3$ (0.169 g, 1.6 mmol, 2.0 equiv) and the mixture was purged with $N_2$ gas for 10 min, followed by the addition of $Pd(PPh_2)Cl_2$ (0.028 g, 0.04 mmol. 0.05 equiv). The resulting reaction mixture was heated at 100° C. for overnight. Product formation was confirmed by LCMS. After the completion of reaction the reaction mixture was diluted with water (30 mL) and washed with ethyl acetate (50 mL×2). Aqueous layer was separated and dried over lyophilizer to obtain (E)-6-styrylquinoline-4-carboxylic acid (0.300 g, Quant. Yield) as a yellow solid.

LCMS 276.0 [M+H]+

Step 2: Synthesis of (S,E)-N-(2-(2-cyano-4,4-difluoropyrrolidin-1-yl)-2-oxoethyl)-6-styrylquinoline-4-carboxamide. To a stirred solution of (E)-6-styrylquinoline-4-carboxylic acid (0.3 g, 1.08 mmol, 1.0 equiv) in DMF (7 mL), was added (S)-4,4-difluoro-1-glycylpyrrolidine-2-carbonitrile hydrochloride (0.336 g, 0.51 mmol, 1.5 equiv), EDCI.HCl (0.312 g, 1.63 mmol, 1.5 equiv) and HOBt (0.220 g, 1.63 mmol, 1.5 equiv) followed by the addition of triethylamine (0.32 g, 3.24 mmol, and 3.0 equiv). The resulting reaction mixture was allowed to stir at RT for overnight. Product formation was confirmed by LCMS. After completion of reaction, the reaction mixture was diluted with water (25 mL) and extracted with ethyl acetate (50 mL×2). Combined organic extracts were washed with water (20 mL×4), dried over anhydrous Na$_2$SO$_4$ and concentrated under reduced pressure. The crude product was purified by flash chromatography (0-5% MeOH in DCM as an eluent) followed by reversed phase HPLC purification to obtain (S,E)-N-(2-(2-cyano-4,4-difluoropyrrolidin-1-yl)-2-oxoethyl)-6-styrylquinoline-4-carboxamide (0.025 g, 5.2% Yield) as a white solid.

LCMS 447.4 [M+H]$^+$ $^1$H NMR (400 MHz, DMSO-d$_6$) δ 9.18 (t, J=6.14 Hz, 1H) 8.93 (d, J=4.39 Hz, 1H) 8.59 (s, 1H) 8.14 (dd, J=8.77, 1.75 Hz, 1H) 8.07 (d, J=8.77 Hz, 1H) 7.71 (d, J=7.45 Hz, 2H) 7.50-7.64 (m, 2H) 7.37-7.49 (m, 2H) 7.26-7.36 (m, 1H) 5.23 (dd, J=9.21, 2.19 Hz, 1H) 4.11-4.41 (m, 4H) 2.96 (br. s., 1H) 2.87 (d, J=16.66 Hz, 1H).

Example 5-15

Synthesis of (S)—N-(2-(2-cyano-4,4-difluoropyrrolidin-1-yl)-2-oxoethyl)-6-(6-(dimethylamino)naphthalen-2-yl)quinoline-4-carboxamide

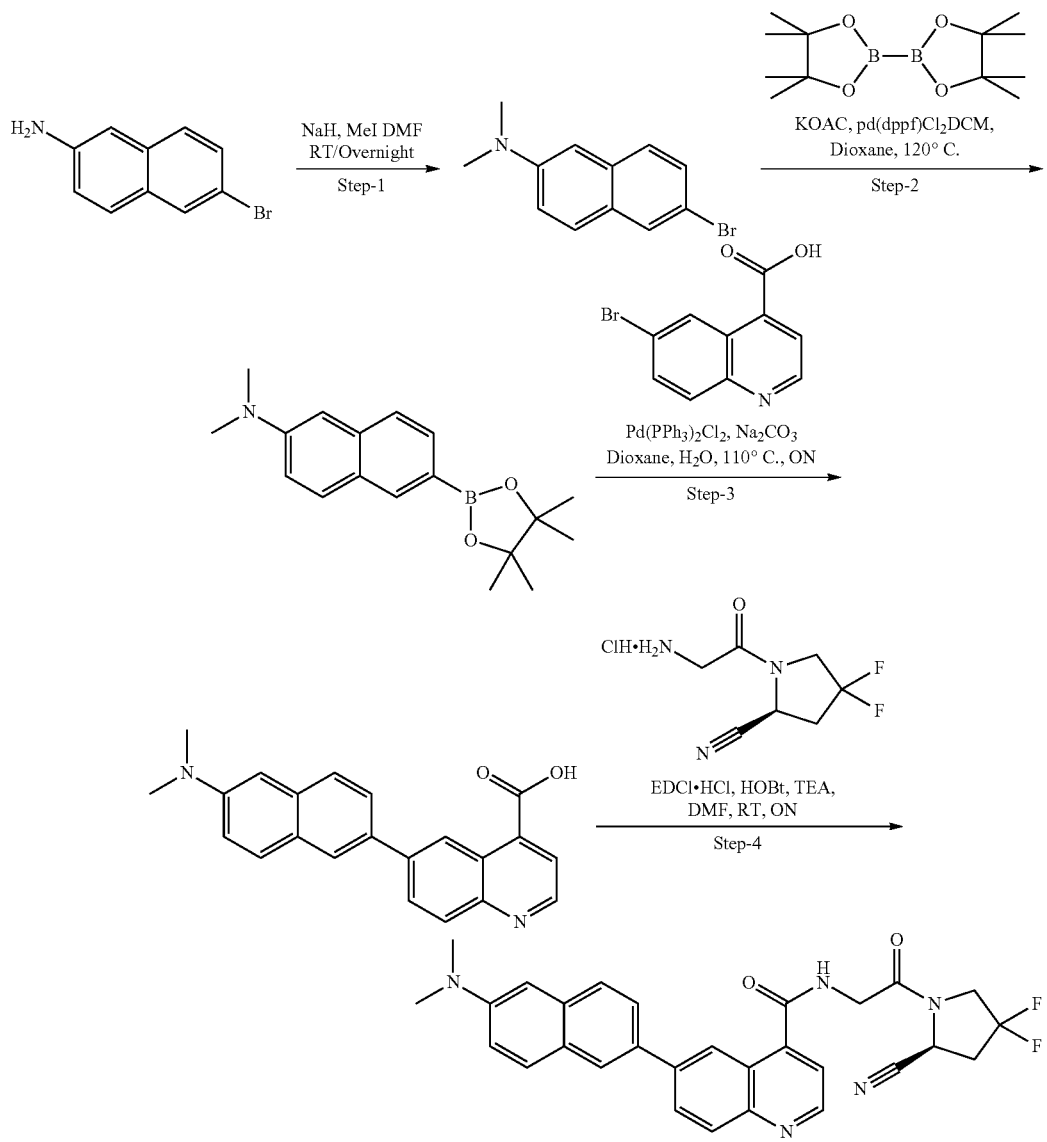

Compound 15

Step 1: Synthesis of 6-bromo-N,N-dimethylnaphthalen-2-amine. To a stirred solution 6-bromonaphthalen-2-amine (0.25 g, 1.1261 mmol, 1.0 equiv) in DMF (5 mL), was added NaH (0.053 g, 2.252 mmol, 1.1 equiv) at 0° C. Methyl Iodide (0.1 ml, 2.252 mmol, 2.0 equiv) was added and the mixture was allowed to stir at RT for overnight. Product formation was confirmed by TLC. After completion of reaction, the reaction mixture was diluted with water solution (20 mL) and extracted with ethyl acetate (50 mL×2). Combined organic extracts were washed with water (20 mL×4), dried over anhydrous Na$_2$SO$_4$ and concentrated. The crude product was purified by flash chromatography (0-10% ethyl acetate in hexane as an eluent) to obtain 6-bromo-N,N-dimethylnaphthalen-2-amine (0.100 g, 35.7% Yield) as an off-white solid.

LCMS 249.9 [M+H]$^+$ $^1$H NMR (400 MHz, DMSO-d$_6$) δ 7.94 (s, 1H) 7.72 (d, J=9.21 Hz, 1H) 7.62 (d, J=8.77 Hz, 1H) 7.42 (dd, J=8.77, 1.75 Hz, 1H) 7.27 (dd, J=8.99, 2.41 Hz, 1H) 6.94 (d, J=2.19 Hz, 1H) 3.00 (s, 6H).

Step 2: Synthesis of N,N-dimethyl-6-(4,4,5,5-tetramethyl-1,3,2-dioxaborolan-2-yl)naphthalen-2-amine. To a solution of 6-bromo-N,N-dimethylnaphthalen-2-amine (0.2 g, 0.80 mmol, 1.0 equiv) in dioxane (4 mL) was added 4,4,4',4',5,5,5',5'-octamethyl-2,2'-bi(1,3,2-dioxaborolane) (0.20 g, 0.80 mmol, 1.0 equiv), KOAC (0.235 g, 1.2 mmol, 3.0 equiv) and the mixture purged with N$_2$ gas for 10 min, followed by the addition of PdCl$_2$(dppf).DCM (0.032 g, 0.02 mmol. 0.05 equiv). The resulting reaction mixture was heated at 120° C. for overnight. Product formation was confirmed by LCMS. After the completion of reaction, the mixture was diluted with water (20 mL) and extracted with ethyl acetate (50 mL×2). Combined organic extracts were washed with water (20 mL×4), dried over anhydrous Na$_2$SO$_4$ and concentrated under reduced pressure. The crude product was purified by flash chromatography (0-10% ethyl acetate in hexane as an eluent) to obtain N,N-dimethyl-6-(4,4,5,5-tetramethyl-1,3,2-dioxaborolan-2-yl)naphthalen-2-amine (0.12 g, 50.0% yield) as an off-white solid.

LCMS 298.2 [M+H]$^+$ $^1$H NMR (400 MHz, DMSO-d$_6$) δ 8.09 (s, 1H) 7.80 (d, J=9.21 Hz, 1H) 7.60 (d, J=8.33 Hz, 1H) 7.53 (d, J=8.33 Hz, 1H) 7.21 (dd, J=9.21, 2.19 Hz, 1H) 6.90 (s, 1H) 3.03 (s, 6H) 1.31 (s, 9H).

Step 3: Synthesis of 6-(6-(dimethylamino)naphthalen-2-yl)quinoline-4-carboxylic acid. To a solution of N,N-dimethyl-6-(4,4,5,5-tetramethyl-1,3,2-dioxaborolan-2-yl)naphthalen-2-amine (0.1 g, 0.335 mmol, 1.0 equiv) in dioxane (5 mL) was added 6-bromoquinoline-4-carboxylic acid (0.084 g, 0.33 mmol, 1.0 equiv), Na$_2$CO$_3$ (0.071 g, 0.671 mmol, 2.0 equiv) in water (1 ml) and the mixture purged with N$_2$ gas for 10 min, followed by the addition of Pd(PPh$_3$)$_2$Cl$_2$ (0.011 g, 0.016 mmol. 0.05 equiv). The resulting reaction mixture was heated at 110° C. for overnight. Product formation was confirmed by LCMS. After the completion of reaction the reaction mixture was diluted with water (30 mL) and washed with ethyl acetate (50 mL×2). Aqueous layer was separated and dried over lyophilizer to obtain 6-(6-(dimethylamino)naphthalen-2-yl)quinoline-4-carboxylic acid (0.1 g, 87% yield) as a yellow solid.

LCMS 343.1 [M+H]$^+$ $^1$H NMR (400 MHz, DMSO-d$_6$) δ 9.08 (s, 1H) 8.72-8.84 (m, 2H) 7.96-8.16 (m, 3H) 7.74-7.92 (m, 2H) 7.39-7.55 (m, 2H) 7.28 (d, J=8.77 Hz, 1H) 3.11 (s, 6H).

Step 4: Synthesis of (S)—N-(2-(2-cyano-4,4-difluoropyrrolidin-1-yl)-2-oxoethyl)-6-(6-(dimethylamino)naphthalen-2-yl)quinoline-4-carboxamide. To a stirred solution of 6-(6-(dimethylamino)naphthalen-2-yl)quinoline-4-carboxylic acid (0.1 g, 0.291 mmol, 1.0 equiv) in DMF (4 mL), was added (S)-4,4-difluoro-1-glycylpyrrolidine-2-carbonitrile hydrochloride (0.065 g, 0.291 mmol, 1.0 equiv), EDCI.HCl (0.083 g, 0.437 mmol, 1.2 equiv) and HOBt (0.059 g, 0.437 mmol, 1.2 equiv) followed by the TEA (0.2 mL). The resulting reaction mixture was allowed to stir at RT for overnight. Product formation was confirmed by LCMS and TLC. After completion of reaction, the reaction mixture was diluted with water (20 mL) and extracted with ethyl acetate (50 mL×2). Combined organic extracts were washed with water (20 mL×4), dried over anhydrous Na$_2$SO$_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-(dimethylamino)naphthalen-2-yl)quinoline-4-carboxamide (0.030 g, 4% Yield) as an off-white solid.

LCMS 514.4 [M+H]$^+$ $^1$H NMR (400 MHz, DMSO-d$_6$) δ9.22 (t, J=5.92 Hz, 1H) 8.96 (d, J=4.39 Hz, 1H) 8.73-8.86 (m, 1H) 8.45 (s, 1H) 8.32 (d, J=3.95 Hz, 1H) 8.17 (d, J=9.21 Hz, 1H) 7.84-8.11 (m, 2H) 7.81 (d, J=8.77 Hz, 1H) 7.58 (d, J=4.38 Hz, 1H) 7.27 (dd, J=9.21, 2.63 Hz, 1H) 6.97 (br. s., 1H) 5.22 (d, J=9.21 Hz, 1H) 4.11-4.41 (m, 4H) 3.17 (s., 6H) 2.76-2.95 (m, 2H).

Example 5-16

Synthesis of (S)—N-(2-(2-cyano-4,4-difluoropyrrolidin-1-yl)-2-oxoethyl)-2'-oxo-1',2',3',4'-tetrahydro-[6,6'-biquinoline]-4-carboxamide

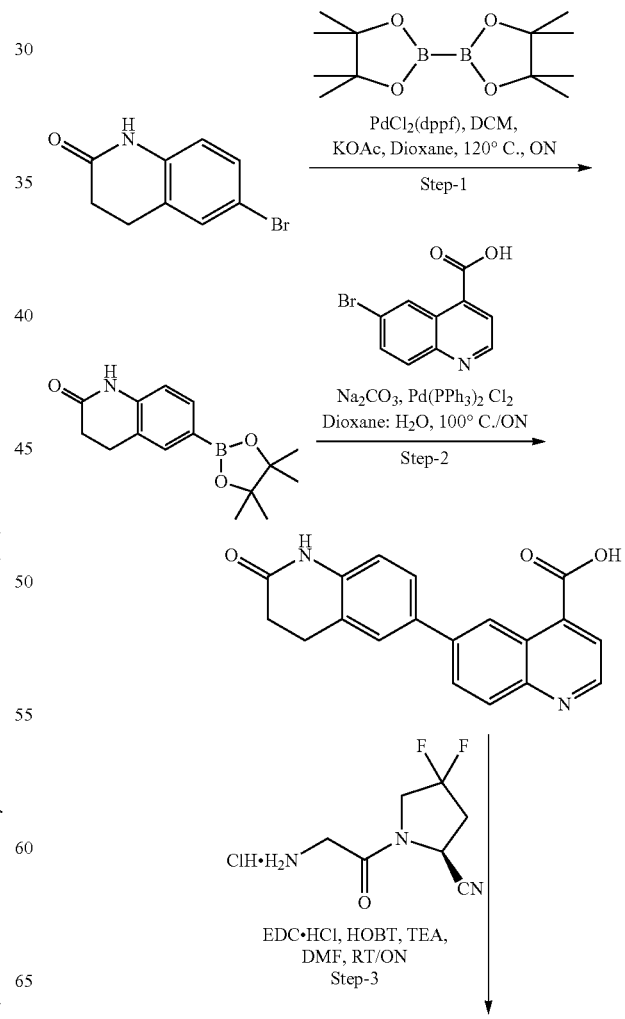

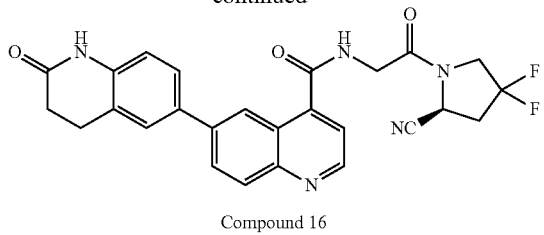

Compound 16

Step 1: Synthesis of 6-(4,4,5,5-tetramethyl-1,3,2-dioxaborolan-2-yl)-3,4-dihydroquinolin-2(1H)-one. To a solution of 6-bromo-3,4-dihydroquinolin-2(1H)-one (500 mg, 2.21 mmol, 1.0 equiv) in Dioxane (10 mL) was added 4,4,4',4',5,5,5',5'-octamethyl-2,2'-bi(1,3,2-dioxaborolane) (561 mg, 2.21 mmol, 1.0 equiv), KOAc (650 mg, 6.63 mmol, 3.0 equiv) and the mixture purged with $N_2$ gas for 10 min, followed by the addition of $PdCl_2(dppf)$.DCM (90 mg, 0.11 mmol. 0.05 equiv). The resulting reaction mixture was heated at 120° C. for overnight. After the completion of reaction (monitored by TLC & LCMS), the mixture was diluted with water (100 mL) and extracted with ethyl acetate (2×100 mL). Combined organic extracts were washed with water (50 mL×2), dried over anhydrous $Na_2SO_4$ and concentrated to obtain 6-(4,4,5,5-tetramethyl-1,3,2-dioxaborolan-2-yl)-3,4-dihydroquinolin-2(1H)-one (300 mg, 50% Yield) as an off white solid.

LCMS 274.0 $[M+H]^+$ $^1$H NMR (400 MHz, DMSO-$d_6$) δ 10.23 (s, 1H), 7.39-7.52 (m, 2H), 6.83 (d, J=7.89 Hz, 1H), 2.87 (t, J=7.67 Hz, 2H), 2.39-2.47 (m, 2H), 1.16-1.35 (m, 12H).

Step 2: Synthesis of 2'-oxo-1',2',3',4'-tetrahydro-[6,6'-biquinoline]-4-carboxylic acid. To the solution of 6-(4,4,5,5-tetramethyl-1,3,2-dioxaborolan-2-yl)-3,4-dihydroquinolin-2(1H)-one (100 mg, 0.36 mmol, 1.0 equiv) in Dioxane: water (5:2 mL), was added 6-bromoquinoline-4-carboxylic acid (92 mg, 0.36 mmol, 1.0 equiv), $Na_2CO_3$ (77 mg, 0.72 mmol, 2.0 equiv) followed by the addition of $Pd(PPh_3)_2Cl_2$ (13 mg, 0.018 mmol, 0.05 equiv). The resulting reaction mixture was heated at 100° C. for overnight. Product formation was confirmed by LCMS, after the completion of reaction the reaction mixture was diluted with water (30 mL) and washed with ethyl acetate (50 mL×2). Aqueous layer was separated and dried over lyophilizer to obtain 2'-oxo-1',2',3',4'-tetrahydro-[6,6'-biquinoline]-4-carboxylic acid (100 mg, 86% Yield) as an off white solid.

LCMS 319.1 $[M+H]^+$

Step 3: Synthesis of (S)—N-(2-(2-cyano-4,4-difluoropyrrolidin-1-yl)-2-oxoethyl)-2'-oxo-1',2',3',4'-tetrahydro-[6,6'-biquinoline]-4-carboxamide. To a stirred solution of 2'-oxo-1',2',3',4'-tetrahydro-[6,6'-biquinoline]-4-carboxylic acid (100 mg, 0.31 mmol, 1.0 equiv) in DMF (05 mL), was added (S)-4,4-difluoro-1-glycylpyrrolidine-2-carbonitrile hydrochloride (70 mg, 0.31 mmol, 1.0 equiv), HOBT (63 mg, 0.46 mmol, 1.5 equiv) and EDC.HCl (89 mg, 0.46 mmol, 1.5 equiv) followed by the addition of triethyl amine (0.10 mL). The resulting reaction mixture was allowed to stir at RT for overnight. Product formation was confirmed by LCMS and TLC. After completion of reaction, the reaction mixture was diluted with water (20 mL) and extracted with ethyl acetate (50 mL×2). Combined organic extracts were washed with water (20 mL×4), dried over anhydrous $Na_2SO_4$ and concentrated. The crude product obtained was purified reversed phase HPLC to obtain (S)—N-(2-(2-cyano-4,4-difluopyrrolidin-1-yl)-2-oxoethyl)-2'-oxo-1',2',3',4'-tetrahydro-[6,6'-biquinoline]-4-carboxamide (05 mg, 3% Yield) as a yellow solid.

LCMS 490.4 $[M+H]^+$ $^1$H NMR (400 MHz, DMSO-$d_6$) δ 10.24 (s, 1H), 9.19 (br. s., 1H), 8.95 (d, J=3.95 Hz, 1H), 8.71 (s, 1H), 8.11-8.22 (m, 2H), 7.76-7.84 (m, 1H), 7.68 (d, J=7.02 Hz, 1H), 7.56 (d, J=4.39 Hz, 1H), 7.00 (d, J=7.89 Hz, 1H), 5.19 (d, J=9.21 Hz, 1H), 4.35 (br. s., 2H), 4.08-4.22 (m, 2H), 2.95-3.07 (m, 2H), 2.86 (d, J=16.66 Hz, 2H), 2.67 (br. s., 2H).

Example 5-17

Synthesis of (S)—N-(2-(2-cyano-4,4-difluoropyrrolidin-1-yl)-2-oxoethyl)-6-(6-oxo-1,6-dihydropyridin-3-yl)quinoline-4-carboxamide

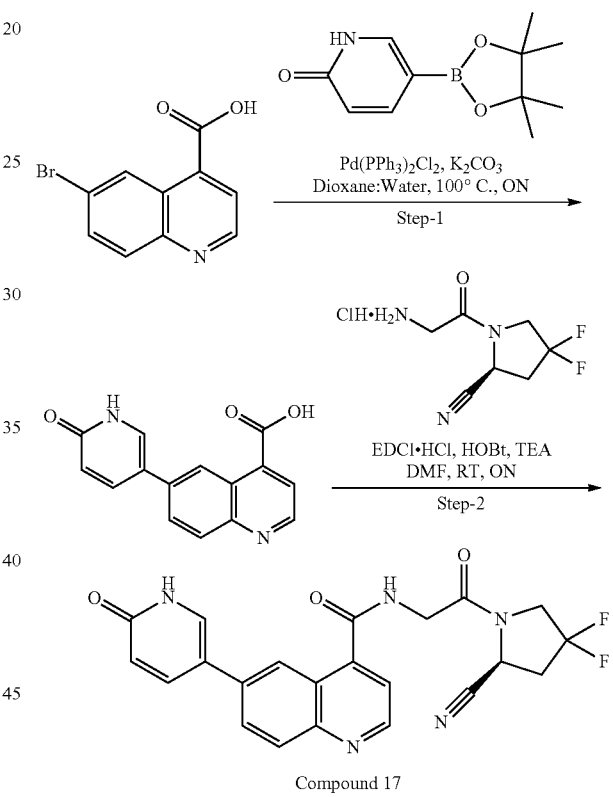

Compound 17

Step 1: Synthesis of 6-(6-hydroxypyridin-3-yl)quinoline-4-carboxylic acid. To a stirred solution of 6-bromoquinoline-4-carboxylic acid (0.100 g, 0.396 mmol, 1.0 equiv) in Dioxane (4 mL) was added 5-(4,4,5,5-tetramethyl-1,3,2-dioxaborolan-2-yl)pyridin-2(1H)-one (0.131 g, 5.595 mmol, 1.5 equiv) and a solution of $K_2CO_3$ (0.109 g, 0.793 mmol, 2.0 equiv) in water (1 mL), and the mixture was purged with $N_2$ gas for 10 min, followed by the addition of $Pd(PPh_3)Cl_2$ (0.013 g, 0.019 mmol. 0.05 equiv). The resulting reaction mixture was heated at 100° C. for overnight. Product formation was confirmed by LCMS. After the completion of reaction the reaction mixture was diluted with water (30 mL) washed with ethyl acetate (20 mL×2). Aqueous layer was separated and freeze dried over lyophilizer to obtain 6-(6-oxo-1,6-dihydropyridin-3-yl)quinoline-4-carboxylic acid (0.150 g, 94% Yield) as a yellow solid.

LCMS 266.9 $[M+H]^+$ $^1$H NMR (400 MHz, DMSO-d$_6$) δ 8.89 (d, J=1.75 Hz, 1H) 8.69-8.80 (m, 1H) 7.91-7.98 (m, 1H) 7.76-7.91 (m, 3H) 7.49 (d, J=4.38 Hz, 1H) 7.27-7.45 (m, 1H) 6.46 (d, J=9.21 Hz, 1H) 6.29 (d, J=9.21 Hz, 1H).

Step 2: Synthesis of (S)—N-(2-(2-cyano-4,4-difluoropyrrolidin-1-yl)-2-oxoethyl)-6-(6-oxo-1,6-dihydropyridin-3-yl)quinoline-4-carboxamide. To a stirred solution of 6-(6-hydroxypyridin-3-yl)quinoline-4-carboxylic acid (0.250 g, 0.939 mmol, 1.0 equiv) in DMF (5 mL), was added (S)-4,4-difluoro-1-glycylpyrrolidine-2-carbonitrile hydrochloride (0.317 g, 1.409 mmol, 1.5 equiv), HOBt (0.190 g, 1.409 mmol, 1.5 equiv) and EDC.HCl (0.269 g, 1.409 mmol, 1.5 equiv) followed by the addition of TEA (0.27 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous Na$_2$SO$_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-oxo-1,6-dihydropyridin-3-yl)quinoline-4-carboxamide (0.010 g, 2.43% Yield) as a white solid.

LCMS 438.4 [M+H]$^+$ $^1$H NMR (400 MHz, DMSO-d$_6$) δ 9.16 (d, J=6.14 Hz, 1H) 8.93 (d, J=3.95 Hz, 1H) 8.69 (d, J=1.32 Hz, 1H) 7.97-8.21 (m, 3H) 7.55 (d, J=4.38 Hz, 1H) 6.81 (d, J=9.21 Hz, 1H) 6.53 (d, J=9.21 Hz, 1H) 5.15-5.31 (m, 1H) 4.24-4.49 (m, 2H) 4.08-4.24 (m, 1H) 2.96 (br. s., 1H) 2.88 (d, J=17.10 Hz, 2H).

Example 5-18

Synthesis of (S)—N-(2-(2-cyano-4,4-difluoropyrrolidin-1-yl)-2-oxoethyl)-6-(1-oxo-1,2,3,4-tetrahydroisoquinolin-6-yl)quinoline-4-carboxamide

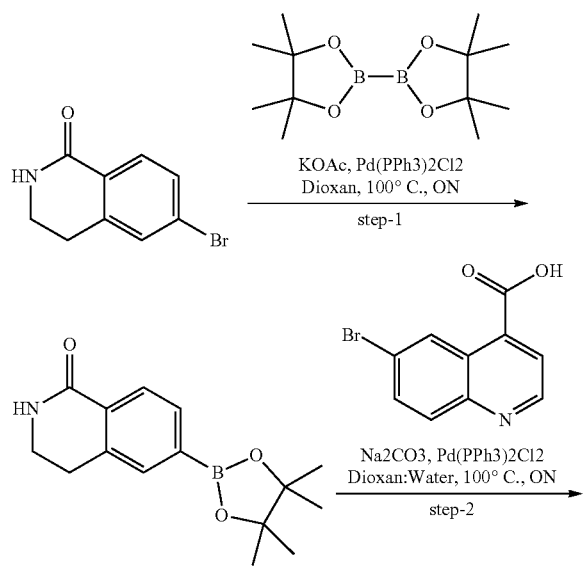

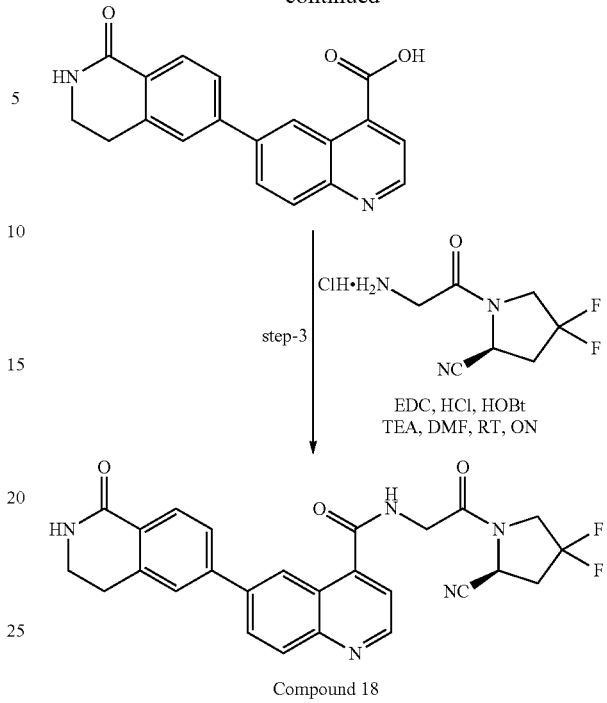

Compound 18

Step 1: Synthesis of 6-(4,4,5,5-tetramethyl-1,3,2-dioxaborolan-2-yl)-3,4-dihydroisoquinolin-1(2H)-one. To a solution of 6-bromo-3,4-dihydroisoquinolin-1(2H)-one (1.00 g, 4.424 mmol, 1.0 equiv) in Dioxane (30 mL) was added 4,4,4',4',5,5,5',5'-octamethyl-2,2'-bi(1,3,2-dioxaborolane) (1.360 g, 5.309 mmol, 1.2 equiv), KOAc (0.868 g, 8.849 mmol, 2.0 equiv) followed by the addition of PdCl$_2$(dppf).DCM (0.181 g, 0.221 mmol. 0.05 equiv). The resulting reaction mixture was heated at 100° C. for overnight. After the completion of reaction (monitored by TLC & LCMS), the reaction mixture was diluted with water (50 mL) and extracted with ethyl acetate (2×100 mL). Combined organic was dried over anhydrous Na$_2$SO$_4$ and concentrated. The crude product was purified by flash chromatography (0-60% Ethyl acetate in hexane as an eluent) to obtain 6-(4,4,5,5-tetramethyl-1,3,2-dioxaborolan-2-yl)-3,4-dihydroisoquinolin-1(2H)-one (0.350 g, 29% Yield) as an off white solid.

LCMS 274.1 [M+H]$^+$ $^1$H NMR (400 MHz, DMSO-d$_6$) δ7.99 (br. s., 1H) 7.83 (d, J=7.45 Hz, 1H) 7.54-7.68 (m, 2H) 3.34-3.44 (m, 2H) 2.91 (t, J=6.36 Hz, 2H) 1.30 (s, 12H).

Step 2: Synthesis of 6-(1-oxo-1,2,3,4-tetrahydroisoquinolin-6-yl)quinoline-4-carboxylic acid. To the solution of 6-bromoquinoline-4-carboxylic acid (0.250 g, 0.992 mmol, 1.0 equiv) was added 6-(4,4,5,5-tetramethyl-1,3,2-dioxaborolan-2-yl)-3,4-dihydroisoquinolin-1(2H)-one (0.325 g, 1.190 mmol, 1.2 equiv) in Dioxane:water (10:05 mL), Na$_2$CO$_3$ (0.315 g, 2.976 mmol, 3.0 equiv) followed by the addition of Pd(PPh$_3$)$_2$Cl$_2$ (0.035 g, 0.050 mmol, 0.05 equiv). The resulting reaction mixture was heated at 100° C. for overnight. Product formation was confirmed by LCMS, after completion of reaction the reaction mixture was diluted with water (30 mL). Aqueous layer was washed with ethyl acetate (20 mL×2), separated and freeze dried to obtain 6-(1-oxo-1,2,3,4-tetrahydroisoquinolin-6-yl)quinoline-4-carboxylic acid (0.300 g, Quant. Yield) as an off white solid.

LCMS 319.2 [M+H]$^+$ $^1$H NMR (400 MHz, DMSO-d$_6$) δ 9.10 (s, 1H) 8.80 (d, J=4.39 Hz, 1H) 8.03 (s, 2H) 7.97 (d, J=7.89 Hz, 2H) 7.64-7.77 (m, 2H) 7.52 (d, J=4.39 Hz, 1H) 3.39-3.51 (m, 2H) 3.02 (t, J=6.58 Hz, 2H).

Step 3: Synthesis of (S)—N-(2-(2-cyano-4,4-difluoropyrrolidin-1-yl)-2-oxoethyl)-6-(1-oxo-1,2,3,4-tetrahydroisoquinolin-6-yl)quinoline-4-carboxamide. To a stirred solution of 6-(1-oxo-1,2,3,4-tetrahydroisoquinolin-6-yl)quinoline-4-carboxylic acid (0.300 g, 0.879 mmol, 1.0 equiv) in DMF (5 mL), was added (S)-4,4-difluoro-1-glycylpyrrolidine-2-carbonitrile hydrochloride (0.297 g, 1.319 mmol, 1.5 equiv), HOBT (0.238 g, 1.759 mmol, 2.0 equiv) and EDC.HCl (0.338 g, 1.759 mmol, 2.0 equiv) followed by the addition of TEA (0.4 mL). The resulting reaction mixture was allowed to stir at RT for overnight. Product formation was confirmed by LCMS and TLC. After completion of reaction, the reaction mixture was diluted with water (25 mL) and extracted with ethyl acetate (50 mL×2). Combined organic layer was washed with water (20 mL×4), dried over anhydrous Na$_2$SO$_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(1-oxo-1,2,3,4-tetrahydroisoquinolin-6-yl)quinoline-4-carboxamide (0.65 g, 14% Yield) as an off-white solid.

LCMS 490.4 [M+H]$^+$ $^1$H NMR (400 MHz, DMSO-d$_6$) δ 9.22 (t, J=5.92 Hz, 1H) 9.00 (d, J=4.38 Hz, 1H) 8.88 (d, J=1.75 Hz, 1H) 8.16-8.31 (m, 2H) 7.87-8.02 (m, 3H) 7.60 (d, J=4.38 Hz, 1H) 5.21 (dd, J=9.43, 2.41 Hz, 1H) 4.10-4.40 (m, 4H) 3.38-3.49 (m, 2H) 3.06 (t, J=6.58 Hz, 2H) 2.75-3.03 (m, 2H).

Example 5-19

Synthesis of (S,E)-N-(2-(2-cyano-4,4-difluoropyrrolidin-1-yl)-2-oxoethyl)-6-(2-(pyridin-4-yl)vinyl)quinoline-4-carboxamide

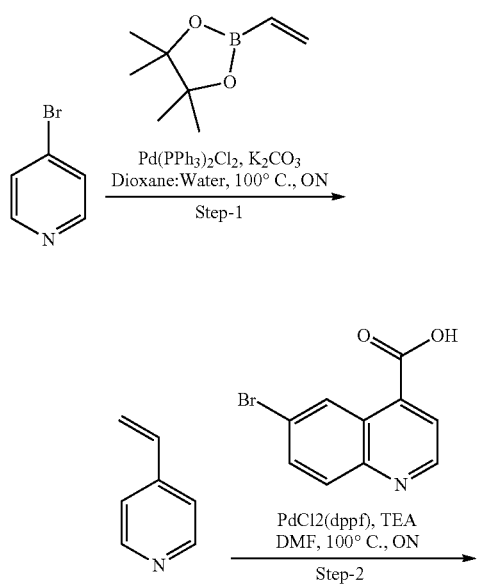

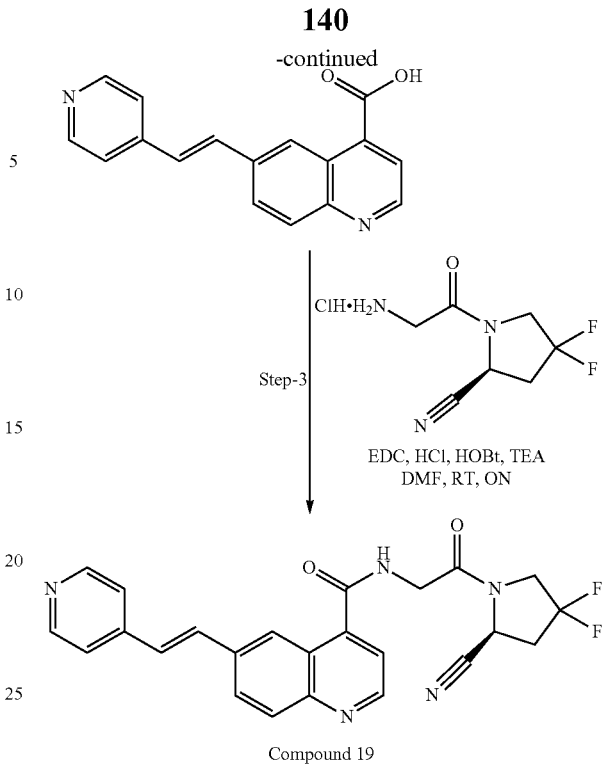

Compound 19

Step 1: Synthesis of 4-vinylpyridine. To a stirred solution of 4-Bromopyridine hydrochloride (0.500 g, 2.577 mmol, 1.0 equiv) in Dioxane (8 mL) was added 2-Vinyl-4,4,5,5-tetramethyl-1,3,2-dioxaoborolane (0.595 g, 3.865 mmol, 1.5 equiv) and a solution of K$_2$CO$_3$ (0.711 g, 5.154 mmol, 2.0 equiv) in water (4 mL), and the mixture was purged with N$_2$ gas for 10 min, followed by the addition of Pd(PPh$_3$)Cl$_2$ (0.090 g, 0.128 mmol. 0.05 equiv). The resulting reaction mixture was heated at 100° C. for overnight. Product formation was confirmed by TLC. Reaction mixture was cooled to RT, diluted with water (50 mL) extracted with ethyl acetate (100 mL×2). Combined organic extracts were washed with water (50 mL×2) & brine (50 mL), dried over anhydrous Na$_2$SO$_4$ and concentrated. The crude product was purified by flash chromatography (0-15% EA in hexane as an eluent) to obtain 4-Vinylpyridine (0.150 g, 55.55% Yield) as a Semi-solid.

$^1$H NMR (400 MHz, CHLOROFORM-d) δ 8.42-8.68 (m, 2H) 7.14-7.38 (m, 2H) 6.66 (dd, J=17.54, 10.96 Hz, 1H) 5.97 (d, J=17.54 Hz, 1H) 5.48 (d, J=10.52 Hz, 1H).

Step 2: Synthesis of (E)-6-(2-(pyridin-4-yl)vinyl)quinoline-4-carboxylic acid. To a stirred solution of 6-bromoquinoline-4-carboxylic acid (0.100 g, 0.395 mmol, 1.0 equiv) in DMF (5 mL) was added 4-Vinylpyridine (0.062 g, 0.595 mmol, 1.5 equiv) and triethyl amine (0.17 ml, 1.190 mmol, 3.0 equiv). The resulting reaction mixture was purged with N$_2$ gas for 5 min followed by addition of Pd(dppf)Cl$_2$ (0.029 g, 0.039 mmol, 0.1 equiv). The reaction mixture was heated at 100° C. for overnight. Product formation was confirmed by LCMS. Reaction mixture was cool to RT, diluted with water (50 mL) washed with ethyl acetate (100 mL×2). The aqueous layer was separated and freeze dried over lyophilyzer to obtained (E)-6-(2-(pyridin-4-yl)vinyl)quinoline-4-carboxylic acid (0.100 g, 91% Yield) as a yellow solid.

LCMS 277.0 [M+H]$^+$ $^1$H NMR (400 MHz, DMSO-d$_6$) δ10.08 (s, 1H) 8.73-8.95 (m, 2H) 8.57 (d, J=5.70 Hz, 2H) 8.16 (d, J=8.77 Hz, 1H)

8.03 (d, J=8.77 Hz, 1H) 7.78 (s, 1H) 7.61-7.73 (m, 2H) 7.57 (br. s., 1H) 7.39 (d, J=16.66 Hz, 1H).

Step 3: Synthesis of (S,E)-N-(2-(2-cyano-4,4-difluoropyrrolidin-1-yl)-2-oxoethyl)-6-(2-(pyridin-4-yl)vinyl)quinoline-4-carboxamide. To a stirred solution of (E)-6-(2-(pyridin-4-yl)vinyl)quinoline-4-carboxylic acid (0.200 g, 0.724 mmol, 1.0 equiv) in DMF (5 mL), was added (S)-4,4-difluoro-1-glycylpyrrolidine-2-carbonitrile hydrochloride (0.244 g, 1.086 mmol, 1.5 equiv), HOBt (0.147 g, 1.086 mmol, 1.5 equiv) and EDCI.HCl (0.207 g, 1.086 mmol, 1.5 equiv) followed by the addition of TEA (0.2 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous Na₂SO₄ and concentrated. The crude product was purified by flash chromatography (0-5% MeOH in DCM as an eluent) to obtain (S,E)-N-(2-(2-cyano-4,4-difluoropyrrolidin-1-yl)-2-oxoethyl)-6-(2-(pyridin-4-yl)vinyl)quinoline-4-carboxamide (0.040 g, 13% Yield) as an off white solid.

LCMS 448.4 [M+H]$^+$ $^1$H NMR (400 MHz, DMSO-d₆) δ 9.20 (t, J=6.14 Hz, 1H) 8.97 (d, J=3.95 Hz, 1H) 8.68 (s, 1H) 8.57 (d, J=6.14 Hz, 2H) 8.04-8.24 (m, 2H) 7.69-7.84 (m, 1H) 7.65 (d, J=5.70 Hz, 2H) 7.50-7.61 (m, 2H) 5.24 (dd, J=9.21, 2.63 Hz, 1H) 4.12-4.41 (m, 4H) 3.02 (s, 1H) 2.88 (d, J=14.91 Hz, 1H).

Example 5-20

Synthesis of (S,E)-N-(2-(2-cyano-4,4-difluoropyrrolidin-1-yl)-2-oxoethyl)-6-(2-(pyridin-3-yl)vinyl)quinoline-4-carboxamide

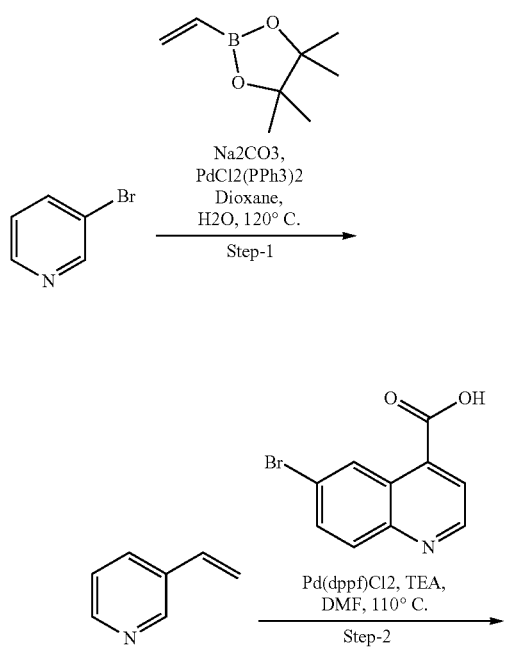

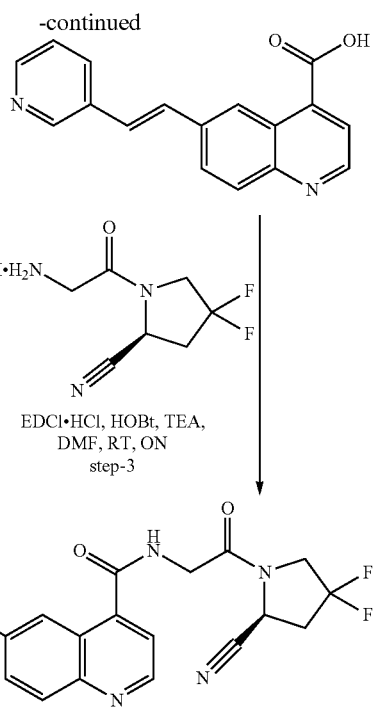

Step 1: Synthesis of 3-vinylpyridine. To a solution of 3-bromopyridine (0.25 g, 1.582 mmol, 1.0 equiv) in Dioxane (10 mL) was added 4,4,5,5-tetramethyl-2-vinyl-1,3,2-dioxaborolane (0.24 g, 1.582 mmol, 1.0 equiv), Na₂CO₃ (0.335 g, 3.164 mmol, 2.0 equiv) in H₂O (2 ml) and resulting reaction mixture was purged with N₂ gas for 10 min, followed by the addition of Pd(PPh₃)₂Cl₂ (0.055 g, 0.079 mmol. 0.05 equiv). The resulting reaction mixture was heated at 120° C. for overnight. Product formation was confirmed by LCMS. After the completion of reaction, the reaction mixture was diluted with water (20 mL) and extracted with ethyl acetate (40 mL×2). Combined organic extracts were washed with water (10 mL×4), dried over anhydrous Na₂SO₄ and concentrated. The crude product was purified by flash chromatography to 3-vinylpyridine (0.2 g, 40.0% yield) as a yellow oil.

LCMS 105.8 [M+H]$^+$ $^1$H NMR (400 MHz, DMSO-d₆) δ 8.47 (d, J=3.07 Hz, 1H) 7.81-7.98 (m, 1H) 7.38 (dd, J=7.67, 4.60 Hz, 1H) 6.77 (dd, J=17.98, 10.96 Hz, 1H) 5.98 (d, J=17.98 Hz, 1H) 5.40 (d, J=10.96 Hz, 1H).

Step 2: Synthesis of (E)-6-(2-(pyridin-3-yl)vinyl)quinoline-4-carboxylic acid. To a solution of 3-vinylpyridine (0.1 g, 0.632 mmol, 1.0 equiv) in DMF (4 mL) was added 6-bromoquinoline-4-carboxylic acid (0.159 g, 0.632 mmol, 1.0 equiv), TEA(0.2 ml) and the resulting reaction mixture was purged with N₂ gas for 10 min, followed by the addition of Pd₂(dppf)Cl₂ (0.046 g, 0.063 mmol. 0.1 equiv). The resulting reaction mixture was heated at 110° C. for overnight. Product formation was confirmed by LCMS. After the completion of reaction, the mixture was diluted with water solution (20 mL) and washed with ethyl acetate (10 mL×2). The aqueous layer was separated and freeze dried over lyophilizer to obtain (E)-6-(2-(pyridin-3-yl)vinyl)quinoline-4-carboxylic acid (0.200 g, 45% yield) as an off-white solid.

LCMS 277.0 [M+H]$^+$

Step 3: Synthesis of (S,E)-N-(2-(2-cyano-4,4-difluoropyrrolidin-1-yl)-2-oxoethyl)-6-(2-(pyridin-3-yl)vinyl)quinoline-4-carboxamide. To a stirred solution of (E)-6-(2-(pyridin-3-yl)vinyl)quinoline-4-carboxylic acid (0.1 g, 0.362 mmol, 1.0 equiv) in DMF (5 mL), was added (S)-4,4-difluoro-1-glycylpyrrolidine-2-carbonitrile hydrochloride (0.081 g, 0.362 mmol, 1.0 equiv), EDC.HCl (0.104 g, 0.543 mmol, 1.5 equiv) and HOBt (0.073 g, 0.543 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (20 mL) and extracted with ethyl acetate (50 mL×2). Combined organic extracts were washed with water (20 mL×3) and brine (20 mL), dried over anhydrous $Na_2SO_4$ and concentrated. The crude product was purified by flash chromatography (0-5% MeOH in DCM as an eluent) to obtain (S,E)-N-(2-(2-cyano-4,4-difluoropyrrolidin-1-yl)-2-oxoethyl)-6-(2-(pyridin-3-yl)vinyl)quinoline-4-carboxamide (0.010 g, 6.21% Yield) as an off-white solid.

LCMS 448.3 [M+H]$^+$ $^1$H NMR (400 MHz, DMSO-d$_6$) δ 9.19 (s, 1H) 8.95 (d, J=4.38 Hz, 1H) 8.87 (br. s., 1H) 8.60 (s, 1H) 8.50 (br. s., 1H) 8.01-8.29 (m, 3H) 7.51-7.78 (m, 2H) 7.44 (br. s., 2H) 5.23 (d, J=8.77 Hz, 1H) 4.36 (br. s., 1H) 4.28 (s, 2H) 4.18 (br. s., 1H) 2.89 (br. s., 2H).

Example 5-21

Synthesis of (S,E)-N-(2-(2-cyano-4,4-difluoropyrrolidin-1-yl)-2-oxoethyl)-6-(2-(pyridin-2-yl)vinyl)quinoline-4-carboxamide

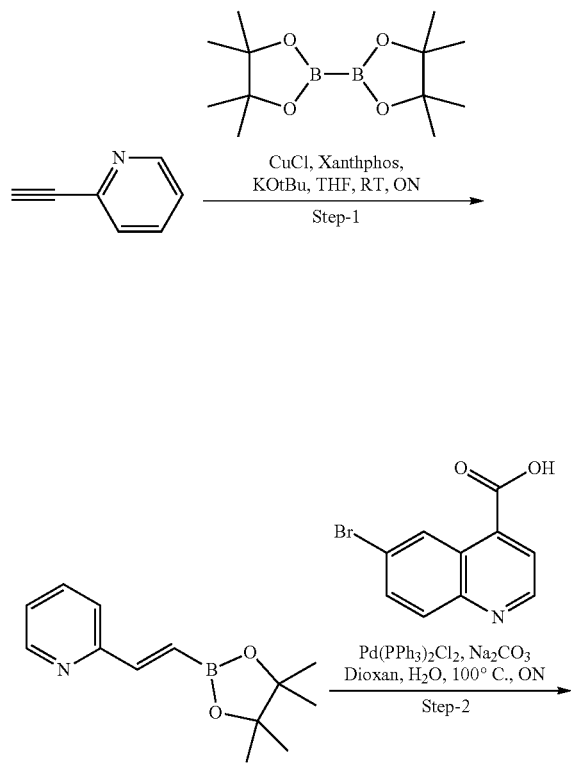

Compound 21

Step 1: Synthesis of (E)-2-(2-(4,4,5,5-tetramethyl-1,3,2-dioxaborolan-2-yl)vinyl)pyridine. To a stirred solution 4,4,4',4',5,5,5',5'-octamethyl-2,2'-bi(1,3,2-dioxaborolane) (1.3 g, 5.33 mmol, 1.1 equiv) in dry THF (30 mL), was added CuCl (0.004 mg, 0.048 mmol, 0.01 equiv), Xanthphos (27 mg, 0.048 mmol, 0.01 equiv) and KOtBu (0.651 g, 5.82 mmol, 1.2 equiv) at RT. The resulting mixture was allowed to stir at RT for 30 min. 2-ethynylpyridine (0.5 g, 4.85 mmol, 1.0 equiv) in THF (5 mL) was added into above reaction mixture and allowed to stir at RT for overnight. Product formation was confirmed by TLC. After completion of reaction, the reaction mixture was diluted with water (50 mL) and extracted with ethyl acetate (100 mL×2). Combined organic extracts were washed with water (50 mL×2), dried over anhydrous $Na_2SO_4$ and concentrated. The crude product was purified by flash chromatography (0-5% EtOAc in Hexane as an eluent) to obtain (E)-2-(2-(4,4,5,5-tetramethyl-1,3,2-dioxaborolan-2-yl)vinyl)pyridine (0.160 g, 14% Yield) as yellow solid.

$^1$H NMR (400 MHz, DMSO-d$_6$) δ 8.59 (s, 1H) 7.80 (d, J=1.75 Hz, 1H) 7.60 (d, J=7.89 Hz, 1H) 7.23-7.49 (m, 2H) 6.56 (d, J=17.98 Hz, 1H) 1.25 (s, 12H).

Step 2: Synthesis of (E)-6-(2-(pyridin-2-yl)vinyl)quinoline-4-carboxylic acid. To a solution of 6-bromoquinoline-4-carboxylic acid (0.138 g, 0.554 mmol, 0.8 equiv) and (E)-4,4,5,5-tetramethyl-2-1,3,2-dioxaborolane-2-yl)vinyl)pyridine (0.160 g, 0.692 mmol, 1.0 equiv) in dioxane (10 ml) and water (1 ml) was added in $K_2CO_3$ (0.145 g, 1.38 mmol, 2.0 equiv) and resulting reaction mixture was purged with $N_2$ gas for 10 min, followed by the addition of Pd(PPh$_2$)$_2$Cl$_2$ (0.024 g, 0.034 mmol. 0.05 equiv). The resulting reaction mixture was heated at 100° C. for overnight. Product formation was confirmed by LCMS. After the completion of reaction, the reaction mixture was quenched with water (10 mL) and aqueous layer was washed with ethyl acetate (10 mL). Aqueous layer was separated and freeze dried over lyophilizer to obtain (E)-6-(2-(pyridin-2-yl)vinyl)quinoline-4-carboxylic acid (0.120 g, 79% Yield) as a yellow solid.

LCMS 227.2 [M+H]$^+$

Step 3: Synthesis of (S,E)-6-(2(pyridine-2-yl)vinyl-N-(2-(2-cyano-4,4-difluoropyrrolidin-1-yl)-2-oxoethyl)quinoline-4-carboxamide. To a stirred solution of (E)-6-(2(pyridine-2-yl)vinyl)quinoline-4-carboxylic acid (0.120 g, 0.43 mmol, 1.0 equiv) in DMF (5 mL), was added (S)-4,4-difluoro-1-glycylpyrrolidine-2-carbonitrile hydrochloride (0.146 g, 0.652 mmol, 1.5 equiv), EDCI.HCl (0.125 g, 0.652 mmol, 1.5 equiv) and HOBt (0.088 g, 0.65 mmol, 1.5 equiv) followed by the addition of TEA (0.2 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) followed by reversed phase HPLC purification to obtain (S,E)-6-(2(pyridine-2-yl)vinyl-N-(2-(2-cyano-4,4-difluoropyrrolidin-1-yl)-2-oxoethyl)quinoline-4-carboxamide (0.045 g, 14% Yield) as a yellow solid.

LCMS 448.4 $[M+H]^+$ $^1$H NMR (400 MHz, DMSO-$d_6$) δ 9.14-9.25 (m, 1H) 8.96 (d, J=4.38 Hz, 1H) 8.61 (br. s., 2H) 8.16-8.23 (m, 1H) 8.09 (d, J=8.77 Hz, 1H) 7.76-7.91 (m, 2H) 7.52-7.67 (m, 3H) 7.30 (dd, J=7.24, 5.04 Hz, 1H) 5.25 (d, J=9.21 Hz, 1H) 4.20-4.40 (m, 3H) 4.16 (d, J=11.84 Hz, 1H) 2.87 (d, J=18.42 Hz, 2H).

Example S-22

Synthesis of methyl (S,E)-3-(4-((2-(2-cyano-4,4-difluoropyrrolidin-1-yl)-2-oxoethyl)carbamoyl)quinolin-6-yl)acrylate

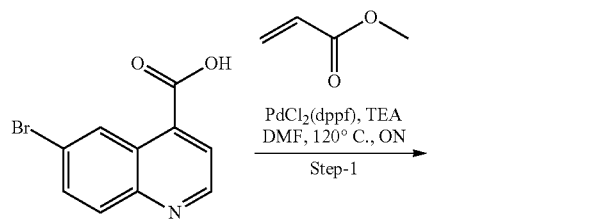

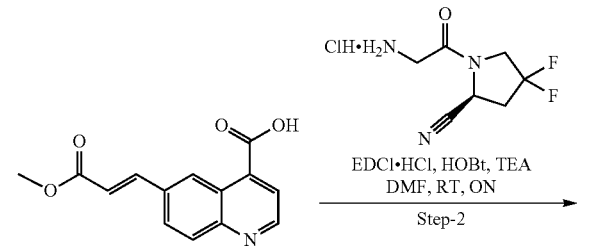

Compound 22

Step 1: Synthesis of (E)-6-(3-methoxy-3-oxoprop-1-en-1-yl)quinoline-4-carboxylic acid. To a stirred solution of 6-bromoquinoline-4-carboxylic acid (0.100 g, 0.396 mmol, 1.0 equiv) in DMF (3 mL) was added methyl acrylate (0.068 g, 0.793 mmol, 2.0 equiv) and triethyl amine (0.171 ml, 1.99 mmol, 3.0 equiv). The resulting reaction mixture was purged with $N_2$ gas for 5 min followed by the addition of Pd(dppf)$Cl_2$(0.014 g, 0.0198 mmol, 0.05 equiv). The reaction mixture was heated at 120° C. for overnight. Product formation was confirmed by LCMS. Reaction mixture was cooled to RT, diluted with water (50 mL) washed with ethyl acetate (20 mL×2). Aqueous layer was separated and freeze dried over lyophilyzer to obtain (E)-6-(3-methoxy-3-oxoprop-1-en-1-yl)quinoline-4-carboxylic acid (0.100 g, Quant. Yield) as a Yellow solid.

LCMS 257.9 $[M+H]^+$ $^1$H NMR (400 MHz, DMSO-$d_6$) δ10.32 (br. s., 1H) 8.83-9.05 (m, 2H) 8.17 (d, J=8.77 Hz, 1H) 8.03 (d, J=8.77 Hz, 1H) 7.72-7.87 (m, 2H) 6.76 (d, J=15.79 Hz, 1H) 3.76 (s, 3H).

Step 2: Synthesis of methyl (S,E)-3-(4-((2-(2-cyano-4,4-difluoropyrrolidin-1-yl)-2-oxoethyl)carbamoyl)quinolin-6-yl)acrylate. To a stirred solution of (E)-6-(3-methoxy-3-oxoprop-1-en-1-yl)quinoline-4-carboxylic acid (0.200 g, 0.778 mmol, 1.0 equiv) in DMF (10 mL), was added (S)-4,4-difluoro-1-glycylpyrrolidine-2-carbonitrile hydrochloride (0.262 g, 1.167 mmol, 1.5 equiv), HOBt (0.157 g, 1.167 mmol, 1.5 equiv) and EDC.HCl (0.222 g, 1.167 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain methyl (S,E)-3-(4-((2-(2-cyano-4,4-difluoropyrrolidin-1-yl)-2-oxoethyl)carbamoyl)quinolin-6-yl)acrylate (0.090 g, 27% Yield) as white solid.

LCMS 429.3 $[M+H]^+$ $^1$H NMR (400 MHz, DMSO-$d_6$) δ 9.19 (t, J=5.92 Hz, 1H) 9.01 (d, J=4.38 Hz, 1H) 8.64 (s, 1H) 8.23 (d, J=8.77 Hz, 1H) 8.10 (d, J=8.77 Hz, 1H) 7.80 (d, J=15.79 Hz, 1H) 7.61 (d, J=4.38 Hz, 1H) 6.89 (d, J=16.22 Hz, 1H) 5.20 (d, J=7.02 Hz, 1H) 4.09-4.39 (m, 4H) 3.76 (s, 3H) 2.75-3.00 (m, 2H).

Example S-23

Synthesis of (S)—N-(2-(2-cyano-4,4-difluoropyrrolidin-1-yl)-2-oxoethyl)-6-(6-methylpyridin-3-yl)quinoline-4-carboxamide

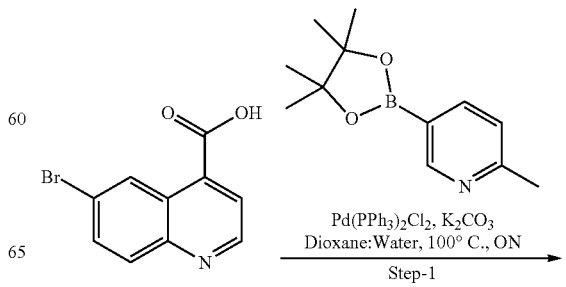

Hz, 1H) 5.19 (d, J=7.89 Hz, 1H) 4.35 (br. s., 1H) 4.09-4.32 (m, 2H) 3.90 (br. s., 1H) 2.76-3.02 (m, 2H) 2.54 (s, 3H).

Example S-24

Synthesis of (S)—N-(2-(2-cyano-4,4-difluoropyrrolidin-1-yl)-2-oxoethyl)-6-(2,3-dihydrobenzo[b][1,4]dioxin-6-yl)quinoline-4-carboxamide

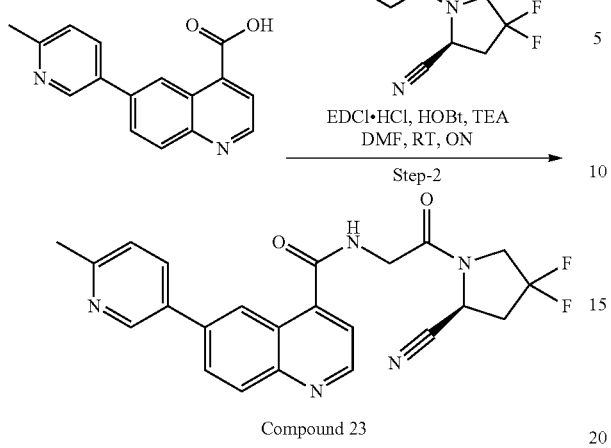

Compound 23

Step 1: Synthesis of 6-(6-methylpyridin-3-yl)quinoline-4-carboxylic acid. To a stirred solution of 6-bromoquinoline-4-carboxylic acid (0.250 g, 0.992 mmol, 1.0 equiv) in Dioxane (5 mL) was added 2-Methyl-5-(4,4,5,5-tetramethyl-1,3,2-dioxaborolan-2-yl)pyridine (0.260 g, 1.190 mmol, 1.5 equiv) and a solution of K$_2$CO$_3$ (0.273 g, 1.984 mmol, 2.0 equiv) in water (2 mL), and resulting reaction mixture was purged with N$_2$ gas for 10 min, followed by the addition of Pd(PPh$_3$)Cl$_2$ (0.034 g, 0.049 mmol. 0.05 equiv). The resulting reaction mixture was heated at 100° C. for overnight. Product formation was confirmed by LCMS. Reaction mixture was cooled to RT, diluted with water (60 mL) washed with ethyl acetate (50 mL×3). The aqueous layer was separated and freeze dried over lyophilyzer to obtain 6-(6-methylpyridin-3-yl)quinoline-4-carboxylic acid (0.260 g, 99.23% Yield) as a yellow solid.

LCMS 264.9 [M+H]$^+$ $^1$H NMR (400 MHz, DMSO-d$_6$) δ 9.06 (d, J=1.75 Hz, 1H) 8.82 (d, J=2.19 Hz, 1H) 8.78 (d, J=4.39 Hz, 1H) 7.91-8.11 (m, 3H) 7.51 (d, J=3.95 Hz, 1H) 7.40 (d, J=8.33 Hz, 1H) 2.54 (s, 3H).

Step 2: Synthesis of (S)—N-(2-(2-cyano-4,4-difluoropyrrolidin-1-yl)-2-oxoethyl)-6-(6-methylpyridin-3-yl)quinoline-4-carboxamide. To a stirred solution of 6-(6-methylpyridin-3-yl)quinoline-4-carboxylic acid (0.250 g, 0.946 mmol, 1.0 equiv) in DMF (5 mL), was added (S)-4,4-difluoro-1-glycylpyrrolidine-2-carbonitrile hydrochloride (0.319 g, 1.420 mmol, 1.5 equiv), HOBt (0.191 g, 1.420 mmol, 1.5 equiv) and EDC.HCl (0.271 g, 1.420 mmol, 1.5 equiv) followed by the addition of TEA (0.27 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous Na$_2$SO$_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-methylpyridin-3-yl)quinoline-4-carboxamide (0.260 g, 63.41% Yield) as white solid.

LCMS 436.3 [M+H]$^+$ $^1$H NMR (400 MHz, DMSO-d$_6$) δ 9.21 (t, J=5.48 Hz, 1H) 9.00 (d, J=3.95 Hz, 1H) 8.95 (br. s., 1H) 8.78 (s, 1H) 8.09-8.31 (m, 3H) 7.61 (d, J=4.38 Hz, 1H) 7.41 (d, J=7.89

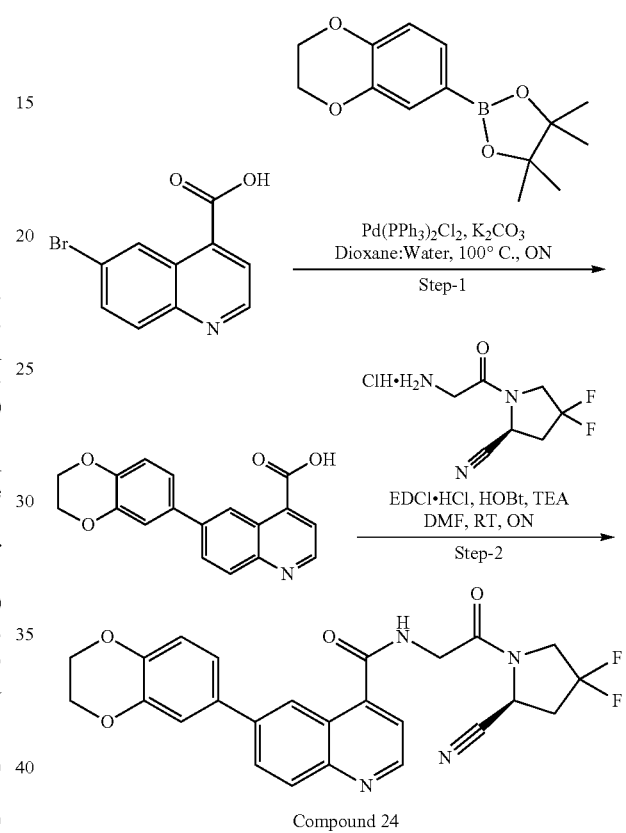

Compound 24

Step 1: Synthesis of 6-(2,3-dihydrobenzo[b][1,4]dioxin-6-yl)quinoline-4-carboxylic acid. To a stirred solution of 6-bromoquinoline-4-carboxylic acid (0.250 g, 0.992 mmol, 1.0 equiv) in Dioxane (6 mL) was added 1,4-Benzodioxane-6-boronic acid, pinacol ester (0.389 g, 1.488 mmol, 1.5 equiv) and a solution of K$_2$CO$_3$ (0.273 g, 1.984 mmol, 2.0 equiv) in water (2 mL), and resulting reaction mixture was purged with N$_2$ gas for 10 min, followed by the addition of Pd(PPh$_3$)Cl$_2$ (0.034 g, 0.049 mmol. 0.05 equiv). The resulting reaction mixture was heated at 100° C. for 16 hr. Product formation was confirmed by LCMS. Reaction mixture was cooled to RT, diluted with water (60 mL) washed with ethyl acetate (50 mL×3). The aqueous layer was acidified with 1N HCl and extracted with ethyl acetate (60 mL×3). Combined organic extracts were washed with water (20 mL×2) and brine (20 mL), dried over anhydrous Na$_2$SO$_4$ and concentrated under reduced pressure to obtain 6-(2,3-dihydrobenzo[b][1,4]dioxin-6-yl)quinoline-4-carboxylic acid (0.250 g, 82% Yield) as a yellow solid.

LCMS 308.0 [M+H]$^+$ $^1$H NMR (400 MHz, DMSO-d$_6$) δ 8.93 (s, 1H) 8.72 (d, J=4.38 Hz, 1H) 7.81-8.00 (m, 2H) 7.44 (d, J=3.95 Hz, 1H) 7.09-7.33 (m, 2H) 6.99 (d, J=8.77 Hz, 1H) 4.30 (s, 4H).

Step 2: Synthesis of (S)—N-(2-(2-cyano-4,4-difluoropyrrolidin-1-yl)-2-oxoethyl)-6-(2,3-dihydrobenzo[b][1,4]dioxin-6-yl)quinoline-4-carboxamide. To a stirred solution of 6-(2,3-dihydrobenzo[b][1,4]dioxin-6-yl)quinoline-4-carboxylic acid (0.250 g, 0.814 mmol, 1.0 equiv) in DMF (5 mL), was added (S)-4,4-difluoro-1-glycylpyrrolidine-2-carbonitrile hydrochloride (0.274 g, 1.221 mmol, 1.5 equiv), HOBt (0.164 g, 1.221 mmol, 1.5 equiv) and EDC.HCl (0.233 g, 1.221 mmol, 1.5 equiv) followed by the addition of TEA (0.27 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(2,3-dihydrobenzo[b][1,4]dioxin-6-yl)quinoline-4-carboxamide (0.170 g, 44% Yield) as an off-white solid.

LCMS 479.4 $[M+H]^+$ $^1$H NMR (400 MHz, DMSO-$d_6$) δ 9.16 (t, J=5.92 Hz, 1H) 8.95 (d, J=4.38 Hz, 1H) 8.63 (s, 1H) 8.03-8.23 (m, 2H) 7.57 (d, J=4.39 Hz, 1H) 7.23-7.49 (m, 2H) 7.00 (d, J=8.33 Hz, 1H) 5.18 (dd, J=9.21, 2.19 Hz, 1H) 4.33 (d, J=6.14 Hz, 2H) 4.08-4.31 (m, 5H) 4.03 (d, J=7.45 Hz, 1H) 2.75-3.04 (m, 2H).

Example 5-25

Synthesis of (S)—N-(2-(2-cyano-4,4-difluoropyrrolidin-1-yl)-2-oxoethyl)-6-(6-cyclopropylpyridin-3-yl)quinoline-4-carboxamide

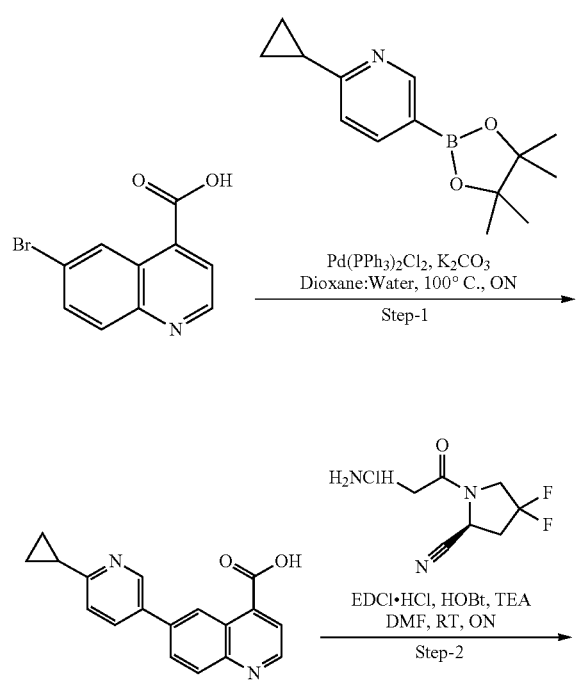

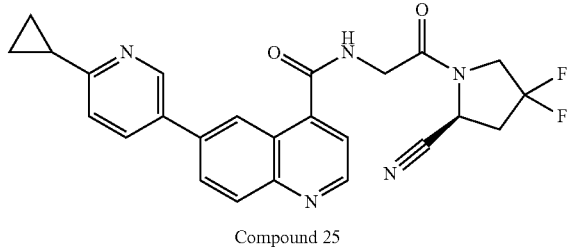

Compound 25

Step 1: Synthesis of 6-(6-cyclopropylpyridin-3-yl)quinoline-4-carboxylic acid. To a stirred solution of 6-bromoquinoline-4-carboxylic acid (0.050 g, 0.198 mmol, 1.0 equiv) in Dioxane (1 mL) was added 2-Cyclopropyl-5-(4,4,5,5-tetramethyl-1,3,2-dioxaborolan-2-yl)pyridine (0.058 g, 0.238 mmol, 1.2 equiv), $K_2CO_3$ (0.054 g, 0.396 mmol, 2.0 equiv) in water (0.5 mL) was added and mixture was purged with $N_2$ gas for 10 min followed by the addition of Pd(PPh$_3$)Cl$_2$ (0.069 g, 0.009 mmol. 0.05 equiv). The resulting reaction mixture was heated at 120° C. for overnight. Product formation was confirmed by LCMS. Reaction mixture was cooled to RT, diluted with water (50 mL) washed with ethyl acetate (20 mL×3). The aqueous layer was separated and freeze dried over lyophilyzer to obtain 6-(6-cyclopropylpyridin-3-yl)quinoline-4-carboxylic acid (0.060 g) as a yellow solid.

LCMS 291.0 $[M+H]^+$ $^1$H NMR (400 MHz, DMSO-$d_6$) δ 9.04 (d, J=1.75 Hz, 1H) 8.71-8.84 (m, 2H) 7.87-8.11 (m, 3H) 7.52 (d, J=4.39 Hz, 1H) 7.43 (d, J=8.33 Hz, 1H) 2.17 (br. s., 1H) 0.88-1.04 (m, 4H).

Step 2: Synthesis of (S)—N-(2-(2-cyano-4,4-difluoropyrrolidin-1-yl)-2-oxoethyl)-6-(6-cyclopropylpyridin-3-yl)quinoline-4-carboxamide. To a stirred solution of 6-(6-cyclopropylpyridin-3-yl)quinoline-4-carboxylic acid (0.060 g, 0.206 mmol, 1.0 equiv) in DMF (2 mL), was added (S)-4,4-difluoro-1-glycylpyrrolidine-2-carbonitrile hydrochloride (0.069 g, 0.310 mmol, 1.5 equiv), HOBt (0.041 g, 0.310 mmol, 1.5 equiv) and EDC.HCl (0.059 g, 0.310 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-cyclopropylpyridin-3-yl)quinoline-4-carboxamide (0.015 g, 16% Yield) as an off-white solid.

LCMS 462.4 $[M+H]^+$ $^1$H NMR (400 MHz, DMSO-$d_6$) δ 9.20 (t, J=5.92 Hz, 1H) 8.99 (d, J=3.95 Hz, 1H) 8.89 (d, J=1.75 Hz, 1H) 8.75 (d, J=1.75 Hz, 1H) 8.13-8.25 (m, 3H) 7.60 (d, J=4.39 Hz, 1H) 7.44 (d, J=8.33 Hz, 1H) 5.19 (dd, J=9.21, 2.63 Hz, 1H) 4.10-4.39 (m, 4H) 2.75-3.04 (m, 2H) 2.09-2.23 (m, 1H) 0.83-1.13 (m, 4H).

Example S-26

Synthesis of 6-(4-chlorophenyl)-N—((R)-1-((S)-2-cyano-4,4-difluoropyrrolidin-1-yl)-1-oxopropan-2-yl)quinoline-4-carboxamide

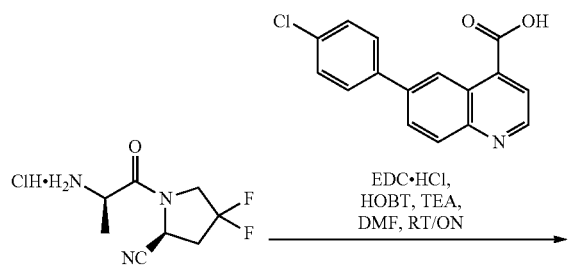

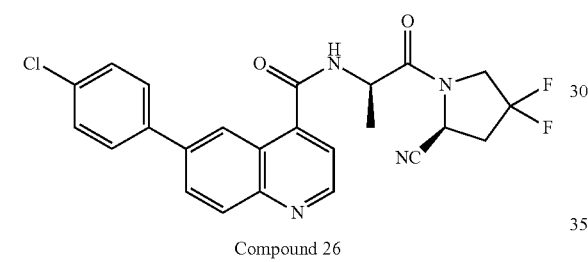

Compound 26

Synthesis of 6-(4-chlorophenyl)-N—((R)-1-((S)-2-cyano-4,4-difluoropyrrolidin-1-yl)-1-oxopropan-2-yl)quinoline-4-carboxamide. To a stirred solution of 6-(4-chlorophenyl) quinoline-4-carboxylic acid (100 mg, 0.35 mmol, 1.0 equiv) in DMF (05 mL) was added (S)-1-(D-alanyl)-4,4-difluoropyrrolidine-2-carbonitrile hydrochloride (85 mg, 0.35 mmol, 1.0 equiv), HOBT (57 mg, 0.42 mmol, 1.2 equiv) and EDC.HCl (81 mg, 0.42 mmol, 1.2 equiv) followed by the addition of TEA (0.2 mL, 0.70 mmol, 2.0 equiv). The resulting reaction mixture was allowed to stir at RT for overnight. The reaction progress was monitored by NMR and TLC. The reaction mixture was diluted with cold water (50 mL) and extracted with ethyl acetate (100 mL×2). Combined organic extracts were washed with water by (50 mL×2), dried over anhydrous sodium sulphate and concentrated under reduced pressure. The crude product was purified by reversed phase HPLC to obtain 6-(4-chlorophenyl)-N—((R)-1-((S)-2-cyano-4,4-difluoropyrrolidin-1-yl)-1-oxopropan-2-yl)quinoline-4-carboxamide (10 mg, 06% Yield) as an off-white solid.

LCMS 469.3 [M+H]$^+$ $^1$H NMR (400 MHz, DMSO-d$_6$) δ 9.32 (d, J=6.58 Hz, 1H), 8.99 (d, J=4.38 Hz, 1H), 8.56 (s, 1H), 8.06-8.27 (m, 2H), 7.84-8.05 (m, 2H), 7.48-7.68 (m, 2H), 5.16 (dd, J=3.95, 9.21 Hz, 1H), 4.72-4.85 (m, 1H), 4.18-4.41 (m, 2H), 2.84-3.07 (m, 2H), 1.27-1.48 (m, 3H).

Example S-27

Synthesis of 6-(4-chlorophenyl)-N—((S)-1-((S)-2-cyano-4,4-difluoropyrrolidin-1-yl)-1-oxopropan-2-yl)quinoline-4-carboxamide

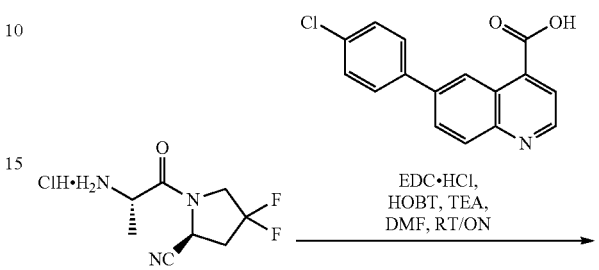

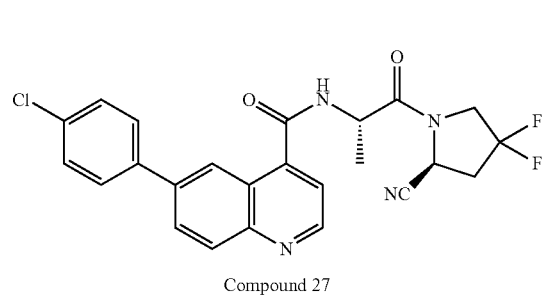

Compound 27

Synthesis of 6-(4-chlorophenyl)-N—((S)-1-((S)-2-cyano-4,4-difluoropyrrolidin-1-yl)-1-oxopropan-2-yl)quinoline-4-carboxamide. To a stirred solution of 6-(4-chlorophenyl) quinoline-4-carboxylic acid (100 mg, 0.35 mmol, 1.0 equiv) in DMF (05 mL) was added (S)-1-(L-alanyl)-4,4-difluoropyrrolidine-2-carbonitrile hydrochloride (85 mg, 0.35 mmol, 1.0 equiv), HOBT (57 mg, 0.42 mmol, 1.2 equiv) and EDC.HCl (81 mg, 0.42 mmol, 1.2 equiv) followed by the addition of TEA (0.2 mL, 0.70 mmol, 2.0 equiv). The resulting reaction mixture was allowed to stir at RT for overnight. The reaction progress was monitored by NMR and TLC. The reaction mixture was diluted with cold water (50 mL) and extracted with ethyl acetate (100 mL×2). Combined organic extracts were washed with water by (50 mL×2), dried over anhydrous sodium sulphate and concentrated under reduced pressure. The crude product was purified by reversed phase HPLC to obtain 6-(4-chlorophenyl)-N—((S)-1-((S)-2-cyano-4,4-difluoropyrrolidin-1-yl)-1-oxopropan-2-yl)quinoline-4-carboxamide (15 mg, 9% Yield) as an off-white solid.

LCMS 469.3 [M+H]$^+$ $^1$H NMR (400 MHz, DMSO-d$_6$) δ 9.32 (d, J=6.58 Hz, 1H), 8.99 (d, J=4.38 Hz, 1H), 8.56 (s, 1H), 8.06-8.27 (m, 2H), 7.84-8.05 (m, 2H), 7.48-7.68 (m, 2H), 5.16 (dd, J=3.95, 9.21 Hz, 1H), 4.72-4.85 (m, 1H), 4.18-4.41 (m, 2H), 2.84-3.07 (m, 2H), 1.27-1.48 (m, 3H).

Example S-28

Synthesis of 6-(4-chlorophenyl)-N—((R)-14(5)-2-cyano-4,4-difluoropyrrolidin-1-yl)-3-methyl-1-oxobutan-2-yl)quinoline-4-carboxamide

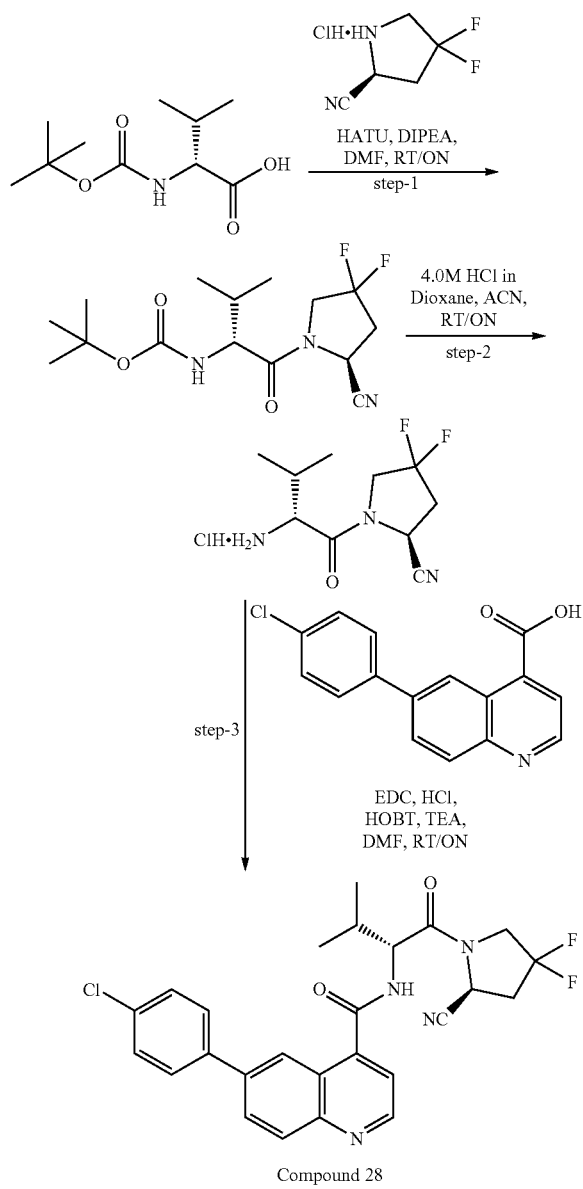

Compound 28

Step 1: Synthesis of tert-butyl ((R)-1-((S)-2-cyano-4,4-difluoropyrrolidin-1-yl)-3-methyl-1-oxobutan-2-yl)carbamate. To a stirred solution of (tert-butoxycarbonyl)-D-valine (642 mg, 2.9 mmol, 1.0 equiv) and HATU(2204 mg, 5.8 mmol, 2.0 equiv) in DMF (5 mL was added (S)-4,4-difluoropyrrolidine-2-carbonitrile hydrochloride (500 mg, 2.9 mmol, 1.0 equiv) and stirred for 10 min. DIPEA (1.5 mL, 8.7 mmol, 3.0 equiv) was added and the reaction mixture was allowed to stir for overnight at RT. Reaction progress was monitored by NMR and TLC. The reaction mixture was diluted with cold water (100 ml) and extracted with ethyl acetate (100 mL×2). Combined organic extracts were washed with water (50 mL×2), dried over anhydrous sodium sulphate and concentrated under reduced pressure to obtain tert-butyl ((R)-1-((S)-2-cyano-4,4-difluoropyrrolidin-1-yl)-3-methyl-1-oxobutan-2-yl)carbamate (300 mg, 30% Yield) as a brown solid.

$^1$H NMR (400 MHz, DMSO-$d_6$) δ 7.30 (d, J=8.33 Hz, 1H) 4.98-5.11 (m, 1H) 4.22-4.36 (m, 1H) 4.06-4.20 (m, 1H) 2.81-2.95 (m, 2H) 1.94 (dd, J=14.69, 6.80 Hz, 1H) 1.31-1.40 (m, 9H) 0.74-0.91 (m, 6H).

Step 2: Synthesis of (S)-1-(D-valyl)-4,4-difluoropyrrolidine-2-carbonitrile hydrochloride. To a stirred solution of tert-butyl ((R)-1-((S)-2-cyano-4,4-difluoropyrrolidin-1-yl)-3-methyl-1-oxobutan-2-yl)carbamate (300 mg, 0.906 mmol, 1.0 equiv) in acetonitrile (15 mL) was added 4.0 M HCl in Dioxan (5.0 ml) dropwise at 0° C. over a period of 10 min. The reaction resulting mixture was allowed to stir at RT for overnight. The reaction progress was monitored by NMR. The solvent was evaporated under reduced pressure to obtain residue which was washed with 20 mL ethyl acetate and hexane (1:1) to obtain (S)-1-(D-valyl)-4,4-difluoropyrrolidine-2-carbonitrile hydrochloride (150 mg, 62% Yield) as a yellow semi solid.

$^1$H NMR (400 MHz, DMSO-$d_6$) δ 8.25 (br. s., 2H), 5.15 (d, J=7.89 Hz, 1H), 4.27-4.43 (m, 1H), 3.92-4.12 (m, 2H), 2.97 (br. s., 1H), 2.84-2.93 (m, 1H), 0.82-1.10 (m, 6H).

Step 3: Synthesis of 6-(4-chlorophenyl)-N—((R)-1-((S)-2-cyano-4,4-difluoropyrrolidin-1-yl)-3-methyl-1-oxobutan-2-yl)quinoline-4-carboxamide. To a stirred solution of 6-(4-chlorophenyl)quinoline-4-carboxylic acid (100 mg, 0.35 mmol, 1.0 equiv.) in DMF (05 mL) was added (S)-1-(D-valyl)-4,4-difluoropyrrolidine-2-carbonitrile hydrochloride (94 mg, 0.35 mmol, 1.0 equiv), HOBT (70 mg, 0.52 mmol, 1.5 equiv) and EDC.HCl (100 mg, 0.52 mmol, 1.5 equiv) followed by the addition of TEA (0.14 mL, 1.05 mmol, 3.0 equiv). The resulting reaction mixture was allowed to stir at RT for overnight. The reaction progress was monitored by NMR and TLC. The reaction mixture was diluted with cold water (50 mL) and extracted with ethyl acetate (100 mL×2). Combined organic extracts were washed with water by (50 mL×2), dried over anhydrous sodium sulphate and concentrated under reduced pressure. The crude product was purified by reversed phase HPLC to obtain 6-(4-chlorophenyl)-N—((R)-1-((S)-2-cyano-4,4-difluoropyrrolidin-1-yl)-3-methyl-1-oxobutan-2-yl)quinoline-4-carboxamide (30 mg, 17% Yield) as a yellow solid.

LCMS 497.1 [M+H]$^+$ $^1$H NMR (400 MHz, DMSO-$d_6$) δ 9.38 (d, J=7.45 Hz, 1H), 9.01 (d, J=4.38 Hz, 1H), 8.38 (s, 1H), 8.12-8.25 (m, 2H), 7.83-7.95 (m, 2H), 7.49-7.67 (m, 3H), 5.18 (d, J=7.45 Hz, 1H), 4.41-4.62 (m, 2H), 4.21-4.31 (m, 1H), 2.88-3.04 (m, 2H), 0.91-1.15 (m, 6H).

Example S-29

Synthesis of 6-(4-chlorophenyl)-N—((S)-1-((S)-2-cyano-4,4-difluoropyrrolidin-1-yl)-3-methyl-1-oxobutan-2-yl)quinoline-4-carboxamide

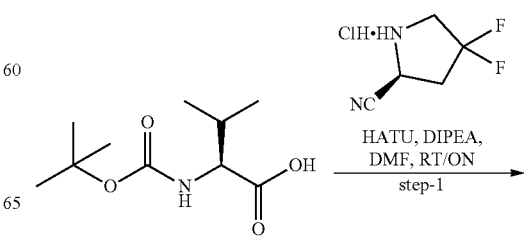

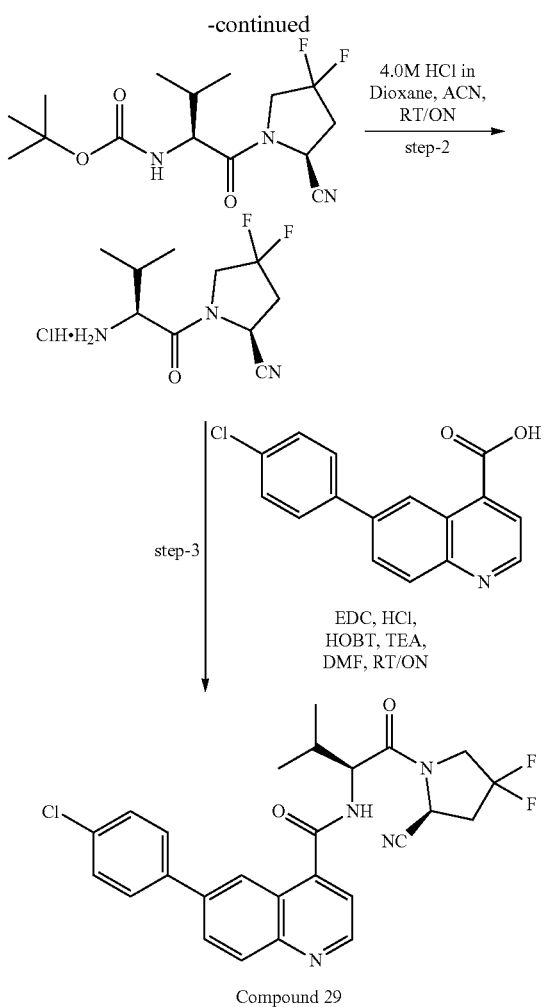

Compound 29

Step 1: Synthesis of tert-butyl ((S)-1-((S)-2-cyano-4,4-difluoropyrrolidin-1-yl)-3-methyl-1-oxobutan-2-yl)carbamate. To a stirred solution of (tert-butoxycarbonyl)-L-valine (642 mg, 2.9 mmol, 1.0 equiv) and HATU(2204 mg, 5.8 mmol, 2.0 equiv) in DMF (5 mL was added (S)-4,4-difluoropyrrolidine-2-carbonitrile hydrochloride (500 mg, 2.9 mmol, 1.0 equiv) and stirred for 10 min. DIPEA (1.5 mL, 8.7 mmol, 3.0 equiv) was added and the reaction mixture was allowed to stir for overnight at RT. Reaction progress was monitored by NMR and TLC. The reaction mixture was diluted with cold water (100 ml) and extracted with ethyl acetate (100 mL×2). Combined organic extracts were washed with water (50 mL×2), dried over anhydrous sodium sulphate and concentrated under reduced pressure to obtain tert-butyl ((S)-1-((S)-2-cyano-4,4-difluoropyrrolidin-1-yl)-3-methyl-1-oxobutan-2-yl)carbamate (300 mg, 30% Yield) as a brown solid.

$^1$H NMR (400 MHz, DMSO-$d_6$) δ 7.30 (d, J=8.33 Hz, 1H) 4.98-5.11 (m, 1H) 4.22-4.36 (m, 1H) 4.06-4.20 (m, 1H) 2.81-2.95 (m, 2H) 1.94 (dd, J=14.69, 6.80 Hz, 1H) 1.31-1.40 (m, 9H) 0.74-0.91 (m, 6H).

Step 2: Synthesis of (S)-1-(L-valyl)-4,4-difluoropyrrolidine-2-carbonitrile hydrochloride. To a stirred solution of tert-butyl ((S)-1-((S)-2-cyano-4,4-difluoropyrrolidin-1-yl)-3-methyl-1-oxobutan-2-yl)carbamate (300 mg, 0.906 mmol, 1.0 equiv) in acetonitrile (15 mL) was added 4.0 M HCl in Dioxan (5.0 ml) dropwise at 0° C. over a period of 10 min. The reaction resulting mixture was allowed to stir at RT for overnight. The reaction progress was monitored by NMR. The solvent was evaporated under reduced pressure to obtain residue which was washed with 20 mL ethyl acetate and hexane (1:1) to obtain (S)-1-(L-valyl)-4,4-difluoropyrrolidine-2-carbonitrile hydrochloride (150 mg, 62% Yield) as a yellow semi solid.

$^1$H NMR (400 MHz, DMSO-$d_6$) δ 8.25 (br. s., 2H), 5.15 (d, J=7.89 Hz, 1H), 4.27-4.43 (m, 1H), 3.92-4.12 (m, 2H), 2.97 (br. s., 1H), 2.84-2.93 (m, 1H), 0.82-1.10 (m, 6H).

Step 3: Synthesis of 6-(4-chlorophenyl)-N—((S)-1-((S)-2-cyano-4,4-difluoropyrrolidin-1-yl)-3-methyl-1-oxobutan-2-yl)quinoline-4-carboxamide. To a stirred solution of 6-(4-chlorophenyl)quinoline-4-carboxylic acid (100 mg, 0.35 mmol, 1.0 equiv.) in DMF (05 mL) was added (S)-1-(L-valyl)-4,4-difluoropyrrolidine-2-carbonitrile hydrochloride (94 mg, 0.35 mmol, 1.0 equiv), HOBT (70 mg, 0.52 mmol, 1.5 equiv) and EDC.HCl (100 mg, 0.52 mmol, 1.5 equiv) followed by the addition of TEA (0.14 mL, 1.05 mmol, 3.0 equiv). The resulting reaction mixture was allowed to stir at RT for overnight. The reaction progress was monitored by NMR and TLC. The reaction mixture was diluted with cold water (50 mL) and extracted with ethyl acetate (100 mL×2). Combined organic extracts were washed with water by (50 mL×2), dried over anhydrous sodium sulphate and concentrated under reduced pressure. The crude product was purified by reversed phase HPLC to obtain 6-(4-chlorophenyl)-N—((S)-1-((S)-2-cyano-4,4-difluoropyrrolidin-1-yl)-3-methyl-1-oxobutan-2-yl)quinoline-4-carboxamide (20 mg, 12% Yield) as a yellow solid.

LCMS 497.1 [M+H]$^+$ $^1$H NMR (400 MHz, DMSO-$d_6$) δ 9.38 (d, J=7.45 Hz, 1H), 9.01 (d, J=4.38 Hz, 1H), 8.38 (s, 1H), 8.12-8.25 (m, 2H), 7.83-7.95 (m, 2H), 7.49-7.67 (m, 3H), 5.18 (d, J=7.45 Hz, 1H), 4.41-4.62 (m, 2H), 4.21-4.31 (m, 1H), 2.88-3.04 (m, 2H), 0.91-1.15 (m, 6H).

Example 5-30

Synthesis of (S)—N-(2-(2-cyano-4,4-difluoropyrrolidin-1-yl)-2-oxoethyl)-6-(4-methoxyphenyl)quinoline-4-carboxamide

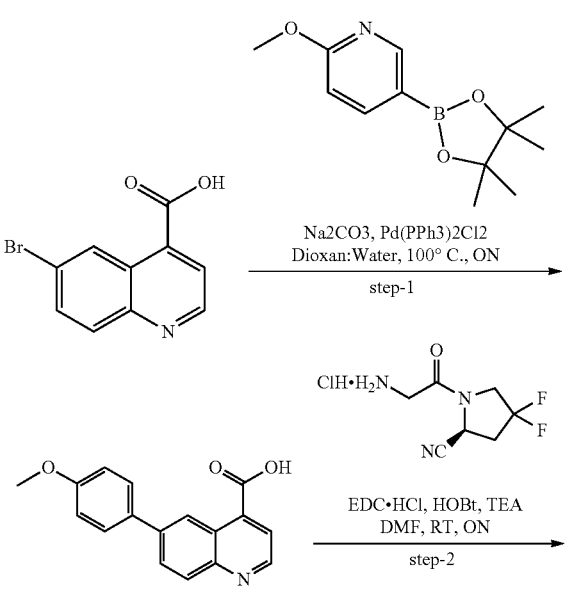

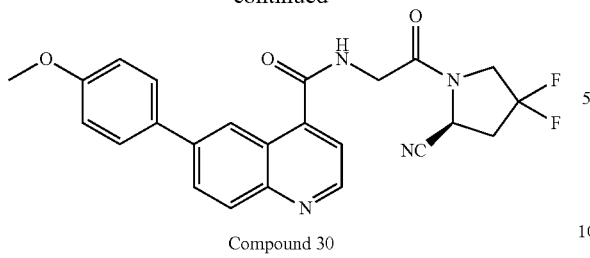

Compound 30

Step 1: Synthesis of 6-(4-methoxyphenyl)quinoline-4-carboxylic acid. To the solution of 2-(4-methoxyphenyl)-4,4,5,5-tetramethyl-1,3,2-dioxaborolane (100 mg, 0.42 mmol, 1.0 equiv) in Dioxane:water (05:02 mL), was added 6-bromoquinoline-4-carboxylic acid (108 mg, 0.42 mmol, 1.0 equiv), Na$_2$CO$_3$ (89 mg, 0.84 mmol, 2.0 equiv) followed by the addition of Pd(PPh$_3$)$_2$Cl$_2$ (15 mg, 0.021 mmol, 0.05 equiv). The resulting reaction mixture was heated at 100° C. for overnight. Product formation was confirmed by LCMS. After completion of reaction the reaction mixture was diluted with water (30 mL). Aqueous layer was washed with extracted with ethyl acetate (50 mL×2) separated and freeze dried over lyophilizer to obtain 6-(4-methoxyphenyl)quinoline-4-carboxylic acid (100 mg, 80% Yield) as an off white solid.

LCMS 280.1 [M+H]$^+$

Step 2: Synthesis of (S)—N-(2-(2-cyano-4,4-difluoropyrrolidin-1-yl)-2-oxoethyl)-6-(4-methoxyphenyl)quinoline-4-carboxamide. To a stirred solution of 6-(4-methoxyphenyl)quinoline-4-carboxylic acid (100 mg, 0.35 mmol, 1.0 equiv) in DMF (05 mL), was added (S)-4,4-difluoro-1-glycylpyrrolidine-2-carbonitrile hydrochloride (81 mg, 0.35 mmol, 1.0 equiv), HOBT (70 mg, 0.52 mmol, 1.5 equiv) and EDC.HCl (100 mg, 0.52 mmol, 1.5 equiv). The mixture was allowed to stir at RT for 10 min. Triethyl amine (0.14 mL) was added and the mixture was allowed to stir at RT for overnight. Product formation was confirmed by LCMS and TLC. After completion of reaction, the mixture was diluted with water (50 mL) and extracted with ethyl acetate (50 mL×2). Combined organic extracts were washed with water (20 mL×4), dried over anhydrous Na$_2$SO$_4$ and concentrated. The crude product obtained was purified reversed phase HPLC to obtain (S)—N-(2-(2-cyano-4,4-difluoropyrrolidin-1-yl)-2-oxoethyl)-6-(4-methoxyphenyl)quinoline-4-carboxamide (20 mg, 13% Yield) as a yellow solid.

LCMS 451.4 [M+H]$^+$ $^1$H NMR (400 MHz, DMSO-d$_6$) δ 9.18 (t, J=5.92 Hz, 1H) 8.96 (d, J=4.39 Hz, 1H) 8.74 (d, J=1.75 Hz, 1H) 8.09-8.23 (m, 2H) 7.83-7.92 (m, 2H) 7.58 (d, J=4.39 Hz, 1H) 7.10 (m, J=8.77 Hz, 2H) 5.20 (dd, J=9.21, 2.63 Hz, 1H) 4.28-4.43 (m, 2H) 4.06-4.22 (m, 2H) 3.77-3.85 (m, 3H) 2.80-3.01 (m, 2H).

Example 5-31

Synthesis of (S)—N-(2-(2-cyano-4,4-difluoropyrrolidin-1-yl)-2-oxoethyl)-6-(4-(trifluoromethoxy)phenyl)quinoline-4-carboxamide

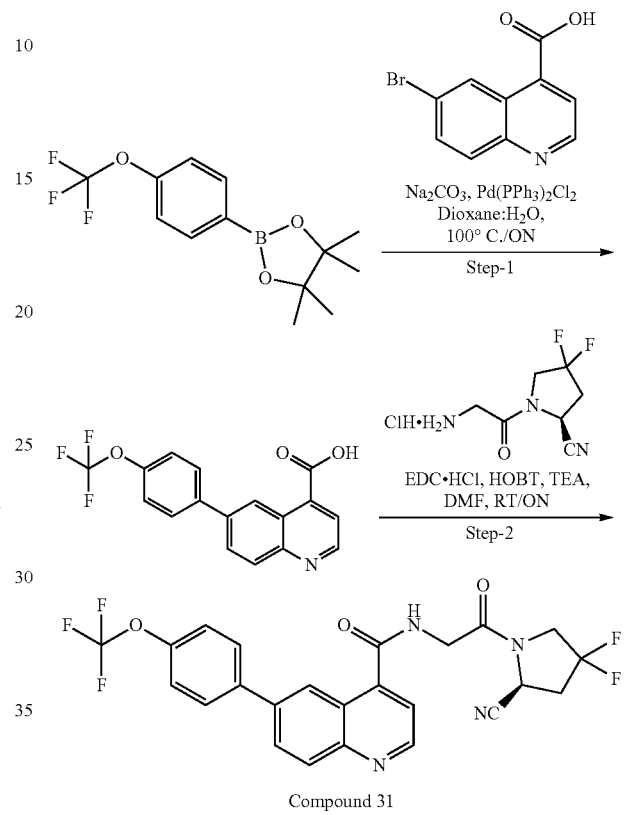

Compound 31

Step 1: Synthesis of 6-(4-(trifluoromethoxy)phenyl)quinoline-4-carboxylic acid. To the solution of 4,4,5,5-tetramethyl-2-(4-(trifluoromethoxy)phenyl)-1,3,2-dioxaborolane (100 mg, 0.34 mmol, 1.0 equiv) in Dioxane: water (05:02 mL), was added 6-bromoquinoline-4-carboxylic acid (86 mg, 0.34 mmol, 1.0 equiv), Na$_2$CO$_3$ (72 mg, 0.68 mmol, 2.0 equiv) followed by the addition of Pd(PPh$_3$)$_2$Cl$_2$ (12 mg, 0.017 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(4-(trifluoromethoxy)phenyl)quinoline-4-carboxylic acid (100 mg, 86% Yield) as an off white solid.

LCMS 334.0 [M+H]$^+$

Step 2: Synthesis of (S)—N-(2-(2-cyano-4,4-difluoropyrrolidin-1-yl)-2-oxoethyl)-6-(4-(trifluoromethoxy)phenyl)quinoline-4-carboxamide. To a stirred solution of 6-(4-(trifluoromethoxy)phenyl)quinoline-4-carboxylic acid (100 mg, 0.30 mmol, 1.0 equiv) in DMF (05 mL), was added (S)-4,4-difluoro-1-glycylpyrrolidine-2-carbonitrile hydrochloride (68 mg, 0.30 mmol, 1.0 equiv), HOBT (61 mg, 0.45 mmol, 1.5 equiv) and EDC.HCl (86 mg, 0.45 mmol, 1.5 equiv). The mixture was allowed to stir at RT for 10 min. Triethyl amine (0.10 mL) was added and the mixture was allowed to stir at RT for overnight. Product formation was confirmed by LCMS and TLC. After completion of reaction, the reaction mixture was diluted with water (50 mL) and extracted with ethyl acetate (50 mL×2). Combined organic extracts were washed with water (20 mL×4), dried over anhydrous Na$_2$SO$_4$ and concentrated. The crude product obtained was purified reversed phase HPLC to obtain (S)—N-(2-(2-cyano-4,4-difluoropyrrolidin-1-yl)-2-oxoethyl)-6-(4-(trifluoromethoxy)phenyl)quinoline-4-carboxamide (10 mg, 07% Yield) as an off-white solid.

LCMS 505.4 [M+H]$^+$ $^1$H NMR (400 MHz, DMSO-d$_6$) δ 9.19 (br. s., 1H), 9.00 (d, J=4.38 Hz, 1H), 8.87 (s, 1H), 8.16-8.28 (m, 2H), 8.00-8.12 (m, J=8.77 Hz, 2H), 7.60 (d, J=4.38 Hz, 1H), 7.45-7.57 (m, J=8.33 Hz, 2H), 5.21 (d, J=6.58 Hz, 1H), 4.27-4.36 (m, 2H), 4.08-4.22 (m, 2H), 2.95 (br. s., 1H), 2.89 (br. s., 1H).

Example S-32

Synthesis of (S)—N-(2-(2-cyano-4,4-difluoropyrrolidin-1-yl)-2-oxoethyl)-6-(4-((4-methylpiperazin-1-yl)methyl)phenyl)quinoline-4-carboxamide

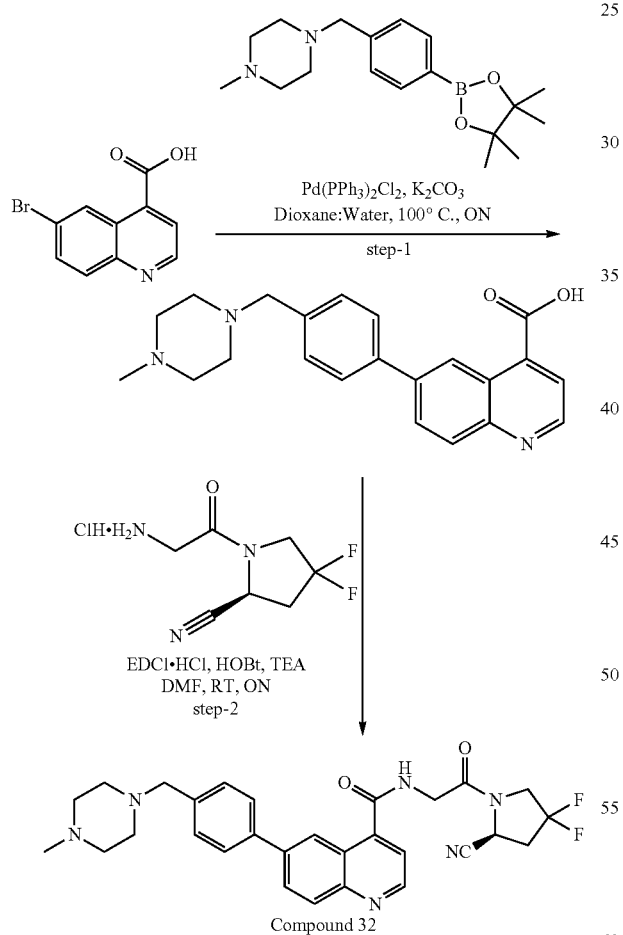

Compound 32

Step 1: Synthesis of 6-(4-((4-methylpiperazin-1-yl)methyl)phenyl)quinoline-4-carboxylic acid. To a stirred solution of 6-bromoquinoline-4-carboxylic acid (0.239 g, 0.949 mmol, 1.0 equiv) in Dioxane (10 mL) was added 1-methyl-4-(4-(4,4,5,5-tetramethyl-1,3,2-dioxaborolan-2-yl)benzyl)piperazine (0.300 g, 0.949 mmol, 1.0 equiv) and a solution of K$_2$CO$_3$ (0.262 g, 1.898 mmol, 2.0 equiv) in water (10 mL), the mixture was purged with N$_2$ gas for 10 min, followed by the addition of Pd(PPh$_3$)$_2$Cl$_2$(0.033 g, 0.047 mmol. 0.05 equiv). The resulting reaction mixture was heated at 100° C. for overnight. Product formation was confirmed by LCMS. After the completion of reaction the reaction mixture was diluted with water (30 mL) washed with ethyl acetate (20 mL×2). Aqueous layer was separated and freeze dried over lyophilizer to obtain 6-(4-((4-methylpiperazin-1-yl)methyl)phenyl)quinoline-4-carboxylic acid (0.200 g, 58% Yield) as a yellow solid.

LCMS 362.2 [M+H]$^+$ $^1$H NMR (400 MHz, DMSO-d$_6$) δ 8.96-9.05 (m, 1H) 8.75 (d, J=4.38 Hz, 1H) 7.92-8.03 (m, 2H) 7.69 (d, J=7.89 Hz, 2H) 7.36-7.52 (m, 3H) 3.51 (s, 2H) 2.33 (br. s., 4H). 2.15 (s, 3H).

Step 2: Synthesis of (S)—N-(2-(2-cyano-4,4-difluoropyrrolidin-1-yl)-2-oxoethyl)-6-(4-((4-methylpiperazin-1-yl)methyl)phenyl)quinoline-4-carboxamide. To a stirred solution of 6-(4-((4-methylpiperazin-1-yl)methyl)phenyl)quinoline-4-carboxylic acid (0.200 g, 0.554 mmol, 1.0 equiv) in DMF (5 mL), was added (S)-4,4-difluoro-1-glycylpyrrolidine-2-carbonitrile hydrochloride (0.186 g, 0.831 mmol, 1.5 equiv), HOBt (0.112 g, 0.831 mmol, 1.5 equiv) and EDC.HCl (0.158 g, 0.831 mmol, 1.5 equiv) followed by the addition of TEA (0.15 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous Na$_2$SO$_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(4-((4-methylpiperazin-1-yl)methyl)phenyl)quinoline-4-carboxamide (0.050 g, 17.00% Yield) as a white solid.

LCMS 533.5 [M+H]$^+$ $^1$H NMR (400 MHz, DMSO-d$_6$) δ 9.18 (br. s., 1H) 8.98 (d, J=3.95 Hz, 1H) 8.73 (s, 1H) 8.12-8.24 (m, 2H) 7.87 (m, J=8.33 Hz, 2H) 7.59 (d, J=4.39 Hz, 1H) 7.45 (m, J=7.89 Hz, 2H) 5.18 (d, J=7.45 Hz, 1H) 4.34 (br. s., 2H) 4.28 (d, J=4.39 Hz, 3H) 3.53 (br. s., 3H) 2.86 (d, J=19.29 Hz, 5H) 2.30 (d, J=18.86 Hz, 3H).

Example S-33

Synthesis of (S)—N-(2-(2-cyano-4,4-difluoropyrrolidin-1-yl)-2-oxoethyl)-6-(6-methoxypyridin-3-yl)quinoline-4-carboxamide

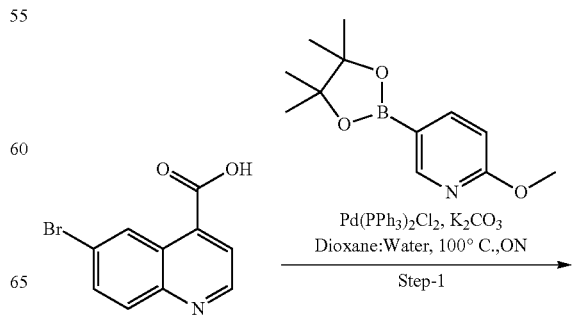

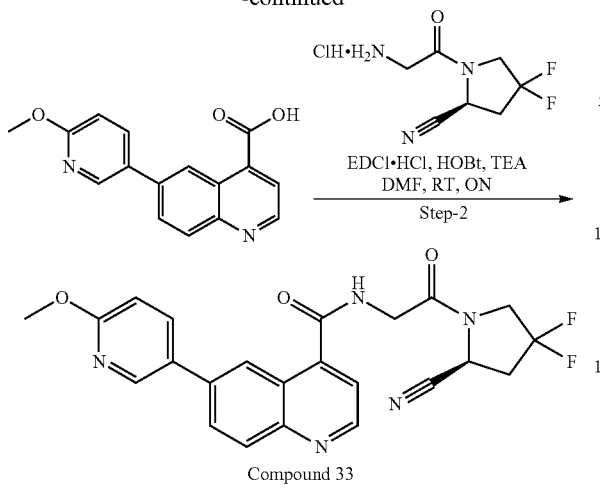

Compound 33

Step 1: Synthesis of 6-(6-methoxypyridin-3-yl)quinoline-4-carboxylic acid. To a stirred solution of 6-bromoquinoline-4-carboxylic acid (0.250 g, 0.992 mmol, 1.0 equiv) in Dioxane (5 mL) was added 2-Methoxypyridine-5-boronic acid pinacol ester (0.279 g, 1.190 mmol, 1.5 equiv) and a solution of $K_2CO_3$ (0.273 g, 1.984 mmol, 2.0 equiv) in water (2 mL), and resulting reaction mixture was purged with $N_2$ gas for 10 min, followed by the addition of $Pd(PPh_3)Cl_2$ (0.034 g, 0.049 mmol. 0.05 equiv). The resulting reaction mixture was heated at 100° C. for overnight. Product formation was confirmed by LCMS. Reaction mixture was cooled to RT, diluted with water (60 mL) washed with ethyl acetate (20 mL×3). The aqueous layer was separated and freeze dried over lyophilyzer to obtain 6-(6-methoxypyridin-3-yl)quinoline-4-carboxylic acid (0.250 g, 90.25% Yield) as a yellow solid.

LCMS 281.1 [M+H]$^+$ $^1$H NMR (400 MHz, DMSO-d$_6$) δ 9.00 (d, J=1.75 Hz, 1H) 8.77 (d, J=4.38 Hz, 1H) 8.49-8.60 (m, 1H) 8.05-8.15 (m, 1H) 7.90-8.05 (m, 2H) 7.50 (d, J=4.38 Hz, 1H) 6.98 (d, J=8.77 Hz, 1H) 3.92 (s, 3H).

Step 2: Synthesis of (S)—N-(2-(2-cyano-4,4-difluoropyrrolidin-1-yl)-2-oxoethyl)-6-(6-methoxypyridin-3-yl)quinoline-4-carboxamide. To a stirred solution of 6-(6-methoxypyridin-3-yl)quinoline-4-carboxylic acid (0.250 g, 0.892 mmol, 1.0 equiv) in DMF (5 mL), was added (S)-4,4-difluoro-1-glycylpyrrolidine-2-carbonitrile hydrochloride (0.301 g, 1.339 mmol, 1.5 equiv), HOBt (0.180 g, 1.339 mmol, 1.5 equiv) and EDC.HCl (0.255 g, 1.339 mmol, 1.5 equiv) followed by the addition of TEA (0.27 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-methoxypyridin-3-yl)quinoline-4-carboxamide (0.160 g, 40% Yield) as a white solid.

LCMS 452.3 [M+H]$^+$ $^1$H NMR (400 MHz, DMSO-d$_6$) δ 9.19 (t, J=5.70 Hz, 1H) 8.98 (d, J=3.95 Hz, 1H) 8.76 (s, 1H) 8.70 (br. s., 1H) 8.30 (d, J=8.33 Hz, 1H) 8.07-8.27 (m, 2H) 7.59 (d, J=4.38 Hz, 1H) 6.99 (d, J=8.77 Hz, 1H) 5.20 (d, J=8.33 Hz, 1H) 4.10-4.39 (m, 4H) 3.93 (s, 3H) 2.73-3.02 (m, 2H).

Example S-34

Synthesis of (S)—N-(2-(2-cyano-4,4-difluoropyrrolidin-1-yl)-2-oxoethyl)-6-(6-isopropoxypyridin-3-yl)quinoline-4-carboxamide

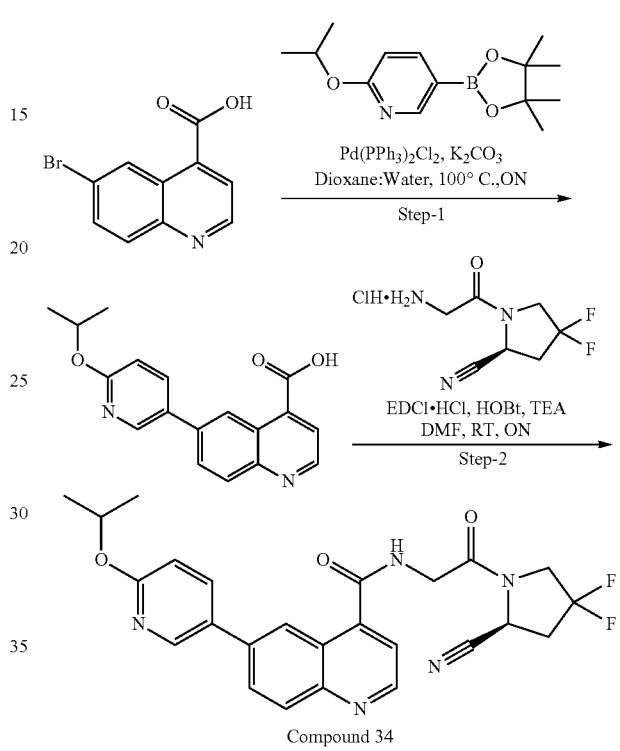

Compound 34

Step 1: Synthesis of 6-(6-isopropoxypyridin-3-yl)quinoline-4-carboxylic acid. To a stirred solution of 6-bromoquinoline-4-carboxylic acid (0.250 g, 0.992 mmol, 1.0 equiv) in Dioxane (5 mL) was added 2-isopropoxy-5-(4,4,5,5-tetramethyl-1,3,2-dioxaborolan-2-yl)pyridine (0.313 g, 1.190 mmol, 1.2 equiv), $K_2CO_3$ (0.273 g, 1.98 mmol, 2.0 equiv) in water (2 mL) was added and mixture was purged with $N_2$ gas for 10 min followed by the addition of $Pd(PPh_3)Cl_2$ (0.034 g, 0.049 mmol. 0.05 equiv). The resulting reaction mixture was heated at 100° C. for overnight. Product formation was confirmed by LCMS. Reaction mixture was cooled to RT, diluted with water (60 mL) washed with ethyl acetate (20 mL×3). The aqueous layer was separated and freeze dried over lyophilyzer to obtain 6-(6-isopropoxypyridin-3-yl)quinoline-4-carboxylic acid (0.250 g, 82% Yield) as a yellow solid.

LCMS 309.0 [M+H]$^+$ $^1$H NMR (400 MHz, DMSO-d$_6$) δ 8.90-9.07 (m, 1H) 8.76 (d, J=4.38 Hz, 1H) 8.52 (d, J=2.19 Hz, 1H) 7.92-8.07 (m, 3H) 7.48 (d, J=4.38 Hz, 1H) 6.89 (d, J=8.77 Hz, 1H) 5.20-5.40 (m, 1H) 1.33 (d, J=6.14 Hz, 6H).

Step 2: Synthesis of (S)—N-(2-(2-cyano-4,4-difluoropyrrolidin-1-yl)-2-oxoethyl)-6-(6-isopropoxypyridin-3-yl)quinoline-4-carboxamide. To a stirred solution of 6-(6-isopropoxypyridin-3-yl)quinoline-4-carboxylic acid (0.100 g, 0.324 mmol, 1.0 equiv) in DMF (2 mL), was added (S)-4,4-difluoro-1-glycylpyrrolidine-2-carbonitrile hydrochloride (0.109 g, 0.487 mmol, 1.5 equiv), HOBt (0.065 g, 0.487 mmol, 1.5 equiv) and EDC.HCl (0.093 g, 0.487 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) followed by reversed phase HPLC purification to obtain (S)—N-(2-(2-cyano-4,4-difluoropyrrolidin-1-yl)-2-oxoethyl)-6-(6-isopropoxypyridin-3-yl)quinoline-4-carboxamide (0.110 g, 70.96% Yield) as an off white solid.

LCMS 480.4 [M+H]$^+$ $^1$H NMR (400 MHz, DMSO-d$_6$) δ 9.20 (t, J=5.92 Hz, 1H) 8.99 (d, J=4.38 Hz, 1H) 8.77 (d, J=1.75 Hz, 1H) 8.68 (d, J=2.63 Hz, 1H) 8.29 (dd, J=8.55, 2.41 Hz, 1H) 8.23 (dd, J=8.99, 1.97 Hz, 1H) 8.17 (d, J=9.21 Hz, 1H) 7.61 (d, J=4.38 Hz, 1H) 6.91 (d, J=8.33 Hz, 1H) 5.33 (dt, J=12.61, 6.19 Hz, 1H) 5.19 (dd, J=9.43, 2.41 Hz, 1H) 4.23-4.41 (m, 3H) 4.03-4.23 (m, 1H) 2.95 (br. s., 1H) 2.76-2.92 (m, 1H) 1.33 (d, J=6.14 Hz, 6H).

Example S-35

Synthesis of (S)—N-(2-(2-cyano-4,4-difluoropyrrolidin-1-yl)-2-oxoethyl)-6-(4-(2-methoxyethoxy)phenyl)quinoline-4-carboxamide

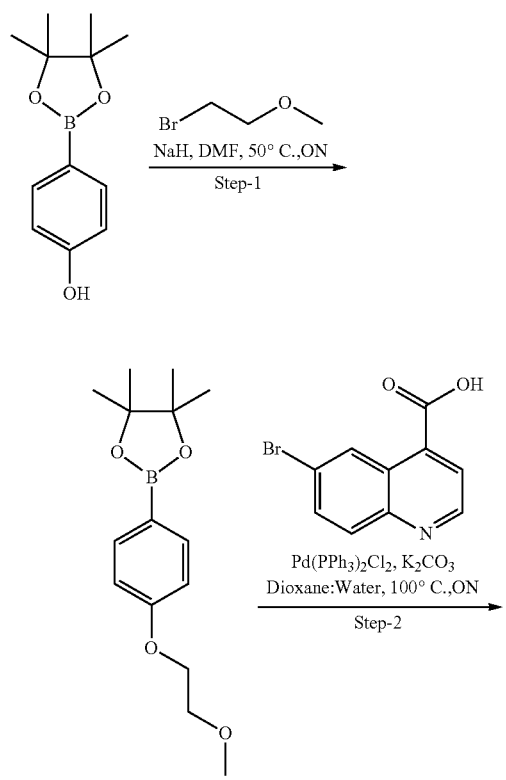

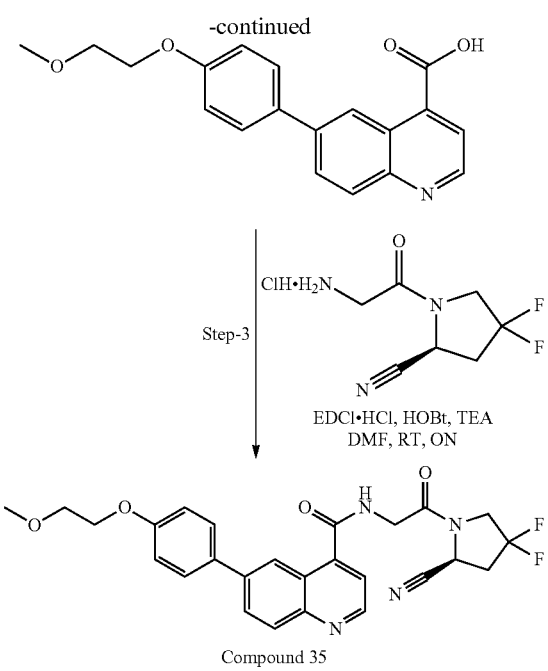

Compound 35

Step 1: Synthesis of 2-(4-(2-Methoxyethoxy) phenyl)-4,4,5,5-tetramethyl-1,3,2-dioxaborolane. To a stirred solution of 4-Hydroxyphenylboronic Acid Pinacol Ester (0.200 g, 0.909 mmol, 1.0 equiv) In DMF (3 mL) was added NaH (0.165 g, 3.450 mmol, 3.8 equiv) portion wise at 0° C. 2-Bromoethyl methyl ether (0.189 g, 1.363 mmol, 1.5 equiv), was added and the resulting reaction mixture was heated at 50° C. for overnight. Product formation was confirmed by LCMS. Reaction mixture was cooled to RT, diluted with ice-cold water (40 mL) and extracted with ethyl acetate (50 mL×3). Combined organic extracts were washed with water (20 mL×3) and brine (20 mL), dried over anhydrous $Na_2SO_4$ and concentrated. The crude product was purified by flash chromatography (0-5% ethyl acetate in Hexane as an eluent) to obtain 2-(4-(2-Methoxyethoxy) phenyl)-4,4,5,5-tetramethyl-1,3,2-dioxaborolane (0.115 g, 45.63% Yield) as a transparent oil.

LCMS 279.0 [M+H]$^+$ $^1$H NMR (400 MHz, CHLOROFORM-d) δ 7.74 (m, J=8.77 Hz, 2H) 6.92 (m, J=8.77 Hz, 2H) 4.14 (d, J=4.82 Hz, 2H) 3.76 (d, J=4.82 Hz, 2H) 3.45 (s, 3H) 1.33 (s, 12H).

Step 2: Synthesis of 6-(4-(2-methoxyethoxy)phenyl)quinoline-4-carboxylic acid. To a stirred solution of 6-bromoquinoline-4-carboxylic acid (0.250 g, 0.992 mmol, 1.0 equiv) in Dioxane (4 mL) was added 2-(4-(2-Methoxyethoxy) phenyl)-4,4,5,5-tetramethyl-1,3,2-dioxaborolane (0.330 g, 1.190 mmol, 1.2 equiv), $K_2CO_3$ (0.273 g, 1.984 mmol, 2.0 equiv) in water (2 mL), and the mixture was purged with $N_2$ gas for 10 min followed by the addition of Pd(PPh$_3$)$_2$Cl$_2$ (0.034 g, 0.049 mmol. 0.05 equiv). The resulting reaction mixture was heated at 100° C. for overnight. Product formation was confirmed by LCMS. Reaction mixture was cooled to RT, diluted with water (60 mL) washed with ethyl acetate (20 mL×2). The aqueous layer was separated and freeze dried over lyophilyzer to obtain 6-(4-(2-methoxyethoxy)phenyl)quinoline-4-carboxylic acid (0.250 g, 78.12% Yield) as an off-white solid.

LCMS 324.0 [M+H]$^+$ $^1$H NMR (400 MHz, DMSO-d$_6$) δ 8.90-9.01 (m, 1H) 8.73 (d, J=4.39 Hz, 1H) 7.88-8.02 (m, 2H) 7.68 (m, J=8.77 Hz, 2H) 7.47 (d, J=4.38 Hz, 1H) 7.09 (m, J=8.77 Hz, 2H) 4.10-4.22 (m, 2H) 3.62-3.73 (m, 2H) 3.35 (s, 3H).

Step 3: Synthesis of (S)—N-(2-(2-cyano-4,4-difluoropyrrolidin-1-yl)-2-oxoethyl)-6-(4-(2-methoxyethoxy)phenyl)quinoline-4-carboxamide. To a stirred solution of 6-(4-(2-methoxyethoxy)phenyl)quinoline-4-carboxylic acid (0.100 g, 0.309 mmol, 1.0 equiv) in DMF (2 mL), was added (S)-4,4-difluoro-1-glycylpyrrolidine-2-carbonitrile hydrochloride (0.104 g, 0.464 mmol, 1.5 equiv), HOBt (0.062 g, 0.464 mmol, 1.5 equiv) EDC.HCl (0.088 g, 0.464 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(4-(2-methoxyethoxy)phenyl)quinoline-4-carboxamide (0.130 g, 85% Yield) as an off white solid.

LCMS 495.4 [M+H]$^+$ $^1$H NMR (400 MHz, DMSO-$d_6$) δ 9.17 (t, J=5.92 Hz, 1H) 8.95 (d, J=3.95 Hz, 1H) 8.73 (d, J=1.75 Hz, 1H) 8.02-8.25 (m, 2H) 7.87 (m, J=8.77 Hz, 2H) 7.56 (d, J=4.39 Hz, 1H) 7.10 (m, J=8.77 Hz, 2H) 5.20 (dd, J=9.21, 2.63 Hz, 1H) 4.24-4.38 (m, 2H) 4.10-4.24 (m, 3H) 3.63-3.75 (m, 2H) 2.77-3.05 (m, 2H).

Example S-36

Synthesis of (S)—N-(2-(2-cyano-4,4-difluoropyrrolidin-1-yl)-2-oxoethyl)-6-(6-(2-methoxyethoxy)pyridin-3-yl)quinoline-4-carboxamide

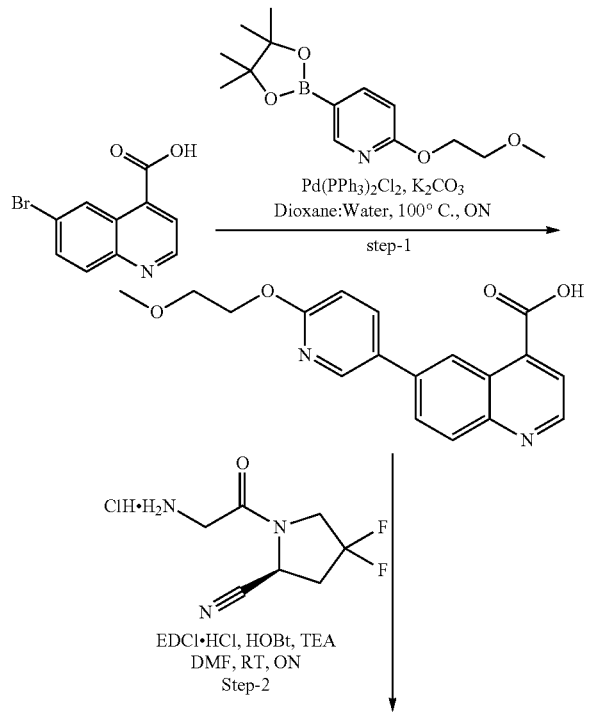

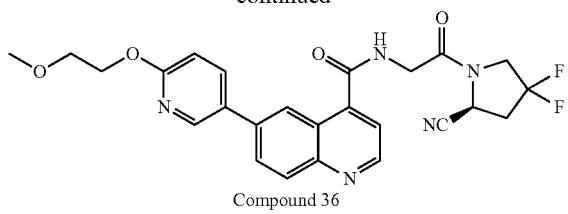

Compound 36

Step 1: Synthesis of 6-(6-(2-methoxyethoxy)pyridin-3-yl)quinoline-4-carboxylic acid. To a stirred solution of 6-bromoquinoline-4-carboxylic acid (0.250 g, 0.992 mmol, 1.0 equiv) in Dioxane (5 mL) was added 2-(2-Methoxy-ethoxy)-5-(4,4,5,5-tetramethyl-[1,3,2]dioxaborolan-2-yl)-pyridine (0.332 g, 1.190 mmol, 1.2 equiv), $K_2CO_3$ (0.273 g, 1.984 mmol, 2.0 equiv) in water (2 mL), was added and mixture was purged with $N_2$ gas for 10 min followed by the addition of $Pd(PPh_3)Cl_2$ (0.034 g, 0.049 mmol. 0.05 equiv). The resulting reaction mixture was heated at 100° C. for overnight. Product formation was confirmed by LCMS. Reaction mixture was cool to RT, diluted with water (60 mL) washed with ethyl acetate (20 mL×3). The aqueous layer was separated and freeze dried over lyophilyzer to obtain 6-(6-(2-methoxyethoxy)pyridin-3-yl)quinoline-4-carboxylic acid (0.250 g, 77.88% Yield) as a yellow solid.

LCMS 325.0 [M+H]$^+$ $^1$H NMR (400 MHz, DMSO-$d_6$) δ 9.00 (s, 1H) 8.76 (d, J=4.38 Hz, 1H) 8.52 (d, J=2.19 Hz, 1H) 8.06 (dd, J=8.55, 2.41 Hz, 1H) 7.88-8.02 (m, 2H) 7.49 (d, J=4.38 Hz, 1H) 6.98 (d, J=8.77 Hz, 1H) 4.36-4.50 (m, 2H) 3.62-3.79 (m, 2H) 3.32 (s, 3H).

Step 2: Synthesis of (S)—N-(2-(2-cyano-4,4-difluoropyrrolidin-1-yl)-2-oxoethyl)-6-(6-(2-methoxyethoxy)pyridin-3-yl)quinoline-4-carboxamide. To a stirred solution of 6-(6-(2-methoxyethoxy)pyridin-3-yl)quinoline-4-carboxylic acid (0.100 g, 0.308 mmol, 1.0 equiv) in DMF (2 mL), was added (S)-4,4-difluoro-1-glycylpyrrolidine-2-carbonitrile hydrochloride (0.104 g, 0.462 mmol, 1.5 equiv), HOBt (0.062 g, 0.462 mmol, 1.5 equiv) and EDC.HCl (0.088 g, 0.462 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(6-(2-methoxyethoxy)pyridin-3-yl)quinoline-4-carboxamide (0.130 g, 85% Yield) as an off white solid.

LCMS 496.4 [M+H]$^+$ $^1$H NMR (400 MHz, DMSO-$d_6$) δ 9.18 (t, J=5.92 Hz, 1H) 8.98 (d, J=4.38 Hz, 1H) 8.77 (s, 1H) 8.68 (d, J=2.19 Hz, 1H) 8.31 (dd, J=8.77, 2.63 Hz, 1H) 8.06-8.28 (m, 2H) 7.59 (d, J=4.38 Hz, 1H) 6.99 (d, J=8.33 Hz, 1H) 5.19 (dd, J=9.21, 2.63 Hz, 1H) 4.40-4.53 (m, 2H) 4.10-4.39 (m, 4H) 3.62-3.78 (m, 2H) 3.33 (s, 3H) 2.73-3.01 (m, 2 H).

Example S-37

Synthesis of (S,E)-N-(2-(2-cyano-4,4-difluoropyrrolidin-1-yl)-2-oxoethyl)-6-(2-(2-oxo-1,2,3,4-tetrahydroquinolin-6-yl)vinyl)quinoline-4-carboxamide

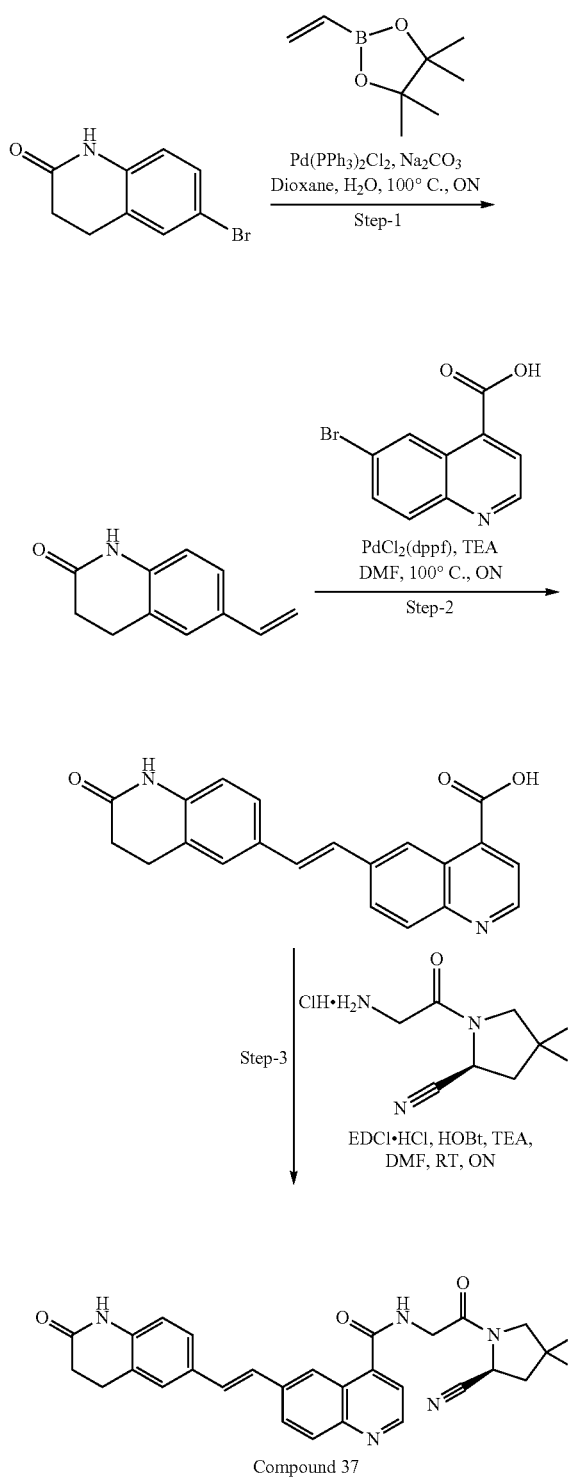

Compound 37

Step 1: Synthesis of 6-vinyl-3,4-dihydroquinolin-2(1H)-one. To a solution of 6-bromo-3,4-dihydroquinolin-2(1H)-one (0.290 g, 1.29 mmol, 0.8 equiv) and 4,4,5,5-tetramethyl-2-vinyl-1,3,2-dioxaborolane (0.250 g, 1.62 mmol, 1.0 equiv), in dioxane (10 mL) and water (1 mL) was added $Na_2CO_3$ (0.343 g, 3.24 mmol, 2.0 equiv). The resulting reaction mixture was purged with $N_2$ gas for 10 min followed by the addition of $Pd(PPh_3)Cl_2$(0.056 g, 0.081 mmol, 0.05 equiv). The resulting reaction mixture was heated at 100° C. for overnight. Product formation was confirmed by LCMS and TLC. After the completion of reaction, the reaction mixture was diluted with water (50 mL) and extracted with ethyl acetate (100 mL×2). Combined organic extracts were washed with water (50 mL×2), dried over anhydrous $Na_2SO_4$ and concentrated under reduced pressure. The crude product was purified by flash chromatography (0-30% ethyl acetate in hexane as an eluent) to obtain 6-vinyl-3,4-dihydroquinolin-2(1H)-one (0.140 g, 60% yield) as a yellow semi solid.

LCMS 173.9 $[M+H]^+$

Step 2: Synthesis of (E)-6-(2-(2-oxo-1,2,3,4-tetrahydroquinolin-6-yl)vinyl)quinoline-4-carboxylic acid. To a solution of 6-bromoquinoline-4-carboxylic acid (0.2 g, 0.796 mmol, 1.0 equiv) and 6-vinyl-3,4-dihydroquinolin-2(1H)-one (0.150 g, 0.876 mmol, 1.1 equiv) in DMF (5 ml) was added TEA (0.241 g, 2.38 mmol, 3.0 equiv). The resulting reaction mixture was purged with $N_2$ gas for 10 min followed by the addition of $Pd(dppf)Cl_2$ (0.042 g, 0.057 mmol. 0.05 equiv) at RT. The resulting reaction mixture was heated at 100° C. for overnight. Product formation was confirmed by LCMS. After the completion of reaction, the mixture was diluted with water (20 mL) and aqueous layer washed with ethyl acetate (10 mL×3). The aqueous layer was separated and freeze dried over lyophilyzer to obtain (E)-6-(2-(2-oxo-1,2,3,4-tetrahydroquinolin-6-yl)vinyl)quinoline-4-carboxylic acid (0.150 g, Quant. Yield).

LCMS 345.2 $[M+H]^+$

Step 3: Synthesis of (S,E)-N-(2-(2-cyano-4,4-difluoropyrrolidin-1-yl)-2-oxoethyl)-6-(2-(2-oxo-1,2,3,4-tetrahydroquinolin-6-yl)vinyl)quinoline-4-carboxamide. To a stirred solution of synthesis of (E)-6-(2-(2-oxo-1,2,3,4-tetrahydroquinolin-6-yl)vinyl)quinoline-4-carboxylic acid (0.150 g, 0.434 mmol, 1.0 equiv) in DMF (7 mL), was added (S)-4,4-difluoro-1-glycylpyrrolidine-2-carbonitrile hydrochloride (0.146 g, 0.652 mmol, 1.5 equiv), HOBt (0.088 g, 0.652 mmol, 1.5 equiv) and EDC.HCl (0.125 g, 0.652 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) followed by the reversed phase HPLC purification to obtain (S,E)-N-(2-(2-cyano-4,4-difluoropyrrolidin-1-yl)-2-oxoethyl)-6-(2-(2-oxo-1,2,3,4-tetrahydroquinolin-6-yl)vinyl)quinoline-4-carboxamide (0.008 g, 4% Yield) as an off-white solid.

LCMS 516.5 $[M+H]^+$ $^1$H NMR (400 MHz, DMSO-$d_6$) δ 10.21 (s, 1H) 9.18 (br. s., 1H) 8.91 (d, J=4.38 Hz, 1H) 8.57 (br. s., 1H) 8.01-8.11 (m, 2H) 7.54 (br. s., 1H) 7.47 (d, J=10.96 Hz, 1H) 7.30 (d, J=16.22 Hz, 1H) 6.87 (d, J=7.89 Hz, 1H) 5.24 (d, J=6.58 Hz, 1H) 4.22-4.39 (m, 4H) 4.18 (br. s., 2H) 2.91 (d, J=7.45 Hz, 2H) 1.23 (br. s., 3H).

Example S-38

Synthesis of (S,E)-N-(2-(2-cyano-4,4-difluoropyrrolidin-1-yl)-2-oxoethyl)-6-(2-(1-oxo-1,2,3,4-tetrahydroisoquinolin-6-yl)vinyl)quinoline-4-carboxamide

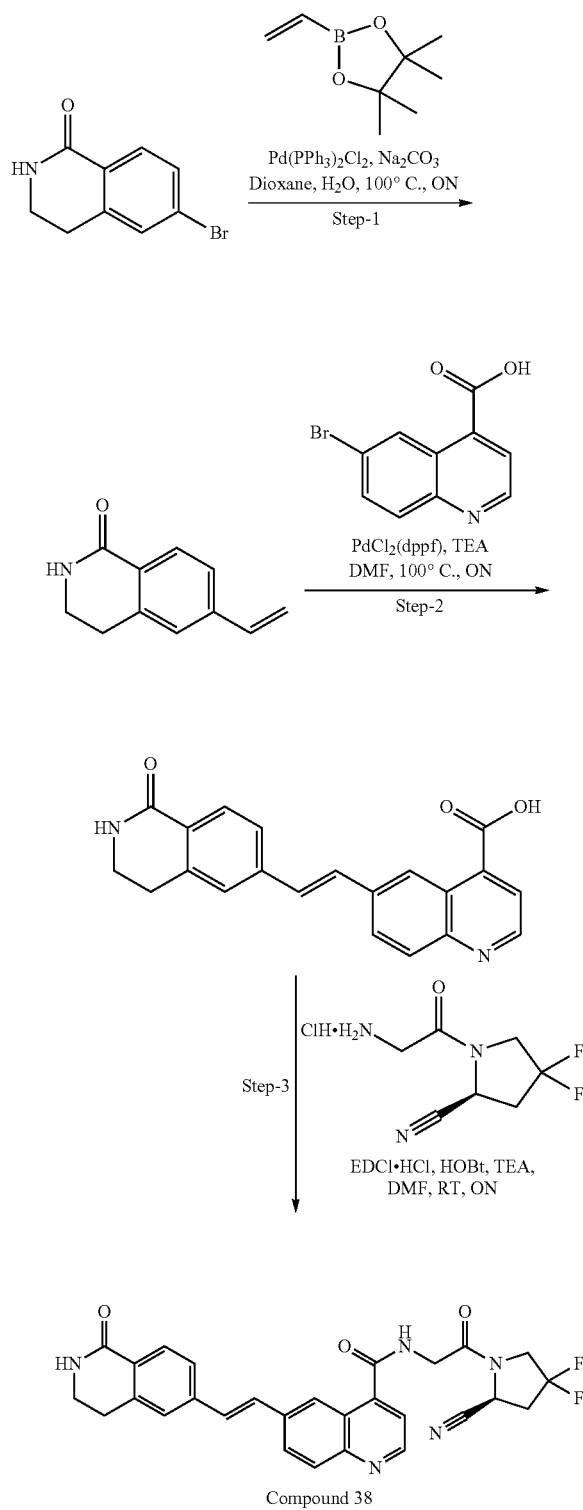

Compound 38

Step 1: Synthesis of 6-vinyl-3,4-dihydroisoquinolin-2(1H)-one. To a solution of 6-bromo-3,4-dihydroisoquinolin-2(1H)-one (0.290 g, 1.29 mmol, 0.8 equiv) and 4,4,5,5-tetramethyl-2-vinyl-1,3,2-dioxaborolane (0.250 g, 1.62 mmol, 1.0 equiv), in dioxane (10 mL) and water (1 mL) was added $Na_2CO_3$ (0.343 g, 3.24 mmol, 2.0 equiv). The resulting reaction mixture was purged with $N_2$ gas for 10 min followed by the addition of $Pd(PPh_3)Cl_2$ (0.056 g, 0.081 mmol, 0.05 equiv). The resulting reaction mixture was heated at 100° C. for overnight. Product formation was confirmed by LCMS and TLC. After the completion of reaction, the reaction mixture was diluted with water (50 mL) and extracted with ethyl acetate (100 mL×2). Combined organic extracts were washed with water (50 mL×2), dried over anhydrous $Na_2SO_4$ and concentrated. The crude product was purified by flash chromatography (0-30% ethyl acetate in hexane as an eluent) to obtain 6-vinyl-3,4-dihydroisoquinolin-2(1H)-one (0.100 g, 45% yield) as a yellow semi solid.

LCMS 174.1 [M+H]$^+$

Step 2: Synthesis of (E)-6-(2-(1-oxo-1,2,3,4-tetrahydroisoquinolin-6-yl)vinyl)quinoline-4-carboxylic acid. To a solution of 6-bromoquinoline-4-carboxylic acid (0.1 g, 0.398 mmol, 1.0 equiv and 6-vinyl-3,4-dihydroisoquinolin-2(1H)-one (0.075 g, 0.438 mmol, 1.1 equiv) in DMF (5 ml) was added in TEA (0.011 g, 0.117 mmol, 3.0 equiv). The resulting reaction mixture was purged with $N_2$ gas for 10 min followed by the addition of $Pd(dppf)Cl_2$ (0.029 g, 0.039 mmol. 0.05 equiv) at RT. The resulting reaction mixture was heated at 100° C. for overnight. Product formation was confirmed by LCMS. After the completion of reaction, the mixture was diluted with water (20 mL) and aqueous layer washed with ethyl acetate (10 mL×3). The aqueous layer was separated and freeze dried over lyophilyzer to obtain (E)-6-(2-(2-oxo-1,2,3,4-tetrahydroisoquinolin-6-yl)vinyl)quinoline-4-carboxylic acid (0.150 g, Quant. Yield).

LCMS 345.2 [M+H]$^+$

Step 3: Synthesis of (S,E)-N-(2-(2-cyano-4,4-difluoropyrrolidin-1-yl)-2-oxoethyl)-6-(2-(1-oxo-1,2,3,4-tetrahydroisoquinolin-6-yl)vinyl)quinoline-4-carboxamide. To a stirred solution of synthesis of (E)-6-(2-(2-oxo-1,2,3,4-tetrahydroisoquinolin-6-yl)vinyl)quinoline-4-carboxylic acid (0.150 g, 0.434 mmol, 1.0 equiv) in DMF (7 mL), was added (S)-4,4-difluoro-1-glycylpyrrolidine-2-carbonitrile hydrochloride (0.146 g, 0.652 mmol, 1.5 equiv), HOBt (0.088 g, 0.652 mmol, 1.5 equiv) and EDC.HCl (0.125 g, 0.652 mmol, 1.5 equiv) followed by the addition of TEA (0.1 mL). The resulting reaction mixture was allowed to stir at RT for overnight. Product formation was confirmed by LCMS and TLC. After completion of reaction, the reaction mixture was diluted with water (50 mL) and extracted with ethyl acetate (100 mL×2). Combined organic extracts were washed with water (50 mL×3) and brine (50 mL), dried over anhydrous $Na_2SO_4$ and concentrated. The crude product was purified by flash chromatography (0-5% MeOH in DCM as an eluent) followed by the reversed phase HPLC purification to obtain (S,E)-N-(2-(2-cyano-4,4-difluoropyrrolidin-1-yl)-2-oxoethyl)-6-(2-(1-oxo-1,2,3,4-tetrahydroisoquinolin-6-yl)vinyl)quinoline-4-carboxamide (0.01 g, 4.5% Yield) as yellow solid.

LCMS 516.5 [M+H]$^+$ $^1$H NMR (400 MHz, DMSO-$d_6$) δ 9.14-9.25 (m, 1H) 8.95 (d, J=4.38 Hz, 1H) 8.68 (s, 1H) 8.06-8.17 (m, 1H) 7.93 (br. s., 1H) 7.86 (d, J=7.89 Hz, 1H) 7.61-7.70 (m, 2H) 7.51-7.60 (m, 2H) 5.10-5.30 (m, 1H) 4.21-4.43 (m, 4H) 4.16 (d, J=9.21 Hz, 1H) 3.50 (br. s., 2H) 3.39 (br. s., 1H) 2.78-3.01 (m, 3H).

Example S-39

Synthesis of N—((R)-1-((S)-2-cyano-4,4-difluoropyrrolidin-1-yl)-1-oxopropan-2-yl)-3-phenylisonicotinamide

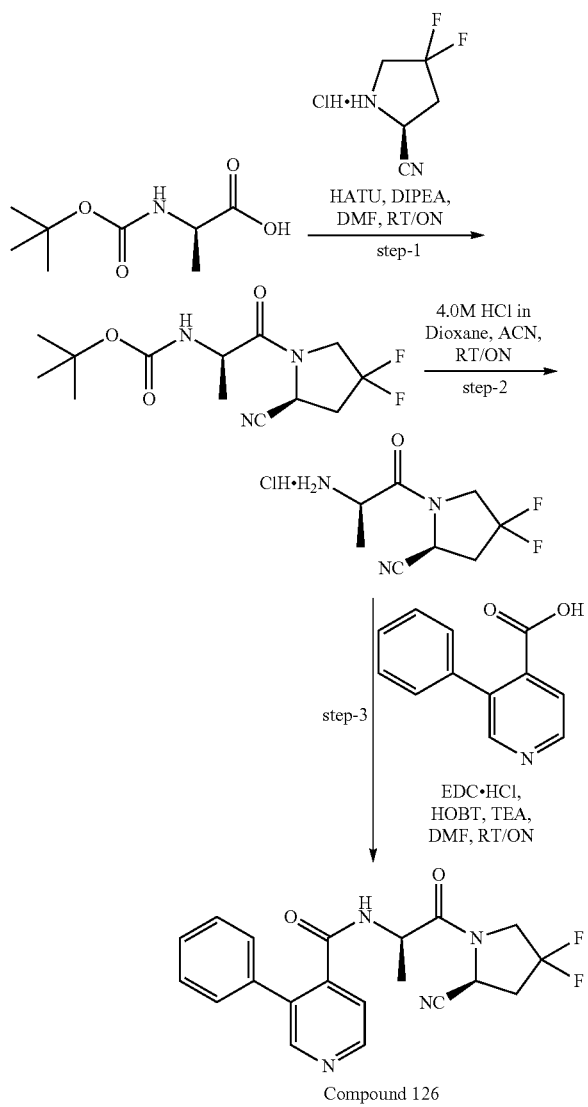

Compound 126

Step 1: Synthesis of tert-butyl ((R)-1-((S)-2-cyano-4,4-difluoropyrrolidin-1-yl)-1-oxopropan-2-yl)carbamate. To a stirred solution of (tert-butoxycarbonyl)-D-alanine (560 mg, 2.9 mmol, 1.0 equiv.) and HATU(2204 mg, 5.8 mmol, 2.0 equiv.) in DMF (10 mL was added (S)-4,4-difluoropyrrolidine-2-carbonitrile hydrochloride (500 mg, 2.9 mmol, 1.0 equiv) and stirred for 10 min. DIPEA (1.5 mL, 8.7 mmol, 3.0 equiv.) was added and the reaction mixture was allowed to stir for overnight at RT. Reaction progress was monitored by NMR and TLC. The reaction mixture was diluted with cold water (100 ml) and extracted with ethyl acetate (200 mL×2). Combined organic extracts were washed with water (100 mL×3), dried over anhydrous sodium sulphate and concentrated under reduced pressure to obtain tert-butyl ((R)-1-((S)-2-cyano-4,4-difluoropyrrolidin-1-yl)-1-oxopropan-2-yl)carbamate (300 mg, 34% Yield) as a brown solid.

$^1$H NMR (400 MHz, DMSO-d$_6$) δ 7.31 (d, J=7.45 Hz, 1H) 5.03 (d, J=8.77 Hz, 1H) 4.11-4.22 (m, 2H) 2.75-2.94 (m, 2H) 1.32-1.42 (m, 9H) 1.06-1.15 (m, 3H).

Step 2: Synthesis of (S)-1-(D-alanyl)-4,4-difluoropyrrolidine-2-carbonitrile hydrochloride. To a stirred solution of tert-butyl ((R)-1-((S)-2-cyano-4,4-difluoropyrrolidin-1-yl)-1-oxopropan-2-yl)carbamate (300 mg, 0.99 mmol, 1.0 equiv) in acetonitrile (10 mL) was added 4.0 M HCl in Dioxan (5.0 ml) dropwise at 0° C. over a period of 10 min. the mixture was allowed to stir at RT for overnight. The reaction progress was monitored by NMR. The solvent was evaporated under reduced pressure to obtain residue which was washed with 20 mL ethyl acetate and hexane (1:1) and dried under vacuum to obtain (S)-1-(D-alanyl)-4,4-difluoropyrrolidine-2-carbonitrile hydrochloride (200 mg, 80% Yield) as a yellow semi solid.

$^1$H NMR (400 MHz, DMSO-d$_6$) δ 8.31 (br. s., 2H), 5.18 (d, J=7.89 Hz, 1H), 3.94 (br. s., 1H), 3.82 (d, J=12.28 Hz, 1H), 2.82-3.03 (m, 1H), 2.75 (br. s., 1H), 1.19-1.32 (m, 3H).

Step 3: Synthesis of N—((R)-1-((S)-2-cyano-4,4-difluoropyrrolidin-1-yl)-1-oxopropan-2-yl)-3-phenylisonicotinamide. To a stirred solution of (S)-1-(D-alanyl)-4,4-difluoropyrrolidine-2-carbonitrile hydrochloride (300 mg, 1.2 mmol, 1.0 equiv.) in DMF (10 mL) was added 3-phenylisonicotinic acid (251 mg, 1.2 mmol, 1.0 equiv) HOBT (189 mg, 1.4 mmol, 1.2 equiv) and EDC.HCl (275 mg, 1.4 mmol, 1.2 equiv) followed by the addition of TEA (0.33 mL, 2.4 mmol, 2.0 equiv). The resulting reaction mixture was allowed to stir at RT for overnight. The reaction progress was monitored by NMR and TLC. The reaction mixture was diluted with cold water (50 mL) and extracted with ethyl acetate (50 mL×2). Combined organic extracts were washed with water (20 mL×2), dried over anhydrous sodium sulphate and concentrated under reduced pressure. The crude product was purified by reversed phase HPLC to obtain N—((R)-1-((S)-2-cyano-4,4-difluoropyrrolidin-1-yl)-1-oxopropan-2-yl)-3-phenylisonicotinamide (30 mg, 07% Yield) as a white solid.

LCMS 385.3 [M+H]$^+$ $^1$H NMR (400 MHz, DMSO-d$_6$) δ 8.99 (d, J=7.02 Hz, 1H) 8.68 (t, J=2.41 Hz, 2H) 7.33-7.56 (m, 6H) 5.03 (dd, J=9.21, 3.95 Hz, 1H) 4.54 (t, J=7.02 Hz, 1H) 4.20 (d, J=7.45 Hz, 1H) 4.00-4.08 (m, 1H) 2.76-2.98 (m, 2H) 1.16 (d, J=7.02 Hz, 3H).

Example S-40

Synthesis of N—((S)-1 WS)-2-cyano-4,4-difluoropyrrolidin-1-yl)-1-oxopropan-2-yl)-3-phenylisonicotinamide

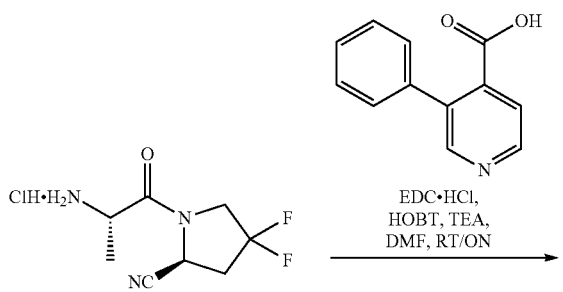

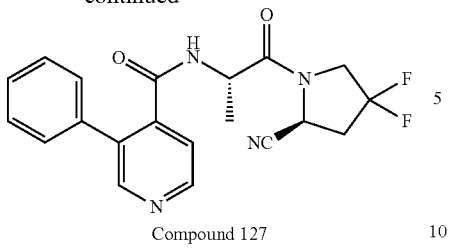

Compound 127

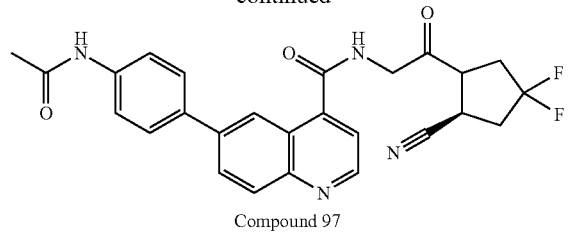

Compound 97

Synthesis of N—((S)-1-((S)-2-cyano-4,4-difluoropyrrolidin-1-yl)-1-oxopropan-2-yl)-3-phenylisonicotinamide. To a stirred solution of (S)-1-(L-alanyl)-4,4-difluoropyrrolidine-2-carbonitrile hydrochloride (300 mg, 1.2 mmol, 1.0 equiv.) in DMF (10 mL) was added 3-phenylisonicotinic acid (251 mg, 1.2 mmol, 1.0 equiv) HOBT (189 mg, 1.4 mmol, 1.2 equiv) and EDC.HCl (275 mg, 1.4 mmol, 1.2 equiv) followed by the addition of TEA (0.33 mL, 2.4 mmol, 2.0 equiv). The resulting reaction mixture was allowed to stir at RT for overnight. The reaction progress was monitored by NMR and TLC. The reaction mixture was diluted with cold water (50 mL) and extracted with ethyl acetate (50 mL×2). Combined organic extracts were washed with water (20 mL×2), dried over anhydrous sodium sulphate and concentrated under reduced pressure. The crude product was purified by reversed phase HPLC to obtain N—((S)-1-((S)-2-cyano-4,4-difluoropyrrolidin-1-yl)-1-oxopropan-2-yl)-3-phenylisonicotinamide (20 mg, 05% Yield) as a white solid.

LCMS 385.3 [M+H]$^+$ $^1$H NMR (400 MHz, DMSO-d$_6$) δ 8.99 (d, J=7.02 Hz, 1H) 8.68 (t, J=2.41 Hz, 2H) 7.33-7.56 (m, 6H) 5.03 (dd, J=9.21, 3.95 Hz, 1H) 4.54 (t, J=7.02 Hz, 1H) 4.20 (d, J=7.45 Hz, 1H) 4.00-4.08 (m, 1H) 2.76-2.98 (m, 2H) 1.16 (d, J=7.02 Hz, 3H).

Example 5-41

Synthesis of (S)-6-(4-acetamidophenyl)-N-(2-(2-cyano-4,4-difluoropyrrolidin-1-yl)-2-oxoethyl)quinoline-4-carboxamide

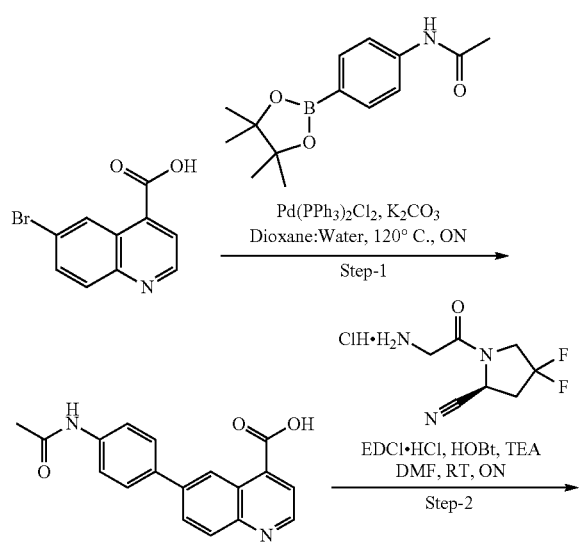

Step 1: Synthesis of 6-(4-acetamidophenyl)quinoline-4-carboxylic acid. To a stirred solution of 6-bromoquinoline-4-carboxylic acid (0.250 g, 0.992 mmol, 1.0 equiv) in Dioxane (5 mL) was added N-(4-(4,4,5,5-tetramethyl-1,3,2-dioxaborolan-2-yl)phenyl)acetamide (0.310 g 1.190 mmol, 1.2 equiv) and a solution of K$_2$CO$_3$ (0.273 g, 1.984 mmol, 2.0 equiv) in water (1.5 mL), and resulting reaction mixture purged with N$_2$ gas for 10 minutes, followed by the addition of Pd(PPh$_3$)$_2$Cl$_2$ (0.034 g, 0.496 mmol. 0.05 equiv). The resulting reaction mixture was heated at 120° C. for overnight. Product formation was confirmed by LCMS. Reaction mixture was cooled to RT, diluted with water (50 mL) washed with ethyl acetate (50 mL×2). Aqueous layer was separated and freeze dried over lyophilizer to obtain 6-(4-acetamidophenyl)quinoline-4-carboxylic acid (0.250 g, Quant.Yield) as a yellow solid.

LCMS 307.0 [M+H]$^+$ $^1$H NMR (400 MHz, DMSO-d$_6$) δ 10.42 (s, 1H) 8.96 (s, 1H) 8.74 (d, J=4.38 Hz, 1H) 7.90-8.05 (m, 2H) 7.77 (m, J=8.77 Hz, 2H) 7.68 (m, J=8.33 Hz, 2H) 7.46 (d, J=4.38 Hz, 1H) 2.08 (s, 3H).

Step 2: Synthesis of (S)-6-(4-acetamidophenyl)-N-(2-(2-cyano-4,4-difluoropyrrolidin-1-yl)-2-oxoethyl)quinoline-4-carboxamide. To a stirred solution of 6-(4-acetamidophenyl)quinoline-4-carboxylic acid (0.250 g, 0.816 mmol, 1.0 equiv) in DMF (3 mL), was added (S)-4,4-difluoro-1-glycylpyrrolidine-2-carbonitrile hydrochloride (0.275 g, 1.225 mmol, 1.5 equiv), HOBt (0.165 g, 1.225 mmol, 1.5 equiv) & EDCI.HCl (0.234 g, 1.225 mmol, 1.5 equiv). The mixture was allowed to stir at RT for 10 min. TEA (0.23 mL) was added and the mixture was allowed to stir at RT for overnight. Product formation was confirmed by LCMS and TLC. After completion of reaction, the mixture was diluted with water (50 mL) and extracted with ethyl acetate (50 mL×3). Combined organic extracts were washed with water (50 mL×2) and brine (50 mL), dried over anhydrous Na$_2$SO$_4$ and concentrated. The crude product obtained was purified by flash chromatography (5% MeOH in DCM as an eluent) followed by reversed phase prep purification to obtain (S)-6-(4-acetamidophenyl)-N-(2-(2-cyano-4,4-difluoropyrrolidin-1-yl)-2-oxoethyl)quinoline-4-carboxamide (0.275 g, 70% Yield) as an off white solid.

LCMS 478.4 [M+H]$^+$ $^1$H NMR (400 MHz, DMSO-d$_6$) δ 10.11 (s, 1H) 9.19 (t, J=5.92 Hz, 1H) 8.96 (d, J=4.38 Hz, 1H) 8.67 (d, J=1.32 Hz, 1H) 8.09-8.22 (m, 2H) 7.79-7.89 (m, 2H) 7.74 (m, J=8.77 Hz, 2H) 7.58 (d, J=4.38 Hz, 1H) 5.18 (dd, J=9.65, 2.63 Hz, 1H) 4.24-4.45 (m, 3H) 4.05-4.24 (m, 1H) 2.95 (br. s., 1H) 2.76-2.92 (m, 1H) 2.08 (s, 3H).

Example S-42

Synthesis of (S)-6-(3-acetamidophenyl)-N-(2-(2-cyano-4,4-difluoropyrrolidin-1-yl)-2-oxoethyl)quinoline-4-carboxamide

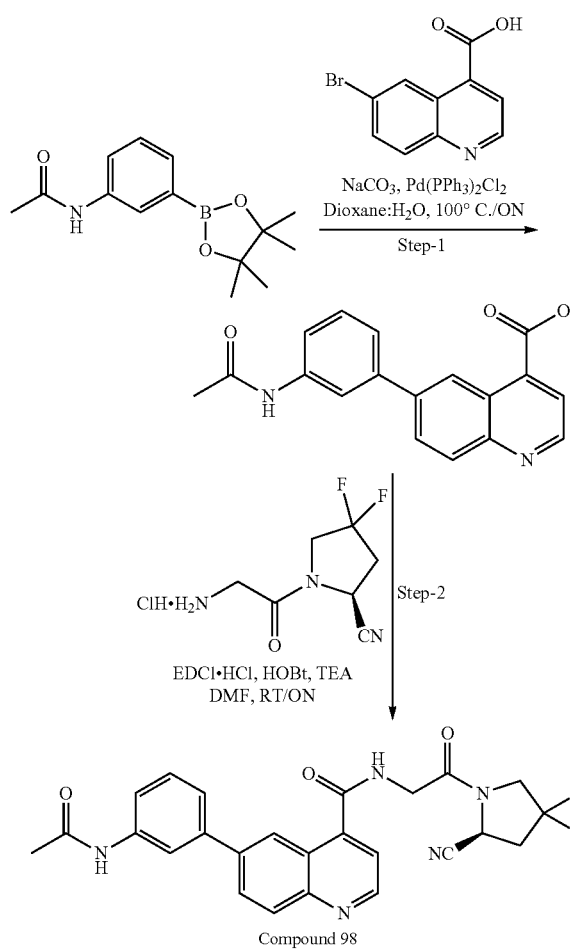

Compound 98

Step 1: Synthesis of 6-(3-acetamidophenyl)quinoline-4-carboxylic acid. To a solution of N-(3-(4,4,5,5-tetramethyl-1,3,2-dioxaborolan-2-yl)phenyl)acetamide (100 mg, 0.38 mmol, 1.0 equiv) in Dioxane: water (5:2 mL), was added 6-bromoquinoline-4-carboxylic acid (97 mg, 0.38 mmol, 1.0 equiv), $Na_2CO_3$ (81 mg, 0.76 mmol, 2.0 equiv) and $Pd(PPh_3)_2Cl_2$ (14 mg, 0.019 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and freeze dried over lyophilizer to obtain 6-(3-acetamidophenyl)quinoline-4-carboxylic acid (100 mg, 86% Yield) as an off white solid.

LCMS 307.1 [M+H]$^+$

Step 2: Synthesis of (S)-6-(3-acetamidophenyl)-N-(2-(2-cyano-4,4-difluoropyrrolidin-1-yl)-2-oxoethyl)quinoline-4-carboxamide. To a stirred solution of 6-(3-acetamidophenyl)quinoline-4-carboxylic acid (100 mg, 0.32 mmol, 1.0 equiv) in DMF (05 mL), was added (S)-4,4-difluoro-1-glycylpyrrolidine-2-carbonitrile hydrochloride (74 mg, 0.32 mmol, 1.0 equiv), HOBT (65 mg, 0.48 mmol, 1.5 equiv) and EDC.HCl (92 mg, 0.48 mmol, 1.5 equiv). The mixture was allowed to stir at RT for 10 min. Triethyl amine (0.13 mL, 0.99 mmols, 3.0 equiv) was added and the mixture was allowed to stir at RT for overnight. Product formation was confirmed by LCMS and TLC. After completion of reaction, the reaction mixture was diluted with water (25 mL) and extracted with ethyl acetate (50 mL×2). Combined organic extracts were washed with water (20 mL×4), dried over anhydrous $Na_2SO_4$ and concentrated. The crude product obtained was purified by reversed phase HPLC to obtain (S)-6-(3-acetamidophenyl)-N-(2-(2-cyano-4,4-difluoropyrrolidin-1-yl)-2-oxoethyl)quinoline-4-carboxamide (50 mg, 25% Yield) as an off-white solid.

LCMS 478.5 [M+H]$^+$ $^1$H NMR (400 MHz, DMSO-d$_6$) δ 10.09 (br. s., 1H) 9.19 (br. s., 1H) 9.00 (d, J=4.39 Hz, 1H) 8.62 (s, 1H) 8.19 (d, J=8.77 Hz, 1H) 8.08 (d, J=8.77 Hz, 1H) 8.00 (s, 1H) 7.60-7.70 (m, 2H) 7.54 (d, J=7.45 Hz, 1H) 7.38-7.46 (m, 1H) 5.18 (d, J=6.58 Hz, 1H) 4.11-4.37 (m, 4H) 2.82-2.98 (m, 2H) 2.08 (s, 3H).

Example S-43

Synthesis of (S)-6-(2-acetamidophenyl)-N-(2-(2-cyano-4,4-difluoropyrrolidin-1-yl)-2-oxoethyl)quinoline-4-carboxamide

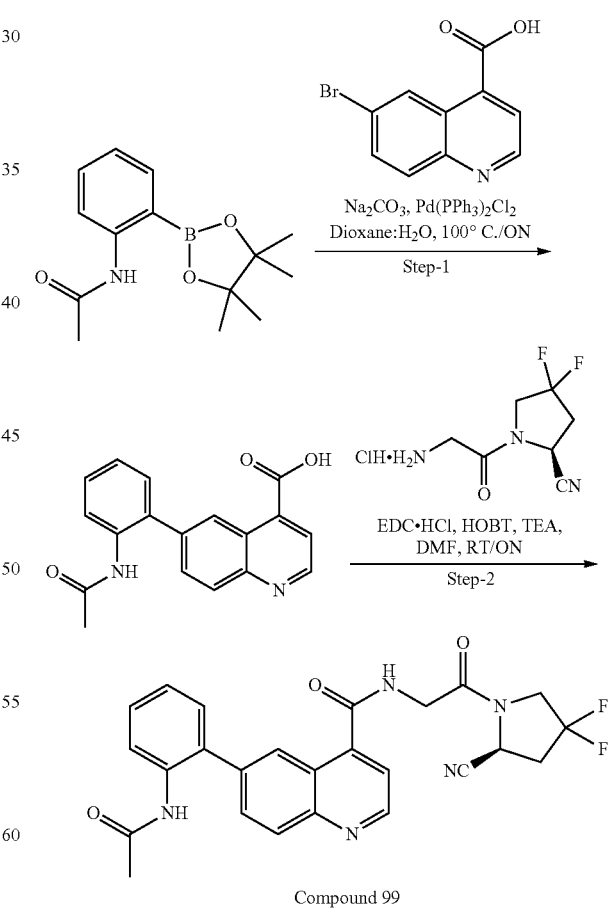

Compound 99

Step 1: Synthesis of 6-(2-acetamidophenyl)quinoline-4-carboxylic acid. To a solution of N-(2-(4,4,5,5-tetramethyl-1,3,2-dioxaborolan-2-yl)phenyl)acetamide (100 mg, 0.38 mmol, 1.0 equiv) in Dioxane: water (05:02 mL), was added 6-bromoquinoline-4-carboxylic acid (97 mg, 0.38 mmol, 1.0 equiv), Na$_2$CO$_3$ (81 mg, 0.76 mmol, 2.0 equiv) and Pd(PPh$_3$)$_2$Cl$_2$(14 mg, 0.019 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and freeze dried over lyophilizer to obtain 6-(2-acetamidophenyl)quinoline-4-carboxylic acid (100 mg, 86% Yield) as an off white solid.

LCMS 307.1 [M+H]$^+$

Step 2: Synthesis of (S)-6-(2-acetamidophenyl)-N-(2-(2-cyano-4,4-difluoropyrrolidin-1-yl)-2-oxoethyl)quinoline-4-carboxamide. To a stirred solution of 6-(2-acetamidophenyl) quinoline-4-carboxylic acid (100 mg, 0.32 mmol, 1.0 equiv) in DMF (05 mL), was added (S)-4,4-difluoro-1-glycylpyrrolidine-2-carbonitrile hydrochloride (74 mg, 0.32 mmol, 1.0 equiv), HOBT (65 mg, 0.48 mmol, 1.5 equiv) and EDC.HCl (92 mg, 0.48 mmol, 1.5 equiv). The mixture was allowed to stir at RT for 10 min. Triethyl amine (0.13 mL, 0.99 mmols, 3.0 equiv) was added and the mixture was allowed to stir at RT for overnight. Product formation was confirmed by LCMS and TLC. After completion of reaction, the reaction mixture was diluted with water (25 mL) and extracted with ethyl acetate (50 mL×2). Combined organic extracts were washed with water (20 mL×4), dried over anhydrous Na$_2$SO$_4$ and concentrated. The crude product obtained was purified by reversed phase HPLC to obtain (S)-6-(2-acetamidophenyl)-N-(2-(2-cyano-4,4-difluoropyrrolidin-1-yl)-2-oxoethyl)quinoline-4-carboxamide (30 mg, 20% Yield) as an off-white solid.

LCMS 478.4 [M+H]$^+$ $^1$H NMR (400 MHz, DMSO-d$_6$) δ 10.09 (br. s., 1H) 9.19 (br. s., 1H) 9.00 (d, J=4.39 Hz, 1H) 8.62 (s, 1H) 8.19 (d, J=8.77 Hz, 1H) 8.08 (d, J=8.77 Hz, 1H) 8.00 (s, 1H) 7.60-7.70 (m, 2H) 7.54 (d, J=7.45 Hz, 1H) 7.38-7.46 (m, 1H) 5.18 (d, J=6.58 Hz, 1H) 4.11-4.37 (m, 4H) 2.82-2.98 (m, 2H) 2.08 (s, 3H).

Example S-44

Synthesis of (S)—N-(2-(2-cyano-4,4-difluoropyrrolidin-1-yl)-2-oxoethyl)-6-(4-(methylcarbamoyl)phenyl)quinoline-4-carboxamide

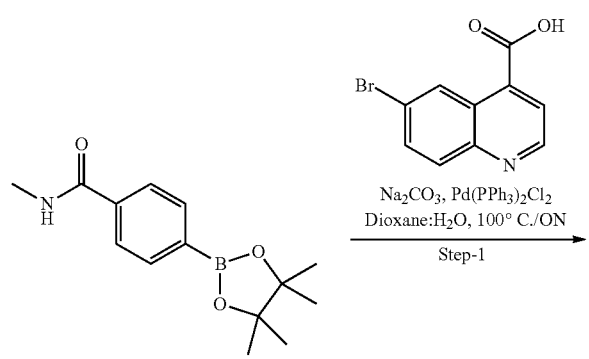

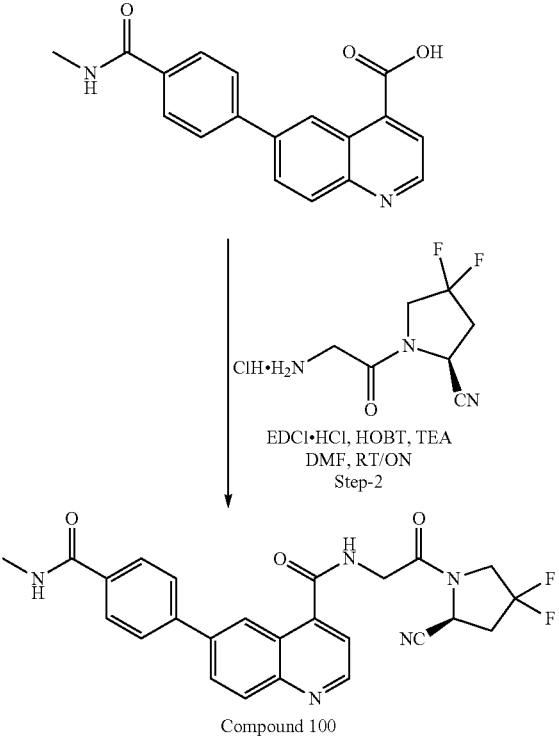

Step 1: Synthesis of 6-(4-(methylcarbamoyl)phenyl)quinoline-4-carboxylic acid. To a solution of N-methyl-4-(4,4,5,5-tetramethyl-1,3,2-dioxaborolan-2-yl)benzamide (100 mg, 0.38 mmol, 1.0 equiv) in Dioxane: water (05:02 mL), was added 6-bromoquinoline-4-carboxylic acid (97 mg, 0.38 mmol, 1.0 equiv), Na$_2$CO$_3$ (81 mg, 0.76 mmol, 2.0 equiv) and Pd(PPh$_3$)$_2$Cl$_2$(14 mg, 0.019 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and dried over lyophilizer to obtain 6-(4-(methylcarbamoyl)phenyl)quinoline-4-carboxylic acid (105 mg, 89% Yield) as an off white solid.

LCMS 307.1 [M+H]$^+$

Step 2: Synthesis of (S)—N-(2-(2-cyano-4,4-difluoropyrrolidin-1-yl)-2-oxoethyl)-6-(4-(methylcarbamoyl)phenyl) quinoline-4-carboxamide. To a stirred solution of 6-(4-(methylcarbamoyl)phenyl)quinoline-4-carboxylic acid (100 mg, 0.32 mmol, 1.0 equiv) in DMF (05 mL), was added (S)-4,4-difluoro-1-glycylpyrrolidine-2-carbonitrile hydrochloride (74 mg, 0.32 mmol, 1.0 equiv), HOBT (65 mg, 0.48 mmol, 1.5 equiv) and EDC.HCl (92 mg, 0.48 mmol, 1.5 equiv). The mixture was allowed to stir at RT for 10 min. Triethyl amine (0.13 mL, 0.99 mmols, 3.0 equiv) was added and the mixture was allowed to stir at RT for overnight. Product formation was confirmed by LCMS and TLC. After completion of reaction, the reaction mixture was diluted with water (25 mL) and extracted with ethyl acetate (50 mL×2). Combined organic extracts were washed with water (20 mL×4), dried over anhydrous Na$_2$SO$_4$ and concentrated. The crude product obtained was purified by reversed phase HPLC to obtain (S)—N-(2-(2-cyano-4,4-difluoropyrrolidin-1-yl)-2-oxoethyl)-6-(4-(methylcarbamoyl)phenyl)quinoline-4-carboxamide (50 mg, 32% Yield) as an off-white solid.

LCMS 478.4 [M+H]$^+$ $^1$H NMR (400 MHz, DMSO-$d_6$) δ 9.22 (t, J=6.36 Hz, 1H) 9.01 (d, J=4.38 Hz, 1H) 8.81 (d, J=1.75 Hz, 1H) 8.52 (d, J=4.82 Hz, 1H) 8.16-8.31 (m, 2H) 8.00 (s, 4H) 7.61 (d, J=4.38 Hz, 1H) 5.16-5.26 (m, 1H) 4.22-4.43 (m, 3H) 4.16 (br. s., 1H) 2.95 (br. s., 1H) 2.88 (br. s., 1H) 2.74-2.87 (d, 3H).

Example S-45

Synthesis of (S)—N-(2-(2-cyano-4,4-difluoropyrrolidin-1-yl)-2-oxoethyl)-6-(1H-indazol-5-yl)quinoline-4-carboxamide

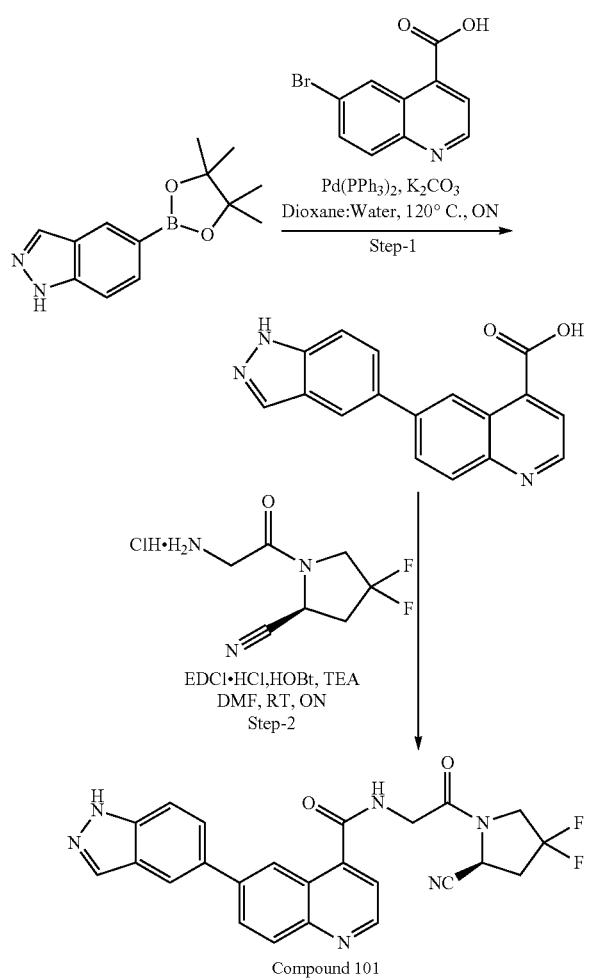

Step 1: Synthesis of 6-(1H-indazol-5-yl)quinoline-4-carboxylic acid. To a stirred solution of 5-(4,4,5,5-tetramethyl-1,3,2-dioxaborolan-2-yl)-1H-indazole (0.100 g, 0.409 mmol, 1.0 equiv) in dioxan (3 mL) and water (1 mL) was added 6-bromoquinoline-4-carboxylic acid (0.103 g, 0.409 mmol, 1.0 equiv), $K_2CO_3$ (0.113 g, 0.819 mmol, 2.0 equiv) and the resulting reaction mixture was purged with $N_2$ gas for 5 minute, followed by the addition of Pd(PPh$_3$)Cl$_2$(0.014 g, 0.020 mmol. 0.05 equiv). The resulting reaction mixture was heated at 120° C. for overnight. Product formation was confirmed by LCMS. Reaction mixture was cooled to RT, diluted with water (30 mL) washed with ethyl acetate (30 mL×2). Aqueous layer was separated freeze dried over lyophilizer to obtain 6-(1H-indazol-5-yl)quinoline-4-carboxylic acid (0.100 g, 84% Yield) as a yellow solid.

LCMS 290.1 [M+H]$^+$

Step 2: Synthesis of (S)—N-(2-(2-cyano-4,4-difluoropyrrolidin-1-yl)-2-oxoethyl)-6-(1H-indazol-5-yl)quinoline-4-carboxamide. To a stirred solution of 6-(1H-indazol-5-yl)quinoline-4-carboxylic acid (0.100 g, 0.346 mmol, 1.0 equiv) in DMF (2 mL), was added (S)-4,4-difluoro-1-glycylpyrrolidine-2-carbonitrile hydrochloride (0.116 g, 0.519 mmol, 1.5 equiv), HOBt (0.070 g, 0.519 mmol, 1.5 equiv) & EDCI.HCl (0.099 g, 0.519 mmol, 1.5 equiv). The mixture was allowed to stir at RT for 2 min. triethylamine (0.1 mL) was added and the mixture was allowed to stir at RT for overnight. Product formation was confirmed by LCMS and TLC. After completion of reaction, the mixture was diluted with water (40 mL) and extracted with ethyl acetate (40 mL×3). Combined organic extracts were washed with water (50 mL×2) and brine (50 mL), dried over anhydrous $Na_2SO_4$ and concentrated. The crude product was purified by flash chromatography (5% MeOH in DCM as an eluent) to obtain (S)—N-(2-(2-cyano-4,4-difluoropyrrolidin-1-yl)-2-oxoethyl)-6-(1H-indazol-5-yl)quinoline-4-carboxamide (0.015 g, 9% Yield) as a yellow solid.

LCMS 461.1 [M+H]$^+$ $^1$H NMR (400 MHz, DMSO-$d_6$) δ 13.18 (br. s., 1H) 9.22 (t, J=5.92 Hz, 1H) 8.98 (d, J=4.38 Hz, 1H) 8.84 (d, J=1.75 Hz, 1H) 8.36 (s, 1H) 8.24-8.33 (m, 1H) 8.13-8.24 (m, 1H) 7.88-8.03 (m, 1H) 7.69 (d, J=8.77 Hz, 1H) 7.60 (d, J=4.39 Hz, 1H) 5.15-5.28 (m, 1H) 4.11-4.41 (m, 4H) 2.73-3.03 (m, 2H).

Example S-46

Synthesis of (S)—N-(2-(2-cyano-4,4-difluoropyrrolidin-1-yl)-2-oxoethyl)-6-(3-(methylcarbamoyl)phenyl)quinoline-4-carboxamide

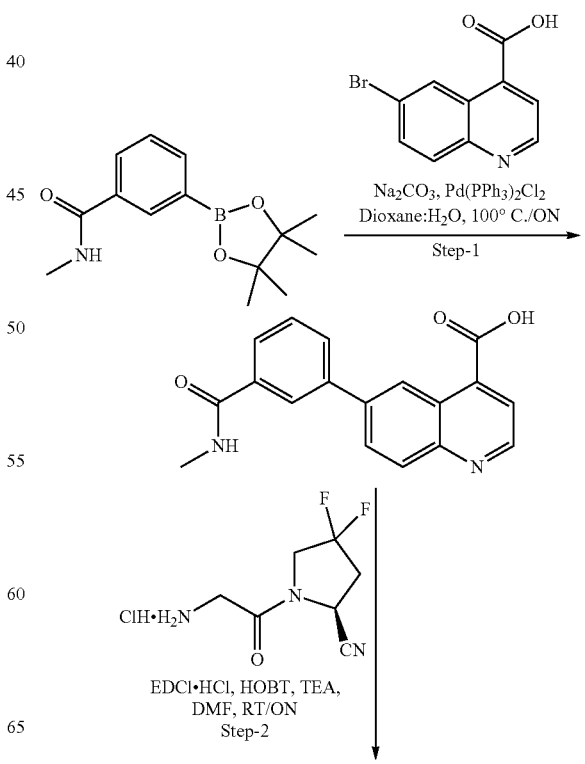

181

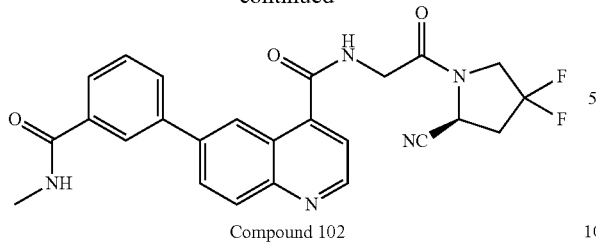

Compound 102

Step 1: Synthesis of 6-(3-(methylcarbamoyl)phenyl)quinoline-4-carboxylic acid. To a solution of N-methyl-3-(4,4,5,5-tetramethyl-1,3,2-dioxaborolan-2-yl)benzamide (100 mg, 0.38 mmol, 1.0 equiv) in Dioxane: water (05:02 mL), was added 6-bromoquinoline-4-carboxylic acid (97 mg, 0.38 mmol, 1.0 equiv), $Na_2CO_3$ (81 mg, 0.76 mmol, 2.0 equiv) and $Pd(PPh_3)_2Cl_2$ (14 mg, 0.019 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and freeze dried over lyophilizer to obtain 6-(3-(methylcarbamoyl) phenyl) quinoline-4-carboxylic acid (100 mg, 86% Yield) as an off white solid.

LCMS 307.1 [M+H]$^+$

Step 2: Synthesis of (S)—N-(2-(2-cyano-4,4-difluoropyrrolidin-1-yl)-2-oxoethyl)-6-(3-(methylcarbamoyl)phenyl)quinoline-4-carboxamide. To a stirred solution of 6-(3-(methylcarbamoyl)phenyl)quinoline-4-carboxylic acid (100 mg, 0.32 mmol, 1.0 equiv) in DMF (05 mL), was added (S)-4,4-difluoro-1-glycylpyrrolidine-2-carbonitrile hydrochloride (74 mg, 0.32 mmol, 1.0 equiv), HOBT (65 mg, 0.48 mmol, 1.5 equiv) and EDC.HCl (92 mg, 0.48 mmol, 1.5 equiv). The mixture was allowed to stir at RT for 10 min. Triethyl amine (0.13 mL, 0.99 mmols, 3.0 equiv) was added and the mixture was allowed to stir at RT for overnight. Product formation was confirmed by LCMS and TLC. After completion of reaction, the reaction mixture was diluted with water (25 mL) and extracted with ethyl acetate (50 mL×2). Combined organic extracts were washed with water (20 mL×4), dried over anhydrous $Na_2SO_4$ and concentrated. The crude product obtained was purified by reversed phase HPLC to obtain (S)—N-(2-(2-cyano-4,4-difluoropyrrolidin-1-yl)-2-oxoethyl)-6-(3-(methylcarbamoyl)phenyl) quinoline-4-carboxamide (25 mg, 17% Yield) as an off-white solid.

LCMS 478.4 [M+H]$^+$ $^1$H NMR (400 MHz, DMSO-d$_6$) δ 9.19 (t, J=5.92 Hz, 1H) 9.01 (d, J=4.38 Hz, 1H) 8.77 (s, 1H) 8.60 (d, J=4.38 Hz, 1H) 8.15-8.34 (m, 3H) 8.07 (d, J=7.89 Hz, 1H) 7.88 (d, J=7.45 Hz, 1H) 7.56-7.70 (m, 2H) 5.21 (dd, J=9.21, 2.19 Hz, 1H) 4.09-4.39 (m, 4H) 2.95 (br. s., 2H) 2.73-2.92 (d, 3H).

182

Example S-47

Synthesis of (S)—N-(2-(2-cyano-4,4-difluoropyrrolidin-1-yl)-2-oxoethyl)-6-(1H-indol-3-yl)quinoline-4-carboxamide

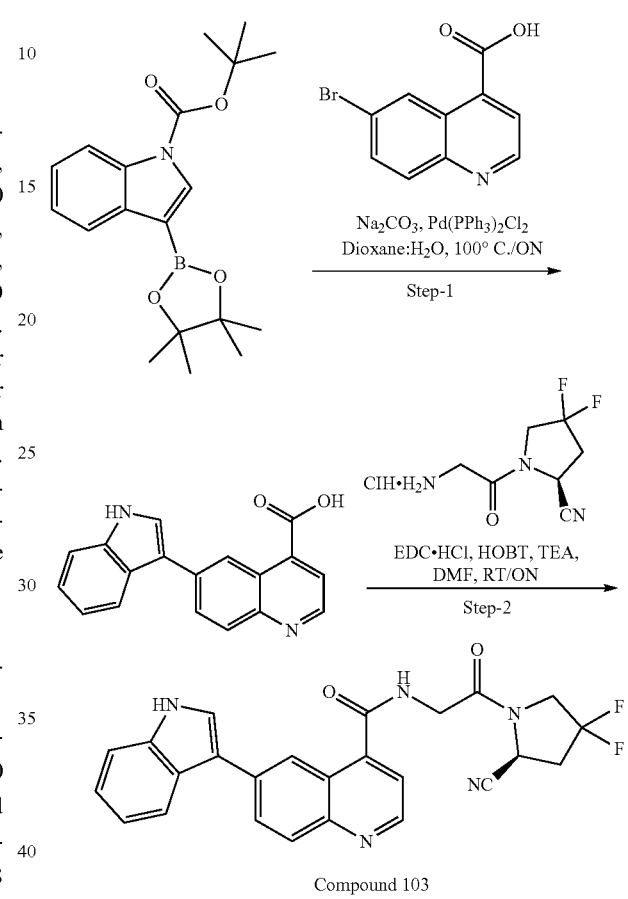

Compound 103

Step 1: Synthesis of 6-(1H-indol-3-yl) quinoline-4-carboxylic acid. To a solution of tert-butyl 3-(4,4,5,5-tetramethyl-1,3,2-dioxaborolan-2-yl)-1H-indole-1-carboxylate (100 mg, 0.29 mmol, 1.0 equiv) in Dioxane: water (05:02 mL), was added 6-bromoquinoline-4-carboxylic acid (74 mg, 0.29 mmol, 1.0 equiv), $Na_2CO_3$ (62 mg, 0.58 mmol, 2.0 equiv) and $Pd(PPh_3)_2Cl_2$ (11 mg, 0.014 mmol, 0.05 equiv). The resulting reaction mixture was heated at 100° C. for overnight. Product formation was confirmed by LCMS, after completion of reaction the reaction mixture was diluted with water (30 mL) and washed with ethyl acetate (50 mL×2). Aqueous layer was separated and freeze dried over lyophilizer to obtain 6-(1H-indol-3-yl) quinoline-4-carboxylic acid (100 mg, Quant. Yield) as an off white solid.

LCMS 289.0 [M+H]$^+$

Step 2: Synthesis of (S)—N-(2-(2-cyano-4,4-difluoropyrrolidin-1-yl)-2-oxoethyl)-6-(1H-indol-3-yl)quinoline-4-carboxamide. To a stirred solution of 6-(1H-indol-3-yl) quinoline-4-carboxylic acid (100 mg, 0.34 mmol, 1.0 equiv) in DMF (05 mL), was added (S)-4,4-difluoro-1-glycylpyrrolidine-2-carbonitrile hydrochloride (78 mg, 0.34 mmol, 1.0 equiv), HOBT (69 mg, 0.51 mmol, 1.5 equiv) and EDC.HCl (98 mg, 0.51 mmol, 1.5 equiv). The mixture was allowed to stir at RT for 10 min. Triethyl amine (0.14 mL, 1.03 mmol, 3.0 equiv) was added and the mixture was allowed to stir at RT for overnight. Product formation was confirmed by LCMS and TLC. After completion of reaction, the reaction mixture was diluted with water (25 mL) and extracted with ethyl acetate (50 mL×2). Combined organic extracts were washed with water (20 mL×4), dried over anhydrous Na$_2$SO$_4$ and concentrated. The crude product obtained was purified by reversed phase HPLC to obtain (S)—N-(2-(2-cyano-4,4-difluoropyrrolidin-1-yl)-2-oxo-ethyl)-6-(1H-indol-3-yl)quinoline-4-carboxamide (15 mg, 10% Yield) as a brown solid.

LCMS 460.1 [M+H]$^+$ $^1$H NMR (400 MHz, DMSO-d$_6$) δ 11.57 (br. s., 1H) 9.19 (t, J=6.14 Hz, 1H) 8.94 (d, J=4.38 Hz, 1H) 8.66 (d, J=1.75 Hz, 1H) 8.22-8.31 (m, 1H) 8.12 (d, J=9.21 Hz, 2H) 7.98 (d, J=2.63 Hz, 1H) 7.61 (d, J=4.82 Hz, 1H) 7.46-7.55 (m, 1H) 7.16-7.27 (m, 2H) 5.10-5.19 (m, 1H) 4.18-4.37 (m, 4H) 2.85-3.00 (m, 2H).

Example S-48

Synthesis of (S)—N-(2-(2-cyano-4,4-difluoropyrro-lidin-1-yl)-2-oxoethyl)-6-(1-oxoisoindolin-5-yl)qui-noline-4-carboxamide equiv), KOAc (0.462 g, 4.716 mmol, 2.0 equiv) and the resulting reaction mixture purged with N$_2$ gas for 5 minute, followed by the addition of Pd(dppf)Cl$_2$(0.172 g, 0.235 mmol. 0.1 equiv). The resulting reaction mixture was heated at 100° C. for 16 h. After the completion of reaction (monitored by TLC & LCMS), the mixture was diluted with water (50 mL) and extracted with ethyl acetate (3×40 mL). Combined organic extracts were washed with water (40 mL×3) & brine (40 mL), dried over anhydrous Na$_2$SO$_4$ and concentrated. The crude product was purified by flash chromatography (50% EtOAc/hexane as an eluent) to obtain 5-(4,4,5,5-tetramethyl-1,3,2-dioxaborolan-2-yl)isoindolin-1-one (0.240 g, 39% yield) as an off white solid.

$^1$H NMR (400 MHz, DMSO-d$_6$) δ 8.63 (br. s., 1H) 7.86 (s, 1H) 7.76 (d, J=7.45 Hz, 1H) 7.67 (d, J=7.45 Hz, 1H) 4.37 (s, 2H) 1.31 (s, 12H).

Step 2: Synthesis of 6-(1-oxoisoindolin-5-yl)quinoline-4-carboxylic acid. To a stirred solution of 6-bromoquinoline-4-carboxylic acid (0.233 g, 0.926 mmol, 1.0 equiv) in dioxan (3 mL) & water (1 mL) was added 5-(4,4,5,5-tetramethyl-1,3,2-dioxaborolan-2-yl)isoindolin-1-one (0.240 g, 0.926 mmol, 1.0 equiv), K$_2$CO$_3$ (0.255 g, 1.853 mmol, 2.0 equiv) and resulting reaction mixture purged with N$_2$ gas for 5 minute, followed by the addition of Pd(PPh$_3$)Cl$_2$ (0.032 g,

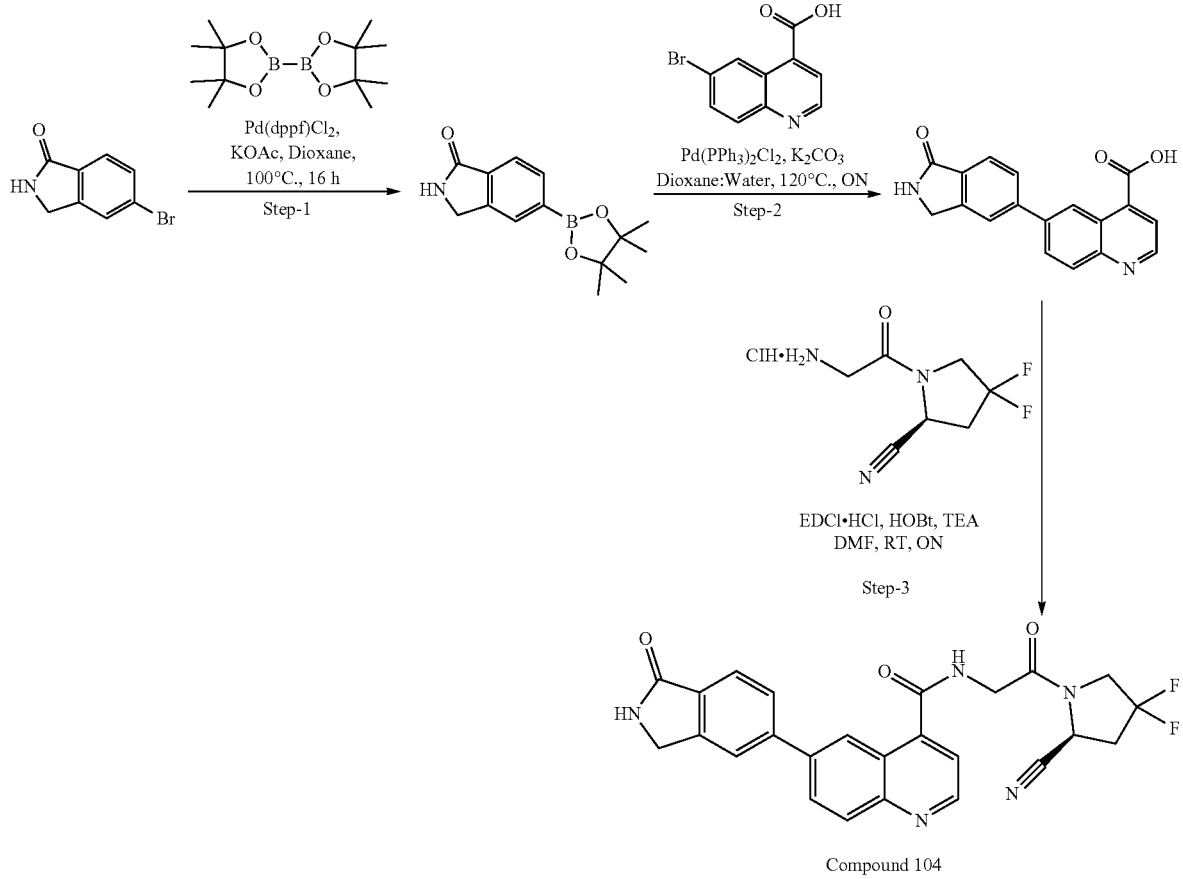

Compound 104

Step 1: Synthesis of 5-(4,4,5,5-tetramethyl-1,3,2-dioxa-borolan-2-yl)isoindolin-1-one. To a stirred solution of 5-Bromoisoindolin-1-one (0.500 g, 2.36 mmol, 1.0 equiv) in 1,4-Dioxane (10 mL) was added 4,4,4',4',5,5,5',5'-octam-ethyl-2,2'-bi(1,3,2-dioxaborolane) (0.718 g, 2.83 mmol, 1.2

0.046 mmol. 0.05 equiv). The resulting reaction mixture was heated at 120° C. for overnight. Product formation was confirmed by LCMS. Reaction mixture was cooled to RT, diluted with water (50 mL) washed with ethyl acetate (40 mL×2). Aqueous layer was separated freeze dried over lyophilizer to obtain 6-(1-oxoisoindolin-5-yl)quinoline-4-carboxylic acid (0.200 g, 71% Yield) as a yellow solid.

LCMS 305.0 [M+H]+

Step 3: Synthesis of (S)—N-(2-(2-cyano-4,4-difluoropyrrolidin-1-yl)-2-oxoethyl)-6-(1-oxoisoindolin-5-yl)quinoline-4-carboxamide. To a stirred solution of 6-(1-oxoisoindolin-5-yl)quinoline-4-carboxylic acid (0.200 g, 0.657 mmol, 1.0 equiv) in DMF (4 mL), was added (S)-4,4-difluoro-1-glycylpyrrolidine-2-carbonitrile hydrochloride (0.222 g, 0.986 mmol, 1.5 equiv), HOBt (0.133 g, 0.986 mmol, 1.5 equiv) & EDCI.HCl (0.188 g, 0.986 mmol, 1.5 equiv). The mixture was allowed to stir at RT for 10 min. triethylamine (0.18 mL) was added and the mixture was allowed to stir at RT for overnight. Product formation was confirmed by LCMS and TLC. After completion of reaction, the mixture was diluted with water (40 mL) and extracted with ethyl acetate (40 mL×3). Combined organic extracts were washed with water (50 mL×2) and brine (50 mL), dried over anhydrous Na2SO4 and concentrated. The crude product was purified by flash chromatography (5% MeOH in DCM as an eluent) followed by reversed phase purification to obtain (S)—N-(2-(2-cyano-4,4-difluoropyrrolidin-1-yl)-2-oxoethyl)-6-(1-oxoisoindolin-5-yl)quinoline-4-carboxamide (0.015 g, 5% Yield) as an off white solid.

LCMS 476.5 [M+H]+

$^1$H NMR (400 MHz, DMSO-$d_6$) δ 9.24 (d, J=5.70 Hz, 1H) 9.01 (d, J=4.39 Hz, 1H) 8.93 (s, 1H) 8.65 (s, 1H) 8.25-8.32 (m, 1H) 8.22 (s, 1H) 8.17 (s, 1H) 8.05 (d, J=7.45 Hz, 1H) 7.83 (d, J=8.33 Hz, 1H) 7.61 (d, J=4.38 Hz, 1H) 5.23 (d, J=6.58 Hz, 1H) 4.43-4.55 (m, 2H) 4.08-4.38 (m, 4H) 2.95 (br. s., 1H) 2.86 (d, J=17.54 Hz, 1H).

Example S-49

Synthesis of (S,E)-N-(2-(2-cyano-4,4-difluoropyrrolidin-1-yl)-2-oxoethyl)-6-(2-(quinolin-6-yl)vinyl)quinoline-4-carboxamide

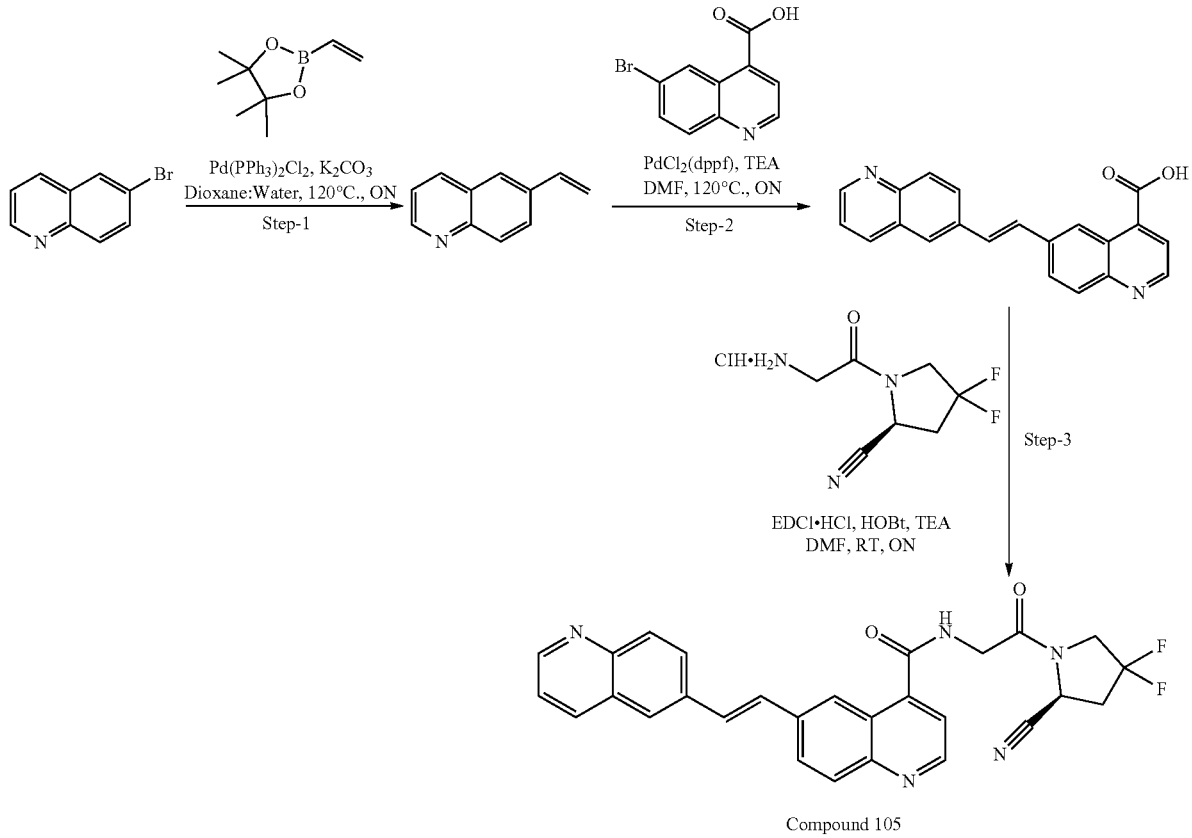

Compound 105

Step 1: Synthesis of 6-vinylquinoline. To a stirred solution of 6-Bromoquinoline (0.500 g, 2.403 mmol, 1.0 equiv) in dioxane (8 mL) was added 2-Vinyl-4,4,5,5-tetramethyl-1,3,2-dioxaoborolane (0.555 g, 3.605 mmol, 1.5 equiv), K2CO3 (0.663 g, 4.807 mmol, 2.0 equiv) in water (4 mL), and the resulting reaction mixture purged with N2 gas for 5 minute, followed by the addition of Pd(PPh3)2Cl2 (0.084 g, 0.120 mmol. 0.05 equiv). The resulting reaction mixture was heated at 120° C. for overnight. Product formation was confirmed by TLC. Reaction mixture was cool to RT, diluted with water (50 mL) extracted with ethyl acetate (50 mL×3). Combined organic extracts were washed with water (50 mL×2) & brine (50 mL), dried over anhydrous Na2SO4 and concentrated. The crude product was purified by flash chromatography (0-15% ethyl acetate in hexane as an eluent) to obtain 6-vinylquinoline (0.250 g, 67% Yield) as an oil.

$^1$H NMR (400 MHz, CHLOROFORM-d) δ 8.87 (dd, J=4.17, 1.53 Hz, 1H) 8.13 (d, J=8.33 Hz, 1H) 8.06 (d, J=8.77 Hz, 1H) 7.87 (dd, J=8.77, 1.75 Hz, 1H) 7.72 (d, J=1.75 Hz, 1H) 7.39 (dd, J=8.33, 4.39 Hz, 1H) 6.89 (dd, J=17.54, 10.96 Hz, 1H) 5.91 (d, J=17.54 Hz, 1H) 5.40 (d, J=10.96 Hz, 1H).

Step 2: Synthesis of (E)-6-(2-(quinolin-6-yl)vinyl)quinoline-4-carboxylic acid. To a stirred solution of 6-bromoquinoline-4-carboxylic acid (0.400 g, 1.587 mmol, 1.0 equiv) in DMF (8 mL) was added 6-vinylquinoline (0.295 g, 1.904 mmol, 1.2 equiv) and triethyl amine (0.68 ml, 4.761 mmol, 3.0 equiv). The resulting reaction mixture was purged with $N_2$ gas for 5 min followed by addition of Pd(dppf)Cl$_2$(0.058 g, 0.079 mmol, 0.05 equiv). The reaction mixture was heated at 120° C. for overnight. Product formation was confirmed by LCMS. Reaction mixture was cooled to RT, diluted with water (40 mL) washed with ethyl acetate (40 mL×3), Aquous layer was separated and freeze dried over lyophilizer to obtain (E)-6-(2-(quinolin-6-yl)vinyl)quinoline-4-carboxylic acid (0.400 g, 77% Yield) as a brown solid.

LCMS 327.1[M+H]$^+$

Step 3: Synthesis of (S,E)-N-(2-(2-cyano-4,4-difluoropyrrolidin-1-yl)-2-oxoethyl)-6-(2-(quinolin-6-yl)vinyl)quinoline-4-carboxamide. To a stirred solution of (E)-6-(2-(quinolin-6-yl)vinyl)quinoline-4-carboxylic acid (0.400 g, 1.226 mmol, 1.0 equiv) in DMF (6 mL), was added (S)-4,4-difluoro-1-glycylpyrrolidine-2-carbonitrile hydrochloride (0.414 g, 1.840 mmol, 1.5 equiv), HOBt (0.248 g, 1.840 mmol, 1.5 equiv) & EDCl.HCl (0.351 g, 1.840 mmol, 1.5 equiv). The mixture was allowed to stir at RT for 10 min. triethylamine (0.35 mL) was added and the mixture was allowed to stir at RT for overnight. Product formation was confirmed by LCMS and TLC. After completion of reaction, the mixture was diluted with water (50 mL) and extracted with ethyl acetate (50 mL×3). Combined organic extracts were washed with water (40 mL×3) and brine (50 mL), dried over anhydrous Na$_2$SO$_4$ and concentrated. The crude product was purified by flash chromatography (5% MeOH in DCM as an eluent) to obtain (S,E)-N-(2-(2-cyano-4,4-difluoropyrrolidin-1-yl)-2-oxoethyl)-6-(2-(quinolin-6-yl)vinyl)quinoline-4-carboxamide (0.150 g, 25% Yield) as off yellow solid.

LCMS 498.5 [M+H]$^+$ $^1$H NMR (400 MHz, DMSO-d$_6$) δ 9.22 (t, J=5.70 Hz, 1H) 8.95 (d, J=3.95 Hz, 1H) 8.88 (dd, J=3.95, 1.32 Hz, 1H) 8.75 (s, 1H) 8.37 (d, J=7.45 Hz, 1H) 8.08-8.27 (m, 3H) 8.03 (d, J=8.33 Hz, 1H) 7.83 (d, J=16.22 Hz, 1H) 7.65 (d, J=16.66 Hz, 1H) 7.50-7.62 (m, 2H) 5.30 (dd, J=9.21, 2.63 Hz, 1H) 4.14-4.43 (m, 4H) 2.80-3.07 (m, 2H).

Example 5-50

Synthesis of (S)—N-(2-(2-cyano-4,4-difluoropyrrolidin-1-yl)-2-oxoethyl)-6-(2-oxoindolin-5-yl)quinoline-4-carboxamide

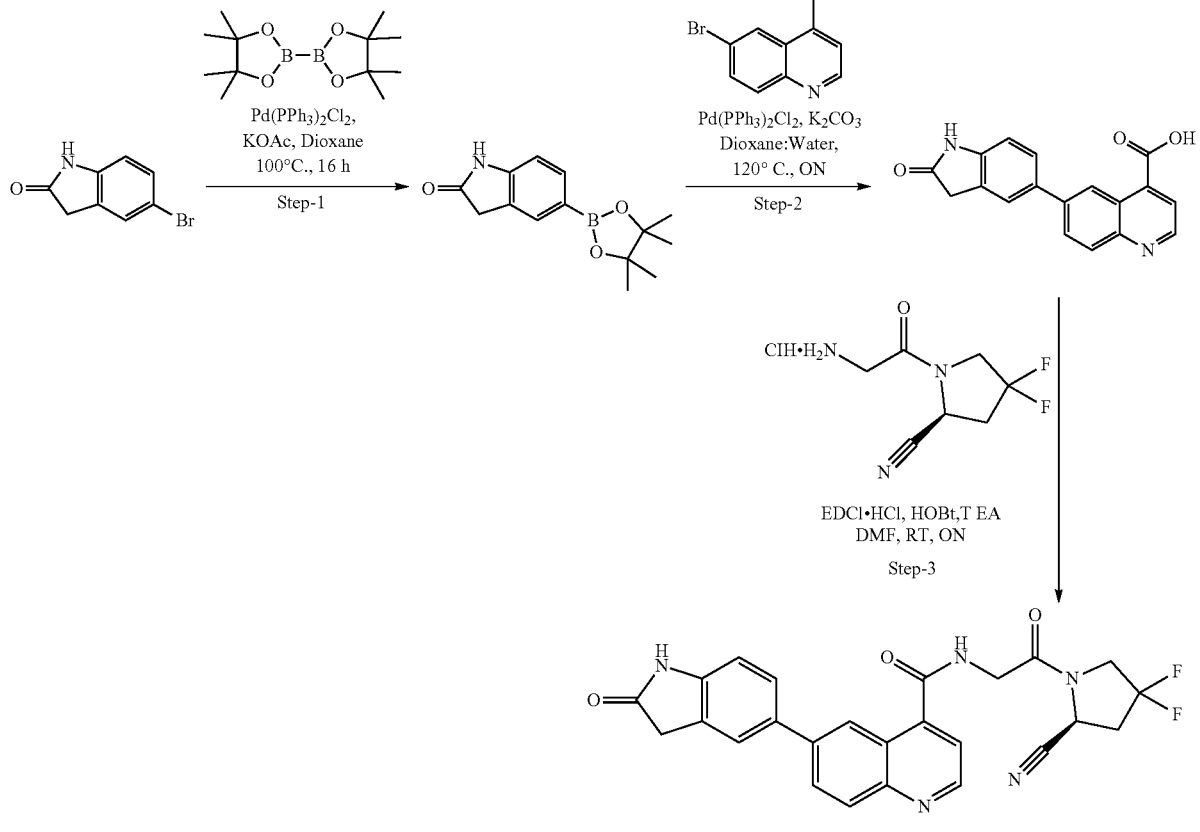

Compound 106

Step 1: Synthesis of 5-(4,4,5,5-tetramethyl-1,3,2-dioxaborolan-2-yl)indolin-2-one. To a stirred solution of 5-Bromoindolin-2-one (0.500 g, 2.358 mmol, 1.0 equiv) in 1,4-Dioxane (10 mL) was added 4,4,4',4',5,5,5',5'-octamethyl-2,2'-bi(1,3,2-dioxaborolane) (0.718 g, 2.830 mmol, 1.2 equiv), KOAc (0.462 g, 4.716 mmol, 2.0 equiv) and the resulting reaction mixture purged with N$_2$ gas for 5 min. followed by the addition of Pd(dppf).DCM (0.096 g, 0.011 mmol. 0.05 equiv). The resulting reaction mixture was heated at 100° C. for 16 h. After the completion of reaction (monitored by TLC & LCMS), the mixture was diluted with water (60 mL) and extracted with ethyl acetate (3×60 mL). Combined organic extracts were washed with water (50 mL) & brine (50 mL), dried over anhydrous $Na_2SO_4$ and concentrated. The crude product was purified by flash chromatography (50% EtOAc/hexane as an eluent) to obtain 5-(4,4,5,5-tetramethyl-1,3,2-dioxaborolan-2-yl)indolin-2-one (0.260 g, 42% Yield) as an off white solid.

LCMS 260.3 $[M+H]^+$ $^1$H NMR (400 MHz, DMSO-$d_6$) δ 10.52 (s, 1H) 7.36-7.64 (m, 2H) 6.81 (d, J=7.89 Hz, 1H) 3.42 (s, 2H) 1.27 (s, 12H).

Step-2: Synthesis of 6-(2-oxoindolin-5-yl)quinoline-4-carboxylic acid. To a stirred solution of 6-bromoquinoline-4-carboxylic acid (0.194 g, 0.772 mmol, 1.0 equiv) in dioxan (4 mL) & water (2 mL) was added 5-(4,4,5,5-tetramethyl-1,3,2-dioxaborolan-2-yl)indolin-2-one (0.200 g, 0.772 mmol, 1.0 equiv), $K_2CO_3$ (0.213 g, 1.554 mmol, 2.0 equiv) and resulting reaction mixture purged with $N_2$ gas for 5 min. followed by the addition of $Pd(PPh_3)Cl_2$ (0.027 g, 0.038 mmol. 0.05 equiv). The resulting reaction mixture was heated at 120° C. for overnight. Product formation was confirmed by LCMS. Reaction mixture was cooled to RT, diluted with water (40 mL) washed with ethyl acetate (50 mL×2). Aquous layer was separated and freeze dried over lyophilizer to obtain 6-(2-oxoindolin-5-yl)quinoline-4-carboxylic acid (0.230 g, 98% Yield) as a yellow solid.

LCMS 305.0 $[M+H]^+$

Step 3: Synthesis of (S)—N-(2-(2-cyano-4,4-difluoropyrrolidin-1-yl)-2-oxoethyl)-6-(2-oxoindolin-5-yl)quinoline-4-carboxamide. To a stirred solution of 6-(2-oxoindolin-5-yl)quinoline-4-carboxylic acid (0.230 g, 0.756 mmol, 1.0 equiv) in DMF (4 mL), was added (S)-4,4-difluoro-1-glycylpyrrolidine-2-carbonitrile hydrochloride (0.255 g, 1.134 mmol, 1.5 equiv), HOBt (0.153 g, 1.134 mmol, 1.5 equiv) & EDCI.HCl (0.216 g, 0.1.134 mmol, 1.5 equiv). The mixture was allowed to stir at RT for 10 min. triethylamine (0.21 mL) was added and the mixture was allowed to stir at RT for overnight. Product formation was confirmed by LCMS and TLC. After completion of reaction, the mixture was diluted with water (50 mL) and extracted with ethyl acetate (50 mL×3). Combined organic extracts were washed with water (50 mL×3) and brine (50 mL), dried over anhydrous $Na_2SO_4$ and concentrated. The crude product was purified by flash chromatography (5% MeOH in DCM as an eluent) followed by reversed phase purification to obtain (S)—N-(2-(2-cyano-4,4-difluoropyrrolidin-1-yl)-2-oxoethyl)-6-(2-oxoindolin-5-yl)quinoline-4-carboxamide (0.060 g, 17% Yield) as a yellow solid.

LCMS 476.5 $[M+H]^+$ $^1$H NMR (400 MHz, DMSO-$d_6$) δ 10.53 (s, 1H) 9.18 (t, J=5.92 Hz, 1H) 8.94 (d, J=4.38 Hz, 1H) 8.73 (s, 1H) 8.07-8.20 (m, 2H) 7.85 (s, 1H) 7.75 (d, J=7.89 Hz, 1H) 7.55 (d, J=4.38 Hz, 1H) 6.97 (d, J=7.89 Hz, 1H) 5.21 (d, J=7.02 Hz, 1H) 4.10-4.40 (m, 4H) 3.60 (d, J=7.02 Hz, 2H) 2.77-3.01 (m, 2H).

Example 5-51

Synthesis of (S)—N-(2-(2-cyano-4,4-difluoropyrrolidin-1-yl)-2-oxoethyl)-6-(1-oxo-1,2,3,4-tetrahydroisoquinolin-7-yl)quinoline-4-carboxamide

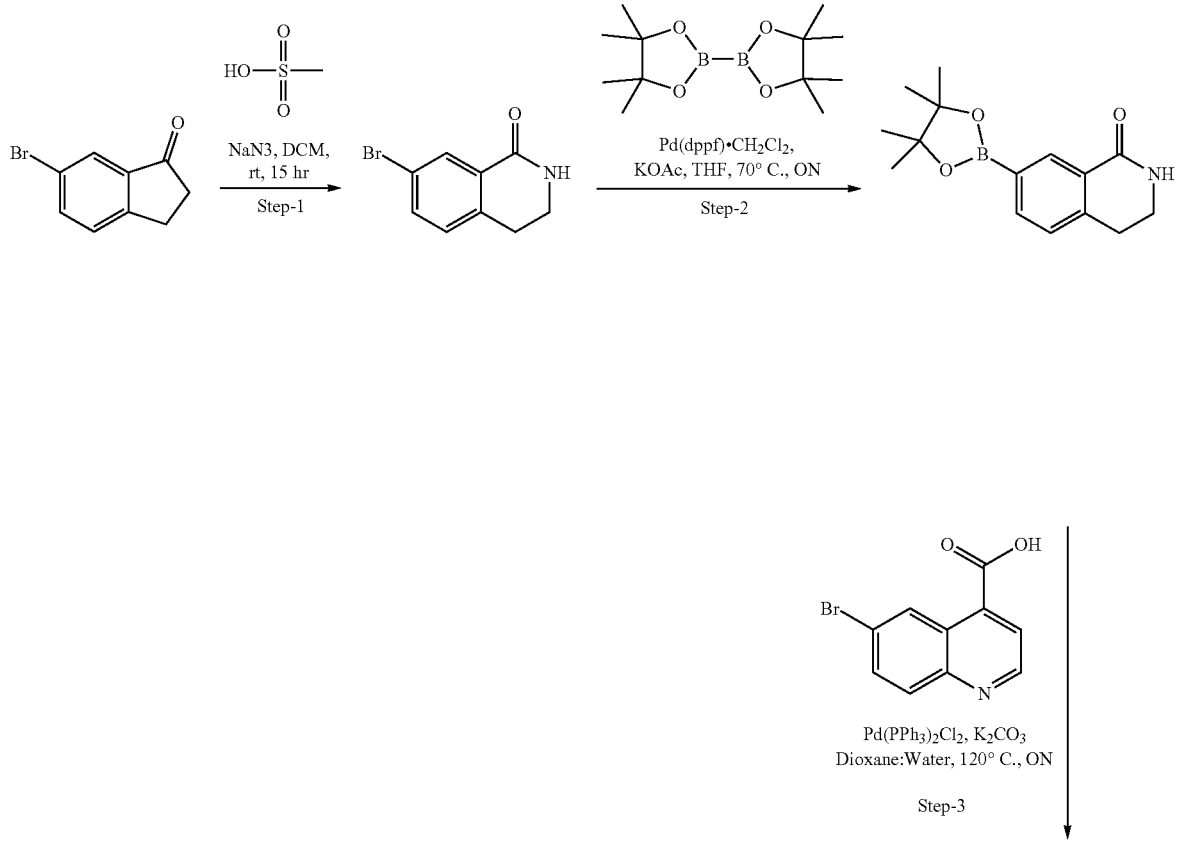

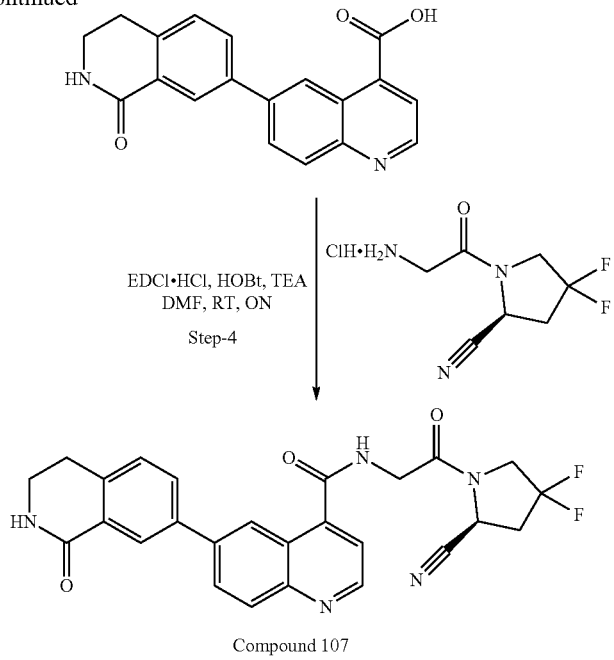

Compound 107

Step 1: Synthesis of 7-bromo-3,4-dihydroisoquinolin-1(2H)-one. Sodium azide (0.924 g, 14.218 mmol, 1.0 equiv) was added slowly to a mixture of 6-bromo-2,3-dihydro-1H-inden-1-one (2.0 g, 9.478 mmol, 1.0 equiv) and methanesulfonic acid (18.1 g, 189.5 mmol, 20.0 equiv) in DCM (60 mL) at 0° C. The mixture was stirred at RT for overnight. The reaction mixture was carefully quenched with 1 M aqueous sodium hydroxide (80 mL). The aqueous layer was extracted with DCM (3×100 mL), and the combined organic layers were washed with water (2×100 mL) and brine (100 mL), dried anhydrous $Na_2SO_4$ and concentrated. The residue was purified by flash chromatography (0-20% ethyl acetate in hexane as an eluent) to obtain 7-bromo-3,4-dihydroisoquinolin-1(2H)-one (0.250 g, 12% Yield) as a white solid.

LCMS 225.9 $[M+H]^+$ $^1$H NMR (400 MHz, CHLOROFORM-d) δ 8.20 (d, J=1.75 Hz, 1H) 7.56 (dd, J=7.89, 2.19 Hz, 1H) 7.26 (s, 1H) 7.11 (d, J=7.89 Hz, 1H) 6.35 (br. s., 1H) 3.57 (td, J=6.69, 2.85 Hz, 2H) 2.96 (t, J=6.58 Hz, 2H).

Step 2: Synthesis of 7-(4,4,5,5-tetramethyl-1,3,2-dioxaborolan-2-yl)-3,4-dihydroisoquinolin-1(2H)-one. To a stirred solution of 7-bromo-3,4-dihydroisoquinolin-1(2H)-one (0.600 g, 2.654 mmol, 1.0 equiv) in THF (20 mL) was added 4,4,4',4',5,5,5',5'-octamethyl-2,2'-bi(1,3,2-dioxaborolane) (1.34 g, 5.309 mmol, 2.0 equiv), KOAc (0.780 g, 7.964 mmol, 3.0 equiv) and resulting reaction mixture purged with $N_2$ gas for 5 min. followed by the addition of Pd(dppf)$CH_2Cl_2$(0.108 g, 0.132 mmol. 0.05 equiv). The resulting reaction mixture was heated at 70° C. for overnight. After the completion of reaction (monitored by TLC & LCMS), the mixture was diluted with water (50 mL) and extracted with ethyl acetate (3×80 mL). Combined organic extracts were washed with water (80 mL×2) & brine (80 mL), dried over anhydrous $Na_2SO_4$ and concentrated. The crude product was purified by flash chromatography (0-30% EtOAc/hexane as an eluent) to obtain 7-(4,4,5,5-tetramethyl-1,3,2-dioxaborolan-2-yl)-3,4-dihydroisoquinolin-1(2H)-one (0.450 g, 72% Yield) as an off white solid.

LCMS 274.1 $[M+H]^+$ $^1$H NMR (400 MHz, DMSO-$d_6$) δ 8.18 (s, 1H) 7.93 (br. s., 1H) 7.72 (d, J=7.45 Hz, 1H) 7.31 (d, J=7.89 Hz, 1H) 3.37 (td, J=6.58, 2.63 Hz, 2H) 2.92 (t, J=6.36 Hz, 2H) 1.30 (s, 12H).

Step 3: Synthesis of 6-(1-oxo-1,2,3,4-tetrahydroisoquinolin-7-yl)quinoline-4-carboxylic acid. To a stirred solution of 6-bromoquinoline-4-carboxylic acid (0.276 g, 1.098 mmol, 1.0 equiv) in dioxan (6 mL) & water (2 mL) was added 7-(4,4,5,5-tetramethyl-1,3,2-dioxaborolan-2-yl)-3,4-dihydroisoquinolin-1(2H)-one (0.300 g, 1.098 mmol, 1.0 equiv), $K_2CO_3$ (0.303 g, 2.197 mmol, 2.0 equiv) and resulting reaction mixture purged with $N_2$ gas for 5 min. followed by the addition of Pd(PPh$_3$)$_2$Cl$_2$(0.038 g, 0.0549 mmol. 0.05 equiv). The resulting reaction mixture was heated at 100° C. for overnight. Product formation was confirmed by LCMS. Reaction mixture was cooled to RT, diluted with water (60 mL) washed with ethyl acetate (50 mL×3). Aqueous layer was separated and freeze dried over lyophilizer to obtain 6-(1-oxo-1,2,3,4-tetrahydroisoquinolin-7-yl)quinoline-4-carboxylic acid (0.300 g, 85% Yield) as a brown solid.

LCMS 319.1 $[M+H]^+$

Step 4: Synthesis of (S)—N-(2-(2-cyano-4,4-difluoropyrrolidin-1-yl)-2-oxoethyl)-6-(1-oxo-1,2,3,4-tetrahydroisoquinolin-7-yl)quinoline-4-carboxamide. To a stirred solution of 6-(1-oxo-1,2,3,4-tetrahydroisoquinolin-7-yl)quinoline-4-carboxylic acid (0.300 g, 0.943 mmol, 1.0 equiv) in DMF (5 mL), was added (S)-4,4-difluoro-1-glycylpyrrolidine-2-carbonitrile hydrochloride (0.318 g, 1.415 mmol, 1.5 equiv), HOBt (0.191 g, 1.415 mmol, 1.5 equiv) & EDCI.HCl (0.270 g, 1.415 mmol, 1.5 equiv). The mixture was allowed to stir at RT for 10 min. triethylamine (0.27 mL) was added and the mixture was allowed to stir at RT for overnight. Product formation was confirmed by LCMS and TLC. After completion of reaction, the mixture was diluted with water (50 mL) and extracted with ethyl acetate (80 mL×3). Combined organic extracts were washed with water (100 mL×2) and brine (100 mL), dried over anhydrous $Na_2SO_4$ and concentrated. The crude product was purified by flash chromatography (0-5% MeOH in DCM as an eluent) to obtain (S)—N-(2-(2-cyano-4,4-difluoropyrrolidin-1-yl)-2-oxoethyl)-6-(1-oxo-1,2,3,4-tetrahydroisoquinolin-7-yl)quinoline-4-carboxamide (0.130 g, 28% Yield) as an off white solid.
LCMS 490.5 [M+H]+
¹H NMR (400 MHz, DMSO-d₆) δ 9.18 (t, J=5.92 Hz, 1H) 9.01 (d, J=3.95 Hz, 1H) 8.74 (s, 1H) 8.29 (s, 1H) 8.19 (s, 2H) 7.98-8.11 (m, 2H) 7.62 (d, J=4.38 Hz, 1H) 7.48 (d, J=8.33 Hz, 1H) 5.24 (m, J=8.77 Hz, 1H) 4.10-4.39 (m, 4H) 3.43 (br. s., 2H) 2.98 (t, J=6.36 Hz, 2H) 2.84 (d, J=13.15 Hz, 2H).
Example S-52
Synthesis of (S)—N-(2-(2-cyano-4,4-difluoropyrrolidin-1-yl)-2-oxoethyl)-2-oxo-1,2,3,4-tetrahydro-[5,6'-biquinoline]-4'-carboxamide
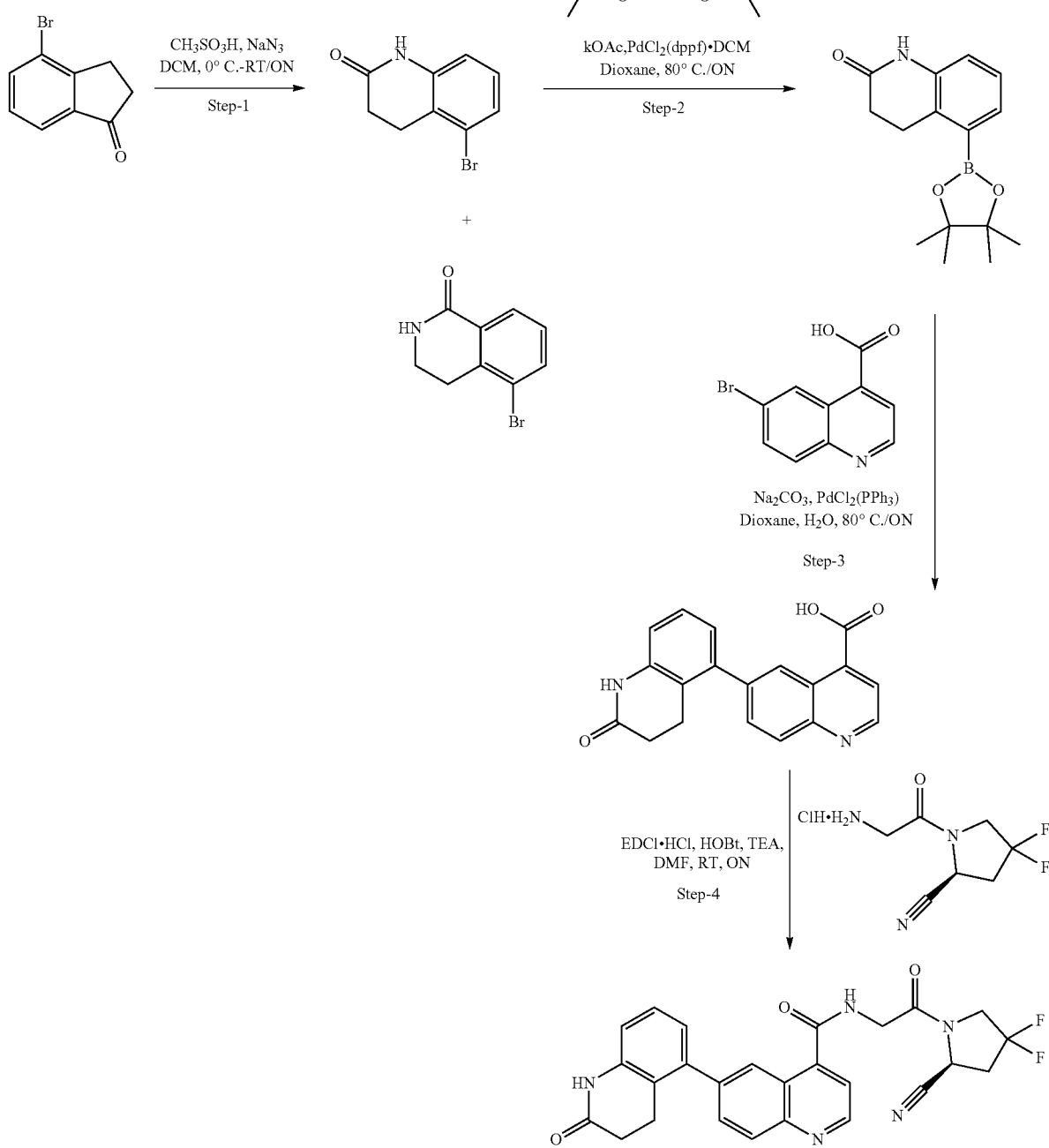
Compound 108

Step 1: Synthesis of 5-bromo-3,4-dihydroquinolin-2(1H)-one. To a stirred solution of 4-bromo-2,3-dihydro-1H-inden-1-one (0.500 g, 2.36 mmol, 1.0 equiv) in DCM (40 ml) was added in methanesulphonic acid (4.6 ml, 35.4 mmol, 15.0 equiv) followed by the addition of NaN$_3$(0.306 g, 4.72 mmol, 2.0 equiv) at 0° C. The resulting reaction mixture was stirred at RT for overnight. Product formation was confirmed by TLC. After the completion of reaction, the reaction mixture was diluted with 2 N NaOH solution (100 mL) and extracted with DCM (150 mL×3). Combined organic extracts were washed with water (50 mL×2) & brine (50 mL), dried over anhydrous Na$_2$SO$_4$ and concentrated. The crude product was purified by flash chromatography (0-30% ethyl acetate in Hexane as an eluent) to obtain 5-bromo-3,4-dihydroquinolin-2(1H)-one (0.500 g) as an off white solid and 5-bromo-3,4-dihydroisoquinolin-1(2H)-one (0.300 g) as a white solid.

$^1$H NMR for 5-bromo-3,4-dihydroquinolin-2(1H)-one (400 MHz, DMSO-d$_6$) δ 10.24 (br. s., 1H) 7.19 (d, J=7.89 Hz, 1H) 7.08 (t, J=7.89 Hz, 1H) 6.86 (d, J=7.89 Hz, 1H) 2.95 (t, J=7.45 Hz, 2H) 2.47 (s, 2H).

$^1$H NMR for 5-bromo-3,4-dihydroisoquinolin-1(2H)-one (400 MHz, DMSO-d$_6$) δ 8.09 (br. s., 1H) 7.88 (d, J=7.45 Hz, 1H) 7.78 (d, J=8.33 Hz, 1H) 7.31 (t, J=7.89 Hz, 1H) 3.40 (td, J=6.69, 2.85 Hz, 2H) 2.96 (t, J=6.58 Hz, 2H).

Step 2: Synthesis of 5-(4,4,5,5-tetramethyl-1,3,2-dioxaborolan-2-yl)-3,4-dihydroquinolin-2(1H)-one. To a solution of 5-bromo-3,4-dihydroquinolin-2(1H)-one (0.200 g, 0.892 mmol, 1.0 equiv), 4,4,4',4',5,5,5',5'-octamethyl-2,2'-bi(1,3,2-dioxaborolane) (0.338 g, 1.33 mmol, 1.5 equiv) and KOAc (0.174 g, 1.78 mmol, 2.0 equiv) in dioxane (10 ml) and resulting reaction mixture was purged with N$_2$ gas for 10 min. followed by the addition of Pd(dppf)Cl$_2$.DCM (0.036 g, 0.044 mmol. 0.05 equiv). The resulting reaction mixture was heated at 80° C. for overnight. Product formation was confirmed by LCMS. After the completion of the reaction, the reaction mixture was diluted with water (50 mL) and extracted with ethyl acetate (100 mL×2). Combined organic extracts were washed with water (50 mL×2) & brine (50 mL), dried over anhydrous Na$_2$SO$_4$ and concentrated. The crude product was purified by flash chromatography (0-5% MeOH in DCM as an eluent) to obtain 5-(4,4,5,5-tetramethyl-1,3,2-dioxaborolan-2-yl)-3,4-dihydroquinolin-2(1H)-one (0.1 g, 41% yield) as a yellow oil.

LCMS 274.2 [M+H]$^+$ $^1$H NMR (400 MHz, DMSO-d$_6$) δ10.03 (s, 1H) 7.23-7.32 (m, 1H) 7.13 (t, J=7.67 Hz, 1H) 6.95 (dd, J=7.89, 0.88 Hz, 1H) 3.09-3.19 (m, 2H) 2.34-2.46 (m, 2H) 1.29 (s, 12 H).

Step 3: Synthesis of 2-oxo-1,2,3,4-tetrahydro-[5,6'-biquinoline]-4'-carboxylic acid. To a solution of 6-bromoquinoline-4-carboxylic acid (0.1 g, 0.396 mmol, 1.0 equiv) and 5-(4,4,5,5-tetramethyl-1,3,2-dioxaborolan-2-yl)-3,4-dihydroquinolin-2(1H)-one (0.162 g, 0.595 mmol, 1.5 equiv), in dioxane (10 mL) and water (2 mL) was added Na$_2$CO$_3$ (0.083 g, 0.792 mmol, 2.0 equiv). The resulting reaction mixture was purged with N$_2$ gas followed by the addition of Pd(PPh$_3$)Cl$_2$ (0.013 g, 0.019 mmol, 0.05 equiv). The resulting reaction mixture was heated at 80° C. for overnight. Product formation was confirmed by LCMS. After completion of reaction, the mixture was concentrated under reduced pressure, diluted with water (50 mL) and washed with ethyl acetate (25 mL×2). Aqueous layer was separated and freeze dried over lyophilizer to obtain 2-oxo-1,2,3,4-tetrahydro-[5,6'-biquinoline]-4'-carboxylic acid (0.200 g, Quant. Yield) as an off white solid.

LCMS 319.1 [M+H]$^+$

Step 4: Synthesis of (S)—N-(2-(2-cyano-4,4-difluoropyrrolidin-1-yl)-2-oxoethyl)-2-oxo-1,2,3,4-tetrahydro-[5,6'-biquinoline]-4'-carboxamide. To a stirred solution of synthesis of 2-oxo-1,2,3,4-tetrahydro-[5,6'-biquinoline]-4'-carboxylic acid (0.2 g, 0.626 mmol, 1.0 equiv) in DMF (10 mL), was added (S)-4,4-difluoro-1-glycylpyrrolidine-2-carbonitrile hydrochloride (0.211 g, 0.940 mmol, 1.5 equiv), HOBt (0.126 g, 0.940 mmol, 1.5 equiv) & EDCI.HCl (0.180 g, 0.940 mmol, 1.5 equiv). The mixture was allowed to stir at RT for 10 min. triethylamine (0.189 g, 1.878 mmol, 3.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous Na$_2$SO$_4$ and concentrated. The crude product was purified by flash chromatography (0-5% MeOH in DCM as an eluent) which was further purified by reversed phase HPLC to obtain (S)—N-(2-(2-cyano-4,4-difluoropyrrolidin-1-yl)-2-oxoethyl)-1'-methyl-2'-oxo-1',2',3',4'-tetrahydro-[6,6'-biquinoline]-4-carboxamide (0.035 g, 11% Yield) as white solid.

LCMS 490.5 [M+H]$^+$ $^1$H NMR (400 MHz, DMSO-d$_6$) δ 10.20 (s, 1H) 9.16 (t, J=5.70 Hz, 1H) 9.02 (d, J=3.95 Hz, 1H) 8.22-8.35 (m, 1H) 8.15 (d, J=8.77 Hz, 1H) 7.84 (dd, J=8.77, 1.75 Hz, 1H) 7.62 (d, J=4.39 Hz, 1H) 7.27 (t, J=7.89 Hz, 1H) 7.01 (d, J=7.02 Hz, 1H) 6.96 (d, J=7.89 Hz, 1H) 5.11 (d, J=7.02 Hz, 1H) 4.05-4.35 (m, 4H) 2.71-3.00 (m, 2H) 2.40 (t, J=7.24 Hz, 2H) 2.33 (br. s., 2H).

Example S-53

Synthesis of (S)—N-(2-(2-cyano-4,4-difluoropyrrolidin-1-yl)-2-oxoethyl)-6-(1-oxo-1,2,3,4-tetrahydroisoquinolin-5-yl)quinoline-4-carboxamide

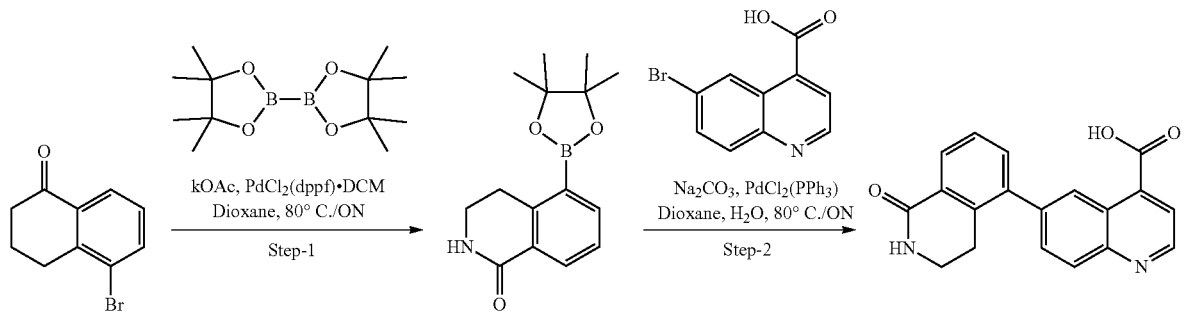

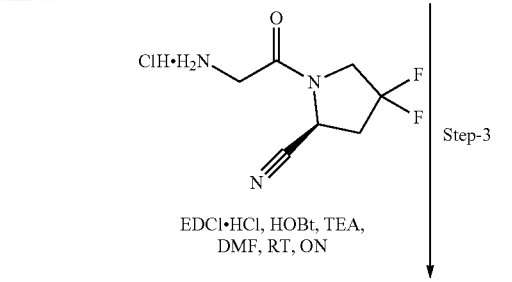

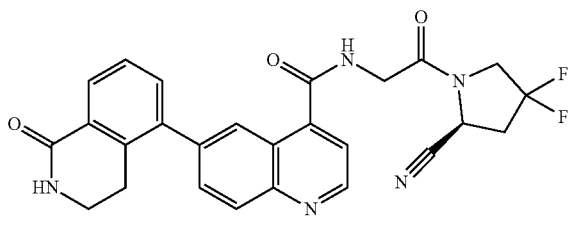

Compound 109

Step 1: Synthesis of 5-(4,4,5,5-tetramethyl-1,3,2-dioxaborolan-2-yl)-3,4-dihydroisoquinolin-1(2H)-one. To a solution of 5-bromo-3,4-dihydroisoquinolin-1(2H)-one (0.1 g, 0.442 mmol, 1.0 equiv), 4,4,4',4',5,5,5',5'-octamethyl-2,2'-bi (1,3,2-dioxaborolane) (0.169 g, 0.669 mmol, 1.5 equiv) and KOAc (0.087 g, 0.892 mmol, 2.0 equiv) in dioxane (10 ml) and resulting reaction mixture was purged with $N_2$ gas for 10 min. followed by the addition of Pd(dppf))$Cl_2$.DCM (0.018 g, 0.022 mmol. 0.05 equiv). The resulting reaction mixture was heated at 80° C. for overnight. Product formation was confirmed by LCMS. After the completion of reaction, the reaction mixture was diluted with water (50 mL) and extracted with ethyl acetate (100 mL×2). Combined organic extracts were washed with water (50 mL×2) & brine (50 mL), dried over anhydrous $Na_2SO_4$ and concentrated. The crude product was purified by flash chromatography (0-5% MeOH in DCM as an eluent) to obtain 5-(4,4,5,5-tetramethyl-1,3,2-dioxaborolan-2-yl)-3,4-dihydroisoquinolin-1 (2H)-one (0.1 g, 83% Yield) as a yellow oil.

LCMS 274.2 $[M+H]^+$

Step 2: Synthesis of 6-(1-oxo-1,2,3,4-tetrahydroisoquinolin-5-yl)quinoline-4-carboxylic acid. To a solution of 6-bromoquinoline-4-carboxylic acid (0.1 g, 0.396 mmol, 1.0 equiv) and 5-(4,4,5,5-tetramethyl-1,3,2-dioxaborolan-2-yl)-3,4-dihydroisoquinolin-1(2H)-one (0.162 g, 0.595 mmol, 1.5 equiv), in dioxane (10 mL) and water (2 mL) was added $Na_2CO_3$ (0.083 g, 0.792 mmol, 2.0 equiv). The resulting reaction mixture was purged with $N_2$ gas, followed by the addition of Pd(PPh$_3$)$Cl_2$(0.013 g, 0.019 mmol, 0.05 equiv). The resulting reaction mixture was heated at 80° C. for overnight. Product formation was confirmed by LCMS. After completion of reaction, the mixture was concentrated under reduced pressure, diluted with water (50 mL) and washed with ethyl acetate (25 mL×2). Aqueous layer was separated and freeze dried over lyophilizer to obtain 6-(1-oxo-1,2,3,4-tetrahydroisoquinolin-5-yl)quinoline-4-carboxylic acid (0.200 g, Quant. Yield) as a yellow solid.

LCMS 319.0 $[M+H]^+$

Step 3: Synthesis of (S)—N-(2-(2-cyano-4,4-difluoropyrrolidin-1-yl)-2-oxoethyl)-6-(1-oxo-1,2,3,4-tetrahydroisoquinolin-5-yl)quinoline-4-carboxamide. To a stirred solution of synthesis of 6-(1-oxo-1,2,3,4-tetrahydroisoquinolin-5-yl)quinoline-4-carboxylic acid (0.200 g, 0.626 mmol, 1.0 equiv) in DMF (5 mL), was added (S)-4,4-difluoro-1-glycylpyrrolidine-2-carbonitrile hydrochloride (0.211 g, 0.939 mmol, 1.5 equiv), HOBt (0.126 g, 0.939 mmol, 1.5 equiv) & EDCI.HCl (0.180 g, 0.939 mmol, 1.5 equiv). The mixture was allowed to stir at RT for 10 min. triethylamine (0.189 g, 1.878 mmol, 3.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product was purified by flash chromatography (0-5% MeOH in DCM as an eluent) which was further purified by reversed phase HPLC to obtain (S)—N-(2-(2-cyano-4,4-difluoropyrrolidin-1-yl)-2-oxoethyl)-6-(1-oxo-1,2,3,4-tetrahydroisoquinolin-5-yl)quinoline-4-carboxamide (0.035 g, 11% Yield) as a white solid.

LCMS 490.5 $[M+H]^+$ $^1$H NMR (400 MHz, DMSO-d$_6$) δ 9.17 (t, J=5.92 Hz, 1H) 9.04 (d, J=3.95 Hz, 1H) 8.29-8.37 (m, 1H) 8.17 (d, J=8.33 Hz, 1H) 8.02 (br. s., 1H) 7.97 (d, J=7.02 Hz, 1H) 7.89 (dd, J=8.77, 1.75 Hz, 1H) 7.63 (d, J=4.38 Hz, 1H) 7.59 (d, J=6.58 Hz, 1H) 7.44-7.53 (m, 1H) 5.11 (dd, J=9.21, 2.19 Hz, 1H) 4.06-4.35 (m, 4H) 2.87-2.98 (m, 2H) 2.81 (d, J=18.86 Hz, 4H).

Example S-54

Synthesis of (S)—N-(2-(2-cyano-4,4-difluoropyrrolidin-1-yl)-2-oxoethyl)-1'-methyl-2'-oxo-1',2',3',4'-tetrahydro-[6,6'-biquinoline]-4-carboxamide

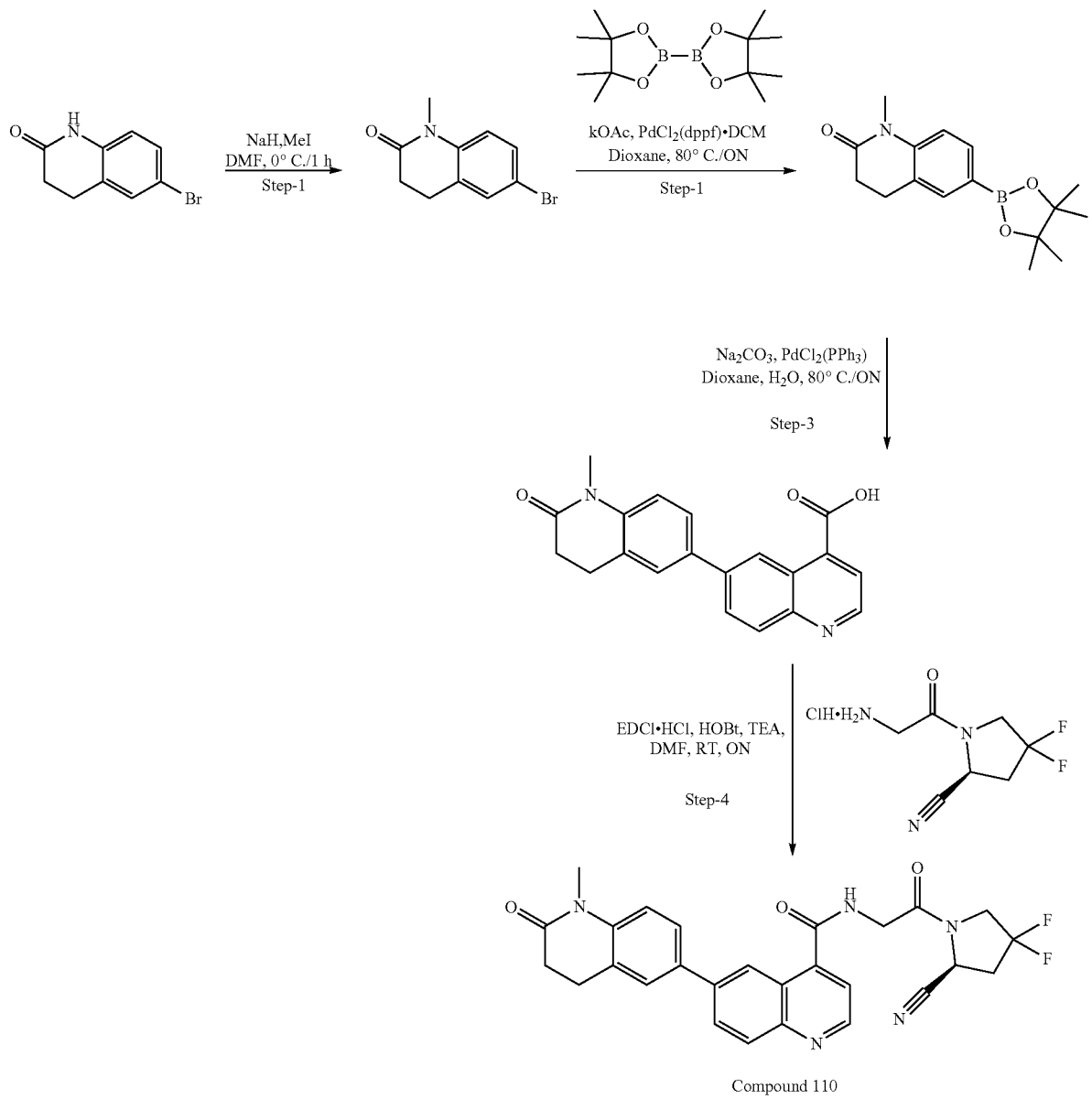

Compound 110

Step 1: Synthesis of 6-bromo-1-methyl-3,4-dihydroquinolin-2(1H)-one. To a stirred solution of 6-bromo-3,4-dihydroquinolin-2(1H)-one (0.250 g, 1.106 mmol, 1.0 equiv) in DMF (2.5 ml) was cooled at 0° C. Sodium hyride (0.050 g, 2.22 mmol, 2.0 equiv) was added slowly in the above reaction mixture and stirred for 20 min. MeI (0.298 g, 2.22 mmol, 2.0 equiv) was added at 0° C. The resulting reaction mixture was stirred at RT for 1 h. Product formation was confirmed by TLC. After the completion of reaction, the reaction mixture was diluted with cold water (50 mL) and extracted with ethyl acetate (50 mL×3). Combined organic extracts were washed with water (50 mL×2) & brine (50 mL), dried over anhydrous $Na_2SO_4$ and concentrated. The crude product was purified by flash chromatography (0-30% ethyl acetate in hexane as an eluent) to obtain 6-bromo-1-methyl-3,4-dihydroquinolin-2(1H)-one (0.15 g, 56% Yield) as a brown solid.

$^1$H NMR (400 MHz, DMSO-$d_6$) δ 7.37-7.47 (m, 2H) 7.03 (d, J=9.21 Hz, 1H) 3.22 (s, 3H) 2.87 (t, J=7.45 Hz, 2H) 2.54 (d, J=7.89 Hz, 2H).

Step 2: Synthesis 1-methyl-6-(4,4,5,5-tetramethyl-1,3,2-dioxaborolan-2-yl)-3,4-dihydroquinolin-2(1H)-one. To a solution of 6-bromo-1-methyl-3,4-dihydroquinolin-2(1H)-one (0.150 g, 0.630 mmol, 1.0 equiv), 4,4,4',4',5,5,5',5'-octamethyl-2,2'-bi(1,3,2-dioxaborolane) (0.239 g, 0.945 mmol, 1.5 equiv) and KOAc (0.123 g, 1.26 mmol, 2.0 equiv) in dioxane (10 ml) and resulting reaction mixture was purged with $N_2$ gas for 10 min. followed by the addition of Pd(dppf))Cl$_2$.DCM (0.025 g, 0.0315 mmol. 0.05 equiv). The resulting reaction mixture was heated at 80° C. for overnight. Product formation was confirmed by LCMS. After the completion of reaction, the reaction mixture was diluted with water (50 mL) and extracted with ethyl acetate (50 mL×3). Combined organic extracts were washed with water (50 mL×2) & brine (50 mL), dried over anhydrous $Na_2SO_4$ and concentrated. The crude product was purified by flash chromatography (0-10% ethyl acetate in hexane) to obtain 1-methyl-6-(4,4,5,5-tetramethyl-1,3,2-dioxaborolan-2-yl)-3,4-dihydroquinolin-2(1H)-one (0.150 g, 83% Yield) as a yellow oil.

LCMS 288.1 $[M+H]^+$ $^1$H NMR (400 MHz, DMSO-$d_6$) δ 7.46-7.62 (m, 2H) 7.08 (d, J=7.89 Hz, 1H) 3.25 (s, 3H) 2.81-2.92 (m, 2H) 2.52-2.59 (m, 2H) 1.22-1.35 (m, 12H).

Step 3: Synthesis 1'-methyl-2'-oxo-1',2',3',4'-tetrahydro-[6,6'-biquinoline]-4-carboxylic acid. To a solution of 6-bromoquinoline-4-carboxylic acid (0.100 g, 0.396 mmol, 1.0 equiv) and 1-methyl-6-(4,4,5,5-tetramethyl-1,3,2-dioxaborolan-2-yl)-3,4-dihydroquinolin-2(1H)-one (0.171 g, 0.594 mmol, 1.5 equiv), in dioxane (7 mL) and water (2 mL) was added $Na_2CO_3$ (0.083 g, 0.792 mmol, 2.0 equiv). The resulting reaction mixture was purged with $N_2$ gas followed by the addition of Pd(PPh$_3$)Cl$_2$ (0.013 g, 0.019 mmol, 0.05 equiv). The resulting reaction mixture was heated at 80° C. for overnight. Product formation was confirmed by LCMS. After completion of reaction, the mixture was concentrated under reduced pressure, diluted with water (25 mL) and washed with ethyl acetate (25 mL×2). Aqueous layer was separated and freeze dried over lyophilizer to obtain 1'-methyl-2'-oxo-1',2',3',4'-tetrahydro-[6,6'-biquinoline]-4-carboxylic acid (0.100 g, 76% Yield) as a yellow solid.

LCMS 333.2 $[M+H]^+$

Step 4: Synthesis of (S)—N-(2-(2-cyano-4,4-difluoropyrrolidin-1-yl)-2-oxoethyl)-1'-methyl-2'-oxo-1',2',3',4'-tetrahydro-[6,6'-biquinoline]-4-carboxamide. To a stirred solution of synthesis of (1'-methyl-2'-oxo-1',2',3',4'-tetrahydro-[6,6'-biquinoline]-4-carboxylic acid (0.100 g, 0.300 mmol, 1.0 equiv) in DMF (5 mL), was added (S)-4,4-difluoro-1-glycylpyrrolidine-2-carbonitrile hydrochloride (0.101 g, 0.450 mmol, 1.5 equiv), HOBt (0.060 g, 0.450 mmol, 1.5 equiv) & EDCI.HCl (0.086 g, 0.450 mmol, 1.5 equiv). The mixture was allowed to stir at RT for 10 min. truiethylamine (0.090 g, 0.9 mmol, 3.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product was purified by flash chromatography (0-5% MeOH in DCM as an eluent) which was further purified by reversed phase HPLC to obtain (S)—N-(2-(2-cyano-4,4-difluoropyrrolidin-1-yl)-2-oxoethyl)-1'-methyl-2'-oxo-1',2',3',4'-tetrahydro-[6,6'-biquinoline]-4-carboxamide (0.007 g, 5% Yield) as a white solid.

LCMS 504.5 $[M+H]^+$ $^1$H NMR (400 MHz, CHLOROFORM-d) δ 8.98 (d, J=4.38 Hz, 1H) 8.53 (s, 1H) 8.23 (d, J=8.77 Hz, 1H) 8.04 (d, J=9.21 Hz, 1H) 7.67 (d, J=6.58 Hz, 1H) 7.53-7.63 (m, 2H) 7.11 (d, J=8.77 Hz, 1H) 6.95 (br. s., 1H) 5.03 (d, J=6.14 Hz, 1H) 4.41 (br. s., 1H) 4.32 (br. s., 2H) 3.94-4.12 (m, 2H) 3.41 (s, 3H) 2.96-3.07 (m, 1H) 2.83 (br. s., 2H) 2.63-2.76 (m, 2H).

Example S-55

Synthesis of (S)—N-(2-(2-cyano-4,4-difluoropyrrolidin-1-yl)-2-oxoethyl)-6-(2-methyl-1-oxo-1,2,3,4-tetrahydroisoquinolin-6-yl)quinoline-4-carboxamide

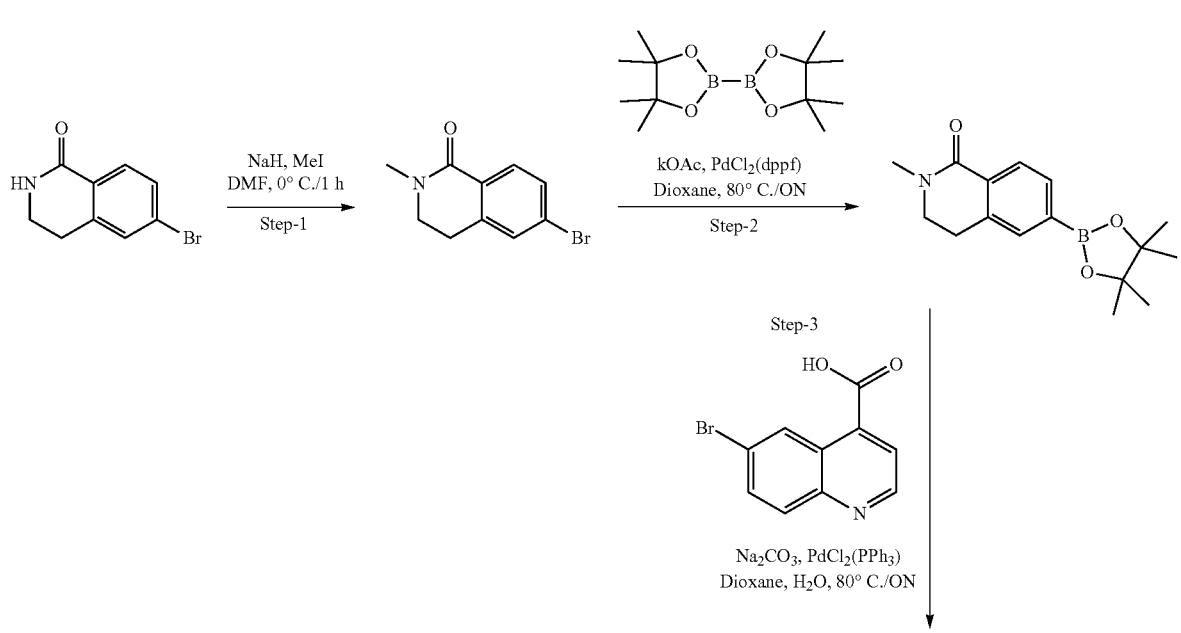

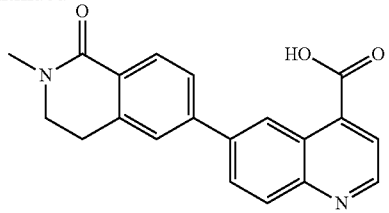

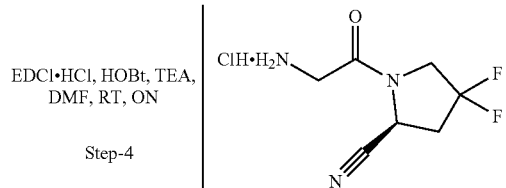

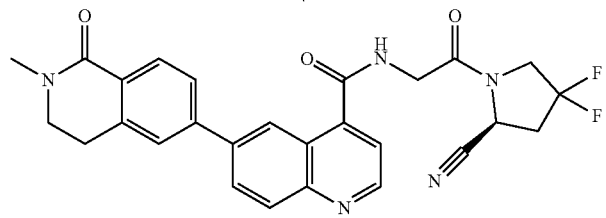

Compound 111

Step 1: Synthesis of 6-bromo-2-methyl-3,4-dihydroisoquinolin-1(2H)-one. To a stirred solution of 6-bromo-3,4-dihydroquinolin-2(1H)-one (0.500 g, 2.23 mmol, 1.0 equiv) in DMF (5 ml) was cooled at 0° C. Sodium hydride (0.102 g, 4.46 mmol, 2.0 equiv) was added slowly in the above reaction mixture and stirred for 20 min. After 20 min. MeI (0.4 ml, 4.46 mmol, 2.0 equiv) was added at 0° C. The resulting reaction mixture was stirred at RT for 1 h. Product formation was confirmed by TLC and LCMS. After the completion of reaction, the reaction mixture was diluted with cold water (100 mL) and extracted with ethyl acetate (150 mL×3). Combined organic extracts were washed with water (50 mL×2) & brine (50 mL), dried over anhydrous Na$_2$SO$_4$ and concentrated. The crude product was purified by flash chromatography (0-30% ethyl acetate in Hexane) to obtain 6-bromo-2-methyl-3,4-dihydroisoquinolin-1(2H)-one (0.200 g, 37% Yield) as a brown solid.

$^1$H NMR (400 MHz, DMSO-d$_6$) δ ppm 7.77 (d, J=8.33 Hz, 1H) 7.55 (d, J=2.19 Hz, 2H) 3.54 (t, J=6.58 Hz, 2H) 2.95-3.10 (m, 5H).

Step 2: Synthesis 2-methyl-6-(4,4,5,5-tetramethyl-1,3,2-dioxaborolan-2-yl)-3,4-dihydroisoquinolin-1(2H)-one. To a solution of 6-bromo-1-methyl-3,4-dihydroquinolin-2(1H)-one (0.200 g, 0.840 mmol, 1.0 equiv), 4,4,4',4',5,5,5',5'-octamethyl-2,2'-bi(1,3,2-dioxaborolane) (0.318 g, 1.26 mmol, 1.0 equiv) and KOAc (0.164 g, 1.26 mmol, 2.0 equiv) in dioxane (10 ml) and resulting reaction mixture was purged with N$_2$ gas for 10 min. followed by the addition of Pd(dppf))Cl$_2$.DCM (0.034 g, 0.042 mmol. 0.05 equiv). The resulting reaction mixture was heated at 80° C. for overnight. Product formation was confirmed by LCMS. After the completion of reaction, the reaction mixture was diluted with cold water (50 mL) and extracted with ethyl acetate (50 mL×3). Combined organic extracts were washed with water (50 mL×2) & brine (50 mL), dried over anhydrous Na$_2$SO$_4$ and concentrated. The crude product was purified by flash chromatography (0-30% ethyl acetate in hexane as an eluent) to obtain 2-methyl-6-(4,4,5,5-tetramethyl-1,3,2-dioxaborolan-2-yl)-3,4-dihydroisoquinolin-1(2H)-one (0.250 g, Quant. Yield) as a yellow oil.

LCMS 288.2 [M+H]$^+$

Step 3: Synthesis of 6-(2-methyl-1-oxo-1,2,3,4-tetrahydroisoquinolin-6-yl)quinoline-4-carboxylic acid. To a solution of 6-bromoquinoline-4-carboxylic acid (0.100 g, 0.396 mmol, 1.0 equiv) and 2-methyl-6-(4,4,5,5-tetramethyl-1,3,2-dioxaborolan-2-yl)-3,4-dihydroisoquinolin-1(2H)-one (0.170 g, 0.595 mmol, 1.5 equiv), in dioxane (10 mL) and water (2 mL) was added Na$_2$CO$_3$ (0.083 g, 0.792 mmol, 2.0 equiv). The resulting reaction mixture was purged with N$_2$ gas followed by the addition of Pd(PPh$_3$)Cl$_2$(0.013 g, 0.019 mmol, 0.05 equiv). The resulting reaction mixture was heated at 80° C. for overnight. Product formation was confirmed by LCMS. After completion of reaction, the mixture was concentrated under reduced pressure, diluted with water (25 mL) and washed with ethyl acetate (25 mL×2). Aqueous layer was separated and freeze dried over lyophilizer to obtain 6-(2-methyl-1-oxo-1,2,3,4-tetrahydroisoquinolin-6-yl)quinoline-4-carboxylic acid (0.300 g, Quant. Yield) as a brown solid.

LCMS 333.1 [M+H]$^+$

Step 4: Synthesis of (S)—N-(2-(2-cyano-4,4-difluoropyrrolidin-1-yl)-2-oxoethyl)-6-(2-methyl-1-oxo-1,2,3,4-tetrahydroisoquinolin-6-yl)quinoline-4-carboxamide. To a stirred solution of synthesis of 6-(2-methyl-1-oxo-1,2,3,4-tetrahydroisoquinolin-6-yl)quinoline-4-carboxylic acid (0.100 g, 0.300 mmol, 1.0 equiv) in DMF (7 mL), was added (S)-4,4-difluoro-1-glycylpyrrolidine-2-carbonitrile hydrochloride (0.101 g, 0.450 mmol, 1.5 equiv), HOBt (0.060 g, 0.450 mmol, 1.5 equiv) & EDCI.HCl (0.086 g, 0.450 mmol, 1.5 equiv). The mixture was allowed to stir at RT for 10 min. triethylamine (0.090 g, 0.9 mmol, 3.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous Na$_2$SO$_4$ and concentrated. The crude product was purified by flash chromatography (0-5% MeOH in DCM as an eluent) which was further purified by reverse phase HPLC to obtain (S)—N-(2-(2-cyano-4,4-difluoropyrrolidin-1-yl)-2-oxoethyl)-6-(2-methyl-1-oxo-1,2,3,4-tetrahydroisoquinolin-6-yl)quinoline-4-carboxamide (0.005 g, 4% Yield) as a white solid.

LCMS 504.5 [M+H]$^+$ $^1$H NMR (400 MHz, DMSO-d$_6$) δ 9.23 (t, J=5.92 Hz, 1H) 9.00 (d, J=3.95 Hz, 1H) 8.88 (d, J=1.75 Hz, 1H) 8.22-8.29 (m, 1H) 8.16-8.22 (m, 1H) 8.01 (d, J=7.89 Hz, 1H) 7.83-7.95 (m, 2H) 7.60 (d, J=4.38 Hz, 1H) 5.14-5.26 (m, 1H) 4.10-4.40 (m, 4H) 3.60 (t, J=6.80 Hz, 2H) 3.14 (d, J=7.45 Hz, 2H) 3.06 (s, 2H) 2.95 (br. s., 1H) 2.86 (d, J=19.29 Hz, 2H).

Example S-56

Synthesis of (S,E)-6-(2-(1H-indazol-5-yl)vinyl)-N-(2-(2-cyano-4,4-difluoropyrrolidin-1-yl)-2-oxoethyl) quinoline-4-carboxamide 0.076 mmol, 0.05 equiv). The resulting reaction mixture was heated at 80° C. for overnight. Product formation was confirmed by LCMS and TLC. After the completion of reaction the mixture was diluted with water (50 mL) and extracted with ethyl acetate (100 mL×2). Combined organic extracts were washed with water (50 mL×4), dried over anhydrous Na$_2$SO$_4$ and concentrated. The crude product was purified by flash chromatography (0-20% ethyl acetate in hexane as an eluent) to obtain 5-vinyl-1H-indazole (0.130 g, 59% yield) as an off white solid.

LCMS 173.9 [M+H]$^+$ $^1$H NMR (400 MHz, DMSO-d$_6$) δ 13.05 (br. s., 1H) 8.03 (s, 1H) 7.74 (s, 1H) 7.43-7.59 (m, 2H) 6.81 (dd, J=17.54, 10.96 Hz, 1H) 5.76 (d, J=17.98 Hz, 1H) 5.17 (d, J=10.96 Hz, 1H).

Step 2: Synthesis of (E)-6-(2-(1H-indazol-5-yl)vinyl)quinoline-4-carboxylic acid. To a solution of 6-bromoquinoline-4-carboxylic acid (0.100 g, 0.396 mmol, 1.0 equiv and 6-vinyl-3,4-dihydroquinolin-2(1H)-one (0.069 g, 0.476 mmol, 1.2 equiv) in DMF (3 ml) was added in triethylamine (0.119 g, 1.18 mmol, 3.0 equiv). The resulting reaction mixture was purged with N$_2$ gas for 10 min. followed by the addition of Pd(dppf)Cl$_2$ (0.014 g, 0.019 mmol. 0.05 equiv) at RT. The resulting reaction mixture was heated at 80° C.

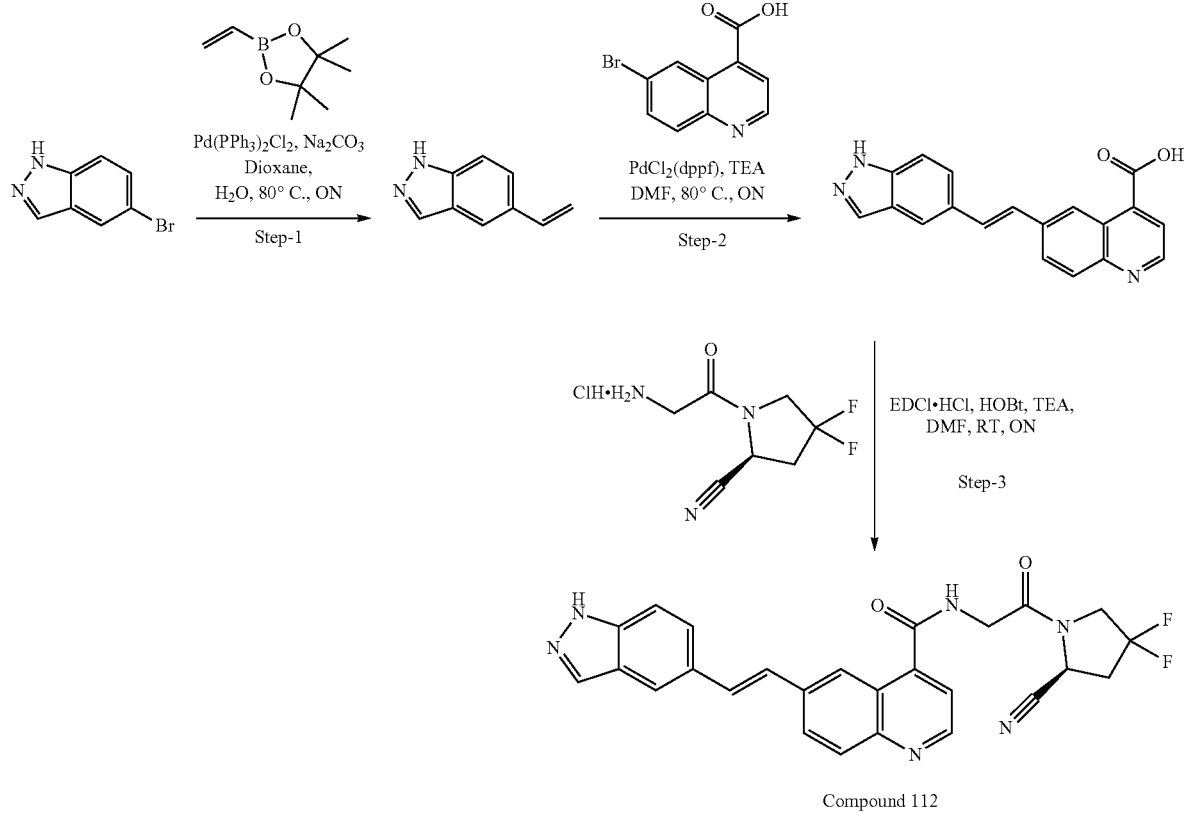

Compound 112

Step 1: Synthesis of 5-vinyl-1H-indazole. To a solution of 5-bromo-1H-indazole (0.300 g, 1.52 mmol, 1.0 equiv) and 4,4,5,5-tetramethyl-2-vinyl-1,3,2-dioxaborolane (0.351 g, 2.28 mmol, 1.5 equiv), in dioxane (7 mL) and water (2 mL) was added Na$_2$CO$_3$ (0.322 g, 3.04 mmol, 2.0 equiv). The resulting reaction mixture was purged with N$_2$ gas for 10 min. followed by the addition of Pd(PPh$_3$)$_2$Cl$_2$ (0.053 g, for overnight. Product formation was confirmed by LCMS. After the completion of reaction, the mixture was diluted with water (10 mL) and aqueous layer washed with ethyl acetate (10 mL×2). Aqueous layer was separated and freeze dried over lyophilizer to obtain (E)-6-(2-(1H-indazol-5-yl)vinyl)quinoline-4-carboxylic acid (0.100 g, 80% yield) as a black solid.

LCMS 316.1 [M+H]$^+$

Step 3: Synthesis of (S,E)-6-(2-(1H-indazol-5-yl)vinyl)-N-(2-(2-cyano-4,4-difluoropyrrolidin-1-yl)-2-oxoethyl)quinoline-4-carboxamide. To a stirred solution of (E)-6-(2-(1H-indazol-5-yl)vinyl)quinoline-4-carboxylic acid (0.100 g, 0.317 mmol, 1.0 equiv) in DMF (7 mL), was added (S)-4,4-difluoro-1-glycylpyrrolidine-2-carbonitrile hydrochloride (0.107 g, 0.456 mmol, 1.5 equiv), HOBt (0.064 g, 0.476 mmol, 1.5 equiv) & EDCI.HCl (0.091 g, 0.476 mmol, 1.5 equiv). The mixture was allowed to stir at RT for 10 min. triethylamine (0.096 g, 0.951 mmol, 3.0 equiv) was added and the mixture was allowed to stir at RT for overnight. Product formation was confirmed by LCMS. After completion of reaction, the mixture was diluted with water (20 mL) and extracted with ethyl acetate (20 mL×2). Combined organic extracts were washed with water (20 mL×4), dried over anhydrous Na$_2$SO$_4$ and concentrated. The crude product was purified reversed phase HPLC to obtain ((S,E)-6-(2-(1H-indazol-5-yl)vinyl)-N-(2-(2-cyano-4,4-difluoropyrrolidin-1-yl)-2-oxoethyl)quinoline-4-carboxamide (0.040 g, 25% Yield) as an orange solid.

LCMS 487.5 [M+H]$^+$ $^1$H NMR (400 MHz, DMSO-d$_6$) δ13.14 (br. s., 1H) 9.20 (t, J=5.48 Hz, 1H) 8.93 (d, J=4.39 Hz, 1H) 8.62 (s, 1H) 8.13-8.21 (m, 2H) 7.97-8.13 (m, 2H) 7.81 (d, J=7.45 Hz, 2H) 7.51-7.63 (m, 2H) 7.40 (d, J=16.22 Hz, 1H) 5.21-5.36 (m, 1H) 4.13-4.43 (m, 4H) 2.82-3.11 (m, 2H).

Example 5-57

Synthesis of (S)—N-(2-(2-cyano-4,4-difluoropyrrolidin-1-yl)-2-oxoethyl)-1',2',3',4'-tetrahydro-[6,6'-biquinoline]-4-carboxamide

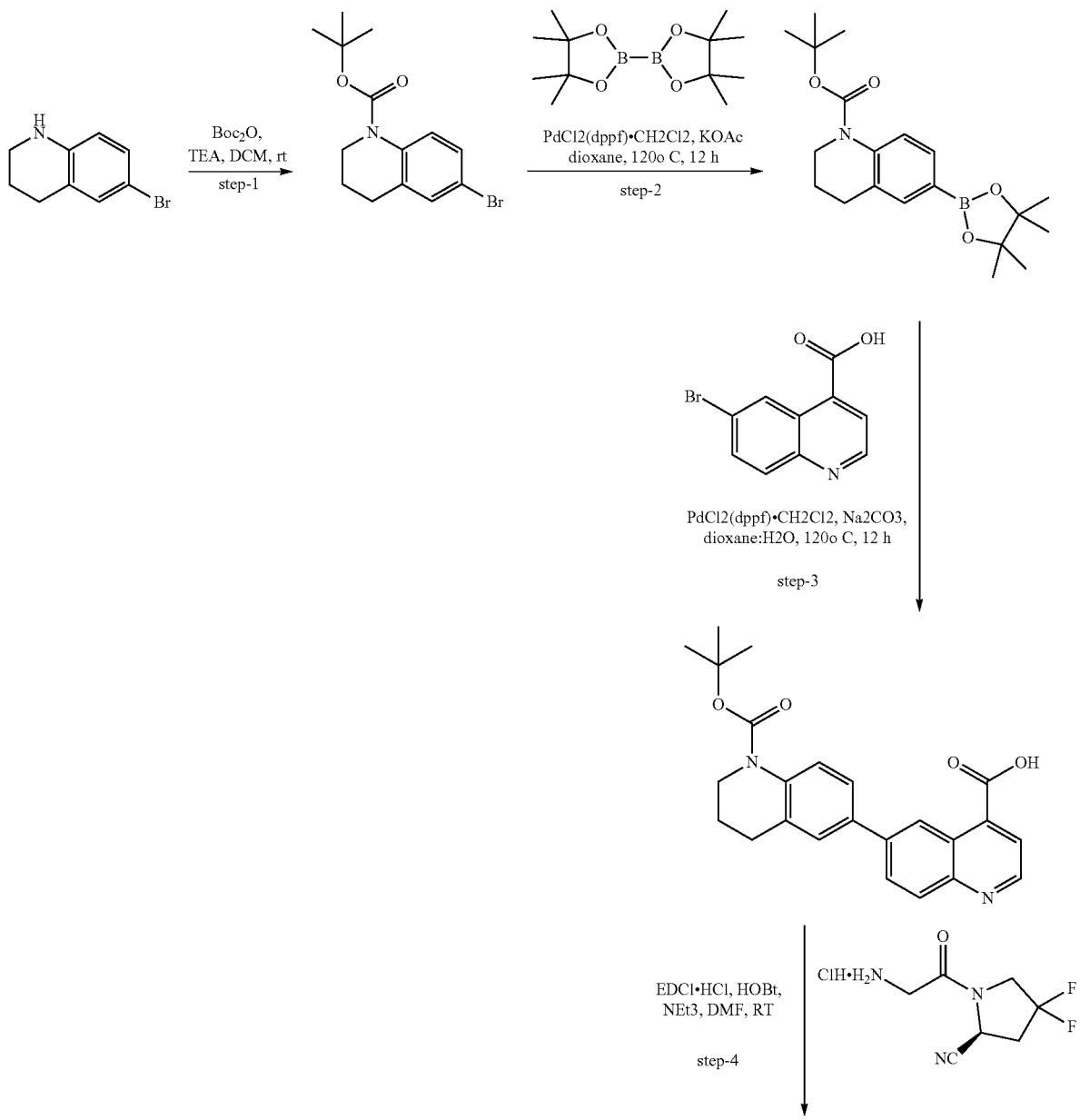

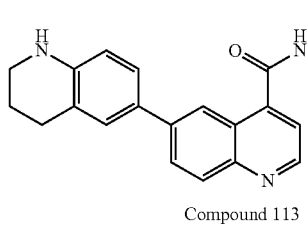

Compound 113

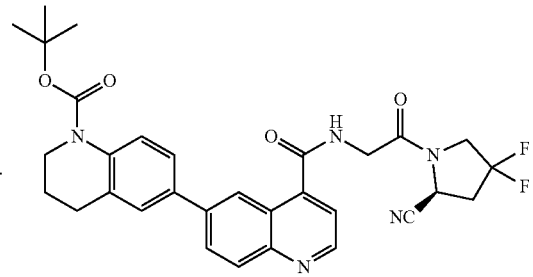

Step 1: Synthesis of tert-butyl 6-bromo-3,4-dihydroquinoline-1(2H)-carboxylate. To a stirred solution of 6-bromo-1,2,3,4-tetrahydroquinoline (1.0 g, 4.71 mmol, 1.0 equiv) in DCM (15 mL) was added di-tert-butyl dicarbonate (2.0 g, 8.49 mmol, 1.8 equiv) and triethylamine (0.609 mL, 6.40 mmol, 1.5 equiv).). The resulting reaction mixture was stirred at rt for 2 hr. After the completion of reaction (monitored by TLC & LCMS), the mixture was diluted with water (100 mL) the resulting precipitate was filtered off, washed with water and hexane. Crude product was purified by flash chromatography (0-3% EtOAc/hexane as an eluent) to obtain tert-butyl 6-bromo-3,4-dihydroquinoline-1(2H)-carboxylate (0.600 g, 41% Yield) as an off white solid.

LCMS 256.0 (acid fragment) [M+H]+

Step 2: Synthesis of tert-butyl 6-(4,4,5,5-tetramethyl-1,3,2-dioxaborolan-2-yl)-3,4-dihydroquinoline-1(2H)-carboxylate. To a solution of t-butyl 6-bromo-3,4-dihydroquinoline-1(2H)-carboxylate (0.350 g, 1.12 mmol, 1.0 equiv) in dioxane (5 mL) was added 4,4,4',4',5,5,5',5'-octamethyl-2,2'-bi(1,3,2-dioxaborolane) (0.342 g, 1.34 mmol, 1.2 equiv), KOAc (0.16 g, 1.68 mmol, 1.5 equiv) and resulting reaction mixture was purged with N$_2$ gas for 10 min. followed by the addition of PdCl$_2$(dppf).DCM (0.27 g, 0.03 mmol. 0.03 equiv). The resulting reaction mixture was heated at 100° C. for overnight. After the completion of reaction (monitored by TLC & LCMS), the mixture was diluted with water (100 mL) and extracted with ethyl acetate (2×100 mL). Combined organic extracts were washed with water (100 mL×2) & brine (100 mL), dried over anhydrous Na$_2$SO$_4$ and concentrated. The crude product was purified by flash chromatography (0-20% EtOAc/hexane as an eluent) to obtain 6-(4,4,5,5-tetramethyl-1,3,2-dioxaborolan-2-yl)-3,4-dihydroquinoline-1(2H)-carboxylate (0.380 g, 94% Yield) as an off white solid.

$^1$H NMR (400 MHz, DMSO-d$_6$) δ 7.61 (d, J=8.77 Hz, 1H) 7.52 (dd, J=6.14, 3.07 Hz, 1H) 7.38-7.43 (m, 1H) 3.57-3.68 (m, 2H) 2.72 (t, J=6.58 Hz, 2H) 1.76-1.86 (m, 2H) 1.46 (s, 9H) 1.21-1.30 (m, 12H).

Step 3: Synthesis of 1'-(tert-butoxycarbonyl)-1',2',3',4'-tetrahydro-[6,6'-biquinoline]-4-carboxylic acid. To a solution of 6-bromoquinoline-4-carboxylic acid (0.420 g, 1.67 mmol, 1.2 equiv) in dioxan (10 mL) & water (3 mL) was added tert-butyl 6-(4,4,5,5-tetramethyl-1,3,2-dioxaborolan-2-yl)-3,4-dihydroquinoline-1(2H)-carboxylate (0.500 g, 1.391 mmol, 1.0 equiv), Na$_2$CO$_3$ (0.113 g, 1.06 mmol, 1.2 equiv) and resulting reaction mixture was purged with N$_2$ gas for 10 min. followed by the addition of PdCl$_2$(dppf).DCM (0.034 g, 0.04 mmol. 0.03 equiv). The resulting reaction mixture was heated at 120° C. for overnight. Product formation was confirmed by LCMS. After completion of reaction, reaction mixture was diluted with water (100 mL) and washed with ethyl acetate (2×50 mL). aqueous layer was freeze dried over lyophillizer to obtain 1'-(tert-butoxycarbonyl)-1',2',3',4'-tetrahydro-[6,6'-biquinoline]-4-carboxylic acid (0.500 g Quant. yield) as a black solid.

LCMS 405.1 [M+H]+

Step 4: Synthesis of tert-butyl (S)-4'-((2-(2-cyano-4,4-difluoropyrrolidin-1-yl)-2-oxoethyl)carbamoyl)-3,4-dihydro-[6,6'-biquinoline]-1(2H)-carboxylate. To a stirred solution of 1'-(tert-butoxycarbonyl)-1',2',3',4'-tetrahydro-[6,6'-biquinoline]-4-carboxylic acid (0.500 g, 1.23 mmol, 1.0 equiv) in DMF (20 mL), was added (S)-4,4-difluoro-1-glycylpyrrolidine-2-carbonitrile hydrochloride (0.30 g, 1.36 mmol, 1.1 equiv), EDCI.HCl (0.286 g, 1.84 mmol, 1.5 equiv) & HOBt (0.240 g, 1.84 mmol, 1.5 equiv). The mixture was allowed to stir at RT for 10 min. triethylamine (0.3 mL) was added and the mixture was allowed to stir at RT for overnight. Product formation was confirmed by LCMS and TLC. After completion of reaction, the mixture was diluted with water (25 mL) and extracted with ethyl acetate (50 mL×2). Combined organic extracts were washed with water (10 mL×4), dried over anhydrous Na$_2$SO$_4$ and concentrated to obtain t-butyl (S)-4'-((2-(2-cyano-4,4-difluoropyrrolidin-1-yl)-2-oxoethyl)carbamoyl)-3,4-dihydro-[6,6'-biquinoline]-1(2H)-carboxylate (0.250 g, as a crude material directly used for next step) as an yellow solid.

LCMS 576.5 [M+H]+

Step 5: Synthesis of (S)—N-(2-(2-cyano-4,4-difluoropyrrolidin-1-yl)-2-oxoethyl)-1',2',3',4'-tetrahydro-[6,6'-biquinoline]-4-carboxamide. To a stirred solution of tert-butyl (S)-4'-((2-(2-cyano-4,4-difluoropyrrolidin-1-yl)-2-oxoethyl)carbamoyl)-3,4-dihydro-[6,6'-biquinoline]-1(2H)-carboxylate (0.250 g, 0.430 mmol, 1.0 equiv) in DCM (5 mL), was added TFA (0.5 mL) the mixture was allowed to stir at RT for overnight. Product formation was confirmed by LCMS TLC. After completion of reaction DCM was evaporated under reduced pressure. The crude product was purified by reversed phase HPLC to obtain (S)—N-(2-(2-cyano-4,4-difluoropyrrolidin-1-yl)-2-oxoethyl)-1',2',3',4'-tetrahydro-[6,6'-biquinoline]-4-carboxamide (0.005 g, 3% Yield) as an off white solid.

LCMS 476.5 [M+H]+

$^1$H NMR (400 MHz, DMSO-d$_6$) δ 9.14 (br. s., 1H) 8.86 (d, J=3.95 Hz, 1H) 8.53 (s, 1H) 8.05 (t, J=9.43 Hz, 2H) 7.50 (d, J=4.38 Hz, 1H) 7.43 (d, J=8.77 Hz, 1H) 6.55 (d, J=8.33 Hz, 1H) 5.98 (br. s., 1H) 4.27 (t, J=5.70 Hz, 3H) 3.23 (br. s., 4H) 2.73-2.94 (m, 3H) 2.67 (br. s., 1H) 2.33 (d, J=1.75 Hz, 2H).

Example S-58

Synthesis of (S)—N-(2-(2-cyano-4,4-difluoropyrrolidin-1-yl)-2-oxoethyl)-6-(1,2,3,4-tetrahydroisoquinolin-6-yl)quinoline-4-carboxamide

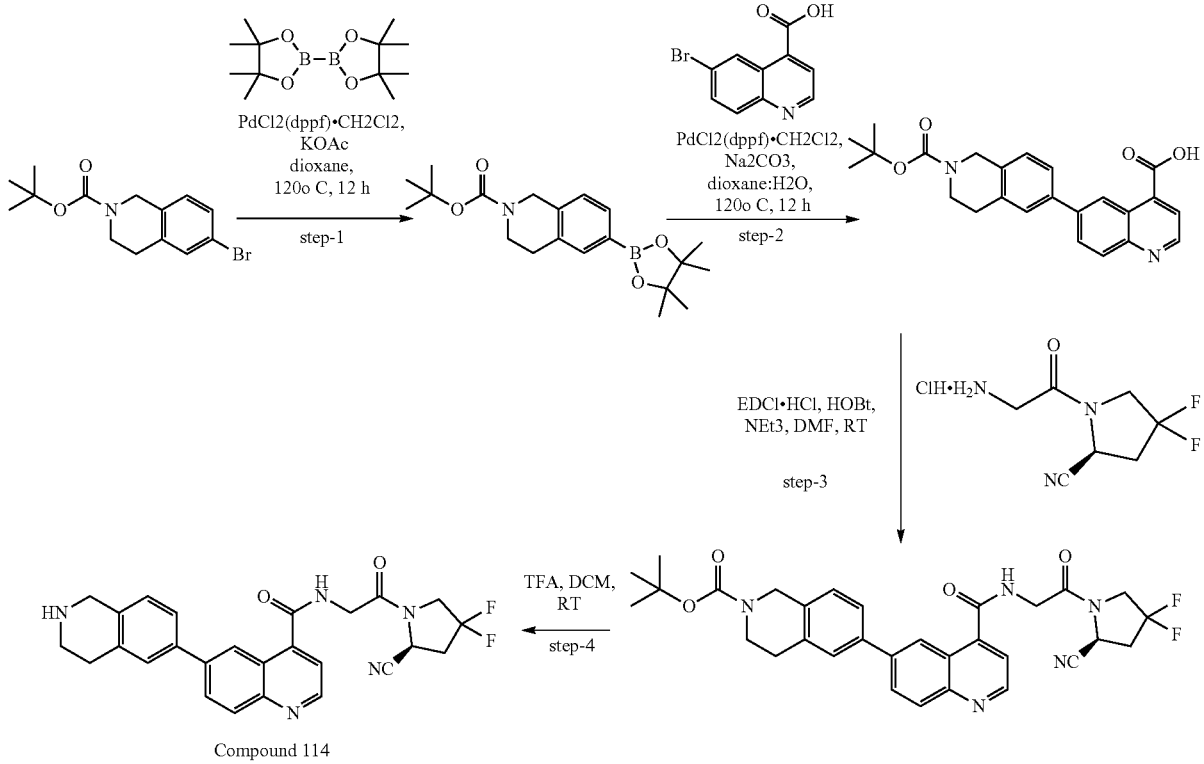

Compound 114

Step 1: Synthesis of tert-butyl 6-(4,4,5,5-tetramethyl-1,3,2-dioxaborolan-2-yl)-3,4-dihydroisoquinoline-2(1H)-carboxylate. To a solution of t-butyl 6-bromo-3,4-dihydroisoquinoline-2(1H)-carboxylate (0.500 g, 1.60 mmol, 1.0 equiv) in dioxane (5 mL) was added 4,4,4',4',5,5,5',5'-octamethyl-2,2'-bi(1,3,2-dioxaborolane) (0.342 g, 1.92 mmol, 1.2 equiv), KOAc (0.23 g, 2.4 mmol, 1.5 equiv) and resulting reaction mixture was purged with $N_2$ gas for 10 min. followed by the addition of $PdCl_2$(dppf).DCM (0.39 g, 0.04 mmol, 0.03 equiv). The resulting reaction mixture was heated at 120° C. for overnight. After the completion of reaction (monitored by TLC & LCMS), the mixture was diluted with water (100 mL) and extracted with ethyl acetate (2×100 mL). Combined organic extracts were washed with water (100 mL×2) & brine (100 mL), dried over anhydrous $Na_2SO_4$ and concentrated. The crude product was purified by flash chromatography (0-20% EtOAc/hexane as an eluent) to obtain tert-butyl 6-(4,4,5,5-tetramethyl-1,3,2-dioxaborolan-2-yl)-3,4-dihydroisoquinoline-2(1H)-carboxylate (0.260 g, 45% Yield) as an off white solid.

LCMS 304.2 (Acid fragment) $[M+H]^+$

Step 2: Synthesis of 6-(2-(tert-butoxycarbonyl)-1,2,3,4-tetrahydroisoquinolin-6-yl)quinoline-4-carboxylic acid. To a solution of 6-bromoquinoline-4-carboxylic acid (0.196 g, 0.77 mmol, 0.8 equiv) in dioxane (5 mL) and water (2 mL) was added t-butyl 6-(4,4,5,5-tetramethyl-1,3,2-dioxaborolan-2-yl)-3,4-dihydroisoquinoline-2(1H)-carboxylate (0.350 g, 0.97 mmol, 1.0 equiv), $Na_2CO_3$ (0.123 g, 1.16 mmol, 1.2 equiv) and resulting reaction mixture was purged with $N_2$ gas for 10 min. followed by the addition of $PdCl_2$(dppf).DCM (0.23 g, 0.021 mmol. 0.03 equiv). The resulting reaction mixture was heated at 100° C. for overnight. Product formation was confirmed by LCMS. After the completion of reaction, reaction mixture was diluted with water (100 mL) and washed with ethyl acetate (2×50 mL). Aqueous layer was separated and freeze dried over lyophillizer to obtain 6-(2-(tert-butoxycarbonyl)-1,2,3,4-tetrahydroisoquinolin-6-yl)quinoline-4-carboxylic acid (0.30 g, quant. yield) as a black solid.

LCMS 405.1 $[M+H]^+$

Step 3: Synthesis of tert-butyl tert-butyl (S)-6-(4-((2-(2-cyano-4,4-difluoropyrrolidin-1-yl)-2-oxoethyl)carbamoyl)quinolin-6-yl)-3,4-dihydroisoquinoline-2(1H)-carboxylate.
To a stirred solution of 6-(2-(tert-butoxycarbonyl)-1,2,3,4-tetrahydroisoquinolin-6-yl)quinoline-4-carboxylic acid (0.250 g, 0.671 mmol, 1.0 equiv) in DMF (10 mL), was added (S)-4,4-difluoro-1-glycylpyrrolidine-2-carbonitrile hydrochloride (0.153 g, 0.67 mmol, 1.1 equiv), EDCI.HCl (0.143 g, 0.92 mmol, 1.5 equiv) & HOBt (0.125 g, 0.92 mmol, 1.5 equiv). The mixture was allowed to stir at RT for 10 min. triethylamine (0.15 mL) was added and the mixture was allowed to stir at RT for overnight. Product formation was confirmed by LCMS and TLC. After completion of reaction, the mixture was diluted with water (25 mL) and extracted with ethyl acetate (50 mL×2). Combined organic extracts were washed with water (25 mL×4), dried over anhydrous $Na_2SO_4$ and concentrated to obtain t-butyl (S)-6-(4-((2-(2-cyano-4,4-difluoropyrrolidin-1-yl)-2-oxoethyl)carbamoyl)quinolin-6-yl)-3,4-dihydroisoquinoline-2(1H)-carboxylate (0.100 g, as a crude product which was directly used for next step) as a yellow solid.

LCMS 576.3 $[M+H]^+$

Step 4: Synthesis of (S)—N-(2-(2-cyano-4,4-difluoropyrrolidin-1-yl)-2-oxoethyl)-6-(1,2,3,4-tetrahydroisoquinolin-6-yl)quinoline-4-carboxamide. To a stirred solution of t-butyl (S)-6-(4-((2-(2-cyano-4,4-difluoropyrrolidin-1-yl)-2-oxoethyl)carbamoyl)quinolin-6-yl)-3,4-dihydroisoquinoline-2(1H)-carboxylate (0.100 g, 0.173 mmol, 1.0 equiv) in DCM (5 mL), was added TFA (0.7 mL) the mixture was allowed to stir at RT for overnight. Product formation was confirmed by LCMS and TLC. After completion of reaction DCM was evaporated under reduced pressure. The crude product was purified by reversed phase HPLC to obtain (S)—N-(2-(2-cyano-4,4-difluoropyrrolidin-1-yl)-2-oxoethyl)-6-(1,2,3,4-tetrahydroisoquinolin-6-yl)quinoline-4-carboxamide (0.013 g, 15% Yield) as an off white solid.

LCMS 476.5 [M+H]$^+$ $^1$H NMR (400 MHz, DMSO-$d_6$) δ 9.21 (br. s., 1H) 8.97 (d, J=3.95 Hz, 1H) 8.77 (s, 1H) 8.11-8.23 (m, 2H) 7.77 (br. s., 1H) 7.73 (d, J=7.89 Hz, 1H) 7.58 (d, J=4.38 Hz, 1H) 7.27 (d, J=7.45 Hz, 1H) 5.18 (d, J=8.33 Hz, 1H) 4.28 (br. s., 3H) 4.05-4.22 (m, 3H) 3.21 (br. s., 3H) 3.00 (br. s., 3H).

Example S-59

Synthesis of (S,E)-N-(2-(2-cyano-4,4-difluoropyrrolidin-1-yl)-2-oxoethyl)-6-(2-(indolin-5-yl)vinyl)quinoline-4-carboxamide

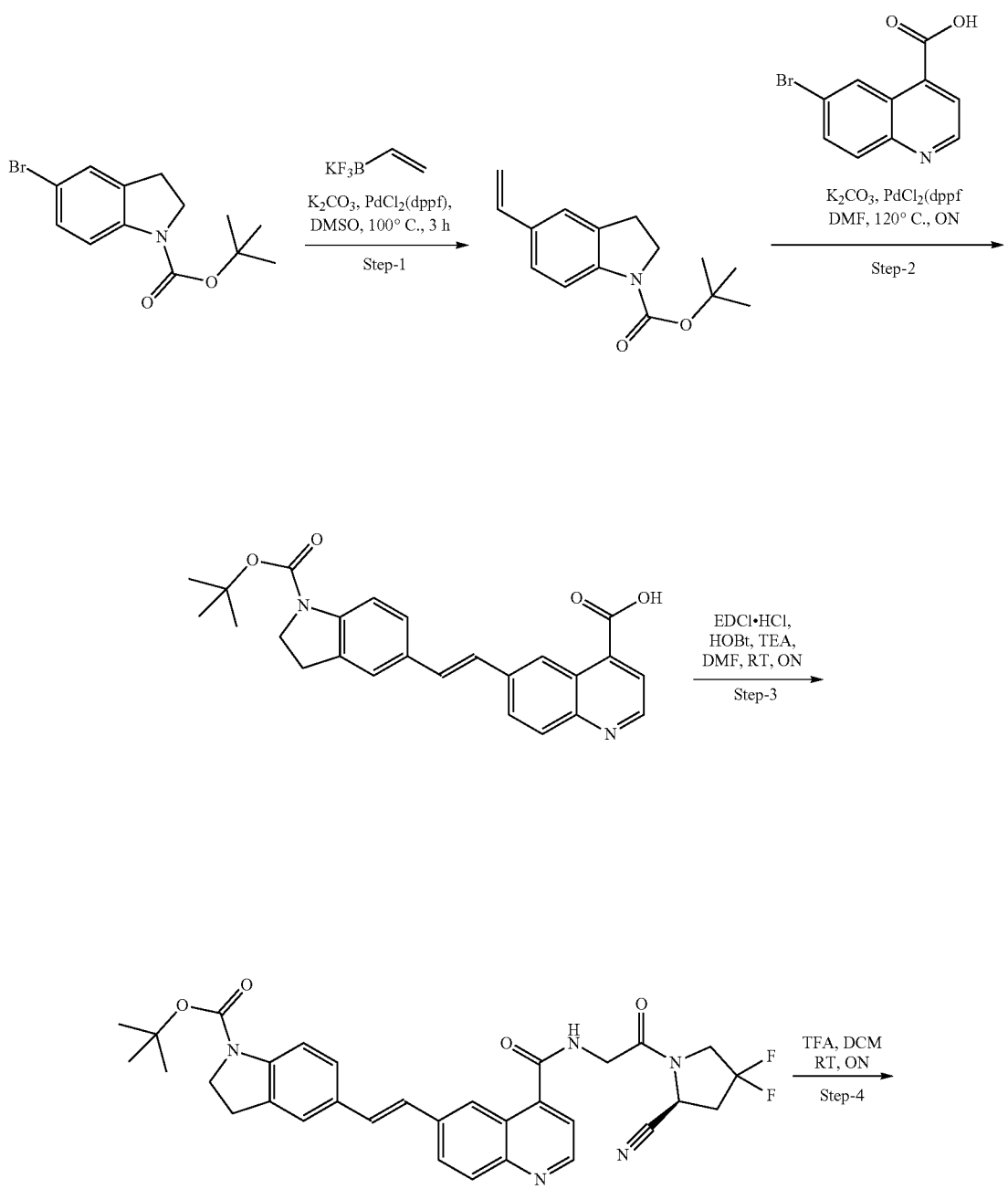

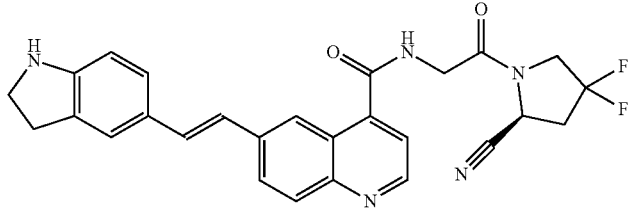

Compound 115

Step 1: Synthesis of tert-butyl 5-vinylindoline-1-carboxylate. To a stirred solution tert-butyl 5-vinylindoline-1-carboxylate (1.00 g, 3.37 mmol, 1 equiv) in dry DMSO (5 mL), was added $K_2CO_3$ (3.0 mg, 10.10 mmol, 3.0 equiv), potassium vinyl trifluoroborate (1.35 g, 10.10 mmol, 3.0 equiv) and $PdCl_2$(dppf) (0.25 g, 0.337 mmol, 0.1 equiv) at RT. Resultant reaction mixture was refluxed at 100° C. for 3 hour. Product formation was confirmed by TLC. After completion of reaction, the mixture was diluted with water (50 mL) and extracted with ethyl acetate (50 mL×2). Combined organic extracts were washed with water (20 mL×3), dried over anhydrous $Na_2SO_4$ and concentrated. The crude product was purified by flash chromatography (100% Hexane as an eluent) to obtain tert-butyl 5-vinylindoline-1-carboxylate (0.470 g, 57% Yield) as a white solid.

$^1$H NMR (400 MHz, DMSO-$d_6$) δ 7.34 (s, 1H), 7.22 (d, J=8.33 Hz, 1H), 6.65 (dd, J=10.96, 17.54 Hz, 1H), 5.68 (d, J=17.54 Hz, 1H), 5.11 (d, J=10.96 Hz, 1H), 3.90 (t, J=8.55 Hz, 2H), 3.05 (t, J=8.55 Hz, 2H), 1.50 (s, 9H).

Step 2: Synthesis of (E)-6-(2-(1-(tert-butoxycarbonyl)indolin-5-yl)vinyl)quinoline-4-carboxylic acid. To a solution of tert-butyl 5-vinylindoline-1-carboxylate (0.470 g, 1.918 mmol, 1.0 equiv) in DMF (20 mL) was added 6-bromoquinoline-4-carboxylic acid (0.385 g, 1.53 mmol, 0.8 equiv), triethylamine (0.8 g, 5.754 mmol, 3.0 equiv) and $PdCl_2$(dppf) (0.14 g, 0.1918 mmol. 0.1 equiv). The resulting reaction mixture was heated at 120° C. for overnight. Product formation was confirmed by LCMS. After the completion of reaction, the mixture was diluted with water (50 mL) and washed with ethyl acetate (10 mL×2). Aqueous layer was separated and acidified with 3 N HCl (pH-5). The resulting yellow precipitate was filtered off and dried under vacuum to obtain (E)-6-(2-(1-(tert-butoxycarbonyl)indolin-5-yl)vinyl)quinoline-4-carboxylic acid (0.180 g, 23% yield) as a yellow oil.

LCMS 417.3 [M+H]$^+$ $^1$H NMR (400 MHz, DMSO-$d_6$) δ 13.88 (br. s., 1H), 8.95 (d, J=4.38 Hz, 1H), 8.70 (s, 1H), 8.20 (d, J=9.21 Hz, 1H), 8.07 (d, J=9.21 Hz, 1H), 7.90 (d, J=4.38 Hz, 1H), 7.62 (s, 1H), 7.47 (d, J=7.89 Hz, 1H), 7.39 (s, 2H), 3.95 (t, J=8.55 Hz, 2H), 3.10 (t, J=8.11 Hz, 2H), 1.52 (br. s., 9H).

Step 3: Synthesis of tert-butyl (S,E)-5-(2-(4-((2-(2-cyano-4,4-difluoropyrrolidin-1-yl)-2-oxoethyl)carbamoyl)quinolin-6-yl)vinyl)indoline-1-carboxylate. To a stirred solution of (E)-6-(2-(1-(tert-butoxycarbonyl)indolin-5-yl)vinyl)quinoline-4-carboxylic acid (0.100 g, 0.24 mmol, 1.0 equiv) in DMF (5 mL), was added (S)-4,4-difluoro-1-glycylpyrrolidine-2-carbonitrile hydrochloride (0.081 g, 0.36 mmol, 1.5 equiv), HATU (0.136 g, 0.36 mmol, 1.5 equiv). The mixture was allowed to stir at RT for 10 min. DIPEA (0.2 mL, 0.96 mmol, 4.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product was purified by flash chromatography (5% MeOH in DCM as an eluent) to obtain tert-butyl (S,E)-5-(2-(4-((2-(2-cyano-4,4-difluoropyrrolidin-1-yl)-2-oxoethyl)carbamoyl)quinolin-6-yl)vinyl)indoline-1-carboxylate (0.140 g, 99% Yield) as an off white solid.

LCMS 588.4 [M+H]$^+$ $^1$H NMR (400 MHz, DMSO-$d_6$) δ 9.17 (br. s., 1H), 8.91 (br. s., 1H), 8.59 (br. s., 1H), 8.06 (br. s., 2H), 7.39-7.62 (m, 5H), 7.30 (d, J=16.66 Hz, 1H), 5.24 (d, J=8.77 Hz, 1H), 4.26-4.51 (m, 2H), 4.23 (br. s., 1H), 4.16 (d, J=11.40 Hz, 1H), 3.93 (d, J=7.89 Hz, 2H), 3.10 (br. s., 2H), 2.96 (br. s., 1H), 2.88 (d, J=17.10 Hz, 1H), 1.52 (br. s., 9H).

Step 4: Synthesis of (S,E)-N-(2-(2-cyano-4,4-difluoropyrrolidin-1-yl)-2-oxoethyl)-6-(2-(indolin-5-yl)vinyl)quinoline-4-carboxamide. To a stirred solution of tert-butyl (S,E)-5-(2-(4-((2-(2-cyano-4,4-difluoropyrrolidin-1-yl)-2-oxoethyl)carbamoyl)quinolin-6-yl)vinyl)indoline-1-carboxylate (0.140 g, 0.0255 mmol, 1.0 equiv) in DCM (5 mL), was added trifloroacetic acid (0.4 mL) at 0° C., allowed to stir at RT overnight. Product formation was confirmed by LCMS. After completion of reaction, the mixture was concentrated. The crude product was purified by revered phase HPLC to obtain (S,E)-N-(2-(2-cyano-4,4-difluoropyrrolidin-1-yl)-2-oxoethyl)-6-(2-(indolin-5-yl)vinyl)quinoline-4-carboxamide (0.030 g, 24% Yield) as a white solid.

LMS 488.5 [M+H]$^+$ $^1$H NMR (400 MHz, DMSO-$d_6$) δ 9.11-9.20 (m, 1H), 8.87 (d, J=3.95 Hz, 1H), 8.45 (s, 1H), 7.91-8.09 (m, 2H), 7.51 (d, J=4.38 Hz, 1H), 7.40 (s, 1H), 7.43 (s, 1H), 7.23 (d, J=8.77 Hz, 1H), 7.06 (s, 1H), 6.48 (d, J=8.33 Hz, 1H), 5.83 (br. s., 1H), 5.22 (d, J=6.14 Hz, 1H), 4.20-4.49 (m, 4H), 4.16 (d, J=10.09 Hz, 2H), 3.47 (t, J=8.33 Hz, 2H), 2.74-3.04 (m, 2H).

Example 5-60

Synthesis of (S)—N-(2-(2-cyano-4,4-difluoropyrrolidin-1-yl)-2-oxoethyl)-6-(3-fluoro-4-(methylcarbamoyl)phenyl)quinoline-4-carboxamide

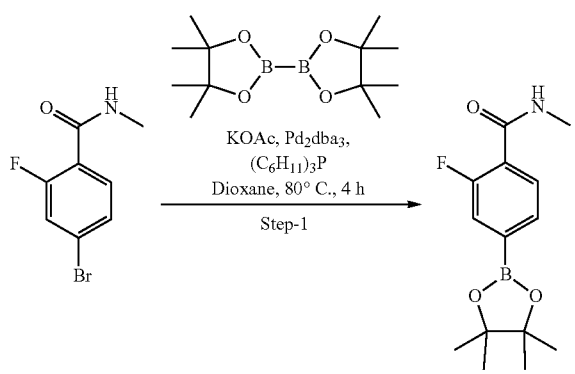

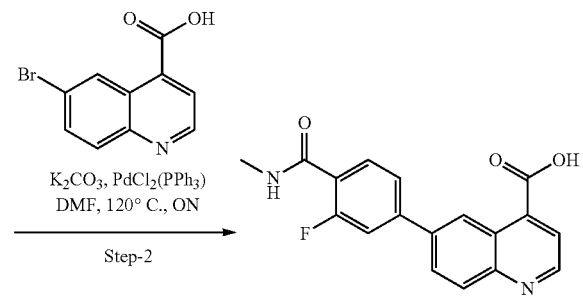

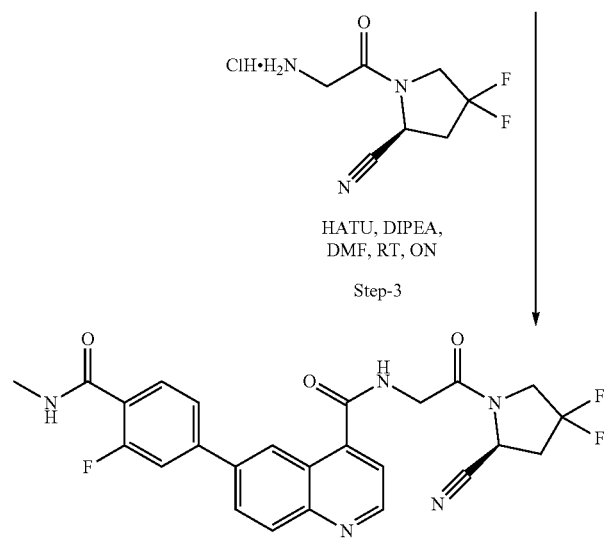

Compound 116

Step-1: Synthesis of 2-fluoro-N-methyl-4-(4,4,5,5-tetramethyl-1,3,2-dioxaborolan-2-yl)benzamide. To a stirred solution 4-bromo-2-fluoro-N-methylbenzamide (0.100 g, 0.431 mmol, 1 equiv) in dioxane (5 mL), was added 4,4,4',4',5,5,5',5'-octamethyl-2,2'-bi(1,3,2-dioxaborolane) (0.166 g, 0.646 mmol, 1.5 equiv), KOAc (0.126 mg, 1.293 mmol, 3.0 equiv), tricyclohexylphosphine (0.12 g, 0.0431 mmol, 0.1 equiv) & Pd$_2$dba$_3$ (0.012 g, 0.043 mmol, 0.1 equiv) at RT. Resultant reaction mixture was refluxed at 80° C. for 4 hour. Product formation was confirmed by TLC. After completion of reaction, the mixture was diluted with water (50 mL) and extracted with ethyl acetate (50 mL×2). Combined organic extracts were washed with water (20 mL×3), dried over anhydrous Na$_2$SO$_4$ and concentrated. The crude product was purified by flash chromatography (100% Hexane as an eluent) to obtain 2-fluoro-N-methyl-4-(4,4,5,5-tetramethyl-1,3,2-dioxaborolan-2-yl)benzamide (0.100 g, 83% Yield) as a white solid.

$^1$H NMR (DMSO-d$_6$, 400 MHz): δ 8.30 (m, 1H), 7.81 (s, J=9.2 Hz, 1H), 7.66-7.79 (m, 1H), 7.40 (d, 1H), 2.78 (d, 3H), 1.38 (s, 12H).

Step 2: Synthesis of 6-(3-fluoro-4-(methylcarbamoyl)phenyl)quinoline-4-carboxylic acid. To a solution of 2-fluoro-N-methyl-4-(4,4,5,5-tetramethyl-1,3,2-dioxaborolan-2-yl)benzamide (0.100 g, 3.968 mmol, 1.0 equiv) in dioxane (2 mL) and water (5 mL) was added 4,4,4',4',5,5,5',5'-octamethyl-2,2'-bi(1,3,2-dioxaborolane) (0.166 g, 0.5956 mmol, 1.5 equiv) and K$_2$CO$_3$ (0.168 g, 1.19 mmol, 3.0 equiv). PdCl$_2$(PPh$_3$)$_2$ (0.028 g, 0.039 mmol. 0.1 equiv). The resulting reaction mixture was heated at 100° C. for overnight. Product formation was confirmed by LCMS. After the completion of reaction, the mixture was diluted with water (25 mL) and washed with ethyl acetate (10 mL×2). Aqueous layer was acidified with 6 N HCl (pH-3 to 4), solid precipitate was filtered off and dried under vacuum to obtain 6-(3-fluoro-4-(methylcarbamoyl)phenyl)quinoline-4-carboxylic acid (0.050 g, 39% Yield) as an off white solid.

LCMS 325.2 [M+H]+ 1H NMR (400 MHz, DMSO-d$_6$) δ 9.08 (d, J=4.38 Hz, 1H), 9.05 (s, 1H), 8.32 (br. s., 1H), 8.22 (s, 2H), 8.01 (d, J=4.38 Hz, 1H), 7.67-7.84 (m, 3H), 2.81 (d, J=4.82 Hz, 3H).

Step 3: Synthesis of (S)—N-(2-(2-cyano-4,4-difluoropyrrolidin-1-yl)-2-oxoethyl)-6-(3-fluoro-4-(methylcarbamoyl)phenyl)quinoline-4-carboxamide. To a stirred solution of 6-(3-fluoro-4-(methylcarbamoyl)phenyl)quinoline-4-carboxylic acid (0.05 g, 0.154 mmol, 1.0 equiv) in DMF (3 mL), was added (S)-4,4-difluoro-1-glycylpyrrolidine-2-carbonitrile hydrochloride (0.052 g, 0.231 mmol, 1.5 equiv), HATU (0.088 g, 0.231 mmol, 1.5 equiv). The mixture was allowed to stir at RT for 10 min. DIPEA (0.1 mL, 0.616 mmol, 4.0 equiv) was added and the mixture was allowed to stir at RT for overnight. Product formation was confirmed by LCMS and TLC. After completion of reaction, the mixture was diluted with water (20 mL) and extracted with ethyl acetate (20 mL×2). Combined organic extracts were washed with water (20 mL×4), dried over anhydrous $Na_2SO_4$ and concentrated. The crude product was purified by flash chromatography (5% MeOH in DCM as an eluent) to obtain (S)—N-(2-(2-cyano-4,4-difluoropyrrolidin-1-yl)-2-oxoethyl)-6-(3-fluoro-4-(methylcarbamoyl)phenyl)quinoline-4-carboxamide (0.025 g, 32.81% Yield) as a white solid.

LCMS 496.5 $[M+H]^+$ $^1$H NMR (400 MHz, DMSO-$d_6$) δ 9.24 (br. s., 1H), 9.03 (d, J=4.38 Hz, 1H), 8.88 (s, 1H), 8.29 (d, J=9.65 Hz, 2H), 8.20 (d, J=8.77 Hz, 1H), 7.89 (d, J=9.21 Hz, 2H), 7.73-7.80 (m, 1H), 7.63 (d, J=3.95 Hz, 1H), 5.18 (d, J=7.02 Hz, 1H), 4.25-4.40 (m, 2H), 4.02-4.25 (m, 2H), 2.95 (br. s., 1H), 2.87 (br. s., 1H), 2.81 (d, J=4.38 Hz, 3H).

Biological Examples

Example B-1

Inhibition of FAPα by test compounds was assessed by in vitro enzymatic activity assays.

FAPα enzymatic exopeptidase (dipeptidase) activity assay. To assay baseline FAPa enzymatic exopeptidase activity, 40 ng of recombinant human FAPα (rhFAPα, R&S system, #3715-SE) or 40 ng of recombinant mouse FAPα (rmFAPα, R&S system, #8647-SE) was incubated with 100 µM of Z-Gly-Pro-AMC peptide (BACHEM, #L-1145) in a FAPα assay buffer (50 mM Tris pH 7.4, 100 mM NaCl, 0.1 mg/ml bovine serum albumin) for 1 h at 37° C. protected from light in 96-well black plates (Nunc, #237108). To assay FAPα enzymatic exopeptidase activity inhibition by test compounds, all test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in duplicate. Val-boroPro, a non-specific prolyl peptidase inhibitor, was used as a positive control. Percent inhibition of rmFAPα or rhFAPα enzymatic exopeptidase activity at 1 µM was determined for certain compounds, as shown in Table 2. For the calculations, the average measurements from reactions containing only vehicle and substrate, without enzyme, were used as a blank and were subtracted from the rest of the measurements. Percent inhibition was calculated using the average measurements from reactions containing vehicle, enzyme, and substrate as the maximum of enzymatic activity. Additionally, $IC_{50}$ for the rmFAPα or rhFAPα enzymatic exopeptidase activity of certain compounds are also shown in Table 2. Measurements were performed as a single point.

FAPα enzymatic endopeptidase (collagenase) activity assay. To assay baseline FAPa enzymatic exopeptidase activity, 50 ng of recombinant human FAPα (rhFAPα) (R&S system, #3715-SE) diluted in FAPα assay buffer (50 mM Tris pH 7.4, 100 mM NaCl, 0.1 mg/ml bovine serum albumin) was incubated with 5 µg of substrate DQ collagen solution (Molecular Probes #D-12060) with for 5 h at 37° C. and protected from light in 384-well optiplates (Perkin Elmer, #384-F). To assay FAPα enzymatic endopeptidase activity inhibition by test compounds, all test compounds were pre-incubated with the enzyme for 30 min at 37° C. before starting the reaction by substrate addition in 384-well OptiPlates (Perkin Elmer, #384-F). Collagen hydrolysis was determined by measuring fluorescence at Ex/Em 495/515 nm using a multifunction Microplate Reader (Synergy 4, Biotek). All measurements were performed as a single point. Val-boroPro, a non-specific prolyl peptidase inhibitor, was used as a positive control. $IC_{50}$ for the rhFAPα enzymatic endopeptidase activity (as determined by the collagenase assay) of certain compounds are also shown in Table 2.

TABLE 2

Exopeptidase or Endopeptidase inhibition of rmFAPα or rhFAPα by Test Compounds

| Compound No. | rmFAPα (% exo inh @ 1 µM) | rhFAPα (% exo inh @ 1 µM) | rmFAPα (exo $IC_{50}$, µM) | rhFAPα (exo $IC_{50}$, µM) | rhFAPα (endo $IC_{50}$, µM) |
|---|---|---|---|---|---|
| Val-boroPro | ++ | − | ++ | ++ | ++ |
| Ref. Comp. 2 | +++ | +++ | +++ | +++ | +++ |
|  | − | +++ | − | +++ | +++ |

Ref. Comp.: Compound 60 as described in Jansen, K., et al., *J Med Chem*, 2014. 57(7): p. 3053-74; for % of inhibition: +++ refers to > 50% inhibition at 1 µM test compound; ++ refers to 25% < % inhibition < 50% at 1 µM test compound; + refers to < 25% inhibition at 1 µM; for $IC_{50}$: +++ refers to $IC_{50}$ < 1 µM; ++ refers to 1 µM < $IC_{50}$ < 10 µM; + refers to $IC_{50}$ > 10 µM; − represents compound not tested; rmFAPα: recombinant mouse fibroblast activation protein alpha; rhFAPα: recombinant human fibroblast activation protein alpha; endo: endopeptidase; exo: exopeptidase; inh: inhibition.

Example B-2

Selectivity of the inhibition of FAPα by test compounds was assessed compared to other prolyl oligopeptidase family S9 members: DPPIV, PREP, and DPP9.

DPPIV enzymatic activity assay. To assay baseline dipeptidyl peptidase-4 (DPPIV) activity, 40 ng of recombinant human DPPIV (rhDPPIV) (R&S system, #1180-SE) or 40 ng of recombinant mouse DPPIV (rmDPPIV) (R&S system, #954-SE) was incubated with 400 µM of H-Gly-Pro-pNA substrate (BACHEM, #L-1880) in a DPPIV assay buffer (25 mM Tris, pH 8.3) for 30 min at 37° C. protected from the light in 96-well black plates (Nunc, #237108). To assay DPPIV inhibition by test compounds, test compounds were pre-incubated with the enzyme for 15 min at 37° C. before starting the reaction by substrate addition in 96-well black plates (Nunc, #237108). Para-nitroaniline (pNA) release was detected by measuring absorbance at 405 nm using a Multifunction Microplate Reader (Synergy 4, Biotek). All measurements were carried out in triplicate. Val-boroPro, a non-specific prolyl peptidase inhibitor, was used as a positive control.

PREP enzymatic activity assay. To assay baseline prolyl endopeptidase (PREP) activity, 20 ng of recombinant human PREP (rhPREP) (R&S system, #4308-SE) or 20 ng of recombinant mouse PREP (rmPREP) (R&S system, #6339-

SE) was incubated with 100 μM of Z-Gly-Pro-AMC peptide (BACHEM, #L-1145) in a PREP assay buffer (25 mM Tris, 250 mM NaCl, 10 mM DTT, pH 7.5) for 30 min at 37° C. protected from light in 96-well black plates (Nunc, #237108). To assay PREP activity inhibition by test compounds, test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in triplicate. Val-boroPro, a non-specific prolyl peptidase inhibitor, was used as a positive control.

DPP9 enzymatic activity assay. To assay baseline dipeptidyl peptidase 9 (DPP9) activity, 40 ng of recombinant human DPP9 (rhDPP9) (R&S system, #5419-SE) was incubated with 100 μM of H-Gly-Pro-AMC peptide (BACHEM, #L-1215) in a DDP9 assay buffer (50 mM HEPES, pH 8) for 30 min at 37° C. in 96-well black plates (Nunc, #237108). To assay rhDPP9 activity inhibition by test compounds, test compounds were pre-incubated with the enzyme for 15 min at 37° C. before starting the reaction by substrate addition in 96-well black plates (Nunc, #237108). 7-Amino-4-Methylcoumarin (AMC) release was detected by measuring fluorescence at Ex/Em 380/460 nm using a Multifunction Microplate Reader (Synergy 4, Biotek). All measurements were carried out in triplicate. Val-boroPro, a non-specific prolyl peptidase inhibitor, was used as a positive control.

To determine if new FAPα inhibitors was selective or if they also inhibited other prolyl peptidases, the $IC_{50}$ for rmDPPIV, rhDPPIV, rmPREP, and/or DPP9 of certain test compounds, a reference compound (compound 60 as described in Jansen, K., et al., J Med Chem, 2014. 57(7): p. 3053-74), and Val-boroPro were determined, as shown in Table 3A.

TABLE 3A

Selectivity of FAPα Inhibition by Test Compounds

| Compound No. | rmFAPα (exo $IC_{50}$, μM) | rhFAPα (exo $IC_{50}$, μM) | rmDPPIV ($IC_{50}$, μM) | rhDPPIV ($IC_{50}$, μM) | rmPREP ($IC_{50}$, μM) | rhPREP ($IC_{50}$, μM) | rhDPP9 ($IC_{50}$, μM) |
|---|---|---|---|---|---|---|---|
| Val-boroPro | + | ++ | +++ | +++ | ++ | ++ | +++ |
| Ref. Comp. | +++ | +++ | + | + | + | ++ | ++ |
| 2 | − | +++ | − | − | − | + | +++ |

Ref. Comp.: Compound 60 as described in Jansen, K., et al., *J Med Chem*, 2014. 57(7): p. 3053-74; for $IC_{50}$: +++ refers to $IC_{50}$ < 1 μM; ++ refers to 1 μM < $IC_{50}$ < 10 μM; + refers to $IC_{50}$ > 10 μM; − represents compound not tested; rmFAPα: recombinant mouse fibroblast activation protein alpha; rhFAPα: recombinant human fibroblast activation protein alpha; rmDPPIV: recombinant mouse dipeptidyl peptidase-4; rhDPPIV: recombinant human dipeptidyl peptidase-4; rmPREP: recombinant mouse prolyl endopeptidase; rhPREP: recombinant human prolyl endopeptidase; rhDPP9: recombinant human dipeptidyl peptidase 9; exo: exopeptidase.

Furthermore, to assay the inhibition of dipeptidyl peptidase 9 (DPP9) activity, aliquots of 10 μL of diluted exemplary compounds, reference compounds or vehicle were mixed in a 96-well black plate with 40 μL of DPP9 assay buffer (25 mM Tris-HCl pH 8.0 and 0.01% BSA) containing 10 ng of recombinant human DPP9 (rhDPP9) (Cat. No. #5419-SE, R&D systems). Compounds were allowed to interact with the enzyme for 15 min at 37° C. before the start of the reaction by adding 50 μL of the synthetic dipeptide substrate, 200 μM H-Gly-ProAMC (Cat. No. #L-1215, Bachem) in DPPIV assay buffer. Reactions were carried out for 30 min at 37° C. protected from light. AMC release was detected by measuring fluorescence at Ex/Em 380/460 nm using a Multifunction Microplate Reader. Results for the inhibition of other prolyl peptidases from S9 family for exemplary compounds are shown in Table 3B.

TABLE 3B

Inhibition of other prolyl peptidases from S9 family members by exemplary compounds

| Compound No. | rhFAPα (% exo inh @ 1 μM) | rhFAPα exo ($IC_{50}$, μM) | rhDPP9 ($IC_{50}$, μM) | rhDPPIV ($IC_{50}$, μM) | rhPREP ($IC_{50}$, μM) |
|---|---|---|---|---|---|
| Ref. Comp. | +++ | +++ | ++ | + | ++ |
| Val-boroPro | ++ | ++ | +++ | +++ | ++ |
| 1 | +++ | +++ | ++ | + | + |
| 2 | +++ | +++ | +++ | + | + |
| 3 | +++ | +++ | +++ | ++ | + |
| 4 | +++ | +++ | ++ | + | + |
| 5 | +++ | +++ | +++ | + | + |
| 6 | +++ | +++ | +++ | + | + |
| 7 | +++ | +++ | +++ | + | + |
| 8 | +++ | +++ | +++ | ++ | + |
| 9 | +++ | +++ | +++ | + | + |
| 10 | +++ | +++ | +++ | + | + |
| 11 | +++ | +++ | +++ | ++ | + |
| 12 | +++ | +++ | +++ | + | + |
| 13 | +++ | +++ | +++ | + | + |
| 14 | +++ | +++ | +++ | + | + |
| 15 | +++ | +++ | +++ | + | + |
| 16 | +++ | +++ | +++ | ++ | + |
| 17 | +++ | +++ | +++ | + | + |
| 18 | +++ | +++ | +++ | +++ | + |
| 19 | +++ | +++ | +++ | ++ | + |
| 20 | +++ | +++ | +++ | + | + |
| 21 | +++ | +++ | +++ | + | + |
| 22 | +++ | +++ | +++ | + | + |
| 23 | +++ | +++ | +++ | ND | ND |
| 24 | +++ | +++ | +++ | ND | ND |
| 25 | +++ | +++ | +++ | ND | ND |
| 26 | ++ | ND | +++ | + | + |
| 27 | + | ND | +++ | + | + |
| 28 | + | ND | + | + | + |
| 29 | + | ND | + | ++ | + |
| 30 | +++ | +++ | +++ | ++ | + |
| 31 | +++ | +++ | +++ | + | + |
| 32 | +++ | +++ | ++ | + | + |
| 33 | +++ | +++ | +++ | ND | ND |
| 34 | +++ | +++ | +++ | ND | ND |

TABLE 3B-continued

Inhibition of other prolyl peptidases from
S9 family members by exemplary compounds

| Compound No. | rhFAPα (% exo inh @ 1 μM) | rhFAPα exo (IC$_{50}$, μM) | rhDPP9 (IC$_{50}$, μM) | rhDPPIV (IC$_{50}$, μM) | rhPREP (IC$_{50}$, μM) |
|---|---|---|---|---|---|
| 35 | +++ | +++ | +++ | ND | ND |
| 36 | +++ | +++ | +++ | + | ND |
| 37 | +++ | +++ | +++ | ND | ND |
| 38 | +++ | +++ | +++ | ND | ND |
| 97 | +++ | +++ | +++ | + | + |
| 98 | +++ | +++ | +++ | + | + |
| 99 | +++ | +++ | ++ | + | + |
| 100 | +++ | +++ | +++ | + | + |
| 101 | +++ | +++ | +++ | ND | ND |
| 102 | +++ | +++ | +++ | + | + |
| 103 | +++ | +++ | +++ | ND | ND |
| 104 | +++ | +++ | +++ | +++ | + |
| 105 | +++ | +++ | ++ | ND | ND |
| 106 | +++ | +++ | +++ | ND | ND |
| 107 | +++ | +++ | +++ | ++ | ND |
| 108 | +++ | +++ | +++ | + | + |
| 109 | +++ | +++ | +++ | + | + |
| 110 | +++ | +++ | +++ | + | ND |
| 111 | +++ | +++ | +++ | ++ | ND |
| 112 | +++ | +++ | +++ | +++ | ND |
| 113 | +++ | +++ | +++ | ++ | ND |
| 114 | +++ | +++ | ++ | + | + |
| 115 | +++ | +++ | +++ | + | ND |
| 116 | +++ | +++ | +++ | + | + |
| 126 | + | + | + | + | + |
| 127 | + | + | + | + | + |

Ref. Comp.: Compound 60 as described in Jansen, K., et al., *J Med Chem*, 2014. 57(7): p. 3053-74; for IC$_{50}$: +++ refers to IC$_{50}$ < 1 μM; ++ refers to 1 μM < IC$_{50}$ < 10 μM; + refers to IC$_{50}$ > 10 μM; ND indicates IC$_{50}$ not determined; rhFAPα: recombinant human fibroblast activation protein alpha; rhDPPIV: recombinant human dipeptidyl peptidase-4; rhPREP: recombinant human prolyl endopeptidase; rhDPP9: recombinant human dipeptidyl peptidase 9; exo: exopeptidase.

Example B-3

Validation of Selective PRXS-AMC Substrate for FAPα Activity Measurements

FAPα activity can be measured by a general fluorescence intensity assay for dipeptidyl-peptidases using a peptide substrate attached to a chemically quenched dye, such as Ala-Pro-7-amino-4-trifluoromethyl-coumarin (AFC) or a substrate containing the consensus Gly-Pro dipeptide such as Z-Gly-Pro-AMC (Levy, M. T., et al., Hepatology, 1999, 29(6): 1768-78; Santos, A. M., et al., J Clin Invest, 2009, 119(12): 3613-25; Park, J. E., et al., J Biol Chem, 1999, 274(51): 36505-12; Niedermeyer, J., et al., Mol Cell Biol, 2000, 20(3): 1089-94; Narra, K., et al., Cancer Biol Ther, 2007, 6(11): 1691-9; Lee, K. N., et al., J Thromb Haemost, 2011, 9(5): 987-96; Li, J., et al., Bioconjug Chem, 2012, 23(8): 1704-11). These substrates are likely targeted also by other circulating proline-specific endopeptidases such as PREP that could be present in the reaction. By contrast, a proprietary substrate reagent, named PRXS-AMC, can specifically monitor FAPa activity.

To validate the high selectivity of this proprietary substrate, enzymatic activity assays for FAP, DPPIV, PREP and DPP9 were carried out using Z-Gly-Pro-AMC or PRXS-AMC as described in Examples B1 and B2.

Figure 1B:
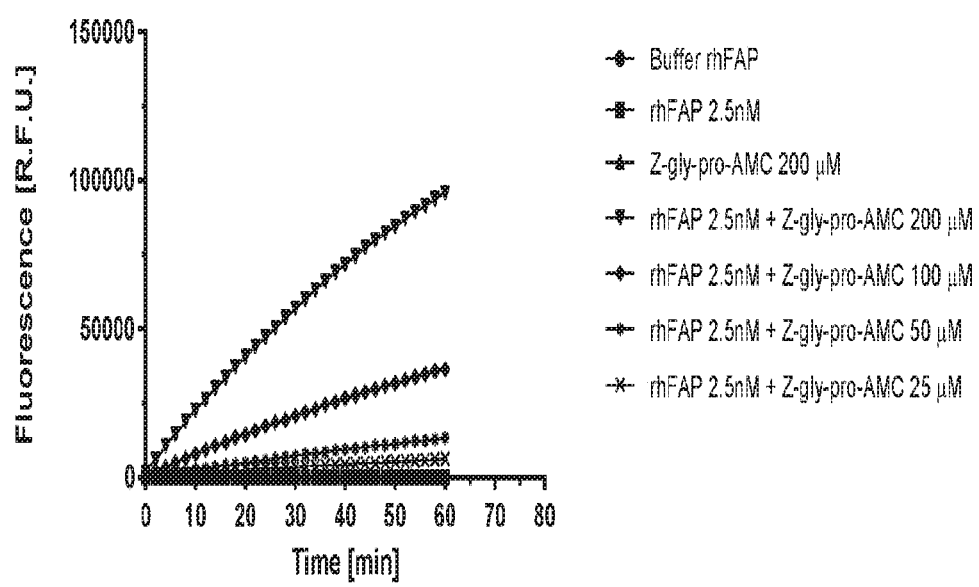
FIG. 1B shows Z-Gly-Pro-AMC degradation over time by rhFAP.

To assay FAPα, DPPIV, DPP9 and PREP enzymatic activities, human recombinant enzymes were used at 5, 2.5, 2.5 and 5 nM final concentrations, respectively. Z-Gly-Pro-AMC or PRXS-AMC were used at 25, 50, 100 and 200 μM final concentrations. Reactions were carried out for 60 min at 37° C. and were protected from light. AMC release was detected by measuring fluorescence at Ex/Em 380/460 nm using a Multifunction Microplate Reader in kinetic mode. Measurements were performed as a single point. Resulting fluorescence over time for PRXS-AMC and Z-gly-pro-AMC in the presence of rhFAPα is shown in FIG. 1A and FIG. 1B, respectively; resulting fluorescence over time for PRXS-AMC and Z-gly-pro-AMC in the presence of rhPREP is shown in FIG. 2A and FIG. 2B, respectively; and resulting fluorescence over time for PRXS-AMC in the presence of rhDPPIV or rhDPP9 is shown in FIG. 3A and FIG. 3B, respectively.

Figure 2A:
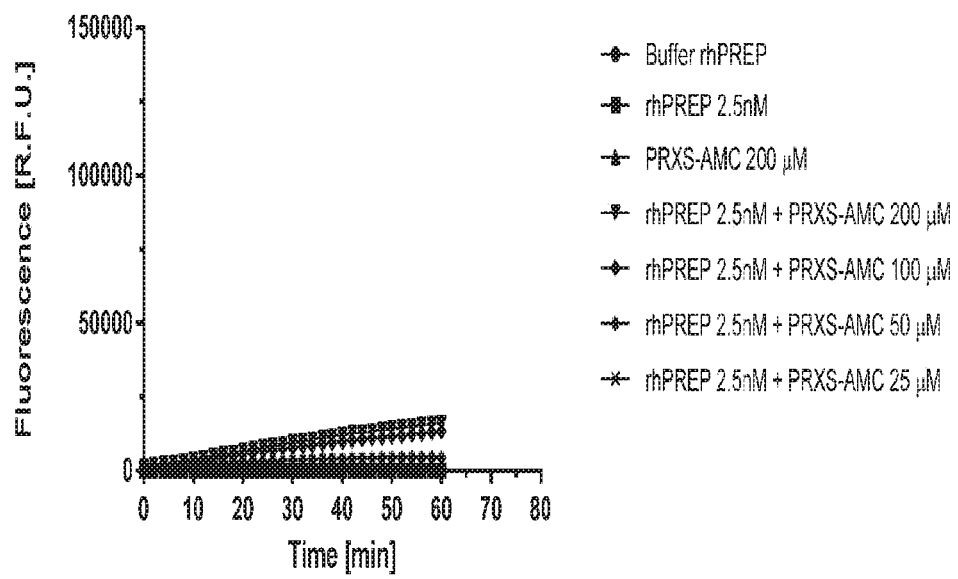
FIG. 2A shows PRXS-AMC degradation over time by rhPREP.
Figure 2B:
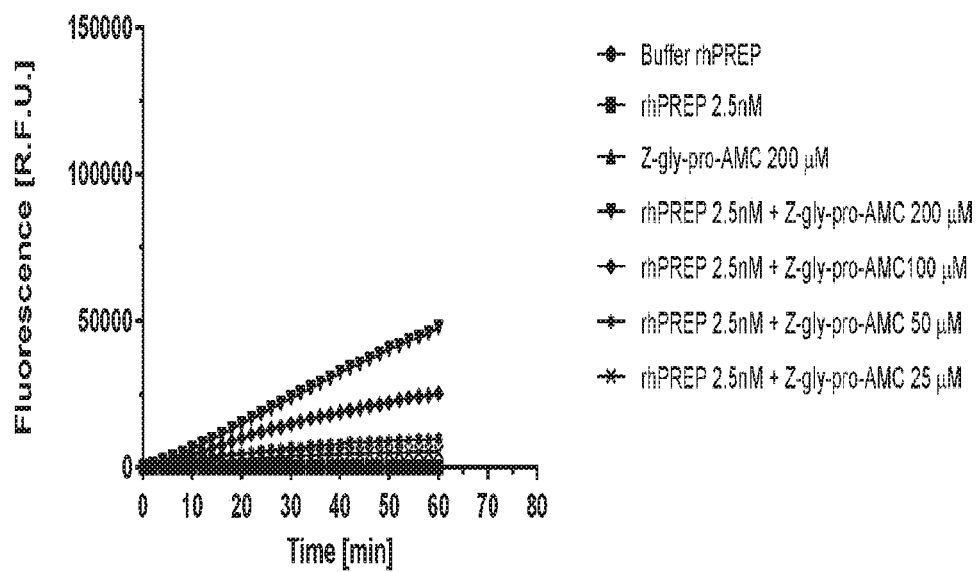
FIG. 2B shows Z-Gly-Pro-AMC degradation over time by rhPREP.
Figure 3A:
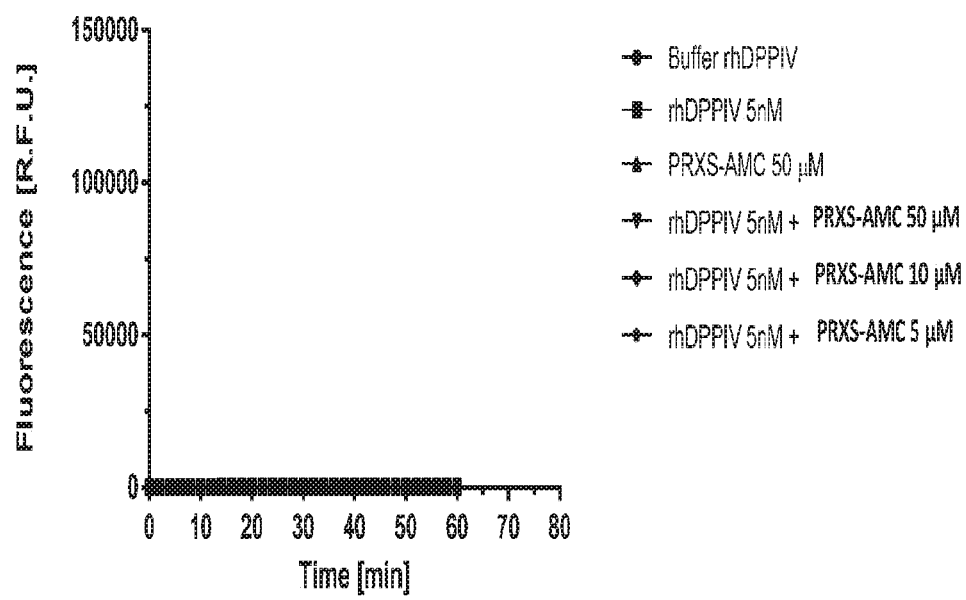
FIG. 3A shows PRXS-AMC degradation over time by rhDPPIV.
Figure 3B:
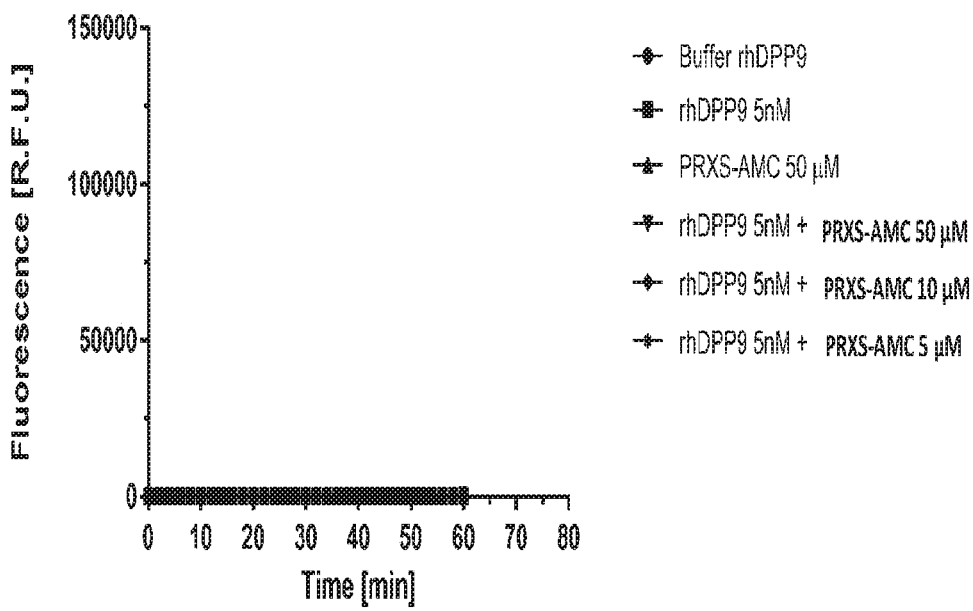
FIG. 3B shows PRXS-AMC degradation over time by rhDPP9.

PRXS-AMC is processed to a lesser extent than Z-Gly-Pro-AMC by the closely related prolyl oligopeptidase PREP at similar concentrations (see FIGS. 2A-2B). PRXS-AMC is not processed by DPPIV or DPP9 (FIGS. 3A-3B). In addition, PRXS-AMC showed an improved solubility in aqueous buffers.

Example B-4

FAPα enzymatic activity in mouse plasma. Approximately 500 μL of whole blood from one $C_{57}BL/6$ mouse is harvested into BD Microtainer® tubes ($K_2$) EDTA (#365974, Becton Dickinson and Co.) via terminal cardiac puncture. The blood sample is immediately centrifuged at approximately 9000 g at 4° C. for 5 minutes. Plasma is separated and stored at −80° C. in aliquots of 300 μL. To assay baseline FAPα enzymatic exopeptidase activity, 5 μL of thawed, plasma is diluted (1:5) with buffer (100 mM Tris-HCl, 400 mM NaCl, 50 mM salicylic acid, 1 mM EDTA, pH 7.5) and mixed with 35 μL of buffer before being pre-incubated with different concentrations of 10 μL of test compounds or DMSO vehicle for 15 minutes at 37° C. in 96-well black plates (Nunc, #237108). After pre-incubation, 50 μL of 200 μM dipeptide substrate Z-Gly-Pro-AMC (Bachem, #L-1145) is added to the mixture. The assay is performed for 1 hour at 37° C. 7-Amino-4-Methylcoumarin (AMC) release is detected measuring fluorescence at an excitation wavelength of 360 nm and an emission wavelength of 460 nm using a Multifunction Microplate Reader (Synergy 4, Biotek). All measurements are carried out at least in duplicate.

DPPIV enzymatic activity in mouse plasma. Approximately 500 μL of whole blood from one $C_{57}BL/6$ mouse is harvested into BD Microtainer® tubes ($K_2$) EDTA (#365974, Becton Dickinson and Co.) via terminal cardiac puncture. The blood sample is immediately centrifuged at approximately 9000 g at 4° C. for 5 minutes. Plasma is separated and stored at −80° C. in aliquots of 300 μL. To assay baseline DPPIV enzymatic exopeptidase activity, 5 μL of thawed, mouse plasma is diluted (1:5) in buffer (100 mM Tris-HCl, 400 mM NaCl, 50 mM salicylic acid, 1 mM EDTA, pH 7.5) and mixed with 35 μL of buffer before being pre-incubated with different concentrations of 10 pt of test compounds or DMSO vehicle for 15 minutes at 37° C. in 96-well black plates (Nunc, #237108). After pre-incubation, 50 μL of 200 μM dipeptide substrate H-Gly-Pro-AMC (Bachem, #L-1225) is added to the mixture. The assay is performed for 1 hour at 37° C. 7-Amino-4-Methylcoumarin (AMC) release is detected measuring fluorescence at an excitation wavelength of 360 nm and an emission wavelength of 460 nm using a Multifunction Microplate Reader (Synergy 4, Biotek). All measurements are carried out at least in duplicate.

Example B-5

In vivo pharmacokinetics and pharmacodynamics of certain compounds.

Solutions of test compounds are prepared at 1 mg/mL in a vehicle containing 50% polyethylene glycol 200 (PEG200, #P3015-1KG: Sigma-Aldrich, Inc.) in distilled water for oral administration.

Female $C_{57}BL/6$ mice (approximately 9-10 weeks old; 20-21 grams) obtained from a vivarium (Fundación Ciencia & Vida, Santiago, Chile) are weighed and divided into different cohorts.

100 μL of whole blood is sampled from the tail vein of each mouse 24 hours prior to dosing. On the day of dosing, mice of all cohorts orally received a single dose (10 mg/kg) of test compound 13 using feeding needles (#FTP-2038/050312, Instech Laboratories, Inc.).

Depending on each cohort, approximately 500 pt of whole blood from each mouse is collected into BD Microtainer® tubes ($K_2$) EDTA (#365974, Becton Dickinson and Co.) via terminal cardiac puncture at the harvesting time point (Table 5). The blood sample is immediately centrifuged at approximately 9000 g at 4° C. for 5 minutes. Plasma is separated and placed into individually labeled cryotube vials (#366656; Thermo Fisher Scientific, Inc.) and stored at −80° C. prior to being assayed for enzymatic activity or LC/MS/MS analysis.

All plasma samples are thawed and diluted with assay buffer (1 part plasma for 5 parts buffer). The assay buffer contained 100 mM Tris-HCl, 400 mM NaCl, 50 mM salicylic acid, 1 mM EDTA, pH 7.5. All plasmas are assayed for FAP and DPPIV activity. To assay the plasma for FAPα or DPPIV enzymatic activity, 5 μL of each diluted plasma sample is loaded into a well of a 96-well black plate (Nunc, #237108), which contained 45 μL of additional assay buffer. The plates are warmed at 37° C. for 15 minutes before the assay began. To start the assay, 50 μL of 200 μM dipeptide substrate Z-Gly-Pro-AMC (Bachem, #L-1145) (FAPα enzymatic activity assay) or 50 μL of 200 μM dipeptide substrate H-Gly-Pro-AMC (Bachem, #L-1225) (DPPIV enzymatic activity assay) is added to each well. 7-Amino-4-Methylcoumarin (AMC) release is detected measuring fluorescence at an excitation wavelength of 360 nm and an emission wavelength of 460 nm using a Multifunction Microplate Reader (Synergy 4, Biotek). All measurements are carried out at least in duplicate.

Example B-6

Female C57/BL6 mice (approximately 8-9 weeks old; 20-21 gr) obtained from the vivarium of Fundación Ciencia & Vida (Santiago, Chile) are maintained in a temperature-controlled room with 12/12 hour light/dark schedule with food and water ad libitum. The mice are acclimated for a minimum period of 4 days upon arrival at the testing facility.

MC38 mouse colon cancer cell line is maintained as monolayer culture in DMEM-F12 (Cat. No.: SH30023.01, Hyclone) supplemented with 10% fetal bovine serum (Cat. No.: 16000, Gibco) and penicillin/streptomycin (Cat. No.: 15140122, Gibco) at 37° C. in an atmosphere with 5% $CO_2$. The cells are routinely subcultured every 3 days to maintain growth at exponential phase. The tumor cells growing in exponential growth phase are harvested using 1×PBS with 0.05% trypsin-EDTA (Cat. No.: 15400054, Gibco), followed by centrifugation at 330 g×3 min in a centrifuge at room temperature. The supernatant is subsequently removed by aspiration. Cell pellet is resuspended in approximately 10× volume of cell culture medium and counted. Cell viability is determined to be >95% by trypan blue staining.

At the day of inoculation, female $C_{57}/B16$ mice (n=15 total) are weighed and identified by marking the tail with numbers using a non-toxic permanent marker. Mice are inoculated subcutaneously in the right lower flank (near the dorsal thigh region) with a single volume of 0.1 mL cell suspension containing approximately $2 \times 10^6$ MC38 cells in 1×PBS. Tumors are measured three times per week with digital calipers and tumors volumes, expressed in $mm^3$, are calculated with the following formula:

$$\text{Tumor volume } (mm^3) = (a \times b^2)/2$$

where "b" is the smallest diameter and "a" is the largest perpendicular diameter.

Seven days after inoculation, mean tumor volume is about 100 $mm^3$. The mice are weighted and randomized into two experimental groups (n=5-6 mice), and receive the following treatments dosed orally twice daily until end: 1) Vehicle (PEG200 50% in water); or 2) 50 mg/kg test compound 24 in PEG200 50%/water. Body weight of the mice and tumor volume is recorded two or three times per week for a total of 22 days. At day 22, mice are sacrificed and all tumor mass are weighed.

Example B-7

FAPα enzymatic activity in murine tumors. Mouse tumor proteins are extracted in a lysis buffer (Tris HCl 50 mM pH 7.6, EDTA 1 mM, Glycerol 10%, protease/phosphatase inhibitors cocktail) for 20 min using an ultra Turrax (IKA, #3737000). To assay baseline FAPα enzymatic exopeptidase activity in the tumor extract, 10 μg of tumor extract sample is incubated with 100 μM Z-Gly-Pro-AMC peptide (BACHEM, #L-1145) in PBS 1× for 1 h at 37° C. in 96-well black plates (Nunc, #237108). Inhibitors are pre-incubated with the tumor extract for 15 min at 37° C. before starting the reaction by substrate addition in 96-well black plates (Nunc, #237108). 7-Amino-4-Methylcoumarin (AMC) release is detected measuring fluorescence at Ex/Em 380/460 nm using a Multifunction Microplate Reader (Synergy 4, Biotek). All measurements are carried out in triplicate.

Example B-8

FAPα enzymatic activity in human plasma. Human plasma is diluted 1/10 in PBS. To assay baseline FAPα enzymatic exopeptidase activity, the diluted plasma is incubated with 100 μM Z-Gly-Pro-AMC peptide (BACHEM, #L-1145) for 1 h at 37° C. in 96-well black plates (Nunc, #237108). Test compounds are pre-incubated with the diluted plasma for 15 min at 37° C. before starting the reaction by substrate addition in 96-well black plates (Nunc, #237108). 7-Amino-4-Methylcoumarin (AMC) release is detected measuring fluorescence at Ex/Em 380/460 nm using a Multifunction Microplate Reader (Synergy 4, Biotek). All measurements are carried out in triplicate.

Example B-9

Ex vivo inhibition of circulating FAPα activity from plasma of different species. Human plasma Human blood was obtained from healthy young volunteers. Blood samples were collected in tubes coated with EDTA-$K_2$ by venipuncture method, mixed gently, then kept on ice and centrifuged at 2,500×g for 15 minutes at 4° C. After plasma separation, samples were stored at −80° C. in aliquots of 300 µL.

To determinate the inhibitory potency of exemplary test compounds over circulating FAPa activity from human plasma, 20 µL of thawed plasma were mixed with 20 µL of assay buffer (50 mM Tris pH 7.4, 100 mM NaCl, 0.1 mg/ml bovine serum albumin) and 10 µL different concentrations of exemplary test compounds or vehicle (DMSO).

Exemplary compounds were allowed to interact with the enzyme for 15 minutes at 37° C. After pre-incubation, 50 µl of 200 µM PRXS-AMC substrate were added to the all mixtures. All reactions were carried out for 1 h at 37° C. protected from light. AMC release was detected measuring fluorescence at an excitation/emission wavelength of 380/460 nm using a Multifunction Microplate Reader. All measurements were carried out as single point.

Results of $IC_{50}$ of exemplary test compounds over circulating FAPα from human are shown in Table 4.

Hamster Plasma

Male Golden Syrian hamsters were provided by National Laboratory Animal Center (NLAC) in Taiwan. The animals were maintained in a hygienic environment under controlled temperature (20-24° C.) and humidity (50%-80%) with 12 hours light/dark cycles. Free access to standard lab diet [MFG (Oriental Yeast Co., Ltd. Japan)] and autoclaved tap water were granted. All aspects of this work including housing, experimentation and disposal of animals were performed in general accordance with the "Guide for the Care and Use of Laboratory Animals: Eighth Edition" (National Academies Press, Washington, D.C., 2011). In addition, the animal care and use protocol was reviewed and approved by the IACUC at Pharmacology Discovery Services Taiwan, Ltd. Immediately after the sacrifice of hamsters, blood samples were collected via terminal cardiac puncture in tubes coated with EDTA-K2, mixed gently, then kept on ice and centrifuged at 2,500×g for 15 minutes at 4° C. After plasma separation, samples were stored at −80° C. in aliquots of 300 pt.

To assay exemplary compounds in hamster plasma, a similar protocol as described for human plasma was performed diluting thawed plasma 1:2 in assay buffer. In a 96-well black plate, 5 µl of diluted hamster plasma were mixed with 35 µl of assay buffer and 10 µl of exemplary test compounds at different concentrations or vehicle (DMSO).

Exemplary test compounds were allowed to interact with the enzyme for 15 minutes at 37° C. After pre-incubation, 50 µl of 200 µM PRXS-AMC substrate were added to the all mixtures. All reactions were carried out for 1 h at 37° C. protected from light. AMC release was detected measuring fluorescence at an excitation/emission wavelength of 380/460 nm using a Multifunction Microplate Reader. All measurements were carried out as single point.

Results of $IC_{50}$ of exemplary test compounds over circulating FAPα from hamster plasma are shown in Table 4.

TABLE 4

Inhibition ex-vivo by exemplary compounds of circulating FAPα activity from human and hamster plasma.

| Compound No. | FAPα activity in human plasma (PRXS-AMC) $IC_{50}$, µM | FAPα activity in hamster plasma (PRXS-AMC) $IC_{50}$, µM |
|---|---|---|
| 2 | +++ | +++ |

For $IC_{50}$: +++ refers to $IC_{50} < 1$ µM; ++ refers to 1 µM $< IC_{50} < 10$ µM; + refers to $IC_{50} > 10$ µM.

Example B-10

Cytoxicity Assays in Human Leukemia Cell Lines

Human acute myeloid leukemia (AML) and non-AML cell lines are purchased from ATCC and cultured following their indications. At the day of the experiment, AML and non-AML cell lines are seeded in white 96-well plate in 100 µL growing medium containing either vehicle (DMSO) or an exemplary compound of the invention at different concentrations. After 48 hours post-treatment, luminescent-based cell viability is determined using Cell-Titer Glo (CTG) assay according to the manufacturer's instructions (Cat.No.: G7573, Promega). Percent of cell viability is calculated by normalizing luminescence signal to the average value from vehicle-treated wells, assumed as the maximum of viability (100%). In every experiment, all treatments are performed in triplicate and reported as % inhibition of viability±standard deviation (SD).

Val-boroPro, a non-specific prolyl peptidase inhibitor, was used as a positive control as described Johnson D C et al, Nature Medicine, 2018. $IC_{50}$ of certain compounds in the cytotoxicity assays using the human AML cell line MV4-11 are shown in Table 5.

TABLE 5

Inhibition of viability of the human AML cell line MV4-11 by certain compounds.

| Compound No. | MV4-11 viability $IC_{50}$, µM |
|---|---|
| Val-boroPro | +++ |
| 2 | ++ |
| 3 | ++ |
| 16 | + |
| 19 | +++ |
| 20 | ++ |
| 30 | ++ |
| 38 | + |
| 105 | +++ |
| 110 | +++ |

For $IC_{50}$: +++ refers to $IC_{50} < 3$ µM; ++ refers to 3 µM $< IC_{50} < 10$ µM; + refers to $IC_{50} > 10$ µM.

All references throughout, such as publications, patents, patent applications and published patent applications, are incorporated herein by reference in their entireties.

What is claimed is:

1. A compound of formula (A):

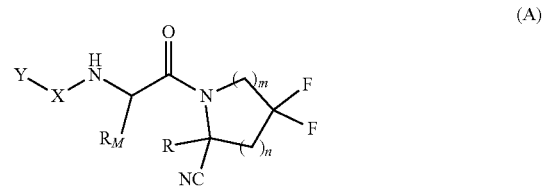

a pharmaceutically acceptable salt, stereoisomer or tautomer thereof, wherein:

R is hydrogen, $C_1$-$C_6$ alkyl, $C_1$-$C_6$ alkoxy, $C_3$-$C_8$ cycloalkyl, 3- to 12-membered heterocyclyl, 5- to 10-membered heteroaryl, or $C_6$-$C_{14}$ aryl, wherein the $C_1$-$C_6$ alkyl, $C_1$-$C_6$ alkoxy, $C_3$-$C_8$ cycloalkyl, 3- to 12-membered heterocyclyl, 5- to 10-membered heteroaryl, and $C_6$-$C_{14}$ aryl of R are independently optionally substituted by $R^d$;

$R_M$ is hydrogen or optionally substituted $C_1$-$C_6$ alkyl;

m is 0, 1, 2, 3, or 4;

n is 0, 1, 2, 3, or 4, wherein m+n is 1, 2, 3, or 4;

X is —C(=O)—, —O—, —CH(OH)—, —S—, —S(=O)—, or —S(=O)$_2$—

Y is

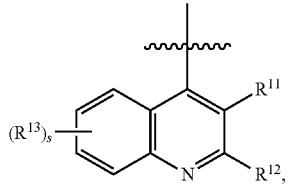

wherein:

the wavy line represents the point of attachment to the rest of the molecule, s is 1, 2, 3, or 4, $R^{11}$ and $R^{12}$ are each independently hydrogen, $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, halogen, cyano, —OR$^{14}$, —NR$^{15}$R$^{16}$, —SR$^{14}$, —NO$_2$, —C=NH(OR$^{14}$), —C(O)R$_{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$, or —P(O)(OR$^{15}$)(OR$^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{11}$ and $R^{12}$ are each independently optionally substituted by one or more of $R^L$;

each $R^{13}$ is independently $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, $C_6$-$C_{14}$ aryl, —NR$^{15}$R$^{16}$, —NO$_2$, —C=NH(OR$^{14}$), —C(O)R$^{14}$, —OC(O)R$^{14}$, —C(O)OR$^{14}$, —C(O)NR$^{15}$R$^{16}$, —NR$^{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$^{15}$, —NR$^{14}$S(O)$_2$R$^{15}$, —S(O)NR$^{15}$R$^{16}$, —S(O)$_2$NR$^{15}$R$^{16}$, or —P(O)(OR$^{15}$)(OR$^{16}$), wherein the $C_1$-$C_6$ alkyl, $C_2$-$C_6$ alkenyl, $C_2$-$C_6$ alkynyl, $C_3$-$C_8$ cycloalkyl, $C_4$-$C_8$ cycloalkenyl, 3- to 12-membered heterocyclyl, 5- to 10-membered heteroaryl, and $C_6$-$C_{14}$ aryl of $R^{13}$ are each independently optionally substituted by one or more $R^L$;

each $R^{14}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{14}$ are independently optionally substituted by halogen, —OH, oxo, cyano, or $C_1$-$C_6$ alkyl optionally substituted by halogen, —OH, or oxo;

$R^{15}$ and $R^{16}$, independently of each other and independently at each occurrence, are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, and 3- to 12-membered heterocyclyl of $R^{15}$ and $R^{16}$ are independently optionally substituted by halogen, —OH, oxo, cyano, or $C_1$-$C_6$ alkyl, optionally substituted by halogen, —OH, or oxo, or $R^{15}$ and $R^{16}$ are taken together with the atom to which they are attached to form a 3- to 6-membered heterocyclyl optionally substituted by halogen, oxo, cyano, or $C_1$-$C_6$ alkyl optionally substituted by halogen, —OH, or oxo;

$R^d$, independently at each occurrence, is halogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5- to 10-membered heteroaryl, 3- to 12-membered heterocyclyl, —OR14, —NR$_{15}$R$_{16}$, cyano, or nitro; and each $R^L$ is independently halogen, $C_1$-$C_6$ alkyl, $C_1$-$C_6$ alkoxy, $C_2$-$C_6$ alkenyl, $C_2$-$C_6$ alkynyl, $C_3$-$C_8$ cycloalkyl, $C_3$-$C_8$ cycloalkenyl, $C_6$-$C_{14}$ aryl, 5- to 10-membered heteroaryl, 3- to 12-membered heterocyclyl, —C(O)R$^{14}$, —OC(O)R$^{14}$, —C(O)OR$^{14}$, —C(O)NR$^{15}$R$^{16}$, —NR$_{14}$C(O)R$^{15}$, —NR$^{14}$C(O)OR$^{15}$, —NR$^{14}$C(O)NR$^{15}$R$^{16}$, —S(O)R$^{14}$, —S(O)$_2$R$^{14}$, —NR$^{14}$S(O)R$_{15}$, —NR$^{14}$(O)$_2$R$^{15}$, —S(O)NR$^{15}$R$^{16}$, —S(O)$_2$NR$^{15}$R$^{16}$, —P(O)(OR$^{15}$)(OR$^{16}$), —NR$^{15}$R$^{16}$, cyano, oxo, or nitro, wherein (1) the $C^1$-$C^6$ alkoxy is optionally substituted by halogen, —OH, oxo, cyano, $C^1$-$C^6$ alkoxy, or $C^1$-$C^6$ alkyl optionally substituted by halogen, —OH, or oxo, (2) the $C_1$-$C_6$ alkyl is optionally substituted by 5- to 10-membered heteroaryl or 3- to 12-membered heterocyclyl, wherein the 3- to 12-membered heterocyclyl is further optionally substituted by $C_1$-$C_6$ alkyl, (3) the 5- to 10-membered heteroaryl is optionally substituted by oxo, and (4) the $C_3$-$C_8$ cycloalkenyl is optionally substituted by halogen, —OH, oxo, cyano, $C_1$-$C_6$ alkoxy, or $C_1$-$C_6$ alkyl.

2. The compound of claim 1, a pharmaceutically acceptable salt, stereoisomer or tautomer thereof, wherein the compound is of formula (I):

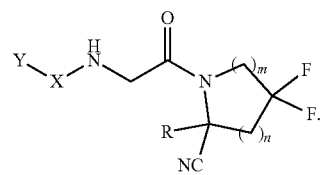

(I)

3. The compound of claim 1, a pharmaceutically acceptable salt, stereoisomer or tautomer thereof, wherein the compound is of formula (Ia):

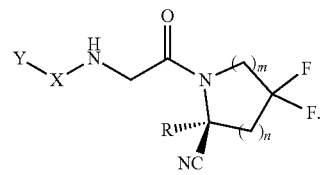

(Ia)

4. The compound of claim 1, a pharmaceutically acceptable salt, stereoisomer or tautomer thereof, wherein the compound is of formula (Ib):

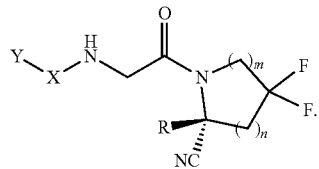

(Ib)

5. The compound of claim 1, a pharmaceutically acceptable salt, stereoisomer or tautomer thereof, wherein the compound is of formula (II):

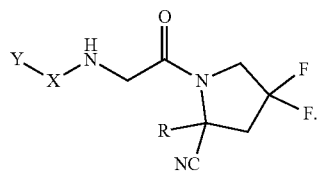

(II)

6. The compound of claim 1, a pharmaceutically acceptable salt, stereoisomer or tautomer thereof, wherein the compound is of formula (IIa):

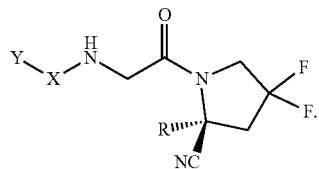

(IIa)

7. The compound of claim 1, a pharmaceutically acceptable salt, stereoisomer or tautomer thereof, wherein the compound is of formula (IIb):

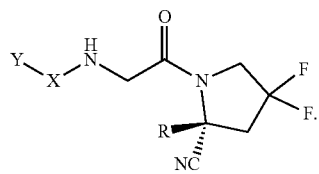

(IIb)

8. The compound of claim 1, a pharmaceutically acceptable salt, stereoisomer or tautomer thereof, wherein the compound is of formula (IIc):

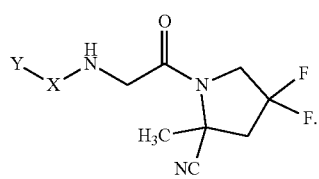

(IIc)

9. The compound of claim 1, a pharmaceutically acceptable salt, stereoisomer or tautomer thereof, wherein X is —C(=O)—.

10. The compound of claim 1, a pharmaceutically acceptable salt, stereoisomer or tautomer thereof, wherein R is hydrogen or $C_1$-$C_6$ alkyl.

11. The compound of claim 1, a pharmaceutically acceptable salt, stereoisomer or tautomer thereof, wherein $R^{11}$ is hydrogen, halogen, or $C_1$-$C_6$ alkyl.

12. The compound of claim 1, a pharmaceutically acceptable salt, stereoisomer or tautomer thereof, wherein $R^{12}$ is hydrogen, halogen, or $C_1$-$C_6$ alkyl.

13. The compound of claim 1, a pharmaceutically acceptable salt, stereoisomer or tautomer thereof, wherein each $R^{13}$ is independently selected from the groups consisting of:

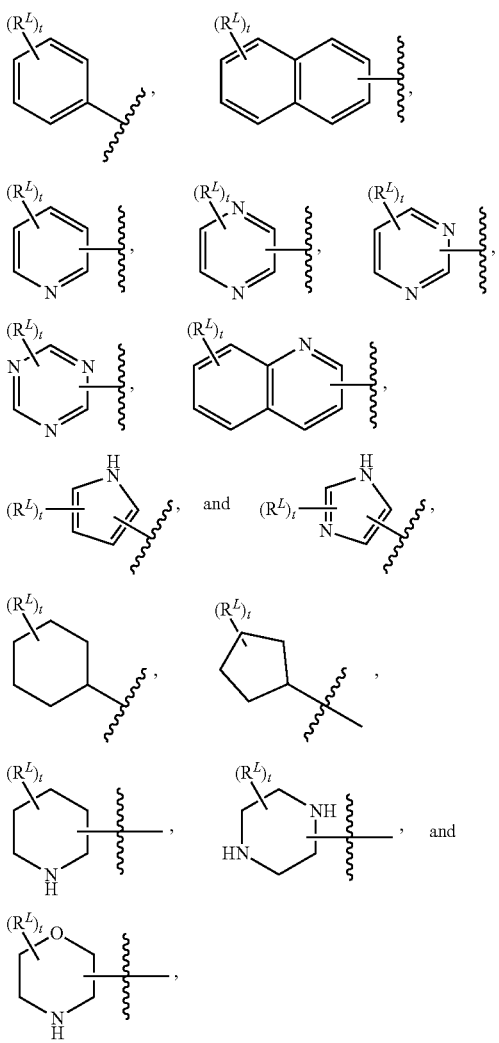

wherein t is 0, 1, 2, 3, 4, or 5; and the wavy line represents the point of attachment to the rest of the molecule.

14. The compound of claim 1, a pharmaceutically acceptable salt, stereoisomer or tautomer thereof, wherein s is 1.

15. The compound of claim 1, a pharmaceutically acceptable salt, stereoisomer or tautomer thereof, wherein s is 2.

16. A compound selected from the group consisting of
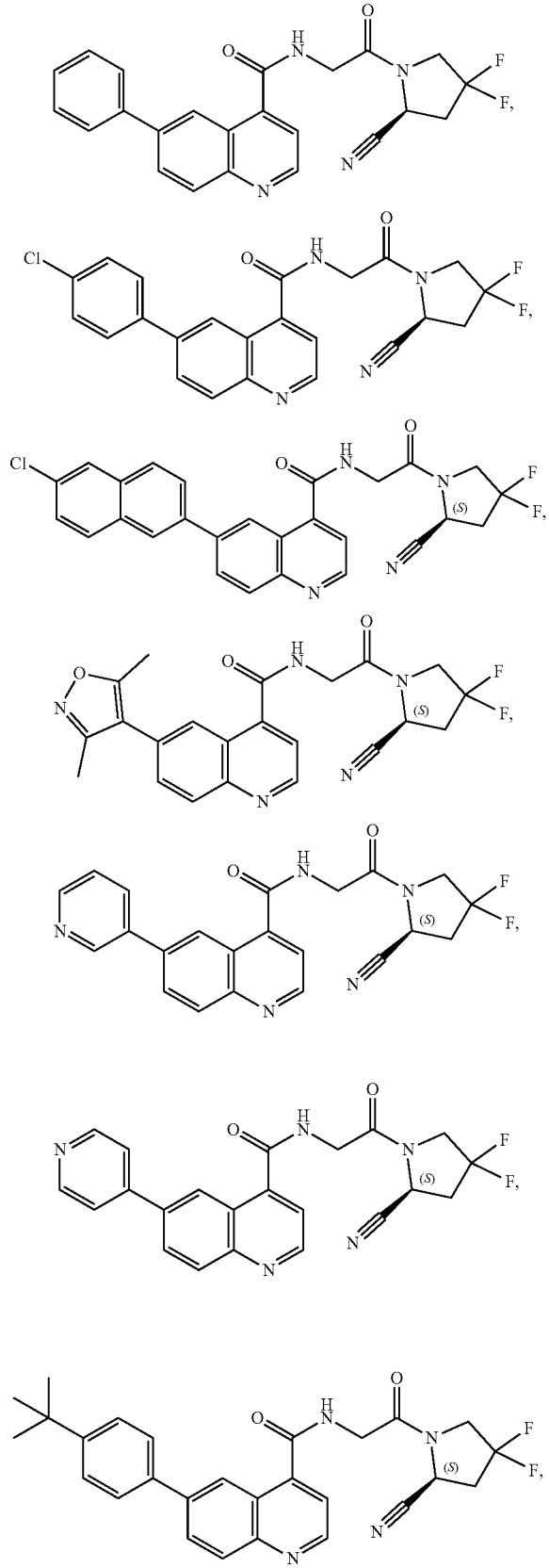
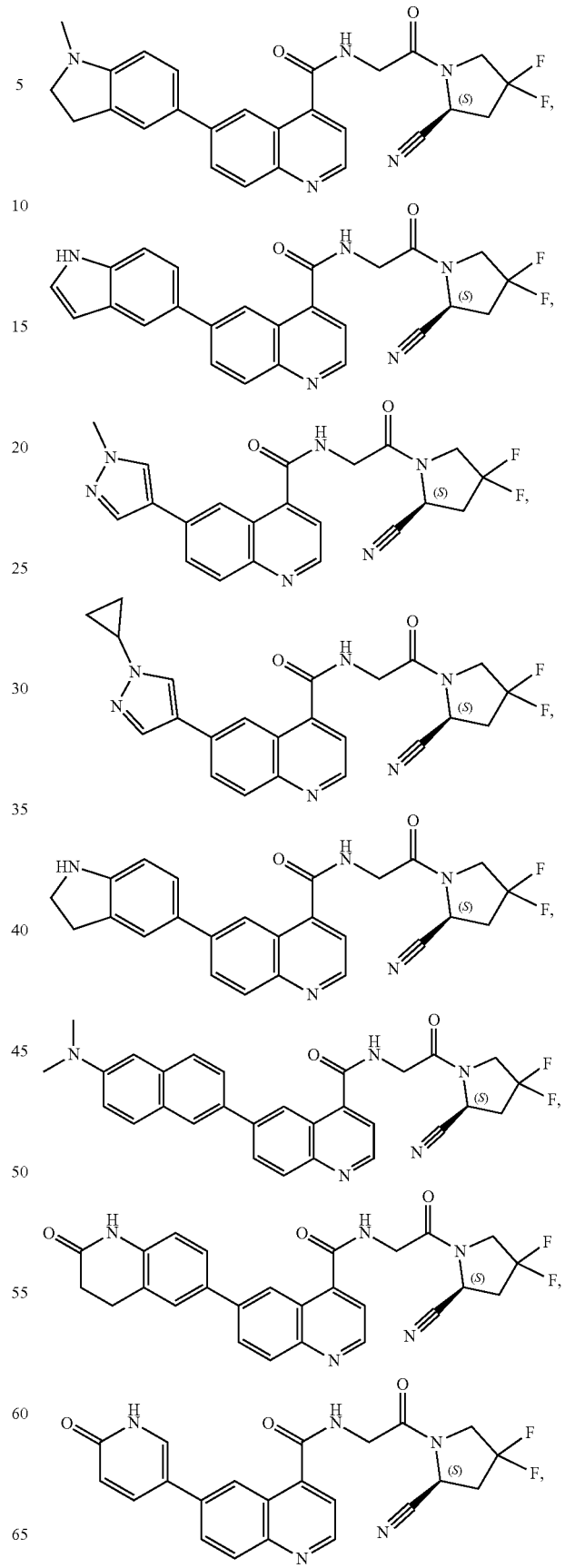

235
-continued
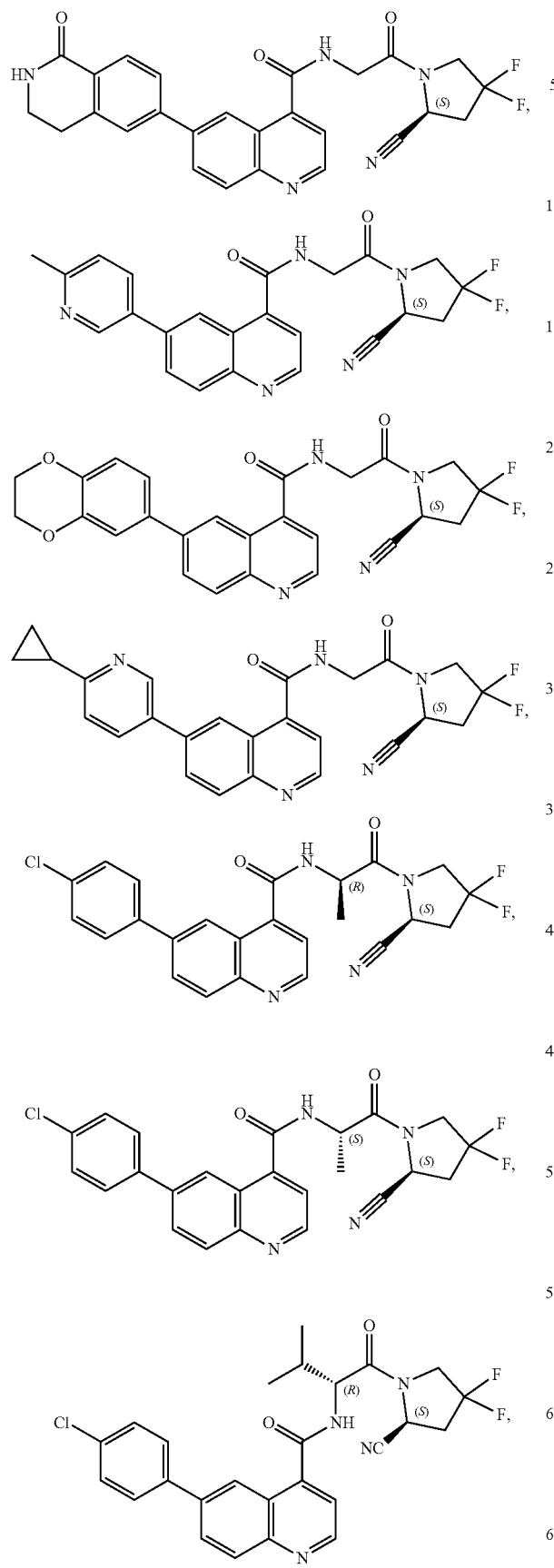
236
-continued
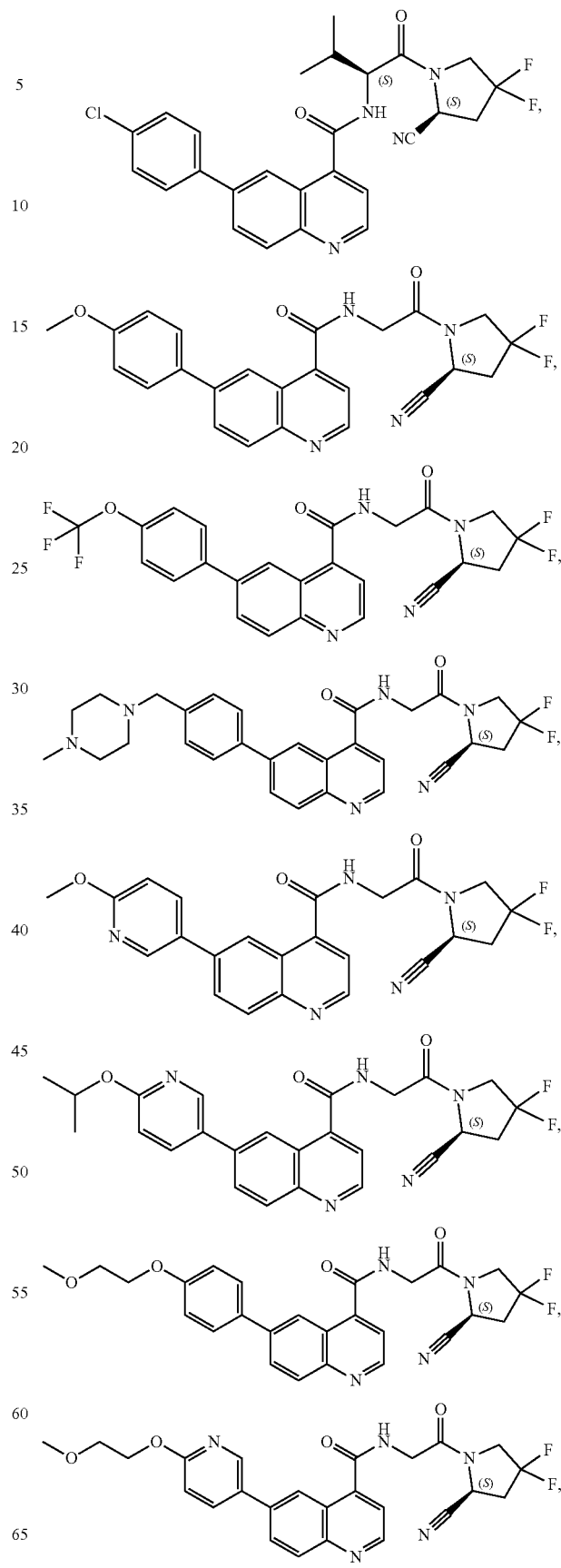

237
-continued
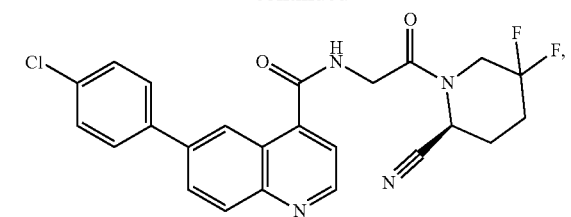
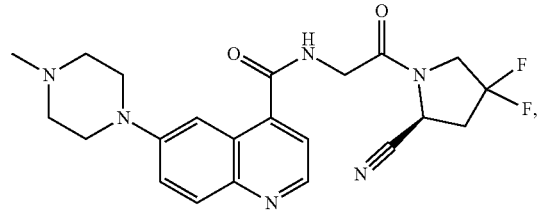
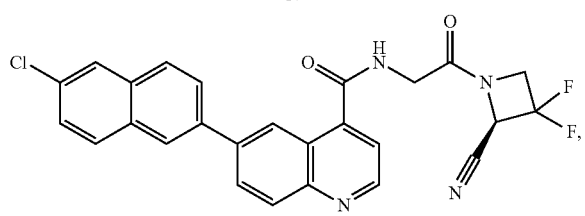
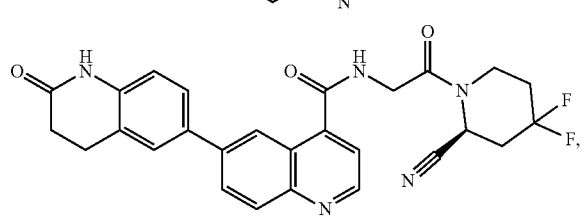
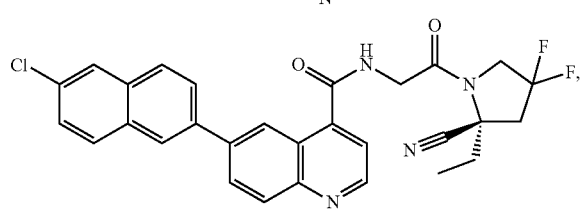
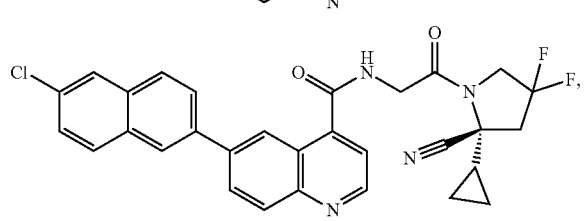
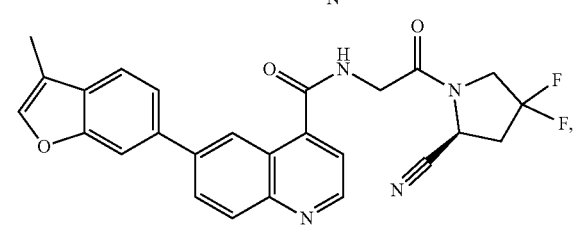
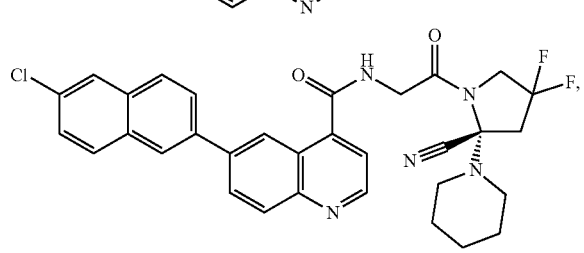
238
-continued
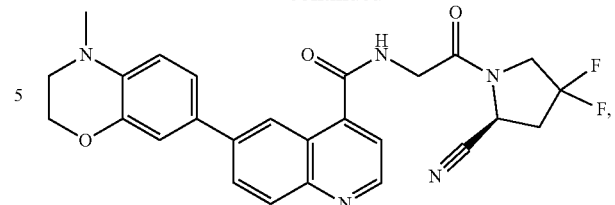
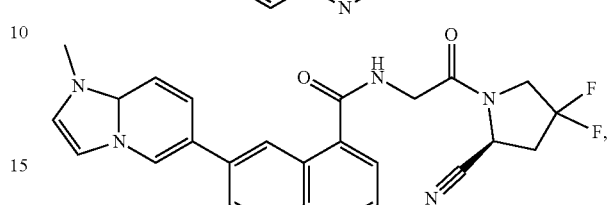
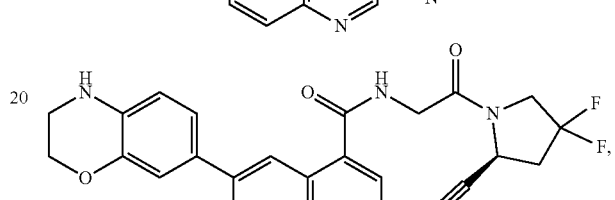
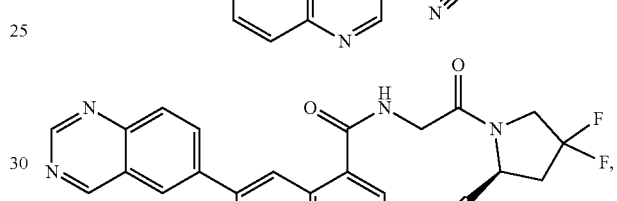
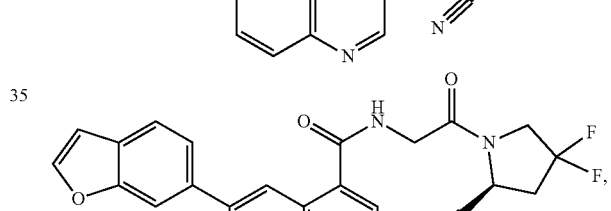
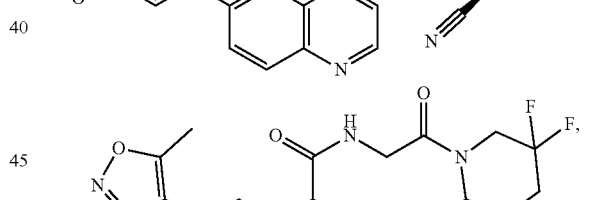
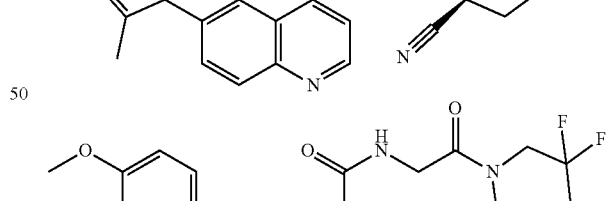
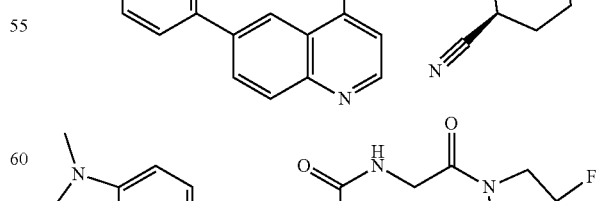
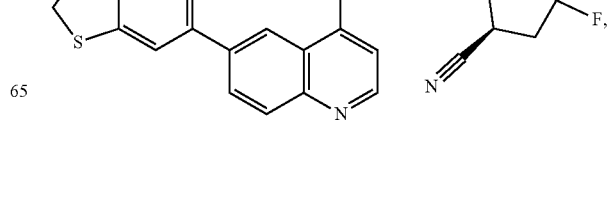

239
-continued
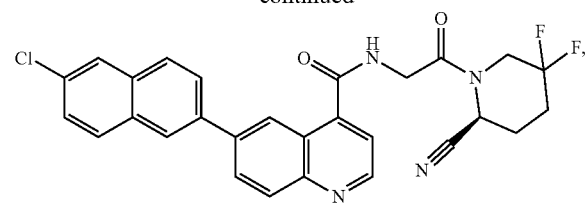
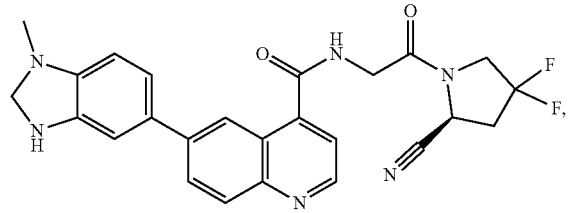
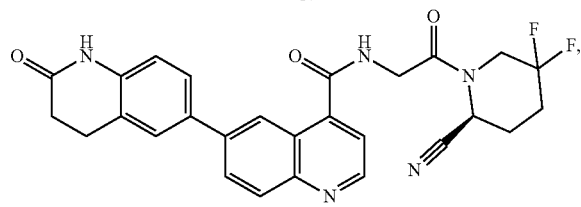
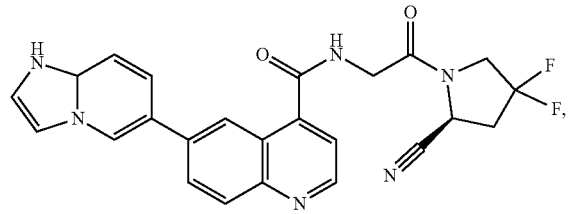
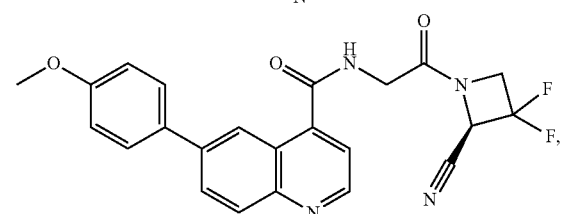
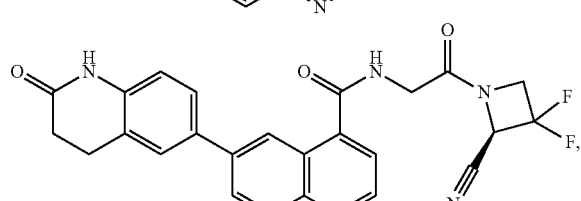
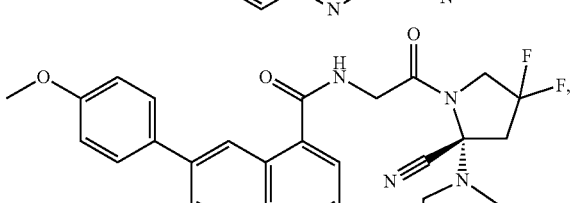
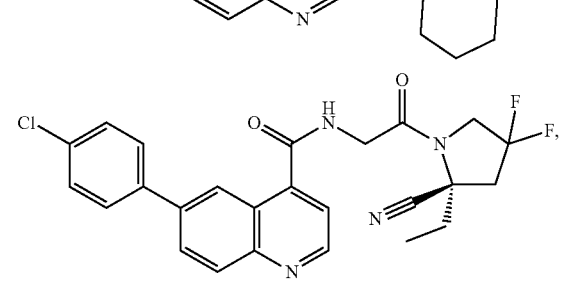
240
-continued
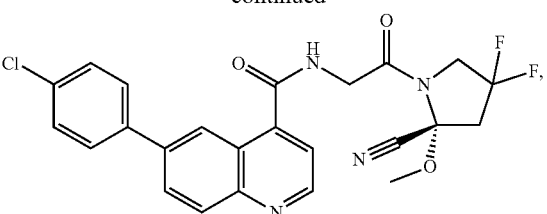
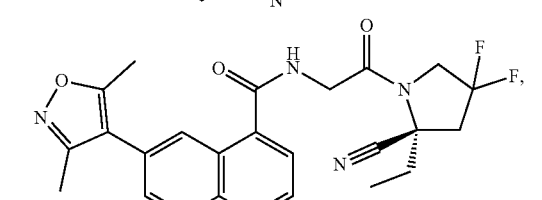
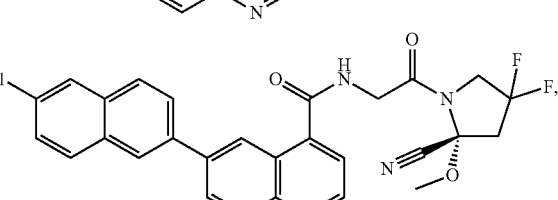
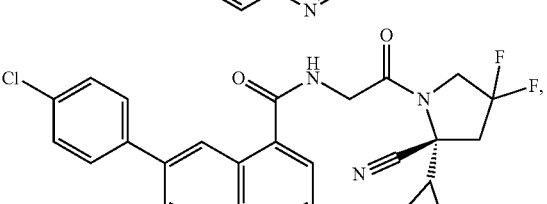
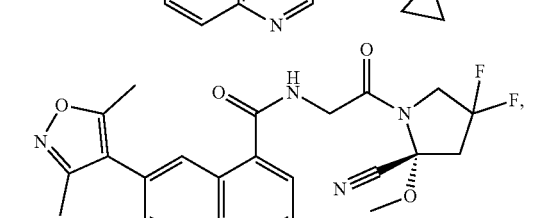
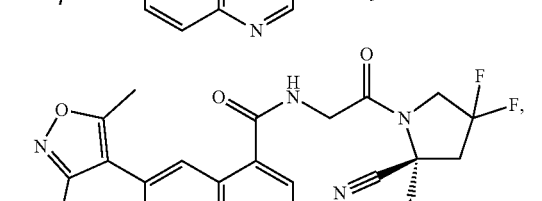
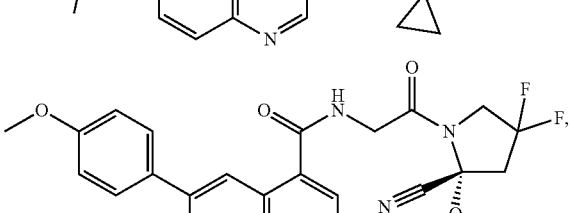
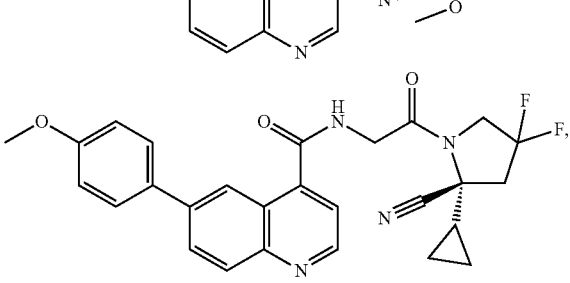

241
-continued
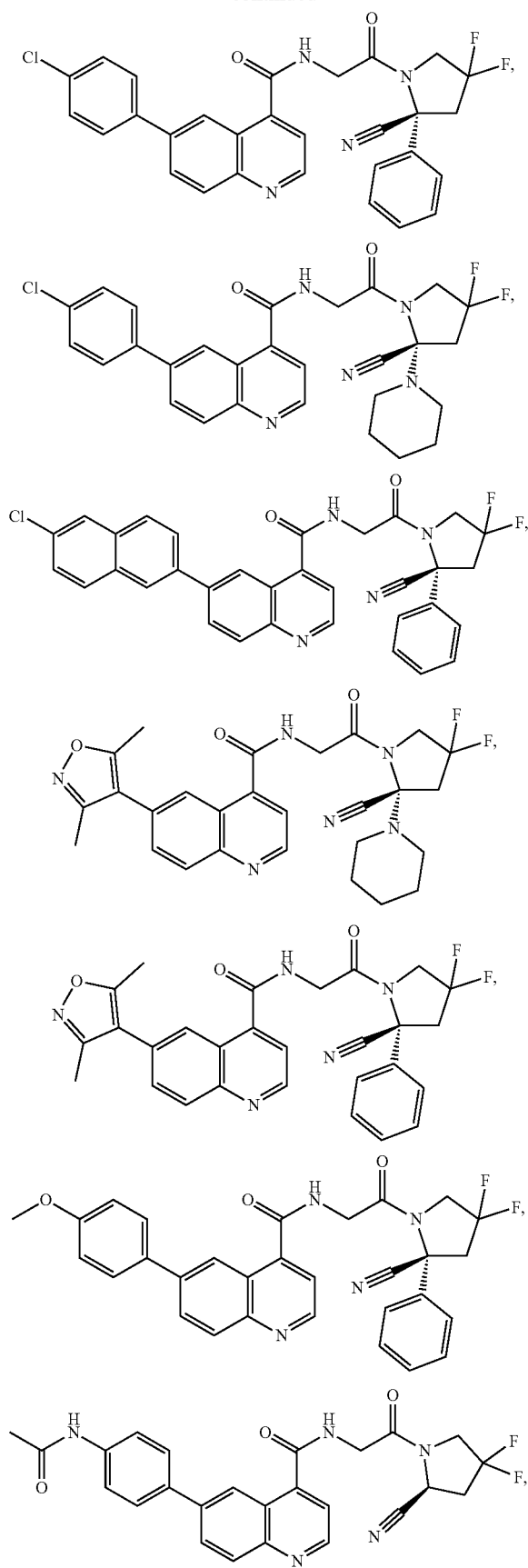
242
-continued
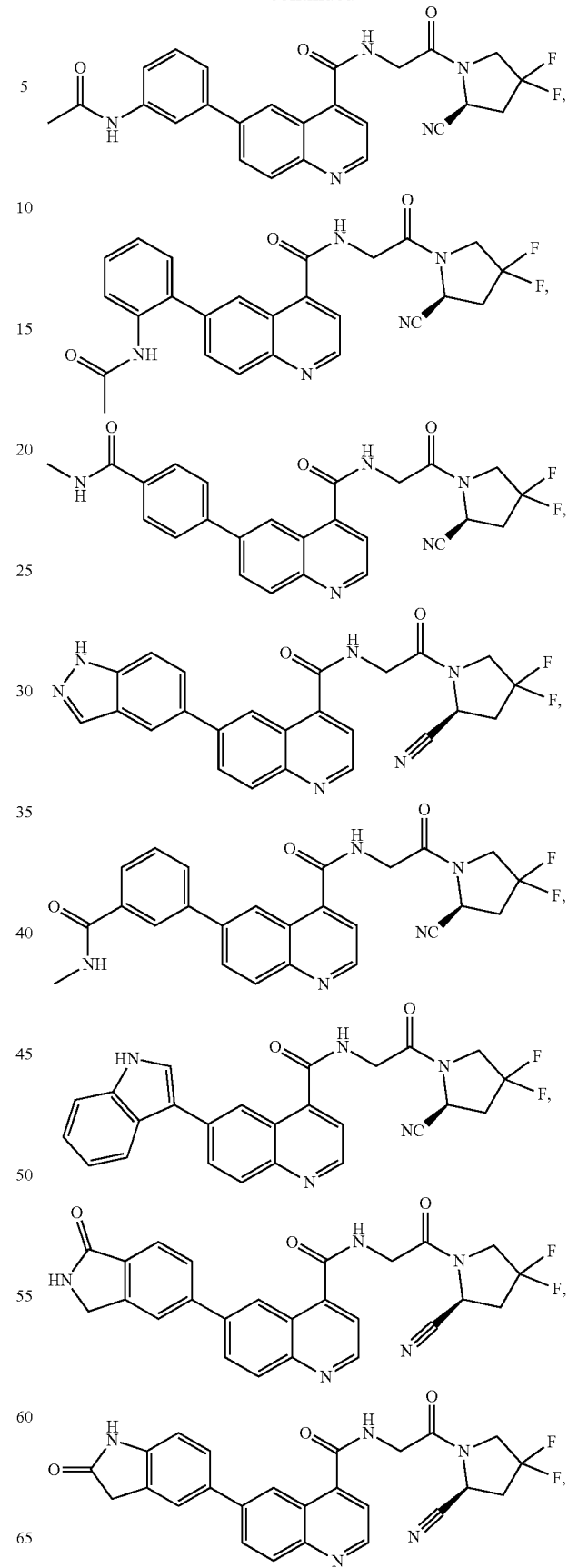

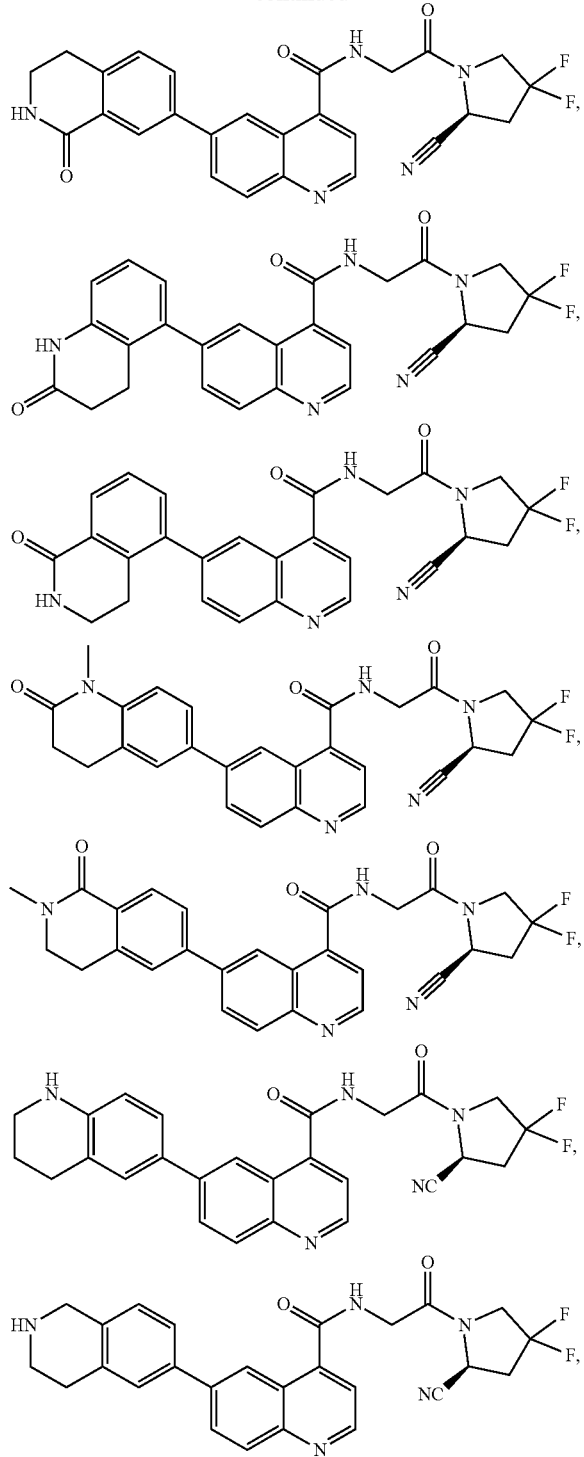

and

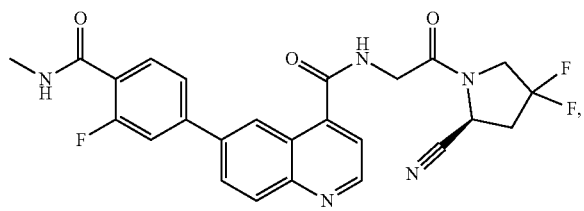

a pharmaceutically acceptable salt, stereoisomer or tautomer thereof.

17. The compound of claim 1, or a pharmaceutically acceptable salt, stereoisomer or tautomer thereof, wherein s is 1 and $R^{13}$ is $C_6$-$C_{14}$ aryl optionally substituted by one $R^L$.

18. The compound of claim 17, or a pharmaceutically acceptable salt, stereoisomer or tautomer thereof, wherein $R^{13}$ is phenyl optionally substituted by one $R^L$.

19. The compound of claim 18, or a pharmaceutically acceptable salt, stereoisomer or tautomer thereof, wherein $R^{13}$ is phenyl substituted by halogen, $C_1$-$C_6$ alkyl, or $C_1$-$C_6$ alkoxy.

20. The compound of claim 1, or a pharmaceutically acceptable salt, stereoisomer or tautomer thereof, wherein s is 1 and $R^{13}$ is 3- to 12-membered heterocyclyl optionally substituted by one $R^L$.

21. The compound of claim 1, or a pharmaceutically acceptable salt, stereoisomer or tautomer thereof, wherein s is 1 and $R^{13}$ is 5- to 10-membered heteroaryl optionally substituted by one $R^L$.

22. The compound of claim 21, or a pharmaceutically acceptable salt, stereoisomer or tautomer thereof, wherein the 5- to 10-membered heteroaryl is imidazolyl, pyrazolyl, isoxazolyl, furyl, pyridyl, pyranyl, tetrahydroquinolinyl, isoindolinyl, benzofuranyl, benzoxazine, benzothiazolyl, or benzimidazolyl.

23. The compound of claim 1, or a pharmaceutically acceptable salt, stereoisomer or tautomer thereof, wherein $R_M$ is $C_1$-$C_6$ alkyl.

24. A compound having the structure of

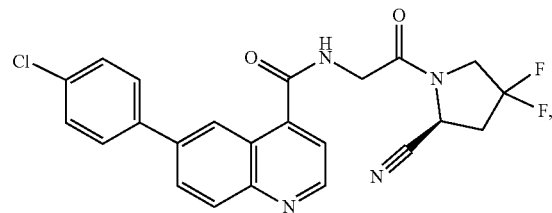 [SMILES: N#C[C@@H]1CC(F)(F)CN1C(=O)CNC(=O)c1ccnc2ccc(-c3ccc(Cl)cc3)cc12]

or a pharmaceutically acceptable salt.

25. A compound having the structure of

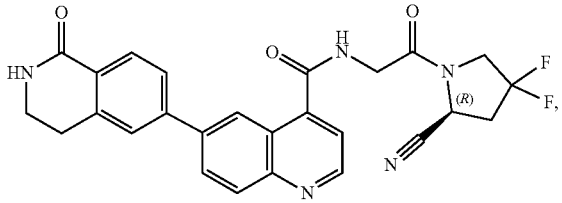

or a pharmaceutically acceptable salt.

26. A compound having the structure of

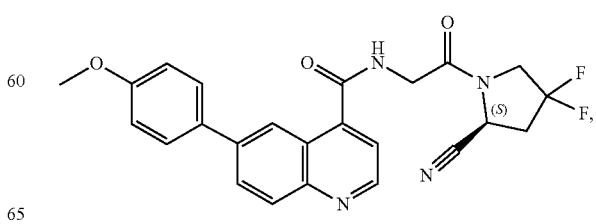

or a pharmaceutically acceptable salt.

27. A pharmaceutical composition comprising a compound of claim 1, or a pharmaceutically acceptable salt, stereoisomer or tautomer thereof, and a pharmaceutically acceptable carrier.

28. A method of inhibiting FAP in an individual comprising administering to the individual a compound of claim 1, or a pharmaceutically acceptable salt, stereoisomer or tautomer thereof.

29. A method of inhibiting FAP in a cell comprising administering or delivering to the cell a compound of claim 1, or a pharmaceutically acceptable salt, stereoisomer or tautomer thereof.

30. A method of inhibiting FAP in a tumor comprising administering or delivering to the tumor a compound of claim 1, or a pharmaceutically acceptable salt, stereoisomer or tautomer thereof.

31. A method of inhibiting FAP in plasma comprising administering or delivering to the plasma a compound of claim 1, or a pharmaceutically acceptable salt, stereoisomer or tautomer thereof.

32. A method of enhancing an immune response in an individual comprising administering (a) an immune checkpoint inhibitor and (b) a compound of claim 1, or a pharmaceutically acceptable salt, stereoisomer or tautomer thereof.

33. A method of increasing the level of FGF21 expression in an individual comprising administering to the individual a compound of claim 1, or a pharmaceutically acceptable salt, stereoisomer or tautomer thereof.

34. A method of treating a disease or disorder associated with FGF21 in an individual in need thereof comprising administering to the individual a therapeutically effective amount of a compound of claim 1, or a pharmaceutically acceptable salt, stereoisomer or tautomer thereof, wherein the disease or disorder is diabetes, obesity, dyslipidemia, metabolic syndrome, non-alcoholic fatty liver diseases, non-alcoholic steatohepatitis or cardiovascular diseases.

35. The method of claim 34, wherein the disease or disorder is diabetes or obesity.

36. The method of claim 35, wherein the diabetes is type I or type II diabetes.

37. A method of inhibiting FAP for treating a disease or disorder in an individual in need thereof comprising administering to the individual a therapeutically effective amount of a compound of claim 1, or a pharmaceutically acceptable salt, stereoisomer or tautomer thereof, wherein the disease or disorder is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma.

* * * * *